(12) United States Patent
Telser et al.

(10) Patent No.: US 10,246,420 B2
(45) Date of Patent: Apr. 2, 2019

(54) PYRAZOLE DERIVATIVES

(71) Applicant: BAYER CROPSCIENCE AKTIENGESELLSCHAFT, Monheim am Rhein (DE)

(72) Inventors: Joachim Telser, Wuppertal (DE); Peter Dahmen, Neuss (DE); Ulrike Wachendorff-Neumann, Neuwied (DE); Pierre Cristau, Lyons (FR); Philippe Rinolfi, Chatillon d Azergues (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/327,531

(22) PCT Filed: Jul. 21, 2015

(86) PCT No.: PCT/EP2015/066603
§ 371 (c)(1),
(2) Date: Jan. 19, 2017

(87) PCT Pub. No.: WO2016/012424
PCT Pub. Date: Jan. 28, 2016

(65) Prior Publication Data
US 2017/0174634 A1 Jun. 22, 2017

(30) Foreign Application Priority Data
Jul. 24, 2014 (EP) ..................................... 14178380

(51) Int. Cl.
| *C07D 231/38* | (2006.01) |
| *C07C 331/28* | (2006.01) |
| *C07C 217/76* | (2006.01) |
| *A01N 43/56* | (2006.01) |
| *C07D 401/04* | (2006.01) |

(52) U.S. Cl.
CPC .......... *C07D 231/38* (2013.01); *A01N 43/56* (2013.01); *C07C 217/76* (2013.01); *C07C 331/28* (2013.01); *C07D 401/04* (2013.01)

(58) Field of Classification Search
None
See application file for complete search history.

(56) References Cited

U.S. PATENT DOCUMENTS

| 6,054,413 A | 4/2000 | Zagar et al. |
| 2011/0319430 A1* | 12/2011 | Long ................... C07D 231/12 514/256 |
| 2013/0296269 A1 | 11/2013 | Benting et al. |
| 2014/0288074 A1 | 9/2014 | Taggi et al. |

FOREIGN PATENT DOCUMENTS

| EP | 0 626 370 A1 | 11/1994 |
| EP | 0863142 A1 | 9/1998 |
| FR | 1351848 A | 2/1964 |
| WO | 9719940 A1 | 6/1997 |
| WO | 2009127612 A1 | 10/2009 |
| WO | 2009137538 A2 | 11/2009 |
| WO | 2010/101973 A1 | 9/2010 |
| WO | 2012023143 A1 | 2/2012 |
| WO | 2012024586 A1 | 2/2012 |
| WO | 2012030922 A1 | 3/2012 |
| WO | 2012031061 A2 | 3/2012 |
| WO | 2012136834 A1 | 10/2012 |
| WO | 2013116251 A2 | 8/2013 |
| WO | 2013126283 A1 | 8/2013 |
| WO | 2013192126 A1 | 12/2013 |
| WO | 2014130241 A1 | 8/2014 |
| WO | 2014130409 A2 | 8/2014 |
| WO | 2015026646 A1 | 2/2015 |

OTHER PUBLICATIONS

Wei et al: "Synthesis and DNA-binding 15 affinity studies of glycosylated intercalators designed as functional mimics of the anthracycline antibiotics", Organic & Biomolecular Chemistry, vol. 7, No. 18, (Jan. 1, 2009), p. 3709, XP055145773.

Tatsuo Tashiro: "The ionization constants of 2-substituted 4,6-diamino-s-triazines: The applicability to the hammett and taft equations", Journal of Heterocyclic Chemistry, vol. 39, No. 4, (Jul. 1, 2002), pp. 615-622, XP055145758.

Harris L. Friedman et al: "Tuberculostatic Compounds. I. Ethers of 2-Hydroxy-5-aminopyridine", Journal of the American Chemical Society, vol. 69, No. 5, May 1, 1947 (May 1, 1947), pp. 1204-1206, XP055145757.

Raffaello Fusco et al: "Intramolecular 1,3-dipolar cycloadditions of aryl azides bearing alkenyl, alkynyl, and nitrile groups", The Journal of Organic Chemistry, vol. 40, No. 13, (Jun. 1, 1975), pp. 1906-1909, XP055145745.

Akito Yasuhara et al: "Convenient Reduction of Nitrobenzenes to Anilines Using Electrochemically Generated Nickel", The Journal of Organic Chemistry, vol. 64, No. 7, (Apr. 1, 1999), pp. 2301-2303, XP055145752.

S E Berezina et al: "Synthesis and Properties of Furazanyl-Substituted Acetylenes and Diacetylenes", Russian Journal of Organic Chemistry, (Nov. 1, 2001), pp. 1629-1637, XP055145771.

(Continued)

*Primary Examiner* — Kamal A Saeed
(74) *Attorney, Agent, or Firm* — McBee Moore Woodward & Vanik IP, LLC

(57) ABSTRACT

The present invention relates to novel pyrazole derivatives, to processes for preparing these compounds, to compositions comprising these compounds, and to the use thereof as biologically active compounds, especially for controlling harmful microorganisms in crop protection and in the protection of materials. Further, the present invention also relates to certain intermediates useful for producing said novel pyrazole derivatives.

15 Claims, No Drawings

(56) References Cited

OTHER PUBLICATIONS

Frank T. Coppo et al: "Synthesis of 1-methyl-7-(trifluoromethyl)-1 H-pyrido[2,3-c] [I,2]thiazin-4(3 H )-one 2,2-dioxide", Journal of Heterocyclic Chemistry, vol. 35, No. 3, (May 1, 1998), pp. 499-501, XP055145738.
Robert P. Mull: "Thionocarbanilates with Anthelmintic Activity", Journal of the American Chemical Society, vol . 77, No. 3, (Feb. 1, 1955), pp. 581-583, XP055145722.
Dubenko, R. G.; Gorbenko, "Investigations in the series of arylhydrazones of substituted glyoxylic acids. XXIX. Arylamides of 2,4-dinitrophenyl(acetyl)thioacetic acids in reactions with arenediazonium salts", Journal of Organic Chemistry USSR (English Translation), vol. 17, 1981, pp. 1521-1527, XP009180677.
Joachim Goerdeler et al: "Zur Darstellung und Tautomerie von 3-0xo-thiocarbonamiden", Chemische Berichte, vol. 113, No. 8, (Aug. 1, 1980), pp. 2814-2817, XP055145716.
EPO Database Abstract, RN 1228584-85-7 (Jun. 2010).

\* cited by examiner

PYRAZOLE DERIVATIVES

CROSS REFERENCE TO RELATED APPLICATIONS

This application is a § 371 National State Application of PCT/EP2015/066603, filed Jul. 21, 2015, which claims priority to European Application No. 14178380.3 filed Jul. 24, 2014.

BACKGROUND OF THE INVENTION

Field of the Invention

The present invention relates to novel pyrazole derivatives, to processes for preparing these compounds, to compositions comprising these compounds, and to the use thereof as biologically active compounds, especially for controlling harmful microorganisms in crop protection and in the protection of materials. Further, the present invention also relates to certain intermediates useful for producing said novel pyrazole derivatives.

Description of Related Art

The control of harmful microorganisms in crop protection is very important for achieving high crop efficiency. Plant disease damage to ornamental, vegetable, field, cereal or fruit crops can cause significant reduction in productivity. There are many active ingredients available today for controlling harmful microorganisms in crop protection, but there continues to be a need for new active ingredients for controlling harmful microorganisms.

It is already known that certain pyrazole derivatives have fungicidal properties (e.g. WO 2009/127612, WO 2009/137538, WO 2010/101973, WO 2012/023143, WO 2012/024586, WO 2012/030922, WO 2012/031061, WO 2013/116251, WO 2013/126283, WO 2013/192126, WO 2014/130241, WO 2014/130409, US 2014/0288074 and WO 2015/026646).

Since the ecological and economic demands made on modern active ingredients, for example fungicides, are increasing constantly, for example with respect to activity spectrum, toxicity, selectivity, application rate, formation of residues and favorable manufacture, and there can also be problems, for example, with resistances, there is a constant need to develop novel fungicidal compositions which have advantages over the known compositions at least in some areas.

SUMMARY

This invention now provides novel pyrazole derivatives of the formula (I)

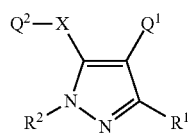

(I)

tautomers and/or salts thereof, wherein
$R^1$ is H, $CH_3$, F, Cl, Br, or $C_1$-$C_4$ alkoxy,
$R^2$ is methyl ($CH_3$) or ethyl ($C_2H_5$),
X is a structure element selected from the group consisting of NH, N($CH_3$), O, S, $CH_2$, CH(OH), and CH($CH_3$) (i.e. X links $Q^2$ to the pyrazole ring),
$Q^1$ is a 5- to 7-membered carbocyclic ring, optionally substituted with up to 5 independently selected substituents $R^{Q1}$ (i.e. 0, 1, 2, 3, 4 or 5 substituents $R^{Q1}$ in case $Q^1$ is a 6-membered carbocyclic ring, and 0, 1, 2, 3 or 4 substituents $R^{Q1}$ in case $Q^1$ is a 5-membered carbocyclic ring);
or a 5- to 7-membered heterocyclic ring containing ring members selected from the group consisting of C, N, O and S, and containing up to 3 (i.e. 1, 2 or 3) heteroatom ring members independently selected from the group O, S, and N, wherein the heterocyclic ring contains as heteroatom ring members up to 1 O atom (i.e. no or one oxygen atom), up to 1 S atom (i.e. no or one sulfur atom), and up to 3 (i.e. 0, 1, 2 or 3) N atoms,
wherein optionally up to 3 (i.e. 0, 1, 2 or 3) carbon ring members are independently selected from C(=O) and C(=S), and, if present, the sulfur atom ring members are independently selected from S, S(O), S(O)$_2$,
wherein the heterocyclic ring is optionally substituted with up to 5 (i.e. 0, 1, 2, 3, 4 or 5) substituents $R^{Q1}$ on carbon atom heterocyclic ring members and optionally substituted with substituents $R^N$ on nitrogen atom heterocyclic ring members, if present (i.e. if one or more nitrogen atom heterocyclic ring members are present),
each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, $CR^C$=NO—$C_1$-$C_4$ alkyl, —$NR^{1N}R^{2N}$ and optionally substituted phenyl,
$Q^2$ is a 5- or 6-membered carbocyclic ring, optionally substituted with up to 5 substituents $R^{Q2}$ (i.e. 0, 1, 2, 3, 4 or 5 substituents $R^{Q2}$ in case $Q^2$ is a 6-membered carbocyclic ring, and 0, 1, 2, 3 or 4 substituents $R^{Q2}$ in case $Q^2$ is a 5-membered carbocyclic ring);
or a 5- to 7-membered heterocyclic ring containing ring members selected from the group consisting of C, N, O and S, and containing up to 3 (i.e. 1, 2 or 3) heteroatom ring members independently selected from the group O, S, and N, wherein the heterocyclic ring contains as heteroatom ring members up to 1 O atom (i.e. no or one oxygen atom), up to 1 S atom (i.e. no or one sulfur atom), and up to 3 (i.e. 0, 1, 2 or 3) N atoms, wherein optionally up to 3 (i.e. 0, 1, 2 or 3) carbon ring members are independently selected from C(=O) and C(=S), and, if present, the sulfur atom ring members are independently selected from S, S(O), S(O)$_2$,
wherein the heterocyclic ring is optionally substituted with up to 5 (i.e. 0, 1, 2, 3, 4 or 5) substituents $R^{Q2}$ on carbon atom heterocyclic ring members and optionally substituted with substituents $R^N$ on nitrogen atom heterocyclic ring members, if present (i.e. if one or more nitrogen atom heterocyclic ring members are present), each $R^{Q2}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, $CR^C=NO$—$C_1$-$C_4$ alkyl, —$NR^{1N}R^{2N}$ and optionally substituted phenyl, wherein each $R^N$ is independently selected from the group consisting of cyano, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl, $C_1$-$C_6$ aminoalkyl, benzyl, $SO_2R^S$, wherein each $R^C$ is independently selected from the group consisting of H and $C_1$-$C_4$ alkyl, wherein $R^{1N}$ and $R^{2N}$ each are independently selected from $C_1$-$C_4$ alkyl and $C_3$-$C_6$ cycloalkyl, wherein each $R^S$ is independently selected from $C_1$-$C_4$ alkyl, $C_1$-$C_4$ haloalkyl, and $C_3$-$C_6$ cycloalkyl, wherein each optionally substituted phenyl is independently selected from phenyl substituted with up to 5 (i.e. 0, 1, 2, 3, 4 or 5) radicals selected from the group consisting of halogen, cyano, $C_1$-$C_4$ alkyl, $C_1$-$C_4$ haloalkyl, ($C_1$-$C_4$)-alkoxy-($C_1$-$C_4$)-alkyl, $C_1$-$C_4$ alkoxy, $C_1$-$C_4$ haloalkoxy, ($C_1$-$C_4$)-alkoxy-($C_1$-$C_4$)-alkoxy, ($C_1$-$C_4$) alkylthio and nitro, in particular phenyl which is optionally substituted by one or more radicals from the group consisting of halogen, $C_1$-$C_4$ alkyl, $C_1$-$C_4$ haloalkyl and $C_1$-$C_4$ alkoxy, provided that at least one substituent $R^{Q2}$ (i.e. one or more substituents $R^{Q2}$) is $C_3$-$C_7$ alkenylalkoxy or $C_3$-$C_7$ alkynylalkoxy.

DETAILED DESCRIPTION OF A PREFERRED EMBODIMENT

Compared to structurally closely related compounds (e.g. compounds disclosed in WO 2010/101973), the compounds of the present invention—in which at least one substituent $R^{Q2}$ is $C_3$-$C_7$ alkenylalkoxy or $C_3$-$C_7$ alkynylalkoxy—show improved fungicidal properties, e.g. a higher efficacy against phytopathogenic fungi, such as *Alternaria solani*, *Phakopsora pachyrhizi*, and *Sphaerotheca fuliginea*.

If in the context of the present invention reference is made to a compound of the formula (I), reference is also made to the tautomers and/or salts thereof.

In the context of the present invention, "propargyl" means prop-2-yn-1-yl, "allyl" means prop-2-en-1-yl, "propargyloxy" means prop-2-yn-1-yloxy, and "allyloxy" means prop-2-en-1-yloxy.

In the formula (I) and in all subsequent formulae, chemical radicals or substituents are referred to by names which are collective terms for the enumeration of individual group members or specifically refer to individual chemical radicals. In general, terms are used which are familiar to the person skilled in the art and/or in particular have the meanings illustrated below.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc.; this applies correspondingly to hydrocarbon radicals in composite meanings, such as hydrocarbonoxy radicals or other hydrocarbon radicals attached via heteroatom groups.

The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$C_1$-$C_4$ alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$C_1$-$C_6$ alkyl", correspondingly also encompass straight-chain or branched alkyl radicals with a greater number of carbon atoms, i.e. according to the example also the alkyl radicals having 5 and 6 carbon atoms.

Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Cycloalkyl is a carbocyclic saturated ring system, for example cyclopropyl, cyclobutyl, cyclopentyl, cyclohexyl or cycloheptyl. In the case of substituted cycloalkyl, cyclic systems with substituents are included, where the substituents may also be bonded by a double bond on the cycloalkyl radical.

Halogen is, for example, fluorine, chlorine, bromine or iodine. Haloalkyl, -alkenyl and -alkynyl are alkyl, alkenyl and alkynyl, respectively, which are partially or fully substituted by identical or different halogen atoms, preferably from the group consisting of fluorine, chlorine, bromine and iodine, in particular from the group consisting of fluorine, chlorine and bromine, very particularly from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals such as, for example, halocycloalkyl.

A heterocyclic radical (heterocyclyl) comprises at least one heterocyclic ring (=carbocyclic ring in which at least one carbon atom is replaced by a heteroatom (from the group consisting of N, O, S), which is saturated, unsaturated or heteroaromatic and may be unsubstituted or substituted, where the point of attachment is located at a ring atom.

Unless defined otherwise it preferably contains one or more, in particular 1, 2 or 3, heteroatoms in the heterocyclic ring from the group consisting of N, O, and S; it is preferably an aliphatic heterocyclyl radical having 5 to 7 ring atoms or a heteroaromatic radical having 5 or 6 ring atoms. The heterocyclic radical may, for example, be a heteroaromatic radical or ring (heteroaryl).

It is preferably a radical of a five- or six-membered heteroaromatic ring, such as pyridyl, pyrrolyl, thienyl or furyl.

it is furthermore preferably a radical of a corresponding heteroaromatic ring having 2, 3 or 4 heteroatoms, for example pyrimidinyl, pyridazinyl, pyrazinyl, triazinyl, thiazolyl, thiadiazolyl, oxazolyl, isoxazolyl, pyrazolyl, imidazolyl or triazolyl.

Here, preference is given to a radical of a heteroaromatic five- or six-membered ring having 1 to 3 heteroatoms, such as, for example, 1,2,3-triazolyl, 1,2,4-triazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, 1,2,3-triazinyl, 1,2,4-triazinyl, 1,3,5-triazinyl, thiazolyl, isothiazolyl, oxazolyl, isoxazolyl, pyrazolyl, imidazolyl.

More preference is given here to heteroaromatic radicals of five-membered heterocycles having 3 nitrogen atoms, such as 1,2,3-triazol-1-yl, 1,2,3-triazol-4-yl, 1,2,3-triazol-5-yl, 1,2,5-triazol-1-yl, 1,2,5-triazol-3-yl, 1,3,4-triazol-1-yl, 1,3,4-triazol-2-yl, 1,2,4-triazol-3-yl, 1,2,4-triazol-5-yl;

more preference is also given here to heteroaromatic radicals of six-membered heterocycles having 3 nitrogen atoms, such as 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl;

more preference is also given here to heteroaromatic radicals of five-membered heterocycles having two nitrogen atoms and one oxygen atom, such as 1,2,4-oxadiazol-3-yl; 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, more preference is also given here to heteroaromatic radicals of five-membered heterocycles having two nitrogen atoms and one sulphur atom, such as 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl.

Furthermore preferably, the heterocyclic radical or ring is a partially or fully hydrogenated heterocyclic radical having one heteroatom from the group of N, O and S, for example oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl. Suitable substituents for a substituted heterocyclic radical are the substituents specified later on below.

When a structural element is substituted "by one or more radicals" from a list of substituents (radicals) or a generically defined group of substituents (radicals), this in each case includes simultaneous substitution by a plurality of identical and/or structurally different substituents (radicals).

Preferred compounds of formula (I) according to the present invention, tautomers and/or salts thereof, are compounds wherein $R^1$ is H, $CH_3$, F, Cl, Br, or methoxy ($OCH_3$), $R^2$ is methyl or ethyl, X is a structure element selected from the group consisting of NH, $N(CH_3)$, O, S, $CH_2$, CH(OH), and $CH(CH_3)$, $Q^1$ is a 5- to 7-membered fully saturated or a fully unsaturated 6-membered carbocyclic ring, optionally substituted with up to 5 substituents $R^{Q1}$;

or a 5- to 7-membered fully saturated or a fully unsaturated 5- or 6-membered heterocyclic ring containing ring members selected from the group consisting of C, N, O and S, and containing up to 3 heteroatom ring members independently selected from the group O, S, and N, wherein the heterocyclic ring contains as heteroatom ring members up to 1 O atom, up to 1 S atom, and up to 3 N atoms, wherein the heterocyclic ring is optionally substituted with up to 3 substituents $R^{Q1}$ on carbon atom heterocyclic ring members and optionally substituted with substituents $R^N$ on nitrogen atom heterocyclic ring members, if present (i.e. if one or more nitrogen atom heterocyclic ring members are present), each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, CH=NO—$C_1$-$C_4$ alkyl, —$NR^{1N}R^{2N}$ and optionally substituted phenyl, $Q^2$ is a fully unsaturated or a fully saturated 5- or 6-membered carbocyclic ring, optionally substituted with up to 5 substituents $R^{Q2}$;

or is a fully unsaturated or a fully saturated 5- or 6-membered heterocyclic ring, wherein the heterocyclic ring is optionally substituted with up to 5 (i.e. 0, 1, 2, 3, 4 or 5) substituents $R^{Q2}$ on carbon atom heterocyclic ring members and optionally substituted with substituents $R^N$ on nitrogen atom heterocyclic ring members, if present (i.e. if one or more nitrogen atom heterocyclic ring members are present), each $R^{Q2}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, CH=NO—$C_1$-$C_4$ alkyl, —$NR^{1N}R^{2N}$ and optionally substituted phenyl, wherein each $R^N$ is independently selected from the group consisting of cyano, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl, $C_1$-$C_6$ aminoalkyl, benzyl, $SO_2R^S$, wherein $R^{1N}$ and $R^{2N}$ each are independently selected from $C_1$-$C_4$ alkyl and $C_3$-$C_6$ cycloalkyl,
wherein each $R^S$ is independently selected from $C_1$-$C_4$ alkyl, $C_1$-$C_4$ haloalkyl, and $C_3$-$C_6$ cycloalkyl,
wherein each optionally substituted phenyl is independently selected from phenyl substituted with up to 5 radicals selected from the group consisting of halogen, cyano, $C_1$-$C_4$ alkyl, $C_1$-$C_4$ haloalkyl, ($C_1$-$C_4$)-alkoxy-($C_1$-$C_4$)-alkyl, $C_1$-$C_4$ alkoxy, $C_1$-$C_4$ haloalkoxy, ($C_1$-$C_4$)-alkoxy-($C_1$-$C_4$)-alkoxy, ($C_1$-$C_4$) alkylthio and nitro, in particular phenyl which is optionally substituted by one or more radicals from the group consisting of halogen, $C_1$-$C_4$ alkyl, $C_1$-$C_4$ haloalkyl and $C_1$-$C_4$ alkoxy,
provided that at least one substituent $R^{Q2}$ is $C_3$-$C_7$ alkenylalkoxy or $C_3$-$C_7$ alkynylalkoxy.

In another preferred embodiment of the present invention, the invention relates to a compound of formula (I) as defined above, tautomers and/or salts thereof, wherein
$R^1$ is H, $CH_3$, F, Cl or Br,
$R^2$ is $CH_3$,
X is a structure element selected from the group consisting of NH, N($CH_3$), O, S, $CH_2$, CH(OH), and CH($CH_3$),
$Q^1$ is a ring selected from the group consisting of phenyl, 5- or 6-membered heteroaromatic rings, 5- to 7-membered fully saturated heterocyclic rings, and 5- to 7-membered fully saturated carbocyclic (i.e. cycloaliphatic) rings, wherein $Q^1$ is optionally substituted with up to 5 substituents $R^{Q1}$;
wherein each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, CH=NO—$C_1$-$C_4$ alkyl, —$NR^{1N}R^{2N}$ and optionally substituted phenyl,
$Q^2$ is a fully unsaturated or a fully saturated 5- or 6-membered carbocyclic or heterocyclic ring, optionally substituted with up to 5 substituents $R^{Q2}$;
wherein each $R^{Q2}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, CH=NO—$C_1$-$C_4$ alkyl, —$NR^{1N}R^{2N}$ and optionally substituted phenyl,
wherein $R^{1N}$ and $R^{2N}$ are independently selected from $C_1$-$C_4$ alkyl and $C_3$-$C_6$ cycloalkyl,
wherein each optionally substituted phenyl is independently selected from phenyl substituted with up to 5 radicals selected from the group consisting of halogen, cyano, $C_1$-$C_4$ alkyl, $C_1$-$C_4$ haloalkyl, ($C_1$-$C_4$)-alkoxy-($C_1$-$C_4$)-alkyl, $C_1$-$C_4$ alkoxy, $C_1$-$C_4$ haloalkoxy, ($C_1$-$C_4$)-alkoxy-($C_1$-$C_4$)-alkoxy, ($C_1$-$C_4$) alkylthio and nitro, in particular phenyl which is optionally substituted by one or more radicals from the group consisting of halogen, $C_1$-$C_4$ alkyl, $C_1$-$C_4$ haloalkyl and $C_1$-$C_4$ alkoxy,
provided that at least one substituent $R^{Q2}$ is $C_3$-$C_7$ alkenylalkoxy or $C_3$-$C_7$ alkynylalkoxy.

In a further preferred embodiment of the present invention, the invention relates to a compound of formula (I) as defined above, tautomers and/or salts thereof, wherein
$R^1$ is $CH_3$ or Cl,
$R^2$ is $CH_3$,
X is a structure element selected from the group consisting of NH, N($CH_3$), O, S, $CH_2$, CH(OH), and CH($CH_3$),
$Q^1$ is a ring selected from the group consisting of phenyl, 5- or 6-membered heteroaromatic rings, 5- to 7-membered fully saturated heterocyclic rings, and 5- or 6-membered fully saturated carbocyclic (i.e. cycloaliphatic) rings, wherein $Q^1$ is optionally substituted with up to 5 substituents $R^{Q1}$;
wherein each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_4$-$C_7$ alkylcycloalkyl, $C_4$-$C_6$ cycloalkylalkyl, $C_1$-$C_4$ alkanoylamino, $SF_5$, SCN, isonitrile, CH=NO—$C_1$-$C_4$ alkyl, —$NR^{1N}R^{2N}$ and optionally substituted phenyl,
$Q^2$ is a ring selected from the group consisting of phenyl, 5-membered heteroaromatic rings and 6-membered heteroaromatic rings (wherein the heteroatoms of said heteroaromatic rings preferably consist of one or two N heteroatom ring members), wherein $Q^2$ is optionally substituted with up to 5 substituents $R^{Q2}$;
wherein each $R^{Q2}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_1$-$C_6$ alkoxy, $C_1$-$C_6$ haloalkoxy, $C_2$-$C_6$ alkenyl, $C_3$-$C_4$ alkenylalkoxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_4$-$C_7$ alkylcycloalkyl, $C_4$-$C_6$ cycloalkylalkyl, $C_1$-$C_4$ alkanoylamino, $SF_5$, SCN, isonitrile, CH=NO—$C_1$-$C_4$ alkyl, —$NR^{1N}R^{2N}$ and optionally substituted phenyl,
wherein $R^{1N}$ and $R^{2N}$ are independently selected from $C_1$-$C_4$ alkyl and $C_3$-$C_6$ cycloalkyl,
wherein each optionally substituted phenyl is independently selected from phenyl substituted with up to 5 radicals selected from the group consisting of halogen, cyano, $C_1$-$C_4$ alkyl, $C_1$-$C_4$ haloalkyl, ($C_1$-$C_4$)-alkoxy-($C_1$-$C_4$)-alkyl, $C_1$-$C_4$ alkoxy, $C_1$-$C_4$ haloalkoxy, ($C_1$-$C_4$)-alkoxy-($C_1$-$C_4$)-alkoxy, ($C_1$-$C_4$) alkylthio and nitro, in particular phenyl which is optionally substituted by one or more radicals from the group consisting of halogen, $C_1$-$C_4$ alkyl, $C_1$-$C_4$ haloalkyl and $C_1$-$C_4$ alkoxy, provided that at least one substituent $R^{Q2}$ is $C_3$-$C_7$ alkenylalkoxy or $C_3$-$C_7$ alkynylalkoxy.

In a more preferred embodiment of the present invention, the invention relates to a compound of formula (I) as defined above, tautomers and/or salts thereof, wherein $R^1$ is $CH_3$ or Cl, $R^2$ is $CH_3$, X is a structure element selected from the group consisting of NH, N($CH_3$), O, S, $CH_2$, CH(OH), and CH($CH_3$), $Q^1$ is a ring selected from the group consisting of phenyl, 5- or 6-membered heteroaromatic rings, 5- to 7-membered fully saturated heterocyclic rings, and 5- or 6-membered fully saturated carbocyclic rings, wherein $Q^1$ is optionally substituted with up to 5 substituents $R^{Q1}$;

wherein each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_4$-$C_7$ alkylcycloalkyl, $C_4$-$C_6$ cycloalkylalkyl, $C_1$-$C_4$ alkanoylamino, $SF_5$, SCN, isonitrile, CH=NO—$C_1$-$C_4$ alkyl, —$NR^{1N}R^{2N}$ and optionally substituted phenyl, wherein $R^{1N}$ and $R^{2N}$ are independently selected from $C_1$-$C_4$ alkyl and $C_3$-$C_6$ cycloalkyl, wherein optionally substituted phenyl is phenyl substituted with up to 5 radicals selected from the group consisting of halogen, cyano, $C_1$-$C_4$ alkyl, $C_1$-$C_4$ haloalkyl, ($C_1$-$C_4$)-alkoxy-($C_1$-$C_4$)-alkyl, $C_1$-$C_4$ alkoxy, $C_1$-$C_4$ haloalkoxy, ($C_1$-$C_4$)-alkoxy-($C_1$-$C_4$)-alkoxy, ($C_1$-$C_4$) alkylthio and nitro, in particular phenyl which is optionally substituted by one or more radicals from the group consisting of halogen, $C_1$-$C_4$ alkyl, $C_1$-$C_4$ haloalkyl and $C_1$-$C_4$ alkoxy, $Q^2$ is a ring selected from the group consisting of phenyl or pyridinyl (preferably pyridin-3-yl), wherein $Q^2$ is optionally substituted with one or more substituents $R^{Q2}$;

wherein each $R^{Q2}$ is independently selected from the group consisting of halogen, cyano, nitro, amino, hydroxy, $C_1$-$C_6$ alkyl, $C_1$-$C_6$ haloalkyl, $C_1$-$C_6$ alkoxy, $C_1$-$C_6$ haloalkoxy, $C_3$-$C_7$ alkenylalkoxy, $C_2$-$C_6$ alkynyl, $C_3$-$C_7$ alkynylalkoxy, $C_3$-$C_7$ alkynyloxy, provided that at least one substituent $R^{Q2}$ (i.e. one or more substituents $R^{Q2}$) is propargyloxy (i.e. prop-2-yn-1-yloxy) or allyloxy (i.e. prop-2-en-1-yloxy).

In the above embodiment, the following definition of $Q^1$ is in turn preferred:

$Q^1$ is a ring selected from the group consisting of phenyl, 5- or 6-membered heteroaromatic rings, 6- or 7-membered fully saturated heterocyclic rings, wherein $Q^1$ is optionally substituted with up to 5 substituents $R^{Q1}$, wherein the definition of $R^{Q1}$ is the one of the above embodiment.

In a more preferred embodiment of the present invention, the invention relates to a compound of formula (I) as defined above, tautomers and/or salts thereof, wherein $R^1$ is $CH_3$ or Cl, $R^2$ is $CH_3$, X is a structure element selected from the group consisting of NH, N($CH_3$), O, S, $CH_2$, CH(OH), and CH($CH_3$), $Q^1$ is a ring selected from the group consisting of phenyl, furanyl, pyridinyl, piperidinyl, azepanyl and morpholinyl, wherein $Q^1$ is optionally substituted with up to 5 substituents $R^{Q1}$;

wherein each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_4$-$C_7$ alkylcycloalkyl, $C_4$-$C_6$ cycloalkylalkyl, $C_1$-$C_4$ alkanoylamino, $SF_5$, SCN, isonitrile, —$NR^{1N}R^{2N}$, wherein $R^{1N}$ and $R^{2N}$ are independently selected from $C_1$-$C_4$ alkyl and $C_3$-$C_6$ cycloalkyl, provided that at least one of the substituents $R^{Q1}$ is selected from the group consisting of halogen, cyano, nitro, amino, hydroxy, $C_1$-$C_6$ alkyl, $C_1$-$C_6$ haloalkyl, $C_1$-$C_6$ alkoxy, $C_1$-$C_6$ haloalkoxy, $C_2$-$C_6$ alkynyl, $C_3$-$C_7$ alkynylalkoxy, $C_3$-$C_7$ alkynyloxy, $Q^2$ is a phenyl ring substituted with one, two, three or four substituents $R^{Q2}$;

wherein each $R^{Q2}$ is independently selected from the group consisting of halogen, cyano, nitro, amino, hydroxy, $C_1$-$C_6$ alkyl, $C_1$-$C_6$ haloalkyl, $C_1$-$C_6$ alkoxy, $C_1$-$C_6$ haloalkoxy, $C_3$-$C_7$ alkenylalkoxy, $C_2$-$C_6$ alkynyl, $C_3$-$C_7$ alkynylalkoxy, $C_3$-$C_7$ alkynyloxy, provided that one, two or three substituents $R^{Q2}$ are propargyloxy or allyloxy.

In the above embodiment, the following definition of $Q^1$ is in turn preferred:

$Q^1$ is a ring selected from the group consisting of phenyl, furanyl, preferably pyridin-5-yl or pyridin-3-yl, piperidin-1-yl, azepan-1-yl, and 4-morpholinyl, wherein $Q^1$ is optionally substituted with up to 5 substituents $R^{Q1}$, wherein the definition of $R^{Q1}$ is the one of the above embodiment.

In an even more preferred embodiment of the present invention, the invention relates to a compound of formula (I) as defined above, tautomers and/or salts thereof, wherein $R^1$ is $CH_3$ or Cl, $R^2$ is $CH_3$, X is NH or O, $Q^1$ is a phenyl or a furanyl ring, wherein $Q^1$ is optionally substituted with one or more substituents $R^{Q1}$ selected from the group consisting of F, Cl, Br, I, cyano, nitro, amino, hydroxy, $C_1$-$C_6$ alkyl, $C_1$-$C_6$ haloalkyl, $C_1$-$C_6$ alkoxy, $C_1$-$C_6$ haloalkoxy, $C_3$-$C_6$ alkenylalkoxy, $C_2$-$C_6$ alkynyl, $C_3$-$C_7$ alkynylalkoxy, $C_3$-$C_7$ alkynyloxy, $Q^2$ is phenyl ring substituted with one, two, three or four substituents $R^{Q2}$;

wherein each $R^{Q2}$ is independently selected from the group consisting of F, Cl, Br, I, cyano, hydroxy, $C_1$-$C_6$ alkyl, $C_1$-$C_6$ haloalkyl, $C_1$-$C_6$ alkoxy, $C_1$-$C_6$ haloalkoxy, $C_3$-$C_6$ alkenylalkoxy, $C_3$-$C_7$ alkynylalkoxy, $C_3$-$C_7$ alkynyloxy, provided that one, two or three substituents $R^{Q2}$ are propargyloxy or allyloxy.

In an even more preferred embodiment of the present invention, the invention relates to a compound of formula (I) as defined above, tautomers and/or salts thereof, wherein $R^1$ is $CH_3$ or Cl, $R^2$ is $CH_3$, X is NH or O, preferably NH, $Q^1$ is a phenyl ring substituted with one or more substituents $R^{Q1}$ selected from the group consisting of F, Cl, Br, I, cyano, nitro, amino, hydroxy, $C_1$-$C_4$ alkyl, $C_1$-$C_4$ haloalkyl, $C_1$-$C_4$ alkoxy, $C_1$-$C_4$ haloalkoxy, $C_3$-$C_6$ alkenylalkoxy, $C_3$-$C_7$ alkynylalkoxy, $C_3$-$C_6$ alkynyloxy, $Q^2$ is a phenyl ring substituted with one, two, three or four substituents $R^{Q2}$;

wherein each $R^{Q2}$ is independently selected from the group consisting of F, Cl, Br, I, cyano, hydroxy, $C_1$-$C_4$ alkyl, $C_1$-$C_4$ haloalkyl, $C_1$-$C_4$ alkoxy, $C_1$-$C_4$ haloalkoxy, $C_3$-$C_6$ alkenylalkoxy, $C_3$-$C_7$ alkynylalkoxy, $C_3$-$C_6$ alkynyloxy, provided that one, two or three substituents $R^{Q2}$ are propargyloxy or allyloxy.

In a particularly preferred embodiment of the present invention, the invention relates to a compound of formula (I) as defined above, tautomers and/or salts thereof, wherein
$R^1$ is $CH_3$,
$R^2$ is $CH_3$,
X is NH or O, preferably NH,
$Q^1$ is a phenyl ring substituted with one or more (preferably two or three) substituents $R^{Q1}$ selected from the group consisting of F, Cl, Br, I, CN, $CH_3$, $CCl_3$, $CHF_2$, $CF_3$, $CH_2CF_3$, $OCH_3$, $OCF_3$, propargyloxy, allyloxy,
$Q^2$ is a phenyl ring substituted with one, two, three or four independently selected substituents $R^{Q2}$ selected from the group consisting of F, Cl, Br, I, CN, $CH_3$, $CCl_3$, $CHF_2$, $CF_3$, $CH_2CF_3$, $OCH_3$, $OCF_3$, propargyloxy and allyloxy,
provided that one, two or three substituents $R^{Q2}$ are propargyloxy or allyloxy.

In a particularly preferred embodiment of the present invention, the invention relates to a compound of formula (I) as defined above, tautomers and/or salts thereof, wherein
$R^1$ is $CH_3$,
$R^2$ is $CH_3$,
X is NH or O, preferably NH,
$Q^1$ is a phenyl ring substituted with two or more (preferably two or three) substituents $R^{Q1}$ selected from the group consisting of F, Cl, Br, I, CN, $CH_3$, $CCl_3$, $CHF_2$, $CF_3$, $CH_2CF_3$, $OCH_3$, $OCF_3$, propargyloxy, allyloxy,
$Q^2$ is a phenyl ring substituted with one or two substituents $R^{Q2}$ selected from the group consisting of propargyloxy and allyloxy, wherein $Q^2$ is optionally further substituted with one or two independently selected substituents $R^{Q2}$ selected from the group consisting of F, Cl, Br, I, CN, $CH_3$, $CCl_3$, $CHF_2$, $CF_3$, $CH_2CF_3$, $OCH_3$, $OCF_3$.

Particularly preferred compounds of the formula (I) according to the invention are those, wherein:
$Q^2$ is selected from the group consisting of 2,6-difluoro-4-propargyloxyphenyl, 4-allyloxy-2,6-difluorophenyl, 2,4-difluoro-6-propargyloxyphenyl, 4-fluoro-2-propargyloxyphenyl, 2-fluoro-6-propargyloxyphenyl, 4-chloro-2-fluoro-6-propargyloxyphenyl, 2-chloro-4-fluoro-6-propargyloxyphenyl, 4-allyloxy-2-fluorophenyl, 2-fluoro-4-propargyloxyphenyl, 2-allyloxyphenyl, 2-propargyloxyphenyl, 2-allyloxy-5-fluorophenyl, 5-fluoro-2-propargyloxyphenyl, 2-allyloxy-4-methylphenyl, 4-methyl-2-propargyloxyphenyl, 2-allyloxy-5-cyanophenyl, 5-cyano-2-propargyloxyphenyl, 5-allyloxy-2-fluorophenyl, 2-fluoro-5-propargyloxyphenyl, 4-allyloxy-2-chlorophenyl, 2-chloro-4-propargyloxyphenyl, 4-allyloxy-3-fluorophenyl, 3-fluoro-4-propargyloxyphenyl, 4-allyloxyphenyl, 4-propargyloxyphenyl, 3-fluoro-5-propargyloxyphenyl, 3-fluoro-5-allyloxyphenyl, 2,5-difluoro-4-propargyloxyphenyl, 2,5-difluoro-4-allyloxyphenyl, 6-allyloxypyridin-3-yl, 6-propargyloxypyridin-3-yl, 2-propargyloxy-6-trifluorophenyl, 2-allyloxy-6-trifluormethylphenyl, 2-chloro-6-propargyloxyphenyl, 2-allyloxy-6-chlorophenyl, 2,4-dimethyl-6-propargyloxyphenyl and 2-allyloxy-4,6-dimethylphenyl.

Particularly preferred compounds of the formula (I) according to the invention are those, wherein:
$Q^1$ is selected from the group consisting of 2-chloro-4-fluorophenyl, 2,4-dichlorophenyl, 2-fluorophenyl, 3,5-dimethoxyphenyl, 2,4-difluorphenyl, 2-fluoro-4-methoxyphenyl, 6-chloropyridin-3-yl, (2-chloropyridin)-5-yl, 4-allyloxy-2-fluorophenyl, 2-propargyloxyphenyl, 2,6-difluoro-4-methoxyphenyl, 2-fluoro-4-propargyloxyphenyl, 4-chloro-2-fluorophenyl, 2-bromo-4-fluorophenyl, 2,4,6-trifluorophenyl, 4-chloro-2,6-difluorophenyl, 3,4-dichlorophenyl, 3,5-dichlorophenyl, 4-fluoro-2-propargyloxyphenyl, 2,6-difluoro-4-propargyloxyphenyl and 2-fluoro-5-(furan-2-yl)phenyl, 4-methylpiperidin-1-yl, azepan-1-yl, and 4-morpholinyl.

More particularly preferred compounds of the formula (I) according to the invention are those, wherein:
$R^1$ is $CH_3$ or Cl,
$R^2$ is $CH_3$,
X is NH or O,
$Q^1$ is selected from the group consisting of 2-chloro-4-fluorophenyl, 2,4-dichlorophenyl, 2-fluorophenyl, 3,5-dimethoxyphenyl, 2,4-difluorphenyl, 2-fluoro-4-methoxyphenyl, 6-chloropyridin-3-yl, (2-chloropyridin)-5-yl, 4-allyloxy-2-fluorophenyl, 2-propargyloxyphenyl, 2,6-difluoro-4-methoxyphenyl, 2-fluoro-4-propargyloxyphenyl, 4-chloro-2-fluorophenyl, 2-bromo-4-fluorophenyl, 2,4,6-trifluorophenyl, 4-chloro-2,6-difluorophenyl, 3,4-dichlorophenyl, 3,5-dichlorophenyl, 4-fluoro-2-propargyloxyphenyl, 2,6-difluoro-4-propargyloxyphenyl and 2-fluoro-5-(furan-2-yl)phenyl,
and
$Q^2$ is selected from the group consisting of 2,6-difluoro-4-propargyloxyphenyl, 4-allyloxy-2,6-difluorophenyl, 2,4-difluoro-6-propargyloxyphenyl, 4-fluoro-2-propargyloxyphenyl, 2-fluoro-6-propargyloxyphenyl, 4-chloro-2-fluoro-6-propargyloxyphenyl, 2-chloro-4-fluoro-6-propargyloxyphenyl, 4-allyloxy-2-fluorophenyl, 2-fluoro-4-propargyloxyphenyl, 2-allyloxyphenyl, 2-propargyloxyphenyl, 2-allyloxy-5-fluorophenyl, 5-fluoro-2-propargyloxyphenyl, 2-allyloxy-4-methylphenyl, 4-methyl-2-propargyloxyphenyl, 2-allyloxy-5-cyanophenyl, 5-cyano-2-propargyloxyphenyl, 5-allyloxy-2-fluorophenyl, 2-fluoro-5-propargyloxyphenyl, 4-allyloxy-2-chlorophenyl, 2-chloro-4-propargyloxyphenyl, 4-allyloxy-3-fluorophenyl, 3-fluoro-4-propargyloxyphenyl, 4-allyloxyphenyl, 4-propargyloxyphenyl, 3-fluoro-5-propargyloxyphenyl, 3-fluoro-5-allyloxyphenyl, 2,5-difluoro-4-propargyloxyphenyl, 2,5-difluoro-4-allyloxyphenyl, 6-allyloxypyridin-3-yl, 6-propargyloxypyridin-3-yl, 2-propargyloxy-6-trifluorophenyl, 2-allyloxy-6-trifluormethylphenyl, 2-chloro-6-propargyloxyphenyl, 2-allyloxy-6-chlorophenyl, 2,4-dimethyl-6-propargyloxyphenyl and 2-allyloxy-4,6-dimethylphenyl.

More particularly preferred compounds of the formula (I) according to the invention are those, wherein:
$R^1$ is $CH_3$ or Cl,
$R^2$ is $CH_3$,
X is NH or O,
$Q^1$ is selected from the group consisting of 2-chloro-4-fluorophenyl, 2,4-dichlorophenyl, 2-fluorophenyl, 3,5-dimethoxyphenyl, 2,4-difluorphenyl, 2-fluoro-4-methoxyphenyl, (2-chloropyridin)-5-yl, 4-allyloxy-2-fluorophenyl, 2-propargyloxyphenyl, 2,6-difluoro-4-methoxyphenyl, 2-fluoro-4-propargyloxyphenyl, 4-chloro-2-fluorophenyl, 2-bromo-4-fluorophenyl, 2,4,6-trifluorophenyl, 4-chloro-2,6-difluorophenyl, 3,4-dichlorophenyl, 3,5-dichlorophenyl, 4-fluoro-2-propargyloxyphenyl, 2,6-difluoro-4-propargyloxyphenyl and 2-fluoro-5-(furan-2-yl)phenyl,
and
$Q^2$ is selected from the group consisting of 2,6-difluoro-4-propargyloxyphenyl, 4-allyloxy-2,6-difluorophenyl, 2,4-difluoro-6-propargyloxyphenyl, 4-fluoro-2-propargyloxyphenyl, 2-fluoro-6-propargyloxyphenyl, 4-chloro-2-fluoro-6- propargyloxyphenyl, 2-chloro-4-fluoro-6-propargyloxyphenyl, 4-allyloxy-2-fluorophenyl, 2-fluoro-4-propargyloxyphenyl, 2-allyloxyphenyl, 2-propargyloxyphenyl, 2-allyloxy-5-fluorophenyl, 5-fluoro-2-propargyloxyphenyl, 2-allyloxy-4-methylphenyl, 4-methyl-2-propargyloxyphenyl, 2-allyloxy-5-cyanophenyl, 5-cyano-2-propargyloxyphenyl, 5-allyloxy-2-fluorophenyl, 2-fluoro-5-propargyloxyphenyl, 4-allyloxy-2-chlorophenyl, 2-chloro-4-propargyloxyphenyl, 4-allyloxy-3-fluorophenyl, 3-fluoro-4-propargyloxyphenyl, 4-allyloxyphenyl, 4-propargyloxyphenyl, 3-fluoro-5-propargyloxyphenyl, 3-fluoro-5-allyloxyphenyl, 2,5-difluoro-4-propargyloxyphenyl, 2,5-difluoro-4-allyloxyphenyl, 6-allyloxypyridin-3-yl, 6-propargyloxypyridin-3-yl, 2-propargyloxy-6-trifluorophenyl, 2-allyloxy-6-trifluormethylphenyl, 2-chloro-6-propargyloxyphenyl, 2-allyloxy-6-chlorophenyl, 2,4-dimethyl-6-propargyloxyphenyl and 2-allyloxy-4,6-dimethylphenyl.

Even more particularly preferred compounds of the formula (I) according to the invention are those, wherein:
$R^1$ is $CH_3$,
$R^2$ is $CH_3$,
X is NH,
$Q^1$ is selected from the group consisting of 2-chloro-4-fluorophenyl, 2,4-dichlorophenyl, 2-fluorophenyl, 3,5-dimethoxyphenyl, 2,4-difluorphenyl, 2-fluoro-4-methoxyphenyl, 6-chloropyridin-3-yl, (2-chloropyridin)-5-yl, 4-allyloxy-2-fluorophenyl, 2-propargyloxyphenyl, 2,6-difluoro-4-methoxyphenyl, 2-fluoro-4-propargyloxyphenyl, 4-chloro-2-fluorophenyl, 2-bromo-4-fluorophenyl, 2,4,6-trifluorophenyl, 4-chloro-2,6-difluorophenyl, 3,4-dichlorophenyl, 3,5-dichlorophenyl, 4-fluoro-2-propargyloxyphenyl, 2,6-difluoro-4-propargyloxyphenyl and 2-fluoro-5-(furan-2-yl)phenyl,
and
$Q^2$ is selected from the group consisting of 2,6-difluoro-4-propargyloxyphenyl, 4-allyloxy-2,6-difluorophenyl, 2,4-difluoro-6-propargyloxyphenyl, 4-fluoro-2-propargyloxyphenyl, 2-fluoro-6-propargyloxyphenyl, 4-chloro-2-fluoro-6-propargyloxyphenyl, 2-chloro-4-fluoro-6-propargyloxyphenyl, 4-allyloxy-2-fluorophenyl, 2-fluoro-4-propargyloxyphenyl, 2-allyloxyphenyl, 2-propargyloxyphenyl, 2-allyloxy-5-fluorophenyl, 5-fluoro-2-propargyloxyphenyl, 2-allyloxy-4-methylphenyl, 4-methyl-2-propargyloxyphenyl, 2-allyloxy-5-cyanophenyl, 5-cyano-2-propargyloxyphenyl, 5-allyloxy-2-fluorophenyl, 2-fluoro-5-propargyloxyphenyl, 4-allyloxy-2-chlorophenyl, 2-chloro-4-propargyloxyphenyl, 4-allyloxy-3-fluorophenyl, 3-fluoro-4-propargyloxyphenyl, 4-allyloxyphenyl, 4-propargyloxyphenyl, 3-fluoro-5-propargyloxyphenyl, 3-fluoro-5-allyloxyphenyl, 2,5-difluoro-4-propargyloxyphenyl, 2,5-difluoro-4-allyloxyphenyl, 6-allyloxypyridin-3-yl, 6-propargyloxypyridin-3-yl, 2-propargyloxy-6-trifluorophenyl, 2-allyloxy-6-trifluormethylphenyl, 2-chloro-6-propargyloxyphenyl, 2-allyloxy-6-chlorophenyl, 2,4-dimethyl-6-propargyloxyphenyl and 2-allyloxy-4,6-dimethylphenyl.

Even more particularly preferred compounds of the formula (I) according to the invention are those, wherein:
$R^1$ is $CH_3$,
$R^2$ is $CH_3$,
X is NH,
$Q^1$ is selected from the group consisting of 2-chloro-4-fluorophenyl, 2,4-dichlorophenyl, 2-fluorophenyl, 3,5-dimethoxyphenyl, 2,4-difluorphenyl, 2-fluoro-4-methoxyphenyl, (2-chloropyridin)-5-yl, 4-allyloxy-2-fluorophenyl, 2-propargyloxyphenyl, 2,6-difluoro-4-methoxyphenyl, 2-fluoro-4-propargyloxyphenyl, 4-chloro-2-fluorophenyl, 2-bromo-4-fluorophenyl, 2,4,6-trifluorophenyl, 4-chloro-2,6-difluorophenyl, 3,4-dichlorophenyl, 3,5-dichlorophenyl, 4-fluoro-2-propargyloxyphenyl, 2,6-difluoro-4-propargyloxyphenyl and 2-fluoro-5-(furan-2-yl)phenyl,
and
$Q^2$ is selected from the group consisting of 2,6-difluoro-4-propargyloxyphenyl, 4-allyloxy-2,6-difluorophenyl, 2,4-difluoro-6-propargyloxyphenyl, 4-fluoro-2-propargyloxyphenyl, 2-fluoro-6-propargyloxyphenyl, 4-chloro-2-fluoro-6-propargyloxyphenyl, 2-chloro-4-fluoro-6-propargyloxyphenyl, 4-allyloxy-2-fluorophenyl, 2-fluoro-4-propargyloxyphenyl, 2-allyloxyphenyl, 2-propargyloxyphenyl, 2-allyloxy-5-fluorophenyl, 5-fluoro-2-propargyloxyphenyl, 2-allyloxy-4-methylphenyl, 4-methyl-2-propargyloxyphenyl, 2-allyloxy-5-cyanophenyl, 5-cyano-2-propargyloxyphenyl, 5-allyloxy-2-fluorophenyl, 2-fluoro-5-propargyloxyphenyl, 4-allyloxy-2-chlorophenyl, 2-chloro-4-propargyloxyphenyl, 4-allyloxy-3-fluorophenyl, 3-fluoro-4-propargyloxyphenyl, 4-allyloxyphenyl, 4-propargyloxyphenyl, 3-fluoro-5-propargyloxyphenyl, 3-fluoro-5-allyloxyphenyl, 2,5-difluoro-4-propargyloxyphenyl, 2,5-difluoro-4-allyloxyphenyl, 6-allyloxypyridin-3-yl, 6-propargyloxypyridin-3-yl, 2-propargyloxy-6-trifluorophenyl, 2-allyloxy-6-trifluormethylphenyl, 2-chloro-6-propargyloxyphenyl, 2-allyloxy-6-chlorophenyl, 2,4-dimethyl-6-propargyloxyphenyl and 2-allyloxy-4,6-dimethylphenyl.

Even more particularly preferred compounds of the formula (I) according to the invention are those, wherein:
$R^1$ is $CH_3$,
$R^2$ is $CH_3$,
X is NH,
$Q^1$ is selected from the group consisting of 2-chloro-4-fluorophenyl, 2,4-dichlorophenyl, 2-fluorophenyl, 3,5-dimethoxyphenyl, 2,4-difluorphenyl, 2-fluoro-4-methoxyphenyl, 4-allyloxy-2-fluorophenyl, 2-propargyloxyphenyl, 2,6-difluoro-4-methoxyphenyl, 2-fluoro-4-propargyloxyphenyl, 4-chloro-2-fluorophenyl, 2-bromo-4-fluorophenyl, 2,4,6-trifluorophenyl, 4-chloro-2,6-difluorophenyl, 3,4-dichlorophenyl, 3,5-dichlorophenyl, 4-fluoro-2-propargyloxyphenyl, and 2,6-difluoro-4-propargyloxyphenyl,
and
$Q^2$ is selected from the group consisting of 2,6-difluoro-4-propargyloxyphenyl, 4-allyloxy-2,6-difluorophenyl, 2,4-difluoro-6-propargyloxyphenyl, 4-fluoro-2-propargyloxyphenyl, 2-fluoro-6-propargyloxyphenyl, 4-chloro-2-fluoro-6-propargyloxyphenyl, 2-chloro-4-fluoro-6-propargyloxyphenyl, 4-allyloxy-2-fluorophenyl, 2-fluoro-4-propargyloxyphenyl, 2-allyloxyphenyl, 2-propargyloxyphenyl, 2-allyloxy-5-fluorophenyl, 5-fluoro-2-propargyloxyphenyl, 2-allyloxy-4-methylphenyl, 4-methyl-2-propargyloxyphenyl, 2-allyloxy-5-cyanophenyl, 5-cyano-2-propargyloxyphenyl, 5-allyloxy-2-fluorophenyl, 2-fluoro-5-propargyloxyphenyl, 4-allyloxy-2-chlorophenyl, 2-chloro-4-propargyloxyphenyl, 4-allyloxy-3-fluorophenyl, 3-fluoro-4-propargyloxyphenyl, 4-allyloxyphenyl, 4-propargyloxyphenyl, 3-fluoro-5-propargyloxyphenyl, 3-fluoro-5-allyloxyphenyl, 2,5-difluoro-4-propargyloxyphenyl, 2,5-difluoro-4-allyloxyphenyl, 2-propargyloxy-6-trifluorophenyl, 2-allyloxy-6-trifluormethylphenyl, 2-chloro-6-propargyloxyphenyl, 2-allyloxy-6-chlorophenyl, 2,4-dimethyl-6-propargyloxyphenyl and 2-allyloxy-4,6-dimethylphenyl.

More specifically, even further preferred compounds of the formula (I) according to the invention are those, wherein:
$Q^2$ is selected from the group consisting of 2,6-difluoro-4-propargyloxyphenyl, 4-allyloxy-2,6-difluorophenyl, 2,4-difluoro-6-propargyloxyphenyl, and 2-allyloxy-4-methylphenyl, and/or $Q^1$ is selected from the group consisting of 2-chloro-4-fluorophenyl, 2,4-difluorphenyl, 2-fluoro-4-methoxyphenyl, 2-bromo-4-fluorophenyl, 2,4,6-trifluorophenyl, and 4-chloro-2,6-difluorophenyl.

In view of their remarkable fungicidal properties, even more particularly preferred compounds of the formula (I) according to the invention are those, wherein:
$R^1$ is $CH_3$,
$R^2$ is $CH_3$,
X is NH,
and/or
$Q^1$ is selected from the group consisting of 2-chloro-4-fluorophenyl, 2,4-difluorphenyl, 2-fluoro-4-methoxyphenyl, 2-bromo-4-fluorophenyl, 2,4,6-trifluorophenyl, and 4-chloro-2,6-difluorophenyl,
and
$Q^2$ is selected from the group consisting of 2,6-difluoro-4-propargyloxyphenyl, 4-allyloxy-2,6-difluorophenyl, 2,4-difluoro-6-propargyloxyphenyl, and 2-allyloxy-4-methylphenyl.

Preferred compounds of formula (I) according to the present invention are listed in the following table.

| $R^1$ | $R^2$ | X | $Q^1$ | $Q^2$ |
|---|---|---|---|---|
| methyl | methyl | —(NH)— | 2-chloro-4-fluorophenyl | 2,6-difluoro-4-propargyloxyphenyl |
| methyl | methyl | —(NH)— | 2-chloro-4-fluorophenyl | 4-allyloxy-2,6-difluorophenyl |
| methyl | methyl | —(NH)— | 2-chloro-4-fluorophenyl | 2,4-difluoro-6-propargyloxyphenyl |
| methyl | methyl | —(NH)— | 2-chloro-4-fluorophenyl | 4-fluoro-2-propargyloxyphenyl |
| methyl | methyl | —(NH)— | 2-chloro-4-fluorophenyl | 2-fluoro-6-propargyloxyphenyl |
| methyl | methyl | —(NH)— | 2-chloro-4-fluorophenyl | 4-chloro-2-fluoro-6-propargyloxyphenyl |
| methyl | methyl | —(NH)— | 2-chloro-4-fluorophenyl | 2-chloro-4-fluoro-6-propargyloxyphenyl |
| methyl | methyl | —(NH)— | 2-chloro-4-fluorophenyl | 4-allyloxy-2-fluorophenyl |
| methyl | methyl | —(NH)— | 2-chloro-4-fluorophenyl | 2-fluoro-4-propargyloxyphenyl |
| methyl | methyl | —(NH)— | 2-chloro-4-fluorophenyl | 2-allyloxyphenyl |
| methyl | methyl | —(NH)— | 2-chloro-4-fluorophenyl | 2-propargyloxyphenyl |
| methyl | methyl | —(NH)— | 2-chloro-4-fluorophenyl | 2-allyloxy-5-fluorophenyl |
| methyl | methyl | —(NH)— | 2-chloro-4-fluorophenyl | 5-fluoro-2-propargyloxyphenyl |
| methyl | methyl | —(NH)— | 2-chloro-4-fluorophenyl | 2-allyloxy-4-methylphenyl |
| methyl | methyl | —(NH)— | 2-chloro-4-fluorophenyl | 4-methyl-2-propargyloxyphenyl |
| methyl | methyl | —(NH)— | 2-chloro-4-fluorophenyl | 2-allyloxy-5-cyanophenyl |
| methyl | methyl | —(NH)— | 2-chloro-4-fluorophenyl | 5-cyano-2-propargyloxyphenyl |
| methyl | methyl | —(NH)— | 2-chloro-4-fluorophenyl | 5-allyloxy-2-fluorophenyl |
| methyl | methyl | —(NH)— | 2-chloro-4-fluorophenyl | 2-fluoro-5-propargyloxyphenyl |
| methyl | methyl | —(NH)— | 2-chloro-4-fluorophenyl | 4-allyloxy-2-chlorophenyl |
| methyl | methyl | —(NH)— | 2-chloro-4-fluorophenyl | 2-chloro-4-propargyloxyphenyl |
| methyl | methyl | —(NH)— | 2-chloro-4-fluorophenyl | 4-allyloxy-3-fluorophenyl |
| methyl | methyl | —(NH)— | 2-chloro-4-fluorophenyl | 3-fluoro-4-propargyloxyphenyl |
| methyl | methyl | —(NH)— | 2-chloro-4-fluorophenyl | 4-allyloxyphenyl |
| methyl | methyl | —(NH)— | 2-chloro-4-fluorophenyl | 4-propargyloxyphenyl |
| methyl | methyl | —(NH)— | 2-chloro-4-fluorophenyl | 3-fluoro-5-propargyloxyphenyl |
| methyl | methyl | —(NH)— | 2-chloro-4-fluorophenyl | 3-fluoro-5-allyloxyphenyl |
| methyl | methyl | —(NH)— | 2-chloro-4-fluorophenyl | 2,5-difluoro-4-propargyloxyphenyl |
| methyl | methyl | —(NH)— | 2-chloro-4-fluorophenyl | 2,5-difluoro-4-allyloxyphenyl |
| methyl | methyl | —(NH)— | 2-chloro-4-fluorophenyl | 6-allyloxypyridin-3-yl |
| methyl | methyl | —(NH)— | 2-chloro-4-fluorophenyl | 6-propargyloxypyridin-3-yl |
| methyl | methyl | —(NH)— | 2-chloro-4-fluorophenyl | 2-propargyloxy-6-trifluorophenyl |
| methyl | methyl | —(NH)— | 2-chloro-4-fluorophenyl | 2-allyloxy-6-trifluormethylphenyl |
| methyl | methyl | —(NH)— | 2-chloro-4-fluorophenyl | 2-chloro-6-propargyloxyphenyl |
| methyl | methyl | —(NH)— | 2-chloro-4-fluorophenyl | 2-allyloxy-6-chlorophenyl |
| methyl | methyl | —(NH)— | 2-chloro-4-fluorophenyl | 2,4-dimethyl-6-propargyloxyphenyl |
| methyl | methyl | —(NH)— | 2-chloro-4-fluorophenyl | 2-allyloxy-4,6-dimethylphenyl |
| methyl | methyl | —(NH)— | 2,4-dichlorophenyl | 2,6-difluoro-4-propargyloxyphenyl |
| methyl | methyl | —(NH)— | 2,4-dichlorophenyl | 4-allyloxy-2,6-difluorophenyl |
| methyl | methyl | —(NH)— | 2,4-dichlorophenyl | 2,4-difluoro-6-propargyloxyphenyl |
| methyl | methyl | —(NH)— | 2,4-dichlorophenyl | 4-fluoro-2-propargyloxyphenyl |
| methyl | methyl | —(NH)— | 2,4-dichlorophenyl | 2-fluoro-6-propargyloxyphenyl |
| methyl | methyl | —(NH)— | 2,4-dichlorophenyl | 4-chloro-2-fluoro-6-propargyloxyphenyl |
| methyl | methyl | —(NH)— | 2,4-dichlorophenyl | 2-chloro-4-fluoro-6-propargyloxyphenyl |
| methyl | methyl | —(NH)— | 2,4-dichlorophenyl | 4-allyloxy-2-fluorophenyl |
| methyl | methyl | —(NH)— | 2,4-dichlorophenyl | 2-fluoro-4-propargyloxyphenyl |
| methyl | methyl | —(NH)— | 2,4-dichlorophenyl | 2-allyloxyphenyl |
| methyl | methyl | —(NH)— | 2,4-dichlorophenyl | 2-propargyloxyphenyl |
| methyl | methyl | —(NH)— | 2,4-dichlorophenyl | 2-allyloxy-5-fluorophenyl |
| methyl | methyl | —(NH)— | 2,4-dichlorophenyl | 5-fluoro-2-propargyloxyphenyl |
| methyl | methyl | —(NH)— | 2,4-dichlorophenyl | 2-allyloxy-4-methylphenyl |
| methyl | methyl | —(NH)— | 2,4-dichlorophenyl | 4-methyl-2-propargyloxyphenyl |
| methyl | methyl | —(NH)— | 2,4-dichlorophenyl | 2-allyloxy-5-cyanophenyl |
| methyl | methyl | —(NH)— | 2,4-dichlorophenyl | 5-cyano-2-propargyloxyphenyl |
| methyl | methyl | —(NH)— | 2,4-dichlorophenyl | 5-allyloxy-2-fluorophenyl |
| methyl | methyl | —(NH)— | 2,4-dichlorophenyl | 2-fluoro-5-propargyloxyphenyl |
| methyl | methyl | —(NH)— | 2,4-dichlorophenyl | 4-allyloxy-2-chlorophenyl |
| methyl | methyl | —(NH)— | 2,4-dichlorophenyl | 2-chloro-4-propargyloxyphenyl |
| methyl | methyl | —(NH)— | 2,4-dichlorophenyl | 4-allyloxy-3-fluorophenyl |
| methyl | methyl | —(NH)— | 2,4-dichlorophenyl | 3-fluoro-4-propargyloxyphenyl |

-continued

| R¹ | R² | X | Q¹ | Q² |
|---|---|---|---|---|
| methyl | methyl | —(NH)— | 2,4-dichlorophenyl | 4-allyloxyphenyl |
| methyl | methyl | —(NH)— | 2,4-dichlorophenyl | 4-propargyloxyphenyl |
| methyl | methyl | —(NH)— | 2,4-dichlorophenyl | 3-fluoro-5-propargyloxyphenyl |
| methyl | methyl | —(NH)— | 2,4-dichlorophenyl | 3-fluoro-5-allyloxyphenyl |
| methyl | methyl | —(NH)— | 2,4-dichlorophenyl | 2,5-difluoro-4-propargyloxyphenyl |
| methyl | methyl | —(NH)— | 2,4-dichlorophenyl | 2,5-difluoro-4-allyloxyphenyl |
| methyl | methyl | —(NH)— | 2,4-dichlorophenyl | 6-allyloxypyridin-3-yl |
| methyl | methyl | —(NH)— | 2,4-dichlorophenyl | 6-propargyloxypyridin-3-yl |
| methyl | methyl | —(NH)— | 2,4-dichlorophenyl | 2-propargyloxy-6-trifluorophenyl |
| methyl | methyl | —(NH)— | 2,4-dichlorophenyl | 2-allyloxy-6-trifluormethylphenyl |
| methyl | methyl | —(NH)— | 2,4-dichlorophenyl | 2-chloro-6-propargyloxyphenyl |
| methyl | methyl | —(NH)— | 2,4-dichlorophenyl | 2-allyloxy-6-chlorophenyl |
| methyl | methyl | —(NH)— | 2,4-dichlorophenyl | 2,4-dimethyl-6-propargyloxyphenyl |
| methyl | methyl | —(NH)— | 2,4-dichlorophenyl | 2-allyloxy-4,6-dimethylphenyl |
| methyl | methyl | —(NH)— | 2-fluorophenyl | 2,6-difluoro-4-propargyloxyphenyl |
| methyl | methyl | —(NH)— | 2-fluorophenyl | 4-allyloxy-2,6-difluorophenyl |
| methyl | methyl | —(NH)— | 2-fluorophenyl | 2,4-difluoro-6-propargyloxyphenyl |
| methyl | methyl | —(NH)— | 2-fluorophenyl | 4-fluoro-2-propargyloxyphenyl |
| methyl | methyl | —(NH)— | 2-fluorophenyl | 2-fluoro-6-propargyloxyphenyl |
| methyl | methyl | —(NH)— | 2-fluorophenyl | 4-chloro-2-fluoro-6-propargyloxyphenyl |
| methyl | methyl | —(NH)— | 2-fluorophenyl | 2-chloro-4-fluoro-6-propargyloxyphenyl |
| methyl | methyl | —(NH)— | 2-fluorophenyl | 4-allyloxy-2-fluorophenyl |
| methyl | methyl | —(NH)— | 2-fluorophenyl | 2-fluoro-4-propargyloxyphenyl |
| methyl | methyl | —(NH)— | 2-fluorophenyl | 2-allyloxyphenyl |
| methyl | methyl | —(NH)— | 2-fluorophenyl | 2-propargyloxyphenyl |
| methyl | methyl | —(NH)— | 2-fluorophenyl | 2-allyloxy-5-fluorophenyl |
| methyl | methyl | —(NH)— | 2-fluorophenyl | 5-fluoro-2-propargyloxyphenyl |
| methyl | methyl | —(NH)— | 2-fluorophenyl | 2-allyloxy-4-methylphenyl |
| methyl | methyl | —(NH)— | 2-fluorophenyl | 4-methyl-2-propargyloxyphenyl |
| methyl | methyl | —(NH)— | 2-fluorophenyl | 2-allyloxy-5-cyanophenyl |
| methyl | methyl | —(NH)— | 2-fluorophenyl | 5-cyano-2-propargyloxyphenyl |
| methyl | methyl | —(NH)— | 2-fluorophenyl | 5-allyloxy-2-fluorophenyl |
| methyl | methyl | —(NH)— | 2-fluorophenyl | 2-fluoro-5-propargyloxyphenyl |
| methyl | methyl | —(NH)— | 2-fluorophenyl | 4-allyloxy-2-chlorophenyl |
| methyl | methyl | —(NH)— | 2-fluorophenyl | 2-chloro-4-propargyloxyphenyl |
| methyl | methyl | —(NH)— | 2-fluorophenyl | 4-allyloxy-3-fluorophenyl |
| methyl | methyl | —(NH)— | 2-fluorophenyl | 3-fluoro-4-propargyloxyphenyl |
| methyl | methyl | —(NH)— | 2-fluorophenyl | 4-allyloxyphenyl |
| methyl | methyl | —(NH)— | 2-fluorophenyl | 4-propargyloxyphenyl |
| methyl | methyl | —(NH)— | 2-fluorophenyl | 3-fluoro-5-propargyloxyphenyl |
| methyl | methyl | —(NH)— | 2-fluorophenyl | 3-fluoro-5-allyloxyphenyl |
| methyl | methyl | —(NH)— | 2-fluorophenyl | 2,5-difluoro-4-propargyloxyphenyl |
| methyl | methyl | —(NH)— | 2-fluorophenyl | 2,5-difluoro-4-allyloxyphenyl |
| methyl | methyl | —(NH)— | 2-fluorophenyl | 6-allyloxypyridin-3-yl |
| methyl | methyl | —(NH)— | 2-fluorophenyl | 6-propargyloxypyridin-3-yl |
| methyl | methyl | —(NH)— | 2-fluorophenyl | 2-propargyloxy-6-trifluorophenyl |
| methyl | methyl | —(NH)— | 2-fluorophenyl | 2-allyloxy-6-trifluormethylphenyl |
| methyl | methyl | —(NH)— | 2-fluorophenyl | 2-chloro-6-propargyloxyphenyl |
| methyl | methyl | —(NH)— | 2-fluorophenyl | 2-allyloxy-6-chlorophenyl |
| methyl | methyl | —(NH)— | 2-fluorophenyl | 2,4-dimethyl-6-propargyloxyphenyl |
| methyl | methyl | —(NH)— | 2-fluorophenyl | 2-allyloxy-4,6-dimethylphenyl |
| methyl | methyl | —(NH)— | 3,5-dimethoxyphenyl | 2,6-difluoro-4-propargyloxyphenyl |
| methyl | methyl | —(NH)— | 3,5-dimethoxyphenyl | 4-allyloxy-2,6-difluorophenyl |
| methyl | methyl | —(NH)— | 3,5-dimethoxyphenyl | 2,4-difluoro-6-propargyloxyphenyl |
| methyl | methyl | —(NH)— | 3,5-dimethoxyphenyl | 4-fluoro-2-propargyloxyphenyl |
| methyl | methyl | —(NH)— | 3,5-dimethoxyphenyl | 2-fluoro-6-propargyloxyphenyl |
| methyl | methyl | —(NH)— | 3,5-dimethoxyphenyl | 4-chloro-2-fluoro-6-propargyloxyphenyl |
| methyl | methyl | —(NH)— | 3,5-dimethoxyphenyl | 2-chloro-4-fluoro-6-propargyloxyphenyl |
| methyl | methyl | —(NH)— | 3,5-dimethoxyphenyl | 4-allyloxy-2-fluorophenyl |
| methyl | methyl | —(NH)— | 3,5-dimethoxyphenyl | 2-fluoro-4-propargyloxyphenyl |
| methyl | methyl | —(NH)— | 3,5-dimethoxyphenyl | 2-allyloxyphenyl |
| methyl | methyl | —(NH)— | 3,5-dimethoxyphenyl | 2-propargyloxyphenyl |
| methyl | methyl | —(NH)— | 3,5-dimethoxyphenyl | 2-allyloxy-5-fluorophenyl |
| methyl | methyl | —(NH)— | 3,5-dimethoxyphenyl | 5-fluoro-2-propargyloxyphenyl |
| methyl | methyl | —(NH)— | 3,5-dimethoxyphenyl | 2-allyloxy-4-methylphenyl |
| methyl | methyl | —(NH)— | 3,5-dimethoxyphenyl | 4-methyl-2-propargyloxyphenyl |
| methyl | methyl | —(NH)— | 3,5-dimethoxyphenyl | 2-allyloxy-5-cyanophenyl |
| methyl | methyl | —(NH)— | 3,5-dimethoxyphenyl | 5-cyano-2-propargyloxyphenyl |
| methyl | methyl | —(NH)— | 3,5-dimethoxyphenyl | 5-allyloxy-2-fluorophenyl |
| methyl | methyl | —(NH)— | 3,5-dimethoxyphenyl | 2-fluoro-5-propargyloxyphenyl |
| methyl | methyl | —(NH)— | 3,5-dimethoxyphenyl | 4-allyloxy-2-chlorophenyl |
| methyl | methyl | —(NH)— | 3,5-dimethoxyphenyl | 2-chloro-4-propargyloxyphenyl |
| methyl | methyl | —(NH)— | 3,5-dimethoxyphenyl | 4-allyloxy-3-fluorophenyl |

| R¹ | R² | X | Q¹ | Q² |
|---|---|---|---|---|
| methyl | methyl | —(NH)— | 3,5-dimethoxyphenyl | 3-fluoro-4-propargyloxyphenyl |
| methyl | methyl | —(NH)— | 3,5-dimethoxyphenyl | 4-allyloxyphenyl |
| methyl | methyl | —(NH)— | 3,5-dimethoxyphenyl | 4-propargyloxyphenyl |
| methyl | methyl | —(NH)— | 3,5-dimethoxyphenyl | 3-fluoro-5-propargyloxyphenyl |
| methyl | methyl | —(NH)— | 3,5-dimethoxyphenyl | 3-fluoro-5-allyloxyphenyl |
| methyl | methyl | —(NH)— | 3,5-dimethoxyphenyl | 2,5-difluoro-4-propargyloxyphenyl |
| methyl | methyl | —(NH)— | 3,5-dimethoxyphenyl | 2,5-difluoro-4-allyloxyphenyl |
| methyl | methyl | —(NH)— | 3,5-dimethoxyphenyl | 6-allyloxypyridin-3-yl |
| methyl | methyl | —(NH)— | 3,5-dimethoxyphenyl | 6-propargyloxypyridin-3-yl |
| methyl | methyl | —(NH)— | 3,5-dimethoxyphenyl | 2-propargyloxy-6-trifluorophenyl |
| methyl | methyl | —(NH)— | 3,5-dimethoxyphenyl | 2-allyloxy-6-trifluormethylphenyl |
| methyl | methyl | —(NH)— | 3,5-dimethoxyphenyl | 2-chloro-6-propargyloxyphenyl |
| methyl | methyl | —(NH)— | 3,5-dimethoxyphenyl | 2-allyloxy-6-chlorophenyl |
| methyl | methyl | —(NH)— | 3,5-dimethoxyphenyl | 2,4-dimethyl-6-propargyloxyphenyl |
| methyl | methyl | —(NH)— | 3,5-dimethoxyphenyl | 2-allyloxy-4,6-dimethylphenyl |
| methyl | methyl | —(NH)— | 2,4-difluorphenyl | 2,6-difluoro-4-propargyloxyphenyl |
| methyl | methyl | —(NH)— | 2,4-difluorphenyl | 4-allyloxy-2,6-difluorophenyl |
| methyl | methyl | —(NH)— | 2,4-difluorphenyl | 2,4-difluoro-6-propargyloxyphenyl |
| methyl | methyl | —(NH)— | 2,4-difluorphenyl | 4-fluoro-2-propargyloxyphenyl |
| methyl | methyl | —(NH)— | 2,4-difluorphenyl | 2-fluoro-6-propargyloxyphenyl |
| methyl | methyl | —(NH)— | 2,4-difluorphenyl | 4-chloro-2-fluoro-6-propargyloxyphenyl |
| methyl | methyl | —(NH)— | 2,4-difluorphenyl | 2-chloro-4-fluoro-6-propargyloxyphenyl |
| methyl | methyl | —(NH)— | 2,4-difluorphenyl | 4-allyloxy-2-fluorophenyl |
| methyl | methyl | —(NH)— | 2,4-difluorphenyl | 2-fluoro-4-propargyloxyphenyl |
| methyl | methyl | —(NH)— | 2,4-difluorphenyl | 2-allyloxyphenyl |
| methyl | methyl | —(NH)— | 2,4-difluorphenyl | 2-propargyloxyphenyl |
| methyl | methyl | —(NH)— | 2,4-difluorphenyl | 2-allyloxy-5-fluorophenyl |
| methyl | methyl | —(NH)— | 2,4-difluorphenyl | 5-fluoro-2-propargyloxyphenyl |
| methyl | methyl | —(NH)— | 2,4-difluorphenyl | 2-allyloxy-4-methylphenyl |
| methyl | methyl | —(NH)— | 2,4-difluorphenyl | 4-methyl-2-propargyloxyphenyl |
| methyl | methyl | —(NH)— | 2,4-difluorphenyl | 2-allyloxy-5-cyanophenyl |
| methyl | methyl | —(NH)— | 2,4-difluorphenyl | 5-cyano-2-propargyloxyphenyl |
| methyl | methyl | —(NH)— | 2,4-difluorphenyl | 5-allyloxy-2-fluorophenyl |
| methyl | methyl | —(NH)— | 2,4-difluorphenyl | 2-fluoro-5-propargyloxyphenyl |
| methyl | methyl | —(NH)— | 2,4-difluorphenyl | 4-allyloxy-2-chlorophenyl |
| methyl | methyl | —(NH)— | 2,4-difluorphenyl | 2-chloro-4-propargyloxyphenyl |
| methyl | methyl | —(NH)— | 2,4-difluorphenyl | 4-allyloxy-3-fluorophenyl |
| methyl | methyl | —(NH)— | 2,4-difluorphenyl | 3-fluoro-4-propargyloxyphenyl |
| methyl | methyl | —(NH)— | 2,4-difluorphenyl | 4-allyloxyphenyl |
| methyl | methyl | —(NH)— | 2,4-difluorphenyl | 4-propargyloxyphenyl |
| methyl | methyl | —(NH)— | 2,4-difluorphenyl | 3-fluoro-5-propargyloxyphenyl |
| methyl | methyl | —(NH)— | 2,4-difluorphenyl | 3-fluoro-5-allyloxyphenyl |
| methyl | methyl | —(NH)— | 2,4-difluorphenyl | 2,5-difluoro-4-propargyloxyphenyl |
| methyl | methyl | —(NH)— | 2,4-difluorphenyl | 2,5-difluoro-4-allyloxyphenyl |
| methyl | methyl | —(NH)— | 2,4-difluorphenyl | 6-allyloxypyridin-3-yl |
| methyl | methyl | —(NH)— | 2,4-difluorphenyl | 6-propargyloxypyridin-3-yl |
| methyl | methyl | —(NH)— | 2,4-difluorphenyl | 2-propargyloxy-6-trifluorophenyl |
| methyl | methyl | —(NH)— | 2,4-difluorphenyl | 2-allyloxy-6-trifluormethylphenyl |
| methyl | methyl | —(NH)— | 2,4-difluorphenyl | 2-chloro-6-propargyloxyphenyl |
| methyl | methyl | —(NH)— | 2,4-difluorphenyl | 2-allyloxy-6-chlorophenyl |
| methyl | methyl | —(NH)— | 2,4-difluorphenyl | 2,4-dimethyl-6-propargyloxyphenyl |
| methyl | methyl | —(NH)— | 2,4-difluorphenyl | 2-allyloxy-4,6-dimethylphenyl |
| methyl | methyl | —(NH)— | 2-fluoro-4-methoxyphenyl | 2,6-difluoro-4-propargyloxyphenyl |
| methyl | methyl | —(NH)— | 2-fluoro-4-methoxyphenyl | 4-allyloxy-2,6-difluorophenyl |
| methyl | methyl | —(NH)— | 2-fluoro-4-methoxyphenyl | 2,4-difluoro-6-propargyloxyphenyl |
| methyl | methyl | —(NH)— | 2-fluoro-4-methoxyphenyl | 4-fluoro-2-propargyloxyphenyl |
| methyl | methyl | —(NH)— | 2-fluoro-4-methoxyphenyl | 2-fluoro-6-propargyloxyphenyl |
| methyl | methyl | —(NH)— | 2-fluoro-4-methoxyphenyl | 4-chloro-2-fluoro-6-propargyloxyphenyl |
| methyl | methyl | —(NH)— | 2-fluoro-4-methoxyphenyl | 2-chloro-4-fluoro-6-propargyloxyphenyl |
| methyl | methyl | —(NH)— | 2-fluoro-4-methoxyphenyl | 4-allyloxy-2-fluorophenyl |
| methyl | methyl | —(NH)— | 2-fluoro-4-methoxyphenyl | 2-fluoro-4-propargyloxyphenyl |
| methyl | methyl | —(NH)— | 2-fluoro-4-methoxyphenyl | 2-allyloxyphenyl |
| methyl | methyl | —(NH)— | 2-fluoro-4-methoxyphenyl | 2-propargyloxyphenyl |
| methyl | methyl | —(NH)— | 2-fluoro-4-methoxyphenyl | 2-allyloxy-5-fluorophenyl |
| methyl | methyl | —(NH)— | 2-fluoro-4-methoxyphenyl | 5-fluoro-2-propargyloxyphenyl |
| methyl | methyl | —(NH)— | 2-fluoro-4-methoxyphenyl | 2-allyloxy-4-methylphenyl |
| methyl | methyl | —(NH)— | 2-fluoro-4-methoxyphenyl | 4-methyl-2-propargyloxyphenyl |
| methyl | methyl | —(NH)— | 2-fluoro-4-methoxyphenyl | 2-allyloxy-5-cyanophenyl |
| methyl | methyl | —(NH)— | 2-fluoro-4-methoxyphenyl | 5-cyano-2-propargyloxyphenyl |
| methyl | methyl | —(NH)— | 2-fluoro-4-methoxyphenyl | 5-allyloxy-2-fluorophenyl |
| methyl | methyl | —(NH)— | 2-fluoro-4-methoxyphenyl | 2-fluoro-5-propargyloxyphenyl |
| methyl | methyl | —(NH)— | 2-fluoro-4-methoxyphenyl | 4-allyloxy-2-chlorophenyl |
| methyl | methyl | —(NH)— | 2-fluoro-4-methoxyphenyl | 2-chloro-4-propargyloxyphenyl |

-continued

| R¹ | R² | X | Q¹ | Q² |
|---|---|---|---|---|
| methyl | methyl | —(NH)— | 2-fluoro-4-methoxyphenyl | 4-allyloxy-3-fluorophenyl |
| methyl | methyl | —(NH)— | 2-fluoro-4-methoxyphenyl | 3-fluoro-4-propargyloxyphenyl |
| methyl | methyl | —(NH)— | 2-fluoro-4-methoxyphenyl | 4-allyloxyphenyl |
| methyl | methyl | —(NH)— | 2-fluoro-4-methoxyphenyl | 4-propargyloxyphenyl |
| methyl | methyl | —(NH)— | 2-fluoro-4-methoxyphenyl | 3-fluoro-5-propargyloxyphenyl |
| methyl | methyl | —(NH)— | 2-fluoro-4-methoxyphenyl | 3-fluoro-5-allyloxyphenyl |
| methyl | methyl | —(NH)— | 2-fluoro-4-methoxyphenyl | 2,5-difluoro-4-propargyloxyphenyl |
| methyl | methyl | —(NH)— | 2-fluoro-4-methoxyphenyl | 2,5-difluoro-4-allyloxyphenyl |
| methyl | methyl | —(NH)— | 2-fluoro-4-methoxyphenyl | 6-allyloxypyridin-3-yl |
| methyl | methyl | —(NH)— | 2-fluoro-4-methoxyphenyl | 6-propargyloxypyridin-3-yl |
| methyl | methyl | —(NH)— | 2-fluoro-4-methoxyphenyl | 2-propargyloxy-6-trifluorophenyl |
| methyl | methyl | —(NH)— | 2-fluoro-4-methoxyphenyl | 2-allyloxy-6-trifluormethylphenyl |
| methyl | methyl | —(NH)— | 2-fluoro-4-methoxyphenyl | 2-chloro-6-propargyloxyphenyl |
| methyl | methyl | —(NH)— | 2-fluoro-4-methoxyphenyl | 2-allyloxy-6-chlorophenyl |
| methyl | methyl | —(NH)— | 2-fluoro-4-methoxyphenyl | 2,4-dimethyl-6-propargyloxyphenyl |
| methyl | methyl | —(NH)— | 2-fluoro-4-methoxyphenyl | 2-allyloxy-4,6-dimethylphenyl |
| methyl | methyl | —(NH)— | (2-chloropyridin)-5-yl | 2,6-difluoro-4-propargyloxyphenyl |
| methyl | methyl | —(NH)— | (2-chloropyridin)-5-yl | 4-allyloxy-2,6-difluorophenyl |
| methyl | methyl | —(NH)— | (2-chloropyridin)-5-yl | 2,4-difluoro-6-propargyloxyphenyl |
| methyl | methyl | —(NH)— | (2-chloropyridin)-5-yl | 4-fluoro-2-propargyloxyphenyl |
| methyl | methyl | —(NH)— | (2-chloropyridin)-5-yl | 2-fluoro-6-propargyloxyphenyl |
| methyl | methyl | —(NH)— | (2-chloropyridin)-5-yl | 4-chloro-2-fluoro-6-propargyloxyphenyl |
| methyl | methyl | —(NH)— | (2-chloropyridin)-5-yl | 2-chloro-4-fluoro-6-propargyloxyphenyl |
| methyl | methyl | —(NH)— | (2-chloropyridin)-5-yl | 4-allyloxy-2-fluorophenyl |
| methyl | methyl | —(NH)— | (2-chloropyridin)-5-yl | 2-fluoro-4-propargyloxyphenyl |
| methyl | methyl | —(NH)— | (2-chloropyridin)-5-yl | 2-allyloxyphenyl |
| methyl | methyl | —(NH)— | (2-chloropyridin)-5-yl | 2-propargyloxyphenyl |
| methyl | methyl | —(NH)— | (2-chloropyridin)-5-yl | 2-allyloxy-5-fluorophenyl |
| methyl | methyl | —(NH)— | (2-chloropyridin)-5-yl | 5-fluoro-2-propargyloxyphenyl |
| methyl | methyl | —(NH)— | (2-chloropyridin)-5-yl | 2-allyloxy-4-methylphenyl |
| methyl | methyl | —(NH)— | (2-chloropyridin)-5-yl | 4-methyl-2-propargyloxyphenyl |
| methyl | methyl | —(NH)— | (2-chloropyridin)-5-yl | 2-allyloxy-5-cyanophenyl |
| methyl | methyl | —(NH)— | (2-chloropyridin)-5-yl | 5-cyano-2-propargyloxyphenyl |
| methyl | methyl | —(NH)— | (2-chloropyridin)-5-yl | 5-allyloxy-2-fluorophenyl |
| methyl | methyl | —(NH)— | (2-chloropyridin)-5-yl | 2-fluoro-5-propargyloxyphenyl |
| methyl | methyl | —(NH)— | (2-chloropyridin)-5-yl | 4-allyloxy-2-chlorophenyl |
| methyl | methyl | —(NH)— | (2-chloropyridin)-5-yl | 2-chloro-4-propargyloxyphenyl |
| methyl | methyl | —(NH)— | (2-chloropyridin)-5-yl | 4-allyloxy-3-fluorophenyl |
| methyl | methyl | —(NH)— | (2-chloropyridin)-5-yl | 3-fluoro-4-propargyloxyphenyl |
| methyl | methyl | —(NH)— | (2-chloropyridin)-5-yl | 4-allyloxyphenyl |
| methyl | methyl | —(NH)— | (2-chloropyridin)-5-yl | 4-propargyloxyphenyl |
| methyl | methyl | —(NH)— | (2-chloropyridin)-5-yl | 3-fluoro-5-propargyloxyphenyl |
| methyl | methyl | —(NH)— | (2-chloropyridin)-5-yl | 3-fluoro-5-allyloxyphenyl |
| methyl | methyl | —(NH)— | (2-chloropyridin)-5-yl | 2,5-difluoro-4-propargyloxyphenyl |
| methyl | methyl | —(NH)— | (2-chloropyridin)-5-yl | 2,5-difluoro-4-allyloxyphenyl |
| methyl | methyl | —(NH)— | (2-chloropyridin)-5-yl | 6-allyloxypyridin-3-yl |
| methyl | methyl | —(NH)— | (2-chloropyridin)-5-yl | 6-propargyloxypyridin-3-yl |
| methyl | methyl | —(NH)— | (2-chloropyridin)-5-yl | 2-propargyloxy-6-trifluorophenyl |
| methyl | methyl | —(NH)— | (2-chloropyridin)-5-yl | 2-allyloxy-6-trifluormethylphenyl |
| methyl | methyl | —(NH)— | (2-chloropyridin)-5-yl | 2-chloro-6-propargyloxyphenyl |
| methyl | methyl | —(NH)— | (2-chloropyridin)-5-yl | 2-allyloxy-6-chlorophenyl |
| methyl | methyl | —(NH)— | (2-chloropyridin)-5-yl | 2,4-dimethyl-6-propargyloxyphenyl |
| methyl | methyl | —(NH)— | (2-chloropyridin)-5-yl | 2-allyloxy-4,6-dimethylphenyl |
| methyl | methyl | —(NH)— | 4-allyloxy-2-fluorophenyl | 2,6-difluoro-4-propargyloxyphenyl |
| methyl | methyl | —(NH)— | 4-allyloxy-2-fluorophenyl | 4-allyloxy-2,6-difluorophenyl |
| methyl | methyl | —(NH)— | 4-allyloxy-2-fluorophenyl | 2,4-difluoro-6-propargyloxyphenyl |
| methyl | methyl | —(NH)— | 4-allyloxy-2-fluorophenyl | 4-fluoro-2-propargyloxyphenyl |
| methyl | methyl | —(NH)— | 4-allyloxy-2-fluorophenyl | 2-fluoro-6-propargyloxyphenyl |
| methyl | methyl | —(NH)— | 4-allyloxy-2-fluorophenyl | 4-chloro-2-fluoro-6-propargyloxyphenyl |
| methyl | methyl | —(NH)— | 4-allyloxy-2-fluorophenyl | 2-chloro-4-fluoro-6-propargyloxyphenyl |
| methyl | methyl | —(NH)— | 4-allyloxy-2-fluorophenyl | 4-allyloxy-2-fluorophenyl |
| methyl | methyl | —(NH)— | 4-allyloxy-2-fluorophenyl | 2-fluoro-4-propargyloxyphenyl |
| methyl | methyl | —(NH)— | 4-allyloxy-2-fluorophenyl | 2-allyloxyphenyl |
| methyl | methyl | —(NH)— | 4-allyloxy-2-fluorophenyl | 2-propargyloxyphenyl |
| methyl | methyl | —(NH)— | 4-allyloxy-2-fluorophenyl | 2-allyloxy-5-fluorophenyl |
| methyl | methyl | —(NH)— | 4-allyloxy-2-fluorophenyl | 5-fluoro-2-propargyloxyphenyl |
| methyl | methyl | —(NH)— | 4-allyloxy-2-fluorophenyl | 2-allyloxy-4-methylphenyl |
| methyl | methyl | —(NH)— | 4-allyloxy-2-fluorophenyl | 4-methyl-2-propargyloxyphenyl |
| methyl | methyl | —(NH)— | 4-allyloxy-2-fluorophenyl | 2-allyloxy-5-cyanophenyl |
| methyl | methyl | —(NH)— | 4-allyloxy-2-fluorophenyl | 5-cyano-2-propargyloxyphenyl |
| methyl | methyl | —(NH)— | 4-allyloxy-2-fluorophenyl | 5-allyloxy-2-fluorophenyl |
| methyl | methyl | —(NH)— | 4-allyloxy-2-fluorophenyl | 2-fluoro-5-propargyloxyphenyl |
| methyl | methyl | —(NH)— | 4-allyloxy-2-fluorophenyl | 4-allyloxy-2-chlorophenyl |

-continued

| R¹ | R² | X | Q¹ | Q² |
|---|---|---|---|---|
| methyl | methyl | —(NH)— | 4-allyloxy-2-fluorophenyl | 2-chloro-4-propargyloxyphenyl |
| methyl | methyl | —(NH)— | 4-allyloxy-2-fluorophenyl | 4-allyloxy-3-fluorophenyl |
| methyl | methyl | —(NH)— | 4-allyloxy-2-fluorophenyl | 3-fluoro-4-propargyloxyphenyl |
| methyl | methyl | —(NH)— | 4-allyloxy-2-fluorophenyl | 4-allyloxyphenyl |
| methyl | methyl | —(NH)— | 4-allyloxy-2-fluorophenyl | 4-propargyloxyphenyl |
| methyl | methyl | —(NH)— | 4-allyloxy-2-fluorophenyl | 3-fluoro-5-propargyloxyphenyl |
| methyl | methyl | —(NH)— | 4-allyloxy-2-fluorophenyl | 3-fluoro-5-allyloxyphenyl |
| methyl | methyl | —(NH)— | 4-allyloxy-2-fluorophenyl | 2,5-difluoro-4-propargyloxyphenyl |
| methyl | methyl | —(NH)— | 4-allyloxy-2-fluorophenyl | 2,5-difluoro-4-allyloxyphenyl |
| methyl | methyl | —(NH)— | 4-allyloxy-2-fluorophenyl | 6-allyloxypyridin-3-yl |
| methyl | methyl | —(NH)— | 4-allyloxy-2-fluorophenyl | 6-propargyloxypyridin-3-yl |
| methyl | methyl | —(NH)— | 4-allyloxy-2-fluorophenyl | 2-propargyloxy-6-trifluorophenyl |
| methyl | methyl | —(NH)— | 4-allyloxy-2-fluorophenyl | 2-allyloxy-6-trifluormethylphenyl |
| methyl | methyl | —(NH)— | 4-allyloxy-2-fluorophenyl | 2-chloro-6-propargyloxyphenyl |
| methyl | methyl | —(NH)— | 4-allyloxy-2-fluorophenyl | 2-allyloxy-6-chlorophenyl |
| methyl | methyl | —(NH)— | 4-allyloxy-2-fluorophenyl | 2,4-dimethyl-6-propargyloxyphenyl |
| methyl | methyl | —(NH)— | 4-allyloxy-2-fluorophenyl | 2-allyloxy-4,6-dimethylphenyl |
| methyl | methyl | —(NH)— | 2-propargyloxyphenyl | 2,6-difluoro-4-propargyloxyphenyl |
| methyl | methyl | —(NH)— | 2-propargyloxyphenyl | 4-allyloxy-2,6-difluorophenyl |
| methyl | methyl | —(NH)— | 2-propargyloxyphenyl | 2,4-difluoro-6-propargyloxyphenyl |
| methyl | methyl | —(NH)— | 2-propargyloxyphenyl | 4-fluoro-2-propargyloxyphenyl |
| methyl | methyl | —(NH)— | 2-propargyloxyphenyl | 2-fluoro-6-propargyloxyphenyl |
| methyl | methyl | —(NH)— | 2-propargyloxyphenyl | 4-chloro-2-fluoro-6-propargyloxyphenyl |
| methyl | methyl | —(NH)— | 2-propargyloxyphenyl | 2-chloro-4-fluoro-6-propargyloxyphenyl |
| methyl | methyl | —(NH)— | 2-propargyloxyphenyl | 4-allyloxy-2-fluorophenyl |
| methyl | methyl | —(NH)— | 2-propargyloxyphenyl | 2-fluoro-4-propargyloxyphenyl |
| methyl | methyl | —(NH)— | 2-propargyloxyphenyl | 2-allyloxyphenyl |
| methyl | methyl | —(NH)— | 2-propargyloxyphenyl | 2-propargyloxyphenyl |
| methyl | methyl | —(NH)— | 2-propargyloxyphenyl | 2-allyloxy-5-fluorophenyl |
| methyl | methyl | —(NH)— | 2-propargyloxyphenyl | 5-fluoro-2-propargyloxyphenyl |
| methyl | methyl | —(NH)— | 2-propargyloxyphenyl | 2-allyloxy-4-methylphenyl |
| methyl | methyl | —(NH)— | 2-propargyloxyphenyl | 4-methyl-2-propargyloxyphenyl |
| methyl | methyl | —(NH)— | 2-propargyloxyphenyl | 2-allyloxy-5-cyanophenyl |
| methyl | methyl | —(NH)— | 2-propargyloxyphenyl | 5-cyano-2-propargyloxyphenyl |
| methyl | methyl | —(NH)— | 2-propargyloxyphenyl | 5-allyloxy-2-fluorophenyl |
| methyl | methyl | —(NH)— | 2-propargyloxyphenyl | 2-fluoro-5-propargyloxyphenyl |
| methyl | methyl | —(NH)— | 2-propargyloxyphenyl | 4-allyloxy-2-chlorophenyl |
| methyl | methyl | —(NH)— | 2-propargyloxyphenyl | 2-chloro-4-propargyloxyphenyl |
| methyl | methyl | —(NH)— | 2-propargyloxyphenyl | 4-allyloxy-3-fluorophenyl |
| methyl | methyl | —(NH)— | 2-propargyloxyphenyl | 3-fluoro-4-propargyloxyphenyl |
| methyl | methyl | —(NH)— | 2-propargyloxyphenyl | 4-allyloxyphenyl |
| methyl | methyl | —(NH)— | 2-propargyloxyphenyl | 4-propargyloxyphenyl |
| methyl | methyl | —(NH)— | 2-propargyloxyphenyl | 3-fluoro-5-propargyloxyphenyl |
| methyl | methyl | —(NH)— | 2-propargyloxyphenyl | 3-fluoro-5-allyloxyphenyl |
| methyl | methyl | —(NH)— | 2-propargyloxyphenyl | 2,5-difluoro-4-propargyloxyphenyl |
| methyl | methyl | —(NH)— | 2-propargyloxyphenyl | 2,5-difluoro-4-allyloxyphenyl |
| methyl | methyl | —(NH)— | 2-propargyloxyphenyl | 6-allyloxypyridin-3-yl |
| methyl | methyl | —(NH)— | 2-propargyloxyphenyl | 6-propargyloxypyridin-3-yl |
| methyl | methyl | —(NH)— | 2-propargyloxyphenyl | 2-propargyloxy-6-trifluorophenyl |
| methyl | methyl | —(NH)— | 2-propargyloxyphenyl | 2-allyloxy-6-trifluormethylphenyl |
| methyl | methyl | —(NH)— | 2-propargyloxyphenyl | 2-chloro-6-propargyloxyphenyl |
| methyl | methyl | —(NH)— | 2-propargyloxyphenyl | 2-allyloxy-6-chlorophenyl |
| methyl | methyl | —(NH)— | 2-propargyloxyphenyl | 2,4-dimethyl-6-propargyloxyphenyl |
| methyl | methyl | —(NH)— | 2-propargyloxyphenyl | 2-allyloxy-4,6-dimethylphenyl |
| methyl | methyl | —(NH)— | 2,6-difluoro-4-methoxyphenyl | 2,6-difluoro-4-propargyloxyphenyl |
| methyl | methyl | —(NH)— | 2,6-difluoro-4-methoxyphenyl | 4-allyloxy-2,6-difluorophenyl |
| methyl | methyl | —(NH)— | 2,6-difluoro-4-methoxyphenyl | 2,4-difluoro-6-propargyloxyphenyl |
| methyl | methyl | —(NH)— | 2,6-difluoro-4-methoxyphenyl | 4-fluoro-2-propargyloxyphenyl |
| methyl | methyl | —(NH)— | 2,6-difluoro-4-methoxyphenyl | 2-fluoro-6-propargyloxyphenyl |
| methyl | methyl | —(NH)— | 2,6-difluoro-4-methoxyphenyl | 4-chloro-2-fluoro-6-propargyloxyphenyl |
| methyl | methyl | —(NH)— | 2,6-difluoro-4-methoxyphenyl | 2-chloro-4-fluoro-6-propargyloxyphenyl |
| methyl | methyl | —(NH)— | 2,6-difluoro-4-methoxyphenyl | 4-allyloxy-2-fluorophenyl |
| methyl | methyl | —(NH)— | 2,6-difluoro-4-methoxyphenyl | 2-fluoro-4-propargyloxyphenyl |
| methyl | methyl | —(NH)— | 2,6-difluoro-4-methoxyphenyl | 2-allyloxyphenyl |
| methyl | methyl | —(NH)— | 2,6-difluoro-4-methoxyphenyl | 2-propargyloxyphenyl |
| methyl | methyl | —(NH)— | 2,6-difluoro-4-methoxyphenyl | 2-allyloxy-5-fluorophenyl |
| methyl | methyl | —(NH)— | 2,6-difluoro-4-methoxyphenyl | 5-fluoro-2-propargyloxyphenyl |
| methyl | methyl | —(NH)— | 2,6-difluoro-4-methoxyphenyl | 2-allyloxy-4-methylphenyl |
| methyl | methyl | —(NH)— | 2,6-difluoro-4-methoxyphenyl | 4-methyl-2-propargyloxyphenyl |
| methyl | methyl | —(NH)— | 2,6-difluoro-4-methoxyphenyl | 2-allyloxy-5-cyanophenyl |
| methyl | methyl | —(NH)— | 2,6-difluoro-4-methoxyphenyl | 5-cyano-2-propargyloxyphenyl |
| methyl | methyl | —(NH)— | 2,6-difluoro-4-methoxyphenyl | 5-allyloxy-2-fluorophenyl |
| methyl | methyl | —(NH)— | 2,6-difluoro-4-methoxyphenyl | 2-fluoro-5-propargyloxyphenyl |

-continued

| R¹ | R² | X | Q¹ | Q² |
|---|---|---|---|---|
| methyl | methyl | —(NH)— | 2,6-difluoro-4-methoxyphenyl | 4-allyloxy-2-chlorophenyl |
| methyl | methyl | —(NH)— | 2,6-difluoro-4-methoxyphenyl | 2-chloro-4-propargyloxyphenyl |
| methyl | methyl | —(NH)— | 2,6-difluoro-4-methoxyphenyl | 4-allyloxy-3-fluorophenyl |
| methyl | methyl | —(NH)— | 2,6-difluoro-4-methoxyphenyl | 3-fluoro-4-propargyloxyphenyl |
| methyl | methyl | —(NH)— | 2,6-difluoro-4-methoxyphenyl | 4-allyloxyphenyl |
| methyl | methyl | —(NH)— | 2,6-difluoro-4-methoxyphenyl | 4-propargyloxyphenyl |
| methyl | methyl | —(NH)— | 2,6-difluoro-4-methoxyphenyl | 3-fluoro-5-propargyloxyphenyl |
| methyl | methyl | —(NH)— | 2,6-difluoro-4-methoxyphenyl | 3-fluoro-5-allyloxyphenyl |
| methyl | methyl | —(NH)— | 2,6-difluoro-4-methoxyphenyl | 2,5-difluoro-4-propargyloxyphenyl |
| methyl | methyl | —(NH)— | 2,6-difluoro-4-methoxyphenyl | 2,5-difluoro-4-allyloxyphenyl |
| methyl | methyl | —(NH)— | 2,6-difluoro-4-methoxyphenyl | 6-allyloxypyridin-3-yl |
| methyl | methyl | —(NH)— | 2,6-difluoro-4-methoxyphenyl | 6-propargyloxypyridin-3-yl |
| methyl | methyl | —(NH)— | 2,6-difluoro-4-methoxyphenyl | 2-propargyloxy-6-trifluorophenyl |
| methyl | methyl | —(NH)— | 2,6-difluoro-4-methoxyphenyl | 2-allyloxy-6-trifluormethylphenyl |
| methyl | methyl | —(NH)— | 2,6-difluoro-4-methoxyphenyl | 2-chloro-6-propargyloxyphenyl |
| methyl | methyl | —(NH)— | 2,6-difluoro-4-methoxyphenyl | 2-allyloxy-6-chlorophenyl |
| methyl | methyl | —(NH)— | 2,6-difluoro-4-methoxyphenyl | 2,4-dimethyl-6-propargyloxyphenyl |
| methyl | methyl | —(NH)— | 2,6-difluoro-4-methoxyphenyl | 2-allyloxy-4,6-dimethylphenyl |
| methyl | methyl | —(NH)— | 2-fluoro-4-propargyloxyphenyl | 2,6-difluoro-4-propargyloxyphenyl |
| methyl | methyl | —(NH)— | 2-fluoro-4-propargyloxyphenyl | 4-allyloxy-2,6-difluorophenyl |
| methyl | methyl | —(NH)— | 2-fluoro-4-propargyloxyphenyl | 2,4-difluoro-6-propargyloxyphenyl |
| methyl | methyl | —(NH)— | 2-fluoro-4-propargyloxyphenyl | 4-fluoro-2-propargyloxyphenyl |
| methyl | methyl | —(NH)— | 2-fluoro-4-propargyloxyphenyl | 2-fluoro-6-propargyloxyphenyl |
| methyl | methyl | —(NH)— | 2-fluoro-4-propargyloxyphenyl | 4-chloro-2-fluoro-6-propargyloxyphenyl |
| methyl | methyl | —(NH)— | 2-fluoro-4-propargyloxyphenyl | 2-chloro-4-fluoro-6-propargyloxyphenyl |
| methyl | methyl | —(NH)— | 2-fluoro-4-propargyloxyphenyl | 4-allyloxy-2-fluorophenyl |
| methyl | methyl | —(NH)— | 2-fluoro-4-propargyloxyphenyl | 2-fluoro-4-propargyloxyphenyl |
| methyl | methyl | —(NH)— | 2-fluoro-4-propargyloxyphenyl | 2-allyloxyphenyl |
| methyl | methyl | —(NH)— | 2-fluoro-4-propargyloxyphenyl | 2-propargyloxyphenyl |
| methyl | methyl | —(NH)— | 2-fluoro-4-propargyloxyphenyl | 2-allyloxy-5-fluorophenyl |
| methyl | methyl | —(NH)— | 2-fluoro-4-propargyloxyphenyl | 5-fluoro-2-propargyloxyphenyl |
| methyl | methyl | —(NH)— | 2-fluoro-4-propargyloxyphenyl | 2-allyloxy-4-methylphenyl |
| methyl | methyl | —(NH)— | 2-fluoro-4-propargyloxyphenyl | 4-methyl-2-propargyloxyphenyl |
| methyl | methyl | —(NH)— | 2-fluoro-4-propargyloxyphenyl | 2-allyloxy-5-cyanophenyl |
| methyl | methyl | —(NH)— | 2-fluoro-4-propargyloxyphenyl | 5-cyano-2-propargyloxyphenyl |
| methyl | methyl | —(NH)— | 2-fluoro-4-propargyloxyphenyl | 5-allyloxy-2-fluorophenyl |
| methyl | methyl | —(NH)— | 2-fluoro-4-propargyloxyphenyl | 2-fluoro-5-propargyloxyphenyl |
| methyl | methyl | —(NH)— | 2-fluoro-4-propargyloxyphenyl | 4-allyloxy-2-chlorophenyl |
| methyl | methyl | —(NH)— | 2-fluoro-4-propargyloxyphenyl | 2-chloro-4-propargyloxyphenyl |
| methyl | methyl | —(NH)— | 2-fluoro-4-propargyloxyphenyl | 4-allyloxy-3-fluorophenyl |
| methyl | methyl | —(NH)— | 2-fluoro-4-propargyloxyphenyl | 3-fluoro-4-propargyloxyphenyl |
| methyl | methyl | —(NH)— | 2-fluoro-4-propargyloxyphenyl | 4-allyloxyphenyl |
| methyl | methyl | —(NH)— | 2-fluoro-4-propargyloxyphenyl | 4-propargyloxyphenyl |
| methyl | methyl | —(NH)— | 2-fluoro-4-propargyloxyphenyl | 3-fluoro-5-propargyloxyphenyl |
| methyl | methyl | —(NH)— | 2-fluoro-4-propargyloxyphenyl | 3-fluoro-5-allyloxyphenyl |
| methyl | methyl | —(NH)— | 2-fluoro-4-propargyloxyphenyl | 2,5-difluoro-4-propargyloxyphenyl |
| methyl | methyl | —(NH)— | 2-fluoro-4-propargyloxyphenyl | 2,5-difluoro-4-allyloxyphenyl |
| methyl | methyl | —(NH)— | 2-fluoro-4-propargyloxyphenyl | 6-allyloxypyridin-3-yl |
| methyl | methyl | —(NH)— | 2-fluoro-4-propargyloxyphenyl | 6-propargyloxypyridin-3-yl |
| methyl | methyl | —(NH)— | 2-fluoro-4-propargyloxyphenyl | 2-propargyloxy-6-trifluorophenyl |
| methyl | methyl | —(NH)— | 2-fluoro-4-propargyloxyphenyl | 2-allyloxy-6-trifluormethylphenyl |
| methyl | methyl | —(NH)— | 2-fluoro-4-propargyloxyphenyl | 2-chloro-6-propargyloxyphenyl |
| methyl | methyl | —(NH)— | 2-fluoro-4-propargyloxyphenyl | 2-allyloxy-6-chlorophenyl |
| methyl | methyl | —(NH)— | 2-fluoro-4-propargyloxyphenyl | 2,4-dimethyl-6-propargyloxyphenyl |
| methyl | methyl | —(NH)— | 2-fluoro-4-propargyloxyphenyl | 2-allyloxy-4,6-dimethylphenyl |
| methyl | methyl | —(NH)— | 4-chloro-2-fluorophenyl | 2,6-difluoro-4-propargyloxyphenyl |
| methyl | methyl | —(NH)— | 4-chloro-2-fluorophenyl | 4-allyloxy-2,6-difluorophenyl |
| methyl | methyl | —(NH)— | 4-chloro-2-fluorophenyl | 2,4-difluoro-6-propargyloxyphenyl |
| methyl | methyl | —(NH)— | 4-chloro-2-fluorophenyl | 4-fluoro-2-propargyloxyphenyl |
| methyl | methyl | —(NH)— | 4-chloro-2-fluorophenyl | 2-fluoro-6-propargyloxyphenyl |
| methyl | methyl | —(NH)— | 4-chloro-2-fluorophenyl | 4-chloro-2-fluoro-6-propargyloxyphenyl |
| methyl | methyl | —(NH)— | 4-chloro-2-fluorophenyl | 2-chloro-4-fluoro-6-propargyloxyphenyl |
| methyl | methyl | —(NH)— | 4-chloro-2-fluorophenyl | 4-allyloxy-2-fluorophenyl |
| methyl | methyl | —(NH)— | 4-chloro-2-fluorophenyl | 2-fluoro-4-propargyloxyphenyl |
| methyl | methyl | —(NH)— | 4-chloro-2-fluorophenyl | 2-allyloxyphenyl |
| methyl | methyl | —(NH)— | 4-chloro-2-fluorophenyl | 2-propargyloxyphenyl |
| methyl | methyl | —(NH)— | 4-chloro-2-fluorophenyl | 2-allyloxy-5-fluorophenyl |
| methyl | methyl | —(NH)— | 4-chloro-2-fluorophenyl | 5-fluoro-2-propargyloxyphenyl |
| methyl | methyl | —(NH)— | 4-chloro-2-fluorophenyl | 2-allyloxy-4-methylphenyl |
| methyl | methyl | —(NH)— | 4-chloro-2-fluorophenyl | 4-methyl-2-propargyloxyphenyl |
| methyl | methyl | —(NH)— | 4-chloro-2-fluorophenyl | 2-allyloxy-5-cyanophenyl |
| methyl | methyl | —(NH)— | 4-chloro-2-fluorophenyl | 5-cyano-2-propargyloxyphenyl |
| methyl | methyl | —(NH)— | 4-chloro-2-fluorophenyl | 5-allyloxy-2-fluorophenyl |

| R¹ | R² | X | Q¹ | Q² |
|---|---|---|---|---|
| methyl | methyl | —(NH)— | 4-chloro-2-fluorophenyl | 2-fluoro-5-propargyloxyphenyl |
| methyl | methyl | —(NH)— | 4-chloro-2-fluorophenyl | 4-allyloxy-2-chlorophenyl |
| methyl | methyl | —(NH)— | 4-chloro-2-fluorophenyl | 2-chloro-4-propargyloxyphenyl |
| methyl | methyl | —(NH)— | 4-chloro-2-fluorophenyl | 4-allyloxy-3-fluorophenyl |
| methyl | methyl | —(NH)— | 4-chloro-2-fluorophenyl | 3-fluoro-4-propargyloxyphenyl |
| methyl | methyl | —(NH)— | 4-chloro-2-fluorophenyl | 4-allyloxyphenyl |
| methyl | methyl | —(NH)— | 4-chloro-2-fluorophenyl | 4-propargyloxyphenyl |
| methyl | methyl | —(NH)— | 4-chloro-2-fluorophenyl | 3-fluoro-5-propargyloxyphenyl |
| methyl | methyl | —(NH)— | 4-chloro-2-fluorophenyl | 3-fluoro-5-allyloxyphenyl |
| methyl | methyl | —(NH)— | 4-chloro-2-fluorophenyl | 2,5-difluoro-4-propargyloxyphenyl |
| methyl | methyl | —(NH)— | 4-chloro-2-fluorophenyl | 2,5-difluoro-4-allyloxyphenyl |
| methyl | methyl | —(NH)— | 4-chloro-2-fluorophenyl | 6-allyloxypyridin-3-yl |
| methyl | methyl | —(NH)— | 4-chloro-2-fluorophenyl | 6-propargyloxypyridin-3-yl |
| methyl | methyl | —(NH)— | 4-chloro-2-fluorophenyl | 2-propargyloxy-6-trifluorophenyl |
| methyl | methyl | —(NH)— | 4-chloro-2-fluorophenyl | 2-allyloxy-6-trifluormethylphenyl |
| methyl | methyl | —(NH)— | 4-chloro-2-fluorophenyl | 2-chloro-6-propargyloxyphenyl |
| methyl | methyl | —(NH)— | 4-chloro-2-fluorophenyl | 2-allyloxy-6-chlorophenyl |
| methyl | methyl | —(NH)— | 4-chloro-2-fluorophenyl | 2,4-dimethyl-6-propargyloxyphenyl |
| methyl | methyl | —(NH)— | 4-chloro-2-fluorophenyl | 2-allyloxy-4,6-dimethylphenyl |
| methyl | methyl | —(NH)— | 2-bromo-4-fluorophenyl | 2,6-difluoro-4-propargyloxyphenyl |
| methyl | methyl | —(NH)— | 2-bromo-4-fluorophenyl | 4-allyloxy-2,6-difluorophenyl |
| methyl | methyl | —(NH)— | 2-bromo-4-fluorophenyl | 2,4-difluoro-6-propargyloxyphenyl |
| methyl | methyl | —(NH)— | 2-bromo-4-fluorophenyl | 4-fluoro-2-propargyloxyphenyl |
| methyl | methyl | —(NH)— | 2-bromo-4-fluorophenyl | 2-fluoro-6-propargyloxyphenyl |
| methyl | methyl | —(NH)— | 2-bromo-4-fluorophenyl | 4-chloro-2-fluoro-6-propargyloxyphenyl |
| methyl | methyl | —(NH)— | 2-bromo-4-fluorophenyl | 2-chloro-4-fluoro-6-propargyloxyphenyl |
| methyl | methyl | —(NH)— | 2-bromo-4-fluorophenyl | 4-allyloxy-2-fluorophenyl |
| methyl | methyl | —(NH)— | 2-bromo-4-fluorophenyl | 2-fluoro-4-propargyloxyphenyl |
| methyl | methyl | —(NH)— | 2-bromo-4-fluorophenyl | 2-allyloxyphenyl |
| methyl | methyl | —(NH)— | 2-bromo-4-fluorophenyl | 2-propargyloxyphenyl |
| methyl | methyl | —(NH)— | 2-bromo-4-fluorophenyl | 2-allyloxy-5-fluorophenyl |
| methyl | methyl | —(NH)— | 2-bromo-4-fluorophenyl | 5-fluoro-2-propargyloxyphenyl |
| methyl | methyl | —(NH)— | 2-bromo-4-fluorophenyl | 2-allyloxy-4-methylphenyl |
| methyl | methyl | —(NH)— | 2-bromo-4-fluorophenyl | 4-methyl-2-propargyloxyphenyl |
| methyl | methyl | —(NH)— | 2-bromo-4-fluorophenyl | 2-allyloxy-5-cyanophenyl |
| methyl | methyl | —(NH)— | 2-bromo-4-fluorophenyl | 5-cyano-2-propargyloxyphenyl |
| methyl | methyl | —(NH)— | 2-bromo-4-fluorophenyl | 5-allyloxy-2-fluorophenyl |
| methyl | methyl | —(NH)— | 2-bromo-4-fluorophenyl | 2-fluoro-5-propargyloxyphenyl |
| methyl | methyl | —(NH)— | 2-bromo-4-fluorophenyl | 4-allyloxy-2-chlorophenyl |
| methyl | methyl | —(NH)— | 2-bromo-4-fluorophenyl | 2-chloro-4-propargyloxyphenyl |
| methyl | methyl | —(NH)— | 2-bromo-4-fluorophenyl | 4-allyloxy-3-fluorophenyl |
| methyl | methyl | —(NH)— | 2-bromo-4-fluorophenyl | 3-fluoro-4-propargyloxyphenyl |
| methyl | methyl | —(NH)— | 2-bromo-4-fluorophenyl | 4-allyloxyphenyl |
| methyl | methyl | —(NH)— | 2-bromo-4-fluorophenyl | 4-propargyloxyphenyl |
| methyl | methyl | —(NH)— | 2-bromo-4-fluorophenyl | 3-fluoro-5-propargyloxyphenyl |
| methyl | methyl | —(NH)— | 2-bromo-4-fluorophenyl | 3-fluoro-5-allyloxyphenyl |
| methyl | methyl | —(NH)— | 2-bromo-4-fluorophenyl | 2,5-difluoro-4-propargyloxyphenyl |
| methyl | methyl | —(NH)— | 2-bromo-4-fluorophenyl | 2,5-difluoro-4-allyloxyphenyl |
| methyl | methyl | —(NH)— | 2-bromo-4-fluorophenyl | 6-allyloxypyridin-3-yl |
| methyl | methyl | —(NH)— | 2-bromo-4-fluorophenyl | 6-propargyloxypyridin-3-yl |
| methyl | methyl | —(NH)— | 2-bromo-4-fluorophenyl | 2-propargyloxy-6-trifluorophenyl |
| methyl | methyl | —(NH)— | 2-bromo-4-fluorophenyl | 2-allyloxy-6-trifluormethylphenyl |
| methyl | methyl | —(NH)— | 2-bromo-4-fluorophenyl | 2-chloro-6-propargyloxyphenyl |
| methyl | methyl | —(NH)— | 2-bromo-4-fluorophenyl | 2-allyloxy-6-chlorophenyl |
| methyl | methyl | —(NH)— | 2-bromo-4-fluorophenyl | 2,4-dimethyl-6-propargyloxyphenyl |
| methyl | methyl | —(NH)— | 2-bromo-4-fluorophenyl | 2-allyloxy-4,6-dimethylphenyl |
| methyl | methyl | —(NH)— | 2,4,6-trifluorophenyl | 2,6-difluoro-4-propargyloxyphenyl |
| methyl | methyl | —(NH)— | 2,4,6-trifluorophenyl | 4-allyloxy-2,6-difluorophenyl |
| methyl | methyl | —(NH)— | 2,4,6-trifluorophenyl | 2,4-difluoro-6-propargyloxyphenyl |
| methyl | methyl | —(NH)— | 2,4,6-trifluorophenyl | 4-fluoro-2-propargyloxyphenyl |
| methyl | methyl | —(NH)— | 2,4,6-trifluorophenyl | 2-fluoro-6-propargyloxyphenyl |
| methyl | methyl | —(NH)— | 2,4,6-trifluorophenyl | 4-chloro-2-fluoro-6-propargyloxyphenyl |
| methyl | methyl | —(NH)— | 2,4,6-trifluorophenyl | 2-chloro-4-fluoro-6-propargyloxyphenyl |
| methyl | methyl | —(NH)— | 2,4,6-trifluorophenyl | 4-allyloxy-2-fluorophenyl |
| methyl | methyl | —(NH)— | 2,4,6-trifluorophenyl | 2-fluoro-4-propargyloxyphenyl |
| methyl | methyl | —(NH)— | 2,4,6-trifluorophenyl | 2-allyloxyphenyl |
| methyl | methyl | —(NH)— | 2,4,6-trifluorophenyl | 2-propargyloxyphenyl |
| methyl | methyl | —(NH)— | 2,4,6-trifluorophenyl | 2-allyloxy-5-fluorophenyl |
| methyl | methyl | —(NH)— | 2,4,6-trifluorophenyl | 5-fluoro-2-propargyloxyphenyl |
| methyl | methyl | —(NH)— | 2,4,6-trifluorophenyl | 2-allyloxy-4-methylphenyl |
| methyl | methyl | —(NH)— | 2,4,6-trifluorophenyl | 4-methyl-2-propargyloxyphenyl |
| methyl | methyl | —(NH)— | 2,4,6-trifluorophenyl | 2-allyloxy-5-cyanophenyl |
| methyl | methyl | —(NH)— | 2,4,6-trifluorophenyl | 5-cyano-2-propargyloxyphenyl |

-continued

| R¹ | R² | X | Q¹ | Q² |
|---|---|---|---|---|
| methyl | methyl | —(NH)— | 2,4,6-trifluorophenyl | 5-allyloxy-2-fluorophenyl |
| methyl | methyl | —(NH)— | 2,4,6-trifluorophenyl | 2-fluoro-5-propargyloxyphenyl |
| methyl | methyl | —(NH)— | 2,4,6-trifluorophenyl | 4-allyloxy-2-chlorophenyl |
| methyl | methyl | —(NH)— | 2,4,6-trifluorophenyl | 2-chloro-4-propargyloxyphenyl |
| methyl | methyl | —(NH)— | 2,4,6-trifluorophenyl | 4-allyloxy-3-fluorophenyl |
| methyl | methyl | —(NH)— | 2,4,6-trifluorophenyl | 3-fluoro-4-propargyloxyphenyl |
| methyl | methyl | —(NH)— | 2,4,6-trifluorophenyl | 4-allyloxyphenyl |
| methyl | methyl | —(NH)— | 2,4,6-trifluorophenyl | 4-propargyloxyphenyl |
| methyl | methyl | —(NH)— | 2,4,6-trifluorophenyl | 3-fluoro-5-propargyloxyphenyl |
| methyl | methyl | —(NH)— | 2,4,6-trifluorophenyl | 3-fluoro-5-allyloxyphenyl |
| methyl | methyl | —(NH)— | 2,4,6-trifluorophenyl | 2,5-difluoro-4-propargyloxyphenyl |
| methyl | methyl | —(NH)— | 2,4,6-trifluorophenyl | 2,5-difluoro-4-allyloxyphenyl |
| methyl | methyl | —(NH)— | 2,4,6-trifluorophenyl | 6-allyloxypyridin-3-yl |
| methyl | methyl | —(NH)— | 2,4,6-trifluorophenyl | 6-propargyloxypyridin-3-yl |
| methyl | methyl | —(NH)— | 2,4,6-trifluorophenyl | 2-propargyloxy-6-trifluorophenyl |
| methyl | methyl | —(NH)— | 2,4,6-trifluorophenyl | 2-allyloxy-6-trifluormethylphenyl |
| methyl | methyl | —(NH)— | 2,4,6-trifluorophenyl | 2-chloro-6-propargyloxyphenyl |
| methyl | methyl | —(NH)— | 2,4,6-trifluorophenyl | 2-allyloxy-6-chlorophenyl |
| methyl | methyl | —(NH)— | 2,4,6-trifluorophenyl | 2,4-dimethyl-6-propargyloxyphenyl |
| methyl | methyl | —(NH)— | 2,4,6-trifluorophenyl | 2-allyloxy-4,6-dimethylphenyl |
| methyl | methyl | —(NH)— | 4-chloro-2,6-difluorophenyl | 2,6-difluoro-4-propargyloxyphenyl |
| methyl | methyl | —(NH)— | 4-chloro-2,6-difluorophenyl | 4-allyloxy-2,6-difluorophenyl |
| methyl | methyl | —(NH)— | 4-chloro-2,6-difluorophenyl | 2,4-difluoro-6-propargyloxyphenyl |
| methyl | methyl | —(NH)— | 4-chloro-2,6-difluorophenyl | 4-fluoro-2-propargyloxyphenyl |
| methyl | methyl | —(NH)— | 4-chloro-2,6-difluorophenyl | 2-fluoro-6-propargyloxyphenyl |
| methyl | methyl | —(NH)— | 4-chloro-2,6-difluorophenyl | 4-chloro-2-fluoro-6-propargyloxyphenyl |
| methyl | methyl | —(NH)— | 4-chloro-2,6-difluorophenyl | 2-chloro-4-fluoro-6-propargyloxyphenyl |
| methyl | methyl | —(NH)— | 4-chloro-2,6-difluorophenyl | 4-allyloxy-2-fluorophenyl |
| methyl | methyl | —(NH)— | 4-chloro-2,6-difluorophenyl | 2-fluoro-4-propargyloxyphenyl |
| methyl | methyl | —(NH)— | 4-chloro-2,6-difluorophenyl | 2-allyloxyphenyl |
| methyl | methyl | —(NH)— | 4-chloro-2,6-difluorophenyl | 2-propargyloxyphenyl |
| methyl | methyl | —(NH)— | 4-chloro-2,6-difluorophenyl | 2-allyloxy-5-fluorophenyl |
| methyl | methyl | —(NH)— | 4-chloro-2,6-difluorophenyl | 5-fluoro-2-propargyloxyphenyl |
| methyl | methyl | —(NH)— | 4-chloro-2,6-difluorophenyl | 2-allyloxy-4-methylphenyl |
| methyl | methyl | —(NH)— | 4-chloro-2,6-difluorophenyl | 4-methyl-2-propargyloxyphenyl |
| methyl | methyl | —(NH)— | 4-chloro-2,6-difluorophenyl | 2-allyloxy-5-cyanophenyl |
| methyl | methyl | —(NH)— | 4-chloro-2,6-difluorophenyl | 5-cyano-2-propargyloxyphenyl |
| methyl | methyl | —(NH)— | 4-chloro-2,6-difluorophenyl | 5-allyloxy-2-fluorophenyl |
| methyl | methyl | —(NH)— | 4-chloro-2,6-difluorophenyl | 2-fluoro-5-propargyloxyphenyl |
| methyl | methyl | —(NH)— | 4-chloro-2,6-difluorophenyl | 4-allyloxy-2-chlorophenyl |
| methyl | methyl | —(NH)— | 4-chloro-2,6-difluorophenyl | 2-chloro-4-propargyloxyphenyl |
| methyl | methyl | —(NH)— | 4-chloro-2,6-difluorophenyl | 4-allyloxy-3-fluorophenyl |
| methyl | methyl | —(NH)— | 4-chloro-2,6-difluorophenyl | 3-fluoro-4-propargyloxyphenyl |
| methyl | methyl | —(NH)— | 4-chloro-2,6-difluorophenyl | 4-allyloxyphenyl |
| methyl | methyl | —(NH)— | 4-chloro-2,6-difluorophenyl | 4-propargyloxyphenyl |
| methyl | methyl | —(NH)— | 4-chloro-2,6-difluorophenyl | 3-fluoro-5-propargyloxyphenyl |
| methyl | methyl | —(NH)— | 4-chloro-2,6-difluorophenyl | 3-fluoro-5-allyloxyphenyl |
| methyl | methyl | —(NH)— | 4-chloro-2,6-difluorophenyl | 2,5-difluoro-4-propargyloxyphenyl |
| methyl | methyl | —(NH)— | 4-chloro-2,6-difluorophenyl | 2,5-difluoro-4-allyloxyphenyl |
| methyl | methyl | —(NH)— | 4-chloro-2,6-difluorophenyl | 6-allyloxypyridin-3-yl |
| methyl | methyl | —(NH)— | 4-chloro-2,6-difluorophenyl | 6-propargyloxypyridin-3-yl |
| methyl | methyl | —(NH)— | 4-chloro-2,6-difluorophenyl | 2-propargyloxy-6-trifluorophenyl |
| methyl | methyl | —(NH)— | 4-chloro-2,6-difluorophenyl | 2-allyloxy-6-trifluormethylphenyl |
| methyl | methyl | —(NH)— | 4-chloro-2,6-difluorophenyl | 2-chloro-6-propargyloxyphenyl |
| methyl | methyl | —(NH)— | 4-chloro-2,6-difluorophenyl | 2-allyloxy-6-chlorophenyl |
| methyl | methyl | —(NH)— | 4-chloro-2,6-difluorophenyl | 2,4-dimethyl-6-propargyloxyphenyl |
| methyl | methyl | —(NH)— | 4-chloro-2,6-difluorophenyl | 2-allyloxy-4,6-dimethylphenyl |
| methyl | methyl | —(NH)— | 4-chloro-2,6-difluorophenyl | 2,6-difluoro-4-propargyloxyphenyl |
| methyl | methyl | —(NH)— | 4-chloro-2,6-difluorophenyl | 4-allyloxy-2,6-difluorophenyl |
| methyl | methyl | —(NH)— | 4-chloro-2,6-difluorophenyl | 2,4-difluoro-6-propargyloxyphenyl |
| methyl | methyl | —(NH)— | 4-chloro-2,6-difluorophenyl | 4-fluoro-2-propargyloxyphenyl |
| methyl | methyl | —(NH)— | 4-chloro-2,6-difluorophenyl | 2-fluoro-6-propargyloxyphenyl |
| methyl | methyl | —(NH)— | 4-chloro-2,6-difluorophenyl | 4-chloro-2-fluoro-6-propargyloxyphenyl |
| methyl | methyl | —(NH)— | 4-chloro-2,6-difluorophenyl | 2-chloro-4-fluoro-6-propargyloxyphenyl |
| methyl | methyl | —(NH)— | 4-chloro-2,6-difluorophenyl | 4-allyloxy-2-fluorophenyl |
| methyl | methyl | —(NH)— | 4-chloro-2,6-difluorophenyl | 2-fluoro-4-propargyloxyphenyl |
| methyl | methyl | —(NH)— | 4-chloro-2,6-difluorophenyl | 2-allyloxyphenyl |
| methyl | methyl | —(NH)— | 4-chloro-2,6-difluorophenyl | 2-propargyloxyphenyl |
| methyl | methyl | —(NH)— | 4-chloro-2,6-difluorophenyl | 2-allyloxy-5-fluorophenyl |
| methyl | methyl | —(NH)— | 4-chloro-2,6-difluorophenyl | 5-fluoro-2-propargyloxyphenyl |
| methyl | methyl | —(NH)— | 4-chloro-2,6-difluorophenyl | 2-allyloxy-4-methylphenyl |
| methyl | methyl | —(NH)— | 4-chloro-2,6-difluorophenyl | 4-methyl-2-propargyloxyphenyl |
| methyl | methyl | —(NH)— | 4-chloro-2,6-difluorophenyl | 2-allyloxy-5-cyanophenyl |

| R¹ | R² | X | Q¹ | Q² |
|---|---|---|---|---|
| methyl | methyl | —(NH)— | 4-chloro-2,6-difluorophenyl | 5-cyano-2-propargyloxyphenyl |
| methyl | methyl | —(NH)— | 4-chloro-2,6-difluorophenyl | 5-allyloxy-2-fluorophenyl |
| methyl | methyl | —(NH)— | 4-chloro-2,6-difluorophenyl | 2-fluoro-5-propargyloxyphenyl |
| methyl | methyl | —(NH)— | 4-chloro-2,6-difluorophenyl | 4-allyloxy-2-chlorophenyl |
| methyl | methyl | —(NH)— | 4-chloro-2,6-difluorophenyl | 2-chloro-4-propargyloxyphenyl |
| methyl | methyl | —(NH)— | 4-chloro-2,6-difluorophenyl | 4-allyloxy-3-fluorophenyl |
| methyl | methyl | —(NH)— | 4-chloro-2,6-difluorophenyl | 3-fluoro-4-propargyloxyphenyl |
| methyl | methyl | —(NH)— | 4-chloro-2,6-difluorophenyl | 4-allyloxyphenyl |
| methyl | methyl | —(NH)— | 4-chloro-2,6-difluorophenyl | 4-propargyloxyphenyl |
| methyl | methyl | —(NH)— | 4-chloro-2,6-difluorophenyl | 3-fluoro-5-propargyloxyphenyl |
| methyl | methyl | —(NH)— | 4-chloro-2,6-difluorophenyl | 3-fluoro-5-allyloxyphenyl |
| methyl | methyl | —(NH)— | 4-chloro-2,6-difluorophenyl | 2,5-difluoro-4-propargyloxyphenyl |
| methyl | methyl | —(NH)— | 4-chloro-2,6-difluorophenyl | 2,5-difluoro-4-allyloxyphenyl |
| methyl | methyl | —(NH)— | 4-chloro-2,6-difluorophenyl | 6-allyloxypyridin-3-yl |
| methyl | methyl | —(NH)— | 4-chloro-2,6-difluorophenyl | 6-propargyloxypyridin-3-yl |
| methyl | methyl | —(NH)— | 4-chloro-2,6-difluorophenyl | 2-propargyloxy-6-trifluorophenyl |
| methyl | methyl | —(NH)— | 4-chloro-2,6-difluorophenyl | 2-allyloxy-6-trifluormethylphenyl |
| methyl | methyl | —(NH)— | 4-chloro-2,6-difluorophenyl | 2-chloro-6-propargyloxyphenyl |
| methyl | methyl | —(NH)— | 4-chloro-2,6-difluorophenyl | 2-allyloxy-6-chlorophenyl |
| methyl | methyl | —(NH)— | 4-chloro-2,6-difluorophenyl | 2,4-dimethyl-6-propargyloxyphenyl |
| methyl | methyl | —(NH)— | 4-chloro-2,6-difluorophenyl | 2-allyloxy-4,6-dimethylphenyl |
| methyl | methyl | —(NH)— | 3,4-dichlorophenyl | 2,6-difluoro-4-propargyloxyphenyl |
| methyl | methyl | —(NH)— | 3,4-dichlorophenyl | 4-allyloxy-2,6-difluorophenyl |
| methyl | methyl | —(NH)— | 3,4-dichlorophenyl | 2,4-difluoro-6-propargyloxyphenyl |
| methyl | methyl | —(NH)— | 3,4-dichlorophenyl | 4-fluoro-2-propargyloxyphenyl |
| methyl | methyl | —(NH)— | 3,4-dichlorophenyl | 2-fluoro-6-propargyloxyphenyl |
| methyl | methyl | —(NH)— | 3,4-dichlorophenyl | 4-chloro-2-fluoro-6-propargyloxyphenyl |
| methyl | methyl | —(NH)— | 3,4-dichlorophenyl | 2-chloro-4-fluoro-6-propargyloxyphenyl |
| methyl | methyl | —(NH)— | 3,4-dichlorophenyl | 4-allyloxy-2-fluorophenyl |
| methyl | methyl | —(NH)— | 3,4-dichlorophenyl | 2-fluoro-4-propargyloxyphenyl |
| methyl | methyl | —(NH)— | 3,4-dichlorophenyl | 2-allyloxyphenyl |
| methyl | methyl | —(NH)— | 3,4-dichlorophenyl | 2-propargyloxyphenyl |
| methyl | methyl | —(NH)— | 3,4-dichlorophenyl | 2-allyloxy-5-fluorophenyl |
| methyl | methyl | —(NH)— | 3,4-dichlorophenyl | 5-fluoro-2-propargyloxyphenyl |
| methyl | methyl | —(NH)— | 3,4-dichlorophenyl | 2-allyloxy-4-methylphenyl |
| methyl | methyl | —(NH)— | 3,4-dichlorophenyl | 4-methyl-2-propargyloxyphenyl |
| methyl | methyl | —(NH)— | 3,4-dichlorophenyl | 2-allyloxy-5-cyanophenyl |
| methyl | methyl | —(NH)— | 3,4-dichlorophenyl | 5-cyano-2-propargyloxyphenyl |
| methyl | methyl | —(NH)— | 3,4-dichlorophenyl | 5-allyloxy-2-fluorophenyl |
| methyl | methyl | —(NH)— | 3,4-dichlorophenyl | 2-fluoro-5-propargyloxyphenyl |
| methyl | methyl | —(NH)— | 3,4-dichlorophenyl | 4-allyloxy-2-chlorophenyl |
| methyl | methyl | —(NH)— | 3,4-dichlorophenyl | 2-chloro-4-propargyloxyphenyl |
| methyl | methyl | —(NH)— | 3,4-dichlorophenyl | 4-allyloxy-3-fluorophenyl |
| methyl | methyl | —(NH)— | 3,4-dichlorophenyl | 3-fluoro-4-propargyloxyphenyl |
| methyl | methyl | —(NH)— | 3,4-dichlorophenyl | 4-allyloxyphenyl |
| methyl | methyl | —(NH)— | 3,4-dichlorophenyl | 4-propargyloxyphenyl |
| methyl | methyl | —(NH)— | 3,4-dichlorophenyl | 3-fluoro-5-propargyloxyphenyl |
| methyl | methyl | —(NH)— | 3,4-dichlorophenyl | 3-fluoro-5-allyloxyphenyl |
| methyl | methyl | —(NH)— | 3,4-dichlorophenyl | 2,5-difluoro-4-propargyloxyphenyl |
| methyl | methyl | —(NH)— | 3,4-dichlorophenyl | 2,5-difluoro-4-allyloxyphenyl |
| methyl | methyl | —(NH)— | 3,4-dichlorophenyl | 6-allyloxypyridin-3-yl |
| methyl | methyl | —(NH)— | 3,4-dichlorophenyl | 6-propargyloxypyridin-3-yl |
| methyl | methyl | —(NH)— | 3,4-dichlorophenyl | 2-propargyloxy-6-trifluorophenyl |
| methyl | methyl | —(NH)— | 3,4-dichlorophenyl | 2-allyloxy-6-trifluormethylphenyl |
| methyl | methyl | —(NH)— | 3,4-dichlorophenyl | 2-chloro-6-propargyloxyphenyl |
| methyl | methyl | —(NH)— | 3,4-dichlorophenyl | 2-allyloxy-6-chlorophenyl |
| methyl | methyl | —(NH)— | 3,4-dichlorophenyl | 2,4-dimethyl-6-propargyloxyphenyl |
| methyl | methyl | —(NH)— | 3,4-dichlorophenyl | 2-allyloxy-4,6-dimethylphenyl |
| methyl | methyl | —(NH)— | 3,5-dichlorophenyl | 2,6-difluoro-4-propargyloxyphenyl |
| methyl | methyl | —(NH)— | 3,5-dichlorophenyl | 4-allyloxy-2,6-difluorophenyl |
| methyl | methyl | —(NH)— | 3,5-dichlorophenyl | 2,4-difluoro-6-propargyloxyphenyl |
| methyl | methyl | —(NH)— | 3,5-dichlorophenyl | 4-fluoro-2-propargyloxyphenyl |
| methyl | methyl | —(NH)— | 3,5-dichlorophenyl | 2-fluoro-6-propargyloxyphenyl |
| methyl | methyl | —(NH)— | 3,5-dichlorophenyl | 4-chloro-2-fluoro-6-propargyloxyphenyl |
| methyl | methyl | —(NH)— | 3,5-dichlorophenyl | 2-chloro-4-fluoro-6-propargyloxyphenyl |
| methyl | methyl | —(NH)— | 3,5-dichlorophenyl | 4-allyloxy-2-fluorophenyl |
| methyl | methyl | —(NH)— | 3,5-dichlorophenyl | 2-fluoro-4-propargyloxyphenyl |
| methyl | methyl | —(NH)— | 3,5-dichlorophenyl | 2-allyloxyphenyl |
| methyl | methyl | —(NH)— | 3,5-dichlorophenyl | 2-propargyloxyphenyl |
| methyl | methyl | —(NH)— | 3,5-dichlorophenyl | 2-allyloxy-5-fluorophenyl |
| methyl | methyl | —(NH)— | 3,5-dichlorophenyl | 5-fluoro-2-propargyloxyphenyl |
| methyl | methyl | —(NH)— | 3,5-dichlorophenyl | 2-allyloxy-4-methylphenyl |
| methyl | methyl | —(NH)— | 3,5-dichlorophenyl | 4-methyl-2-propargyloxyphenyl |

| R¹ | R² | X | Q¹ | Q² |
|---|---|---|---|---|
| methyl | methyl | —(NH)— | 3,5-dichlorophenyl | 2-allyloxy-5-cyanophenyl |
| methyl | methyl | —(NH)— | 3,5-dichlorophenyl | 5-cyano-2-propargyloxyphenyl |
| methyl | methyl | —(NH)— | 3,5-dichlorophenyl | 5-allyloxy-2-fluorophenyl |
| methyl | methyl | —(NH)— | 3,5-dichlorophenyl | 2-fluoro-5-propargyloxyphenyl |
| methyl | methyl | —(NH)— | 3,5-dichlorophenyl | 4-allyloxy-2-chlorophenyl |
| methyl | methyl | —(NH)— | 3,5-dichlorophenyl | 2-chloro-4-propargyloxyphenyl |
| methyl | methyl | —(NH)— | 3,5-dichlorophenyl | 4-allyloxy-3-fluorophenyl |
| methyl | methyl | —(NH)— | 3,5-dichlorophenyl | 3-fluoro-4-propargyloxyphenyl |
| methyl | methyl | —(NH)— | 3,5-dichlorophenyl | 4-allyloxyphenyl |
| methyl | methyl | —(NH)— | 3,5-dichlorophenyl | 4-propargyloxyphenyl |
| methyl | methyl | —(NH)— | 3,5-dichlorophenyl | 3-fluoro-5-propargyloxyphenyl |
| methyl | methyl | —(NH)— | 3,5-dichlorophenyl | 3-fluoro-5-allyloxyphenyl |
| methyl | methyl | —(NH)— | 3,5-dichlorophenyl | 2,5-difluoro-4-propargyloxyphenyl |
| methyl | methyl | —(NH)— | 3,5-dichlorophenyl | 2,5-difluoro-4-allyloxyphenyl |
| methyl | methyl | —(NH)— | 3,5-dichlorophenyl | 6-allyloxypyridin-3-yl |
| methyl | methyl | —(NH)— | 3,5-dichlorophenyl | 6-propargyloxypyridin-3-yl |
| methyl | methyl | —(NH)— | 3,5-dichlorophenyl | 2-propargyloxy-6-trifluorophenyl |
| methyl | methyl | —(NH)— | 3,5-dichlorophenyl | 2-allyloxy-6-trifluormethylphenyl |
| methyl | methyl | —(NH)— | 3,5-dichlorophenyl | 2-chloro-6-propargyloxyphenyl |
| methyl | methyl | —(NH)— | 3,5-dichlorophenyl | 2-allyloxy-6-chlorophenyl |
| methyl | methyl | —(NH)— | 3,5-dichlorophenyl | 2,4-dimethyl-6-propargyloxyphenyl |
| methyl | methyl | —(NH)— | 3,5-dichlorophenyl | 2-allyloxy-4,6-dimethylphenyl |
| methyl | methyl | —(NH)— | 4-fluoro-2-propargyloxyphenyl | 2,6-difluoro-4-propargyloxyphenyl |
| methyl | methyl | —(NH)— | 4-fluoro-2-propargyloxyphenyl | 4-allyloxy-2,6-difluorophenyl |
| methyl | methyl | —(NH)— | 4-fluoro-2-propargyloxyphenyl | 2,4-difluoro-6-propargyloxyphenyl |
| methyl | methyl | —(NH)— | 4-fluoro-2-propargyloxyphenyl | 4-fluoro-2-propargyloxyphenyl |
| methyl | methyl | —(NH)— | 4-fluoro-2-propargyloxyphenyl | 2-fluoro-6-propargyloxyphenyl |
| methyl | methyl | —(NH)— | 4-fluoro-2-propargyloxyphenyl | 4-chloro-2-fluoro-6-propargyloxyphenyl |
| methyl | methyl | —(NH)— | 4-fluoro-2-propargyloxyphenyl | 2-chloro-4-fluoro-6-propargyloxyphenyl |
| methyl | methyl | —(NH)— | 4-fluoro-2-propargyloxyphenyl | 4-allyloxy-2-fluorophenyl |
| methyl | methyl | —(NH)— | 4-fluoro-2-propargyloxyphenyl | 2-fluoro-4-propargyloxyphenyl |
| methyl | methyl | —(NH)— | 4-fluoro-2-propargyloxyphenyl | 2-allyloxyphenyl |
| methyl | methyl | —(NH)— | 4-fluoro-2-propargyloxyphenyl | 2-propargyloxyphenyl |
| methyl | methyl | —(NH)— | 4-fluoro-2-propargyloxyphenyl | 2-allyloxy-5-fluorophenyl |
| methyl | methyl | —(NH)— | 4-fluoro-2-propargyloxyphenyl | 5-fluoro-2-propargyloxyphenyl |
| methyl | methyl | —(NH)— | 4-fluoro-2-propargyloxyphenyl | 2-allyloxy-4-methylphenyl |
| methyl | methyl | —(NH)— | 4-fluoro-2-propargyloxyphenyl | 4-methyl-2-propargyloxyphenyl |
| methyl | methyl | —(NH)— | 4-fluoro-2-propargyloxyphenyl | 2-allyloxy-5-cyanophenyl |
| methyl | methyl | —(NH)— | 4-fluoro-2-propargyloxyphenyl | 5-cyano-2-propargyloxyphenyl |
| methyl | methyl | —(NH)— | 4-fluoro-2-propargyloxyphenyl | 5-allyloxy-2-fluorophenyl |
| methyl | methyl | —(NH)— | 4-fluoro-2-propargyloxyphenyl | 2-fluoro-5-propargyloxyphenyl |
| methyl | methyl | —(NH)— | 4-fluoro-2-propargyloxyphenyl | 4-allyloxy-2-chlorophenyl |
| methyl | methyl | —(NH)— | 4-fluoro-2-propargyloxyphenyl | 2-chloro-4-propargyloxyphenyl |
| methyl | methyl | —(NH)— | 4-fluoro-2-propargyloxyphenyl | 4-allyloxy-3-fluorophenyl |
| methyl | methyl | —(NH)— | 4-fluoro-2-propargyloxyphenyl | 3-fluoro-4-propargyloxyphenyl |
| methyl | methyl | —(NH)— | 4-fluoro-2-propargyloxyphenyl | 4-allyloxyphenyl |
| methyl | methyl | —(NH)— | 4-fluoro-2-propargyloxyphenyl | 4-propargyloxyphenyl |
| methyl | methyl | —(NH)— | 4-fluoro-2-propargyloxyphenyl | 3-fluoro-5-propargyloxyphenyl |
| methyl | methyl | —(NH)— | 4-fluoro-2-propargyloxyphenyl | 3-fluoro-5-allyloxyphenyl |
| methyl | methyl | —(NH)— | 4-fluoro-2-propargyloxyphenyl | 2,5-difluoro-4-propargyloxyphenyl |
| methyl | methyl | —(NH)— | 4-fluoro-2-propargyloxyphenyl | 2,5-difluoro-4-allyloxyphenyl |
| methyl | methyl | —(NH)— | 4-fluoro-2-propargyloxyphenyl | 6-allyloxypyridin-3-yl |
| methyl | methyl | —(NH)— | 4-fluoro-2-propargyloxyphenyl | 6-propargyloxypyridin-3-yl |
| methyl | methyl | —(NH)— | 4-fluoro-2-propargyloxyphenyl | 2-propargyloxy-6-trifluorophenyl |
| methyl | methyl | —(NH)— | 4-fluoro-2-propargyloxyphenyl | 2-allyloxy-6-trifluormethylphenyl |
| methyl | methyl | —(NH)— | 4-fluoro-2-propargyloxyphenyl | 2-chloro-6-propargyloxyphenyl |
| methyl | methyl | —(NH)— | 4-fluoro-2-propargyloxyphenyl | 2-allyloxy-6-chlorophenyl |
| methyl | methyl | —(NH)— | 4-fluoro-2-propargyloxyphenyl | 2,4-dimethyl-6-propargyloxyphenyl |
| methyl | methyl | —(NH)— | 4-fluoro-2-propargyloxyphenyl | 2-allyloxy-4,6-dimethylphenyl |
| methyl | methyl | —(NH)— | 2,6-difluoro-4-propargyloxyphenyl | 2,6-difluoro-4-propargyloxyphenyl |
| methyl | methyl | —(NH)— | 2,6-difluoro-4-propargyloxyphenyl | 4-allyloxy-2,6-difluorophenyl |
| methyl | methyl | —(NH)— | 2,6-difluoro-4-propargyloxyphenyl | 2,4-difluoro-6-propargyloxyphenyl |
| methyl | methyl | —(NH)— | 2,6-difluoro-4-propargyloxyphenyl | 4-fluoro-2-propargyloxyphenyl |
| methyl | methyl | —(NH)— | 2,6-difluoro-4-propargyloxyphenyl | 2-fluoro-6-propargyloxyphenyl |
| methyl | methyl | —(NH)— | 2,6-difluoro-4-propargyloxyphenyl | 4-chloro-2-fluoro-6-propargyloxyphenyl |
| methyl | methyl | —(NH)— | 2,6-difluoro-4-propargyloxyphenyl | 2-chloro-4-fluoro-6-propargyloxyphenyl |
| methyl | methyl | —(NH)— | 2,6-difluoro-4-propargyloxyphenyl | 4-allyloxy-2-fluorophenyl |

-continued

| R¹ | R² | X | Q¹ | Q² |
|---|---|---|---|---|
| methyl | methyl | —(NH)— | 2,6-difluoro-4-propargyloxyphenyl | 2-fluoro-4-propargyloxyphenyl |
| methyl | methyl | —(NH)— | 2,6-difluoro-4-propargyloxyphenyl | 2-allyloxyphenyl |
| methyl | methyl | —(NH)— | 2,6-difluoro-4-propargyloxyphenyl | 2-propargyloxyphenyl |
| methyl | methyl | —(NH)— | 2,6-difluoro-4-propargyloxyphenyl | 2-allyloxy-5-fluorophenyl |
| methyl | methyl | —(NH)— | 2,6-difluoro-4-propargyloxyphenyl | 5-fluoro-2-propargyloxyphenyl |
| methyl | methyl | —(NH)— | 2,6-difluoro-4-propargyloxyphenyl | 2-allyloxy-4-methylphenyl |
| methyl | methyl | —(NH)— | 2,6-difluoro-4-propargyloxyphenyl | 4-methyl-2-propargyloxyphenyl |
| methyl | methyl | —(NH)— | 2,6-difluoro-4-propargyloxyphenyl | 2-allyloxy-5-cyanophenyl |
| methyl | methyl | —(NH)— | 2,6-difluoro-4-propargyloxyphenyl | 5-cyano-2-propargyloxyphenyl |
| methyl | methyl | —(NH)— | 2,6-difluoro-4-propargyloxyphenyl | 5-allyloxy-2-fluorophenyl |
| methyl | methyl | —(NH)— | 2,6-difluoro-4-propargyloxyphenyl | 2-fluoro-5-propargyloxyphenyl |
| methyl | methyl | —(NH)— | 2,6-difluoro-4-propargyloxyphenyl | 4-allyloxy-2-chlorophenyl |
| methyl | methyl | —(NH)— | 2,6-difluoro-4-propargyloxyphenyl | 2-chloro-4-propargyloxyphenyl |
| methyl | methyl | —(NH)— | 2,6-difluoro-4-propargyloxyphenyl | 4-allyloxy-3-fluorophenyl |
| methyl | methyl | —(NH)— | 2,6-difluoro-4-propargyloxyphenyl | 3-fluoro-4-propargyloxyphenyl |
| methyl | methyl | —(NH)— | 2,6-difluoro-4-propargyloxyphenyl | 4-allyloxyphenyl |
| methyl | methyl | —(NH)— | 2,6-difluoro-4-propargyloxyphenyl | 4-propargyloxyphenyl |
| methyl | methyl | —(NH)— | 2,6-difluoro-4-propargyloxyphenyl | 3-fluoro-5-propargyloxyphenyl |
| methyl | methyl | —(NH)— | 2,6-difluoro-4-propargyloxyphenyl | 3-fluoro-5-allyloxyphenyl |
| methyl | methyl | —(NH)— | 2,6-difluoro-4-propargyloxyphenyl | 2,5-difluoro-4-propargyloxyphenyl |
| methyl | methyl | —(NH)— | 2,6-difluoro-4-propargyloxyphenyl | 2,5-difluoro-4-allyloxyphenyl |
| methyl | methyl | —(NH)— | 2,6-difluoro-4-propargyloxyphenyl | 6-allyloxypyridin-3-yl |
| methyl | methyl | —(NH)— | 2,6-difluoro-4-propargyloxyphenyl | 6-propargyloxypyridin-3-yl |
| methyl | methyl | —(NH)— | 2,6-difluoro-4-propargyloxyphenyl | 2-propargyloxy-6-trifluorophenyl |
| methyl | methyl | —(NH)— | 2,6-difluoro-4-propargyloxyphenyl | 2-allyloxy-6-trifluormethylphenyl |
| methyl | methyl | —(NH)— | 2,6-difluoro-4-propargyloxyphenyl | 2-chloro-6-propargyloxyphenyl |
| methyl | methyl | —(NH)— | 2,6-difluoro-4-propargyloxyphenyl | 2-allyloxy-6-chlorophenyl |
| methyl | methyl | —(NH)— | 2,6-difluoro-4-propargyloxyphenyl | 2,4-dimethyl-6-propargyloxyphenyl |
| methyl | methyl | —(NH)— | 2,6-difluoro-4-propargyloxyphenyl | 2-allyloxy-4,6-dimethylphenyl |
| methyl | methyl | —(NH)— | 2-fluoro-5-(furan-2-yl)phenyl | 2,6-difluoro-4-propargyloxyphenyl |
| methyl | methyl | —(NH)— | 2-fluoro-5-(furan-2-yl)phenyl | 4-allyloxy-2,6-difluorophenyl |
| methyl | methyl | —(NH)— | 2-fluoro-5-(furan-2-yl)phenyl | 2,4-difluoro-6-propargyloxyphenyl |
| methyl | methyl | —(NH)— | 2-fluoro-5-(furan-2-yl)phenyl | 4-fluoro-2-propargyloxyphenyl |
| methyl | methyl | —(NH)— | 2-fluoro-5-(furan-2-yl)phenyl | 2-fluoro-6-propargyloxyphenyl |
| methyl | methyl | —(NH)— | 2-fluoro-5-(furan-2-yl)phenyl | 4-chloro-2-fluoro-6-propargyloxyphenyl |
| methyl | methyl | —(NH)— | 2-fluoro-5-(furan-2-yl)phenyl | 2-chloro-4-fluoro-6-propargyloxyphenyl |
| methyl | methyl | —(NH)— | 2-fluoro-5-(furan-2-yl)phenyl | 4-allyloxy-2-fluorophenyl |
| methyl | methyl | —(NH)— | 2-fluoro-5-(furan-2-yl)phenyl | 2-fluoro-4-propargyloxyphenyl |
| methyl | methyl | —(NH)— | 2-fluoro-5-(furan-2-yl)phenyl | 2-allyloxyphenyl |
| methyl | methyl | —(NH)— | 2-fluoro-5-(furan-2-yl)phenyl | 2-propargyloxyphenyl |
| methyl | methyl | —(NH)— | 2-fluoro-5-(furan-2-yl)phenyl | 2-allyloxy-5-fluorophenyl |
| methyl | methyl | —(NH)— | 2-fluoro-5-(furan-2-yl)phenyl | 5-fluoro-2-propargyloxyphenyl |
| methyl | methyl | —(NH)— | 2-fluoro-5-(furan-2-yl)phenyl | 2-allyloxy-4-methylphenyl |
| methyl | methyl | —(NH)— | 2-fluoro-5-(furan-2-yl)phenyl | 4-methyl-2-propargyloxyphenyl |
| methyl | methyl | —(NH)— | 2-fluoro-5-(furan-2-yl)phenyl | 2-allyloxy-5-cyanophenyl |
| methyl | methyl | —(NH)— | 2-fluoro-5-(furan-2-yl)phenyl | 5-cyano-2-propargyloxyphenyl |

-continued

| R¹ | R² | X | Q¹ | Q² |
|---|---|---|---|---|
| methyl | methyl | —(NH)— | 2-fluoro-5-(furan-2-yl)phenyl | 5-allyloxy-2-fluorophenyl |
| methyl | methyl | —(NH)— | 2-fluoro-5-(furan-2-yl)phenyl | 2-fluoro-5-propargyloxyphenyl |
| methyl | methyl | —(NH)— | 2-fluoro-5-(furan-2-yl)phenyl | 4-allyloxy-2-chlorophenyl |
| methyl | methyl | —(NH)— | 2-fluoro-5-(furan-2-yl)phenyl | 2-chloro-4-propargyloxyphenyl |
| methyl | methyl | —(NH)— | 2-fluoro-5-(furan-2-yl)phenyl | 4-allyloxy-3-fluorophenyl |
| methyl | methyl | —(NH)— | 2-fluoro-5-(furan-2-yl)phenyl | 3-fluoro-4-propargyloxyphenyl |
| methyl | methyl | —(NH)— | 2-fluoro-5-(furan-2-yl)phenyl | 4-allyloxyphenyl |
| methyl | methyl | —(NH)— | 2-fluoro-5-(furan-2-yl)phenyl | 4-propargyloxyphenyl |
| methyl | methyl | —(NH)— | 2-fluoro-5-(furan-2-yl)phenyl | 3-fluoro-5-propargyloxyphenyl |
| methyl | methyl | —(NH)— | 2-fluoro-5-(furan-2-yl)phenyl | 3-fluoro-5-allyloxyphenyl |
| methyl | methyl | —(NH)— | 2-fluoro-5-(furan-2-yl)phenyl | 2,5-difluoro-4-propargyloxyphenyl |
| methyl | methyl | —(NH)— | 2-fluoro-5-(furan-2-yl)phenyl | 2,5-difluoro-4-allyloxyphenyl |
| methyl | methyl | —(NH)— | 2-fluoro-5-(furan-2-yl)phenyl | 6-allyloxypyridin-3-yl |
| methyl | methyl | —(NH)— | 2-fluoro-5-(furan-2-yl)phenyl | 6-propargyloxypyridin-3-yl |
| methyl | methyl | —(NH)— | 2-fluoro-5-(furan-2-yl)phenyl | 2-propargyloxy-6-trifluorophenyl |
| methyl | methyl | —(NH)— | 2-fluoro-5-(furan-2-yl)phenyl | 2-allyloxy-6-trifluormethylphenyl |
| methyl | methyl | —(NH)— | 2-fluoro-5-(furan-2-yl)phenyl | 2-chloro-6-propargyloxyphenyl |
| methyl | methyl | —(NH)— | 2-fluoro-5-(furan-2-yl)phenyl | 2-allyloxy-6-chlorophenyl |
| methyl | methyl | —(NH)— | 2-fluoro-5-(furan-2-yl)phenyl | 2,4-dimethyl-6-propargyloxyphenyl |
| methyl | methyl | —(NH)— | 2-fluoro-5-(furan-2-yl)phenyl | 2-allyloxy-4,6-dimethylphenyl |
| methyl | methyl | —O— | 2-chloro-4-fluorophenyl | 2,6-difluoro-4-propargyloxyphenyl |
| methyl | methyl | —O— | 2-chloro-4-fluorophenyl | 4-allyloxy-2,6-difluorophenyl |
| methyl | methyl | —O— | 2-chloro-4-fluorophenyl | 2,4-difluoro-6-propargyloxyphenyl |
| methyl | methyl | —O— | 2-chloro-4-fluorophenyl | 4-fluoro-2-propargyloxyphenyl |
| methyl | methyl | —O— | 2-chloro-4-fluorophenyl | 2-fluoro-6-propargyloxyphenyl |
| methyl | methyl | —O— | 2-chloro-4-fluorophenyl | 4-chloro-2-fluoro-6-propargyloxyphenyl |
| methyl | methyl | —O— | 2-chloro-4-fluorophenyl | 2-chloro-4-fluoro-6-propargyloxyphenyl |
| methyl | methyl | —O— | 2-chloro-4-fluorophenyl | 4-allyloxy-2-fluorophenyl |
| methyl | methyl | —O— | 2-chloro-4-fluorophenyl | 2-fluoro-4-propargyloxyphenyl |
| methyl | methyl | —O— | 2-chloro-4-fluorophenyl | 2-allyloxyphenyl |
| methyl | methyl | —O— | 2-chloro-4-fluorophenyl | 2-propargyloxyphenyl |
| methyl | methyl | —O— | 2-chloro-4-fluorophenyl | 2-allyloxy-5-fluorophenyl |
| methyl | methyl | —O— | 2-chloro-4-fluorophenyl | 5-fluoro-2-propargyloxyphenyl |
| methyl | methyl | —O— | 2-chloro-4-fluorophenyl | 2-allyloxy-4-methylphenyl |
| methyl | methyl | —O— | 2-chloro-4-fluorophenyl | 4-methyl-2-propargyloxyphenyl |
| methyl | methyl | —O— | 2-chloro-4-fluorophenyl | 2-allyloxy-5-cyanophenyl |
| methyl | methyl | —O— | 2-chloro-4-fluorophenyl | 5-cyano-2-propargyloxyphenyl |
| methyl | methyl | —O— | 2-chloro-4-fluorophenyl | 5-allyloxy-2-fluorophenyl |
| methyl | methyl | —O— | 2-chloro-4-fluorophenyl | 2-fluoro-5-propargyloxyphenyl |
| methyl | methyl | —O— | 2-chloro-4-fluorophenyl | 4-allyloxy-2-chlorophenyl |
| methyl | methyl | —O— | 2-chloro-4-fluorophenyl | 2-chloro-4-propargyloxyphenyl |
| methyl | methyl | —O— | 2-chloro-4-fluorophenyl | 4-allyloxy-3-fluorophenyl |
| methyl | methyl | —O— | 2-chloro-4-fluorophenyl | 3-fluoro-4-propargyloxyphenyl |
| methyl | methyl | —O— | 2-chloro-4-fluorophenyl | 4-allyloxyphenyl |
| methyl | methyl | —O— | 2-chloro-4-fluorophenyl | 4-propargyloxyphenyl |
| methyl | methyl | —O— | 2-chloro-4-fluorophenyl | 3-fluoro-5-propargyloxyphenyl |
| methyl | methyl | —O— | 2-chloro-4-fluorophenyl | 3-fluoro-5-allyloxyphenyl |
| methyl | methyl | —O— | 2-chloro-4-fluorophenyl | 2,5-difluoro-4-propargyloxyphenyl |
| methyl | methyl | —O— | 2-chloro-4-fluorophenyl | 2,5-difluoro-4-allyloxyphenyl |
| methyl | methyl | —O— | 2-chloro-4-fluorophenyl | 6-allyloxypyridin-3-yl |
| methyl | methyl | —O— | 2-chloro-4-fluorophenyl | 6-propargyloxypyridin-3-yl |
| methyl | methyl | —O— | 2-chloro-4-fluorophenyl | 2-propargyloxy-6-trifluorophenyl |
| methyl | methyl | —O— | 2-chloro-4-fluorophenyl | 2-allyloxy-6-trifluormethylphenyl |
| methyl | methyl | —O— | 2-chloro-4-fluorophenyl | 2-chloro-6-propargyloxyphenyl |
| methyl | methyl | —O— | 2-chloro-4-fluorophenyl | 2-allyloxy-6-chlorophenyl |
| methyl | methyl | —O— | 2-chloro-4-fluorophenyl | 2,4-dimethyl-6-propargyloxyphenyl |
| methyl | methyl | —O— | 2-chloro-4-fluorophenyl | 2-allyloxy-4,6-dimethylphenyl |
| methyl | methyl | —O— | 2,4-dichlorophenyl | 2,6-difluoro-4-propargyloxyphenyl |
| methyl | methyl | —O— | 2,4-dichlorophenyl | 4-allyloxy-2,6-difluorophenyl |
| methyl | methyl | —O— | 2,4-dichlorophenyl | 2,4-difluoro-6-propargyloxyphenyl |
| methyl | methyl | —O— | 2,4-dichlorophenyl | 4-fluoro-2-propargyloxyphenyl |
| methyl | methyl | —O— | 2,4-dichlorophenyl | 2-fluoro-6-propargyloxyphenyl |
| methyl | methyl | —O— | 2,4-dichlorophenyl | 4-chloro-2-fluoro-6-propargyloxyphenyl |
| methyl | methyl | —O— | 2,4-dichlorophenyl | 2-chloro-4-fluoro-6-propargyloxyphenyl |
| methyl | methyl | —O— | 2,4-dichlorophenyl | 4-allyloxy-2-fluorophenyl |
| methyl | methyl | —O— | 2,4-dichlorophenyl | 2-fluoro-4-propargyloxyphenyl |
| methyl | methyl | —O— | 2,4-dichlorophenyl | 2-allyloxyphenyl |
| methyl | methyl | —O— | 2,4-dichlorophenyl | 2-propargyloxyphenyl |
| methyl | methyl | —O— | 2,4-dichlorophenyl | 2-allyloxy-5-fluorophenyl |
| methyl | methyl | —O— | 2,4-dichlorophenyl | 5-fluoro-2-propargyloxyphenyl |
| methyl | methyl | —O— | 2,4-dichlorophenyl | 2-allyloxy-4-methylphenyl |
| methyl | methyl | —O— | 2,4-dichlorophenyl | 4-methyl-2-propargyloxyphenyl |
| methyl | methyl | —O— | 2,4-dichlorophenyl | 2-allyloxy-5-cyanophenyl |

-continued

| R¹ | R² | X | Q¹ | Q² |
|---|---|---|---|---|
| methyl | methyl | —O— | 2,4-dichlorophenyl | 5-cyano-2-propargyloxyphenyl |
| methyl | methyl | —O— | 2,4-dichlorophenyl | 5-allyloxy-2-fluorophenyl |
| methyl | methyl | —O— | 2,4-dichlorophenyl | 2-fluoro-5-propargyloxyphenyl |
| methyl | methyl | —O— | 2,4-dichlorophenyl | 4-allyloxy-2-chlorophenyl |
| methyl | methyl | —O— | 2,4-dichlorophenyl | 2-chloro-4-propargyloxyphenyl |
| methyl | methyl | —O— | 2,4-dichlorophenyl | 4-allyloxy-3-fluorophenyl |
| methyl | methyl | —O— | 2,4-dichlorophenyl | 3-fluoro-4-propargyloxyphenyl |
| methyl | methyl | —O— | 2,4-dichlorophenyl | 4-allyloxyphenyl |
| methyl | methyl | —O— | 2,4-dichlorophenyl | 4-propargyloxyphenyl |
| methyl | methyl | —O— | 2,4-dichlorophenyl | 3-fluoro-5-propargyloxyphenyl |
| methyl | methyl | —O— | 2,4-dichlorophenyl | 3-fluoro-5-allyloxyphenyl |
| methyl | methyl | —O— | 2,4-dichlorophenyl | 2,5-difluoro-4-propargyloxyphenyl |
| methyl | methyl | —O— | 2,4-dichlorophenyl | 2,5-difluoro-4-allyloxyphenyl |
| methyl | methyl | —O— | 2,4-dichlorophenyl | 6-allyloxypyridin-3-yl |
| methyl | methyl | —O— | 2,4-dichlorophenyl | 6-propargyloxypyridin-3-yl |
| methyl | methyl | —O— | 2,4-dichlorophenyl | 2-propargyloxy-6-trifluorophenyl |
| methyl | methyl | —O— | 2,4-dichlorophenyl | 2-allyloxy-6-trifluormethylphenyl |
| methyl | methyl | —O— | 2,4-dichlorophenyl | 2-chloro-6-propargyloxyphenyl |
| methyl | methyl | —O— | 2,4-dichlorophenyl | 2-allyloxy-6-chlorophenyl |
| methyl | methyl | —O— | 2,4-dichlorophenyl | 2,4-dimethyl-6-propargyloxyphenyl |
| methyl | methyl | —O— | 2,4-dichlorophenyl | 2-allyloxy-4,6-dimethylphenyl |
| methyl | methyl | —O— | 2-fluorophenyl | 2,6-difluoro-4-propargyloxyphenyl |
| methyl | methyl | —O— | 2-fluorophenyl | 4-allyloxy-2,6-difluorophenyl |
| methyl | methyl | —O— | 2-fluorophenyl | 2,4-difluoro-6-propargyloxyphenyl |
| methyl | methyl | —O— | 2-fluorophenyl | 4-fluoro-2-propargyloxyphenyl |
| methyl | methyl | —O— | 2-fluorophenyl | 2-fluoro-6-propargyloxyphenyl |
| methyl | methyl | —O— | 2-fluorophenyl | 4-chloro-2-fluoro-6-propargyloxyphenyl |
| methyl | methyl | —O— | 2-fluorophenyl | 2-chloro-4-fluoro-6-propargyloxyphenyl |
| methyl | methyl | —O— | 2-fluorophenyl | 4-allyloxy-2-fluorophenyl |
| methyl | methyl | —O— | 2-fluorophenyl | 2-fluoro-4-propargyloxyphenyl |
| methyl | methyl | —O— | 2-fluorophenyl | 2-allyloxyphenyl |
| methyl | methyl | —O— | 2-fluorophenyl | 2-propargyloxyphenyl |
| methyl | methyl | —O— | 2-fluorophenyl | 2-allyloxy-5-fluorophenyl |
| methyl | methyl | —O— | 2-fluorophenyl | 5-fluoro-2-propargyloxyphenyl |
| methyl | methyl | —O— | 2-fluorophenyl | 2-allyloxy-4-methylphenyl |
| methyl | methyl | —O— | 2-fluorophenyl | 4-methyl-2-propargyloxyphenyl |
| methyl | methyl | —O— | 2-fluorophenyl | 2-allyloxy-5-cyanophenyl |
| methyl | methyl | —O— | 2-fluorophenyl | 5-cyano-2-propargyloxyphenyl |
| methyl | methyl | —O— | 2-fluorophenyl | 5-allyloxy-2-fluorophenyl |
| methyl | methyl | —O— | 2-fluorophenyl | 2-fluoro-5-propargyloxyphenyl |
| methyl | methyl | —O— | 2-fluorophenyl | 4-allyloxy-2-chlorophenyl |
| methyl | methyl | —O— | 2-fluorophenyl | 2-chloro-4-propargyloxyphenyl |
| methyl | methyl | —O— | 2-fluorophenyl | 4-allyloxy-3-fluorophenyl |
| methyl | methyl | —O— | 2-fluorophenyl | 3-fluoro-4-propargyloxyphenyl |
| methyl | methyl | —O— | 2-fluorophenyl | 4-allyloxyphenyl |
| methyl | methyl | —O— | 2-fluorophenyl | 4-propargyloxyphenyl |
| methyl | methyl | —O— | 2-fluorophenyl | 3-fluoro-5-propargyloxyphenyl |
| methyl | methyl | —O— | 2-fluorophenyl | 3-fluoro-5-allyloxyphenyl |
| methyl | methyl | —O— | 2-fluorophenyl | 2,5-difluoro-4-propargyloxyphenyl |
| methyl | methyl | —O— | 2-fluorophenyl | 2,5-difluoro-4-allyloxyphenyl |
| methyl | methyl | —O— | 2-fluorophenyl | 6-allyloxypyridin-3-yl |
| methyl | methyl | —O— | 2-fluorophenyl | 6-propargyloxypyridin-3-yl |
| methyl | methyl | —O— | 2-fluorophenyl | 2-propargyloxy-6-trifluorophenyl |
| methyl | methyl | —O— | 2-fluorophenyl | 2-allyloxy-6-trifluormethylphenyl |
| methyl | methyl | —O— | 2-fluorophenyl | 2-chloro-6-propargyloxyphenyl |
| methyl | methyl | —O— | 2-fluorophenyl | 2-allyloxy-6-chlorophenyl |
| methyl | methyl | —O— | 2-fluorophenyl | 2,4-dimethyl-6-propargyloxyphenyl |
| methyl | methyl | —O— | 2-fluorophenyl | 2-allyloxy-4,6-dimethylphenyl |
| methyl | methyl | —O— | 3,5-dimethoxyphenyl | 2,6-difluoro-4-propargyloxyphenyl |
| methyl | methyl | —O— | 3,5-dimethoxyphenyl | 4-allyloxy-2,6-difluorophenyl |
| methyl | methyl | —O— | 3,5-dimethoxyphenyl | 2,4-difluoro-6-propargyloxyphenyl |
| methyl | methyl | —O— | 3,5-dimethoxyphenyl | 4-fluoro-2-propargyloxyphenyl |
| methyl | methyl | —O— | 3,5-dimethoxyphenyl | 2-fluoro-6-propargyloxyphenyl |
| methyl | methyl | —O— | 3,5-dimethoxyphenyl | 4-chloro-2-fluoro-6-propargyloxyphenyl |
| methyl | methyl | —O— | 3,5-dimethoxyphenyl | 2-chloro-4-fluoro-6-propargyloxyphenyl |
| methyl | methyl | —O— | 3,5-dimethoxyphenyl | 4-allyloxy-2-fluorophenyl |
| methyl | methyl | —O— | 3,5-dimethoxyphenyl | 2-fluoro-4-propargyloxyphenyl |
| methyl | methyl | —O— | 3,5-dimethoxyphenyl | 2-allyloxyphenyl |
| methyl | methyl | —O— | 3,5-dimethoxyphenyl | 2-propargyloxyphenyl |
| methyl | methyl | —O— | 3,5-dimethoxyphenyl | 2-allyloxy-5-fluorophenyl |
| methyl | methyl | —O— | 3,5-dimethoxyphenyl | 5-fluoro-2-propargyloxyphenyl |
| methyl | methyl | —O— | 3,5-dimethoxyphenyl | 2-allyloxy-4-methylphenyl |
| methyl | methyl | —O— | 3,5-dimethoxyphenyl | 4-methyl-2-propargyloxyphenyl |

-continued

| R¹ | R² | X | Q¹ | Q² |
|---|---|---|---|---|
| methyl | methyl | —O— | 3,5-dimethoxyphenyl | 2-allyloxy-5-cyanophenyl |
| methyl | methyl | —O— | 3,5-dimethoxyphenyl | 5-cyano-2-propargyloxyphenyl |
| methyl | methyl | —O— | 3,5-dimethoxyphenyl | 5-allyloxy-2-fluorophenyl |
| methyl | methyl | —O— | 3,5-dimethoxyphenyl | 2-fluoro-5-propargyloxyphenyl |
| methyl | methyl | —O— | 3,5-dimethoxyphenyl | 4-allyloxy-2-chlorophenyl |
| methyl | methyl | —O— | 3,5-dimethoxyphenyl | 2-chloro-4-propargyloxyphenyl |
| methyl | methyl | —O— | 3,5-dimethoxyphenyl | 4-allyloxy-3-fluorophenyl |
| methyl | methyl | —O— | 3,5-dimethoxyphenyl | 3-fluoro-4-propargyloxyphenyl |
| methyl | methyl | —O— | 3,5-dimethoxyphenyl | 4-allyloxyphenyl |
| methyl | methyl | —O— | 3,5-dimethoxyphenyl | 4-propargyloxyphenyl |
| methyl | methyl | —O— | 3,5-dimethoxyphenyl | 3-fluoro-5-propargyloxyphenyl |
| methyl | methyl | —O— | 3,5-dimethoxyphenyl | 3-fluoro-5-allyloxyphenyl |
| methyl | methyl | —O— | 3,5-dimethoxyphenyl | 2,5-difluoro-4-propargyloxyphenyl |
| methyl | methyl | —O— | 3,5-dimethoxyphenyl | 2,5-difluoro-4-allyloxyphenyl |
| methyl | methyl | —O— | 3,5-dimethoxyphenyl | 6-allyloxypyridin-3-yl |
| methyl | methyl | —O— | 3,5-dimethoxyphenyl | 6-propargyloxypyridin-3-yl |
| methyl | methyl | —O— | 3,5-dimethoxyphenyl | 2-propargyloxy-6-trifluorophenyl |
| methyl | methyl | —O— | 3,5-dimethoxyphenyl | 2-allyloxy-6-trifluormethylphenyl |
| methyl | methyl | —O— | 3,5-dimethoxyphenyl | 2-chloro-6-propargyloxyphenyl |
| methyl | methyl | —O— | 3,5-dimethoxyphenyl | 2-allyloxy-6-chlorophenyl |
| methyl | methyl | —O— | 3,5-dimethoxyphenyl | 2,4-dimethyl-6-propargyloxyphenyl |
| methyl | methyl | —O— | 3,5-dimethoxyphenyl | 2-allyloxy-4,6-dimethylphenyl |
| methyl | methyl | —O— | 2,4-difluorphenyl | 2,6-difluoro-4-propargyloxyphenyl |
| methyl | methyl | —O— | 2,4-difluorphenyl | 4-allyloxy-2,6-difluorophenyl |
| methyl | methyl | —O— | 2,4-difluorphenyl | 2,4-difluoro-6-propargyloxyphenyl |
| methyl | methyl | —O— | 2,4-difluorphenyl | 4-fluoro-2-propargyloxyphenyl |
| methyl | methyl | —O— | 2,4-difluorphenyl | 2-fluoro-6-propargyloxyphenyl |
| methyl | methyl | —O— | 2,4-difluorphenyl | 4-chloro-2-fluoro-6-propargyloxyphenyl |
| methyl | methyl | —O— | 2,4-difluorphenyl | 2-chloro-4-fluoro-6-propargyloxyphenyl |
| methyl | methyl | —O— | 2,4-difluorphenyl | 4-allyloxy-2-fluorophenyl |
| methyl | methyl | —O— | 2,4-difluorphenyl | 2-fluoro-4-propargyloxyphenyl |
| methyl | methyl | —O— | 2,4-difluorphenyl | 2-allyloxyphenyl |
| methyl | methyl | —O— | 2,4-difluorphenyl | 2-propargyloxyphenyl |
| methyl | methyl | —O— | 2,4-difluorphenyl | 2-allyloxy-5-fluorophenyl |
| methyl | methyl | —O— | 2,4-difluorphenyl | 5-fluoro-2-propargyloxyphenyl |
| methyl | methyl | —O— | 2,4-difluorphenyl | 2-allyloxy-4-methylphenyl |
| methyl | methyl | —O— | 2,4-difluorphenyl | 4-methyl-2-propargyloxyphenyl |
| methyl | methyl | —O— | 2,4-difluorphenyl | 2-allyloxy-5-cyanophenyl |
| methyl | methyl | —O— | 2,4-difluorphenyl | 5-cyano-2-propargyloxyphenyl |
| methyl | methyl | —O— | 2,4-difluorphenyl | 5-allyloxy-2-fluorophenyl |
| methyl | methyl | —O— | 2,4-difluorphenyl | 2-fluoro-5-propargyloxyphenyl |
| methyl | methyl | —O— | 2,4-difluorphenyl | 4-allyloxy-2-chlorophenyl |
| methyl | methyl | —O— | 2,4-difluorphenyl | 2-chloro-4-propargyloxyphenyl |
| methyl | methyl | —O— | 2,4-difluorphenyl | 4-allyloxy-3-fluorophenyl |
| methyl | methyl | —O— | 2,4-difluorphenyl | 3-fluoro-4-propargyloxyphenyl |
| methyl | methyl | —O— | 2,4-difluorphenyl | 4-allyloxyphenyl |
| methyl | methyl | —O— | 2,4-difluorphenyl | 4-propargyloxyphenyl |
| methyl | methyl | —O— | 2,4-difluorphenyl | 3-fluoro-5-propargyloxyphenyl |
| methyl | methyl | —O— | 2,4-difluorphenyl | 3-fluoro-5-allyloxyphenyl |
| methyl | methyl | —O— | 2,4-difluorphenyl | 2,5-difluoro-4-propargyloxyphenyl |
| methyl | methyl | —O— | 2,4-difluorphenyl | 2,5-difluoro-4-allyloxyphenyl |
| methyl | methyl | —O— | 2,4-difluorphenyl | 6-allyloxypyridin-3-yl |
| methyl | methyl | —O— | 2,4-difluorphenyl | 6-propargyloxypyridin-3-yl |
| methyl | methyl | —O— | 2,4-difluorphenyl | 2-propargyloxy-6-trifluorophenyl |
| methyl | methyl | —O— | 2,4-difluorphenyl | 2-allyloxy-6-trifluormethylphenyl |
| methyl | methyl | —O— | 2,4-difluorphenyl | 2-chloro-6-propargyloxyphenyl |
| methyl | methyl | —O— | 2,4-difluorphenyl | 2-allyloxy-6-chlorophenyl |
| methyl | methyl | —O— | 2,4-difluorphenyl | 2,4-dimethyl-6-propargyloxyphenyl |
| methyl | methyl | —O— | 2,4-difluorphenyl | 2-allyloxy-4,6-dimethylphenyl |
| methyl | methyl | —O— | 2-fluoro-4-methoxyphenyl | 2,6-difluoro-4-propargyloxyphenyl |
| methyl | methyl | —O— | 2-fluoro-4-methoxyphenyl | 4-allyloxy-2,6-difluorophenyl |
| methyl | methyl | —O— | 2-fluoro-4-methoxyphenyl | 2,4-difluoro-6-propargyloxyphenyl |
| methyl | methyl | —O— | 2-fluoro-4-methoxyphenyl | 4-fluoro-2-propargyloxyphenyl |
| methyl | methyl | —O— | 2-fluoro-4-methoxyphenyl | 2-fluoro-6-propargyloxyphenyl |
| methyl | methyl | —O— | 2-fluoro-4-methoxyphenyl | 4-chloro-2-fluoro-6-propargyloxyphenyl |
| methyl | methyl | —O— | 2-fluoro-4-methoxyphenyl | 2-chloro-4-fluoro-6-propargyloxyphenyl |
| methyl | methyl | —O— | 2-fluoro-4-methoxyphenyl | 4-allyloxy-2-fluorophenyl |
| methyl | methyl | —O— | 2-fluoro-4-methoxyphenyl | 2-fluoro-4-propargyloxyphenyl |
| methyl | methyl | —O— | 2-fluoro-4-methoxyphenyl | 2-allyloxyphenyl |
| methyl | methyl | —O— | 2-fluoro-4-methoxyphenyl | 2-propargyloxyphenyl |
| methyl | methyl | —O— | 2-fluoro-4-methoxyphenyl | 2-allyloxy-5-fluorophenyl |
| methyl | methyl | —O— | 2-fluoro-4-methoxyphenyl | 5-fluoro-2-propargyloxyphenyl |
| methyl | methyl | —O— | 2-fluoro-4-methoxyphenyl | 2-allyloxy-4-methylphenyl |

-continued

| R¹ | R² | X | Q¹ | Q² |
|---|---|---|---|---|
| methyl | methyl | —O— | 2-fluoro-4-methoxyphenyl | 4-methyl-2-propargyloxyphenyl |
| methyl | methyl | —O— | 2-fluoro-4-methoxyphenyl | 2-allyloxy-5-cyanophenyl |
| methyl | methyl | —O— | 2-fluoro-4-methoxyphenyl | 5-cyano-2-propargyloxyphenyl |
| methyl | methyl | —O— | 2-fluoro-4-methoxyphenyl | 5-allyloxy-2-fluorophenyl |
| methyl | methyl | —O— | 2-fluoro-4-methoxyphenyl | 2-fluoro-5-propargyloxyphenyl |
| methyl | methyl | —O— | 2-fluoro-4-methoxyphenyl | 4-allyloxy-2-chlorophenyl |
| methyl | methyl | —O— | 2-fluoro-4-methoxyphenyl | 2-chloro-4-propargyloxyphenyl |
| methyl | methyl | —O— | 2-fluoro-4-methoxyphenyl | 4-allyloxy-3-fluorophenyl |
| methyl | methyl | —O— | 2-fluoro-4-methoxyphenyl | 3-fluoro-4-propargyloxyphenyl |
| methyl | methyl | —O— | 2-fluoro-4-methoxyphenyl | 4-allyloxyphenyl |
| methyl | methyl | —O— | 2-fluoro-4-methoxyphenyl | 4-propargyloxyphenyl |
| methyl | methyl | —O— | 2-fluoro-4-methoxyphenyl | 3-fluoro-5-propargyloxyphenyl |
| methyl | methyl | —O— | 2-fluoro-4-methoxyphenyl | 3-fluoro-5-allyloxyphenyl |
| methyl | methyl | —O— | 2-fluoro-4-methoxyphenyl | 2,5-difluoro-4-propargyloxyphenyl |
| methyl | methyl | —O— | 2-fluoro-4-methoxyphenyl | 2,5-difluoro-4-allyloxyphenyl |
| methyl | methyl | —O— | 2-fluoro-4-methoxyphenyl | 6-allyloxypyridin-3-yl |
| methyl | methyl | —O— | 2-fluoro-4-methoxyphenyl | 6-propargyloxypyridin-3-yl |
| methyl | methyl | —O— | 2-fluoro-4-methoxyphenyl | 2-propargyloxy-6-trifluorphenyl |
| methyl | methyl | —O— | 2-fluoro-4-methoxyphenyl | 2-allyloxy-6-trifluormethylphenyl |
| methyl | methyl | —O— | 2-fluoro-4-methoxyphenyl | 2-chloro-6-propargyloxyphenyl |
| methyl | methyl | —O— | 2-fluoro-4-methoxyphenyl | 2-allyloxy-6-chlorophenyl |
| methyl | methyl | —O— | 2-fluoro-4-methoxyphenyl | 2,4-dimethyl-6-propargyloxyphenyl |
| methyl | methyl | —O— | 2-fluoro-4-methoxyphenyl | 2-allyloxy-4,6-dimethylphenyl |
| methyl | methyl | —O— | (2-chloropyridin)-5-yl | 2,6-difluoro-4-propargyloxyphenyl |
| methyl | methyl | —O— | (2-chloropyridin)-5-yl | 4-allyloxy-2,6-difluorophenyl |
| methyl | methyl | —O— | (2-chloropyridin)-5-yl | 2,4-difluoro-6-propargyloxyphenyl |
| methyl | methyl | —O— | (2-chloropyridin)-5-yl | 4-fluoro-2-propargyloxyphenyl |
| methyl | methyl | —O— | (2-chloropyridin)-5-yl | 2-fluoro-6-propargyloxyphenyl |
| methyl | methyl | —O— | (2-chloropyridin)-5-yl | 4-chloro-2-fluoro-6-propargyloxyphenyl |
| methyl | methyl | —O— | (2-chloropyridin)-5-yl | 2-chloro-4-fluoro-6-propargyloxyphenyl |
| methyl | methyl | —O— | (2-chloropyridin)-5-yl | 4-allyloxy-2-fluorophenyl |
| methyl | methyl | —O— | (2-chloropyridin)-5-yl | 2-fluoro-4-propargyloxyphenyl |
| methyl | methyl | —O— | (2-chloropyridin)-5-yl | 2-allyloxyphenyl |
| methyl | methyl | —O— | (2-chloropyridin)-5-yl | 2-propargyloxyphenyl |
| methyl | methyl | —O— | (2-chloropyridin)-5-yl | 2-allyloxy-5-fluorophenyl |
| methyl | methyl | —O— | (2-chloropyridin)-5-yl | 5-fluoro-2-propargyloxyphenyl |
| methyl | methyl | —O— | (2-chloropyridin)-5-yl | 2-allyloxy-4-methylphenyl |
| methyl | methyl | —O— | (2-chloropyridin)-5-yl | 4-methyl-2-propargyloxyphenyl |
| methyl | methyl | —O— | (2-chloropyridin)-5-yl | 2-allyloxy-5-cyanophenyl |
| methyl | methyl | —O— | (2-chloropyridin)-5-yl | 5-cyano-2-propargyloxyphenyl |
| methyl | methyl | —O— | (2-chloropyridin)-5-yl | 5-allyloxy-2-fluorophenyl |
| methyl | methyl | —O— | (2-chloropyridin)-5-yl | 2-fluoro-5-propargyloxyphenyl |
| methyl | methyl | —O— | (2-chloropyridin)-5-yl | 4-allyloxy-2-chlorophenyl |
| methyl | methyl | —O— | (2-chloropyridin)-5-yl | 2-chloro-4-propargyloxyphenyl |
| methyl | methyl | —O— | (2-chloropyridin)-5-yl | 4-allyloxy-3-fluorophenyl |
| methyl | methyl | —O— | (2-chloropyridin)-5-yl | 3-fluoro-4-propargyloxyphenyl |
| methyl | methyl | —O— | (2-chloropyridin)-5-yl | 4-allyloxyphenyl |
| methyl | methyl | —O— | (2-chloropyridin)-5-yl | 4-propargyloxyphenyl |
| methyl | methyl | —O— | (2-chloropyridin)-5-yl | 3-fluoro-5-propargyloxyphenyl |
| methyl | methyl | —O— | (2-chloropyridin)-5-yl | 3-fluoro-5-allyloxyphenyl |
| methyl | methyl | —O— | (2-chloropyridin)-5-yl | 2,5-difluoro-4-propargyloxyphenyl |
| methyl | methyl | —O— | (2-chloropyridin)-5-yl | 2,5-difluoro-4-allyloxyphenyl |
| methyl | methyl | —O— | (2-chloropyridin)-5-yl | 6-allyloxypyridin-3-yl |
| methyl | methyl | —O— | (2-chloropyridin)-5-yl | 6-propargyloxypyridin-3-yl |
| methyl | methyl | —O— | (2-chloropyridin)-5-yl | 2-propargyloxy-6-trifluorophenyl |
| methyl | methyl | —O— | (2-chloropyridin)-5-yl | 2-allyloxy-6-trifluormethylphenyl |
| methyl | methyl | —O— | (2-chloropyridin)-5-yl | 2-chloro-6-propargyloxyphenyl |
| methyl | methyl | —O— | (2-chloropyridin)-5-yl | 2-allyloxy-6-chlorophenyl |
| methyl | methyl | —O— | (2-chloropyridin)-5-yl | 2,4-dimethyl-6-propargyloxyphenyl |
| methyl | methyl | —O— | (2-chloropyridin)-5-yl | 2-allyloxy-4,6-dimethylphenyl |
| methyl | methyl | —O— | 4-allyloxy-2-fluorophenyl | 2,6-difluoro-4-propargyloxyphenyl |
| methyl | methyl | —O— | 4-allyloxy-2-fluorophenyl | 4-allyloxy-2,6-difluorophenyl |
| methyl | methyl | —O— | 4-allyloxy-2-fluorophenyl | 2,4-difluoro-6-propargyloxyphenyl |
| methyl | methyl | —O— | 4-allyloxy-2-fluorophenyl | 4-fluoro-2-propargyloxyphenyl |
| methyl | methyl | —O— | 4-allyloxy-2-fluorophenyl | 2-fluoro-6-propargyloxyphenyl |
| methyl | methyl | —O— | 4-allyloxy-2-fluorophenyl | 4-chloro-2-fluoro-6-propargyloxyphenyl |
| methyl | methyl | —O— | 4-allyloxy-2-fluorophenyl | 2-chloro-4-fluoro-6-propargyloxyphenyl |
| methyl | methyl | —O— | 4-allyloxy-2-fluorophenyl | 4-allyloxy-2-fluorophenyl |
| methyl | methyl | —O— | 4-allyloxy-2-fluorophenyl | 2-fluoro-4-propargyloxyphenyl |
| methyl | methyl | —O— | 4-allyloxy-2-fluorophenyl | 2-allyloxyphenyl |
| methyl | methyl | —O— | 4-allyloxy-2-fluorophenyl | 2-propargyloxyphenyl |
| methyl | methyl | —O— | 4-allyloxy-2-fluorophenyl | 2-allyloxy-5-fluorophenyl |
| methyl | methyl | —O— | 4-allyloxy-2-fluorophenyl | 5-fluoro-2-propargyloxyphenyl |

-continued

| R¹ | R² | X | Q¹ | Q² |
|---|---|---|---|---|
| methyl | methyl | —O— | 4-allyloxy-2-fluorophenyl | 2-allyloxy-4-methylphenyl |
| methyl | methyl | —O— | 4-allyloxy-2-fluorophenyl | 4-methyl-2-propargyloxyphenyl |
| methyl | methyl | —O— | 4-allyloxy-2-fluorophenyl | 2-allyloxy-5-cyanophenyl |
| methyl | methyl | —O— | 4-allyloxy-2-fluorophenyl | 5-cyano-2-propargyloxyphenyl |
| methyl | methyl | —O— | 4-allyloxy-2-fluorophenyl | 5-allyloxy-2-fluorophenyl |
| methyl | methyl | —O— | 4-allyloxy-2-fluorophenyl | 2-fluoro-5-propargyloxyphenyl |
| methyl | methyl | —O— | 4-allyloxy-2-fluorophenyl | 4-allyloxy-2-chlorophenyl |
| methyl | methyl | —O— | 4-allyloxy-2-fluorophenyl | 2-chloro-4-propargyloxyphenyl |
| methyl | methyl | —O— | 4-allyloxy-2-fluorophenyl | 4-allyloxy-3-fluorophenyl |
| methyl | methyl | —O— | 4-allyloxy-2-fluorophenyl | 3-fluoro-4-propargyloxyphenyl |
| methyl | methyl | —O— | 4-allyloxy-2-fluorophenyl | 4-allyloxyphenyl |
| methyl | methyl | —O— | 4-allyloxy-2-fluorophenyl | 4-propargyloxyphenyl |
| methyl | methyl | —O— | 4-allyloxy-2-fluorophenyl | 3-fluoro-5-propargyloxyphenyl |
| methyl | methyl | —O— | 4-allyloxy-2-fluorophenyl | 3-fluoro-5-allyloxyphenyl |
| methyl | methyl | —O— | 4-allyloxy-2-fluorophenyl | 2,5-difluoro-4-propargyloxyphenyl |
| methyl | methyl | —O— | 4-allyloxy-2-fluorophenyl | 2,5-difluoro-4-allyloxyphenyl |
| methyl | methyl | —O— | 4-allyloxy-2-fluorophenyl | 6-allyloxypyridin-3-yl |
| methyl | methyl | —O— | 4-allyloxy-2-fluorophenyl | 6-propargyloxypyridin-3-yl |
| methyl | methyl | —O— | 4-allyloxy-2-fluorophenyl | 2-propargyloxy-6-trifluorophenyl |
| methyl | methyl | —O— | 4-allyloxy-2-fluorophenyl | 2-allyloxy-6-trifluormethylphenyl |
| methyl | methyl | —O— | 4-allyloxy-2-fluorophenyl | 2-chloro-6-propargyloxyphenyl |
| methyl | methyl | —O— | 4-allyloxy-2-fluorophenyl | 2-allyloxy-6-chlorophenyl |
| methyl | methyl | —O— | 4-allyloxy-2-fluorophenyl | 2,4-dimethyl-6-propargyloxyphenyl |
| methyl | methyl | —O— | 4-allyloxy-2-fluorophenyl | 2-allyloxy-4,6-dimethylphenyl |
| methyl | methyl | —O— | 2-propargyloxyphenyl | 2,6-difluoro-4-propargyloxyphenyl |
| methyl | methyl | —O— | 2-propargyloxyphenyl | 4-allyloxy-2,6-difluorophenyl |
| methyl | methyl | —O— | 2-propargyloxyphenyl | 2,4-difluoro-6-propargyloxyphenyl |
| methyl | methyl | —O— | 2-propargyloxyphenyl | 4-fluoro-2-propargyloxyphenyl |
| methyl | methyl | —O— | 2-propargyloxyphenyl | 2-fluoro-6-propargyloxyphenyl |
| methyl | methyl | —O— | 2-propargyloxyphenyl | 4-chloro-2-fluoro-6-propargyloxyphenyl |
| methyl | methyl | —O— | 2-propargyloxyphenyl | 2-chloro-4-fluoro-6-propargyloxyphenyl |
| methyl | methyl | —O— | 2-propargyloxyphenyl | 4-allyloxy-2-fluorophenyl |
| methyl | methyl | —O— | 2-propargyloxyphenyl | 2-fluoro-4-propargyloxyphenyl |
| methyl | methyl | —O— | 2-propargyloxyphenyl | 2-allyloxyphenyl |
| methyl | methyl | —O— | 2-propargyloxyphenyl | 2-propargyloxyphenyl |
| methyl | methyl | —O— | 2-propargyloxyphenyl | 2-allyloxy-5-fluorophenyl |
| methyl | methyl | —O— | 2-propargyloxyphenyl | 5-fluoro-2-propargyloxyphenyl |
| methyl | methyl | —O— | 2-propargyloxyphenyl | 2-allyloxy-4-methylphenyl |
| methyl | methyl | —O— | 2-propargyloxyphenyl | 4-methyl-2-propargyloxyphenyl |
| methyl | methyl | —O— | 2-propargyloxyphenyl | 2-allyloxy-5-cyanophenyl |
| methyl | methyl | —O— | 2-propargyloxyphenyl | 5-cyano-2-propargyloxyphenyl |
| methyl | methyl | —O— | 2-propargyloxyphenyl | 5-allyloxy-2-fluorophenyl |
| methyl | methyl | —O— | 2-propargyloxyphenyl | 2-fluoro-5-propargyloxyphenyl |
| methyl | methyl | —O— | 2-propargyloxyphenyl | 4-allyloxy-2-chlorophenyl |
| methyl | methyl | —O— | 2-propargyloxyphenyl | 2-chloro-4-propargyloxyphenyl |
| methyl | methyl | —O— | 2-propargyloxyphenyl | 4-allyloxy-3-fluorophenyl |
| methyl | methyl | —O— | 2-propargyloxyphenyl | 3-fluoro-4-propargyloxyphenyl |
| methyl | methyl | —O— | 2-propargyloxyphenyl | 4-allyloxyphenyl |
| methyl | methyl | —O— | 2-propargyloxyphenyl | 4-propargyloxyphenyl |
| methyl | methyl | —O— | 2-propargyloxyphenyl | 3-fluoro-5-propargyloxyphenyl |
| methyl | methyl | —O— | 2-propargyloxyphenyl | 3-fluoro-5-allyloxyphenyl |
| methyl | methyl | —O— | 2-propargyloxyphenyl | 2,5-difluoro-4-propargyloxyphenyl |
| methyl | methyl | —O— | 2-propargyloxyphenyl | 2,5-difluoro-4-allyloxyphenyl |
| methyl | methyl | —O— | 2-propargyloxyphenyl | 6-allyloxypyridin-3-yl |
| methyl | methyl | —O— | 2-propargyloxyphenyl | 6-propargyloxypyridin-3-yl |
| methyl | methyl | —O— | 2-propargyloxyphenyl | 2-propargyloxy-6-trifluorophenyl |
| methyl | methyl | —O— | 2-propargyloxyphenyl | 2-allyloxy-6-trifluormethylphenyl |
| methyl | methyl | —O— | 2-propargyloxyphenyl | 2-chloro-6-propargyloxyphenyl |
| methyl | methyl | —O— | 2-propargyloxyphenyl | 2-allyloxy-6-chlorophenyl |
| methyl | methyl | —O— | 2-propargyloxyphenyl | 2,4-dimethyl-6-propargyloxyphenyl |
| methyl | methyl | —O— | 2-propargyloxyphenyl | 2-allyloxy-4,6-dimethylphenyl |
| methyl | methyl | —O— | 2,6-difluoro-4-methoxyphenyl | 2,6-difluoro-4-propargyloxyphenyl |
| methyl | methyl | —O— | 2,6-difluoro-4-methoxyphenyl | 4-allyloxy-2,6-difluorophenyl |
| methyl | methyl | —O— | 2,6-difluoro-4-methoxyphenyl | 2,4-difluoro-6-propargyloxyphenyl |
| methyl | methyl | —O— | 2,6-difluoro-4-methoxyphenyl | 4-fluoro-2-propargyloxyphenyl |
| methyl | methyl | —O— | 2,6-difluoro-4-methoxyphenyl | 2-fluoro-6-propargyloxyphenyl |
| methyl | methyl | —O— | 2,6-difluoro-4-methoxyphenyl | 4-chloro-2-fluoro-6-propargyloxyphenyl |
| methyl | methyl | —O— | 2,6-difluoro-4-methoxyphenyl | 2-chloro-4-fluoro-6-propargyloxyphenyl |
| methyl | methyl | —O— | 2,6-difluoro-4-methoxyphenyl | 4-allyloxy-2-fluorophenyl |
| methyl | methyl | —O— | 2,6-difluoro-4-methoxyphenyl | 2-fluoro-4-propargyloxyphenyl |
| methyl | methyl | —O— | 2,6-difluoro-4-methoxyphenyl | 2-allyloxyphenyl |
| methyl | methyl | —O— | 2,6-difluoro-4-methoxyphenyl | 2-propargyloxyphenyl |
| methyl | methyl | —O— | 2,6-difluoro-4-methoxyphenyl | 2-allyloxy-5-fluorophenyl |

-continued

| R¹ | R² | X | Q¹ | Q² |
|---|---|---|---|---|
| methyl | methyl | —O— | 2,6-difluoro-4-methoxyphenyl | 5-fluoro-2-propargyloxyphenyl |
| methyl | methyl | —O— | 2,6-difluoro-4-methoxyphenyl | 2-allyloxy-4-methylphenyl |
| methyl | methyl | —O— | 2,6-difluoro-4-methoxyphenyl | 4-methyl-2-propargyloxyphenyl |
| methyl | methyl | —O— | 2,6-difluoro-4-methoxyphenyl | 2-allyloxy-5-cyanophenyl |
| methyl | methyl | —O— | 2,6-difluoro-4-methoxyphenyl | 5-cyano-2-propargyloxyphenyl |
| methyl | methyl | —O— | 2,6-difluoro-4-methoxyphenyl | 5-allyloxy-2-fluorophenyl |
| methyl | methyl | —O— | 2,6-difluoro-4-methoxyphenyl | 2-fluoro-5-propargyloxyphenyl |
| methyl | methyl | —O— | 2,6-difluoro-4-methoxyphenyl | 4-allyloxy-2-chlorophenyl |
| methyl | methyl | —O— | 2,6-difluoro-4-methoxyphenyl | 2-chloro-4-propargyloxyphenyl |
| methyl | methyl | —O— | 2,6-difluoro-4-methoxyphenyl | 4-allyloxy-3-fluorophenyl |
| methyl | methyl | —O— | 2,6-difluoro-4-methoxyphenyl | 3-fluoro-4-propargyloxyphenyl |
| methyl | methyl | —O— | 2,6-difluoro-4-methoxyphenyl | 4-allyloxyphenyl |
| methyl | methyl | —O— | 2,6-difluoro-4-methoxyphenyl | 4-propargyloxyphenyl |
| methyl | methyl | —O— | 2,6-difluoro-4-methoxyphenyl | 3-fluoro-5-propargyloxyphenyl |
| methyl | methyl | —O— | 2,6-difluoro-4-methoxyphenyl | 3-fluoro-5-allyloxyphenyl |
| methyl | methyl | —O— | 2,6-difluoro-4-methoxyphenyl | 2,5-difluoro-4-propargyloxyphenyl |
| methyl | methyl | —O— | 2,6-difluoro-4-methoxyphenyl | 2,5-difluoro-4-allyloxyphenyl |
| methyl | methyl | —O— | 2,6-difluoro-4-methoxyphenyl | 6-allyloxypyridin-3-yl |
| methyl | methyl | —O— | 2,6-difluoro-4-methoxyphenyl | 6-propargyloxypyridin-3-yl |
| methyl | methyl | —O— | 2,6-difluoro-4-methoxyphenyl | 2-propargyloxy-6-trifluorophenyl |
| methyl | methyl | —O— | 2,6-difluoro-4-methoxyphenyl | 2-allyloxy-6-trifluormethylphenyl |
| methyl | methyl | —O— | 2,6-difluoro-4-methoxyphenyl | 2-chloro-6-propargyloxyphenyl |
| methyl | methyl | —O— | 2,6-difluoro-4-methoxyphenyl | 2-allyloxy-6-chlorophenyl |
| methyl | methyl | —O— | 2,6-difluoro-4-methoxyphenyl | 2,4-dimethyl-6-propargyloxyphenyl |
| methyl | methyl | —O— | 2,6-difluoro-4-methoxyphenyl | 2-allyloxy-4,6-dimethylphenyl |
| methyl | methyl | —O— | 2-fluoro-4-propargyloxyphenyl | 2,6-difluoro-4-propargyloxyphenyl |
| methyl | methyl | —O— | 2-fluoro-4-propargyloxyphenyl | 4-allyloxy-2,6-difluorophenyl |
| methyl | methyl | —O— | 2-fluoro-4-propargyloxyphenyl | 2,4-difluoro-6-propargyloxyphenyl |
| methyl | methyl | —O— | 2-fluoro-4-propargyloxyphenyl | 4-fluoro-2-propargyloxyphenyl |
| methyl | methyl | —O— | 2-fluoro-4-propargyloxyphenyl | 2-fluoro-6-propargyloxyphenyl |
| methyl | methyl | —O— | 2-fluoro-4-propargyloxyphenyl | 4-chloro-2-fluoro-6-propargyloxyphenyl |
| methyl | methyl | —O— | 2-fluoro-4-propargyloxyphenyl | 2-chloro-4-fluoro-6-propargyloxyphenyl |
| methyl | methyl | —O— | 2-fluoro-4-propargyloxyphenyl | 4-allyloxy-2-fluorophenyl |
| methyl | methyl | —O— | 2-fluoro-4-propargyloxyphenyl | 2-fluoro-4-propargyloxyphenyl |
| methyl | methyl | —O— | 2-fluoro-4-propargyloxyphenyl | 2-allyloxyphenyl |
| methyl | methyl | —O— | 2-fluoro-4-propargyloxyphenyl | 2-propargyloxyphenyl |
| methyl | methyl | —O— | 2-fluoro-4-propargyloxyphenyl | 2-allyloxy-5-fluorophenyl |
| methyl | methyl | —O— | 2-fluoro-4-propargyloxyphenyl | 5-fluoro-2-propargyloxyphenyl |
| methyl | methyl | —O— | 2-fluoro-4-propargyloxyphenyl | 2-allyloxy-4-methylphenyl |
| methyl | methyl | —O— | 2-fluoro-4-propargyloxyphenyl | 4-methyl-2-propargyloxyphenyl |
| methyl | methyl | —O— | 2-fluoro-4-propargyloxyphenyl | 2-allyloxy-5-cyanophenyl |
| methyl | methyl | —O— | 2-fluoro-4-propargyloxyphenyl | 5-cyano-2-propargyloxyphenyl |
| methyl | methyl | —O— | 2-fluoro-4-propargyloxyphenyl | 5-allyloxy-2-fluorophenyl |
| methyl | methyl | —O— | 2-fluoro-4-propargyloxyphenyl | 2-fluoro-5-propargyloxyphenyl |
| methyl | methyl | —O— | 2-fluoro-4-propargyloxyphenyl | 4-allyloxy-2-chlorophenyl |
| methyl | methyl | —O— | 2-fluoro-4-propargyloxyphenyl | 2-chloro-4-propargyloxyphenyl |
| methyl | methyl | —O— | 2-fluoro-4-propargyloxyphenyl | 4-allyloxy-3-fluorophenyl |
| methyl | methyl | —O— | 2-fluoro-4-propargyloxyphenyl | 3-fluoro-4-propargyloxyphenyl |
| methyl | methyl | —O— | 2-fluoro-4-propargyloxyphenyl | 4-allyloxyphenyl |
| methyl | methyl | —O— | 2-fluoro-4-propargyloxyphenyl | 4-propargyloxyphenyl |
| methyl | methyl | —O— | 2-fluoro-4-propargyloxyphenyl | 3-fluoro-5-propargyloxyphenyl |
| methyl | methyl | —O— | 2-fluoro-4-propargyloxyphenyl | 3-fluoro-5-allyloxyphenyl |
| methyl | methyl | —O— | 2-fluoro-4-propargyloxyphenyl | 2,5-difluoro-4-propargyloxyphenyl |
| methyl | methyl | —O— | 2-fluoro-4-propargyloxyphenyl | 2,5-difluoro-4-allyloxyphenyl |
| methyl | methyl | —O— | 2-fluoro-4-propargyloxyphenyl | 6-allyloxypyridin-3-yl |
| methyl | methyl | —O— | 2-fluoro-4-propargyloxyphenyl | 6-propargyloxypyridin-3-yl |
| methyl | methyl | —O— | 2-fluoro-4-propargyloxyphenyl | 2-propargyloxy-6-trifluorophenyl |
| methyl | methyl | —O— | 2-fluoro-4-propargyloxyphenyl | 2-allyloxy-6-trifluormethylphenyl |
| methyl | methyl | —O— | 2-fluoro-4-propargyloxyphenyl | 2-chloro-6-propargyloxyphenyl |
| methyl | methyl | —O— | 2-fluoro-4-propargyloxyphenyl | 2-allyloxy-6-chlorophenyl |
| methyl | methyl | —O— | 2-fluoro-4-propargyloxyphenyl | 2,4-dimethyl-6-propargyloxyphenyl |
| methyl | methyl | —O— | 2-fluoro-4-propargyloxyphenyl | 2-allyloxy-4,6-dimethylphenyl |
| methyl | methyl | —O— | 4-chloro-2-fluorophenyl | 2,6-difluoro-4-propargyloxyphenyl |
| methyl | methyl | —O— | 4-chloro-2-fluorophenyl | 4-allyloxy-2,6-difluorophenyl |
| methyl | methyl | —O— | 4-chloro-2-fluorophenyl | 2,4-difluoro-6-propargyloxyphenyl |
| methyl | methyl | —O— | 4-chloro-2-fluorophenyl | 4-fluoro-2-propargyloxyphenyl |
| methyl | methyl | —O— | 4-chloro-2-fluorophenyl | 2-fluoro-6-propargyloxyphenyl |
| methyl | methyl | —O— | 4-chloro-2-fluorophenyl | 4-chloro-2-fluoro-6-propargyloxyphenyl |
| methyl | methyl | —O— | 4-chloro-2-fluorophenyl | 2-chloro-4-fluoro-6-propargyloxyphenyl |
| methyl | methyl | —O— | 4-chloro-2-fluorophenyl | 4-allyloxy-2-fluorophenyl |
| methyl | methyl | —O— | 4-chloro-2-fluorophenyl | 2-fluoro-4-propargyloxyphenyl |
| methyl | methyl | —O— | 4-chloro-2-fluorophenyl | 2-allyloxyphenyl |
| methyl | methyl | —O— | 4-chloro-2-fluorophenyl | 2-propargyloxyphenyl |

-continued

| R¹ | R² | X | Q¹ | Q² |
|---|---|---|---|---|
| methyl | methyl | —O— | 4-chloro-2-fluorophenyl | 2-allyloxy-5-fluorophenyl |
| methyl | methyl | —O— | 4-chloro-2-fluorophenyl | 5-fluoro-2-propargyloxyphenyl |
| methyl | methyl | —O— | 4-chloro-2-fluorophenyl | 2-allyloxy-4-methylphenyl |
| methyl | methyl | —O— | 4-chloro-2-fluorophenyl | 4-methyl-2-propargyloxyphenyl |
| methyl | methyl | —O— | 4-chloro-2-fluorophenyl | 2-allyloxy-5-cyanophenyl |
| methyl | methyl | —O— | 4-chloro-2-fluorophenyl | 5-cyano-2-propargyloxyphenyl |
| methyl | methyl | —O— | 4-chloro-2-fluorophenyl | 5-allyloxy-2-fluorophenyl |
| methyl | methyl | —O— | 4-chloro-2-fluorophenyl | 2-fluoro-5-propargyloxyphenyl |
| methyl | methyl | —O— | 4-chloro-2-fluorophenyl | 4-allyloxy-2-chlorophenyl |
| methyl | methyl | —O— | 4-chloro-2-fluorophenyl | 2-chloro-4-propargyloxyphenyl |
| methyl | methyl | —O— | 4-chloro-2-fluorophenyl | 4-allyloxy-3-fluorophenyl |
| methyl | methyl | —O— | 4-chloro-2-fluorophenyl | 3-fluoro-4-propargyloxyphenyl |
| methyl | methyl | —O— | 4-chloro-2-fluorophenyl | 4-allyloxyphenyl |
| methyl | methyl | —O— | 4-chloro-2-fluorophenyl | 4-propargyloxyphenyl |
| methyl | methyl | —O— | 4-chloro-2-fluorophenyl | 3-fluoro-5-propargyloxyphenyl |
| methyl | methyl | —O— | 4-chloro-2-fluorophenyl | 3-fluoro-5-allyloxyphenyl |
| methyl | methyl | —O— | 4-chloro-2-fluorophenyl | 2,5-difluoro-4-propargyloxyphenyl |
| methyl | methyl | —O— | 4-chloro-2-fluorophenyl | 2,5-difluoro-4-allyloxyphenyl |
| methyl | methyl | —O— | 4-chloro-2-fluorophenyl | 6-allyloxypyridin-3-yl |
| methyl | methyl | —O— | 4-chloro-2-fluorophenyl | 6-propargyloxypyridin-3-yl |
| methyl | methyl | —O— | 4-chloro-2-fluorophenyl | 2-propargyloxy-6-trifluorophenyl |
| methyl | methyl | —O— | 4-chloro-2-fluorophenyl | 2-allyloxy-6-trifluormethylphenyl |
| methyl | methyl | —O— | 4-chloro-2-fluorophenyl | 2-chloro-6-propargyloxyphenyl |
| methyl | methyl | —O— | 4-chloro-2-fluorophenyl | 2-allyloxy-6-chlorophenyl |
| methyl | methyl | —O— | 4-chloro-2-fluorophenyl | 2,4-dimethyl-6-propargyloxyphenyl |
| methyl | methyl | —O— | 4-chloro-2-fluorophenyl | 2-allyloxy-4,6-dimethylphenyl |
| methyl | methyl | —O— | 2-bromo-4-fluorophenyl | 2,6-difluoro-4-propargyloxyphenyl |
| methyl | methyl | —O— | 2-bromo-4-fluorophenyl | 4-allyloxy-2,6-difluorophenyl |
| methyl | methyl | —O— | 2-bromo-4-fluorophenyl | 2,4-difluoro-6-propargyloxyphenyl |
| methyl | methyl | —O— | 2-bromo-4-fluorophenyl | 4-fluoro-2-propargyloxyphenyl |
| methyl | methyl | —O— | 2-bromo-4-fluorophenyl | 2-fluoro-6-propargyloxyphenyl |
| methyl | methyl | —O— | 2-bromo-4-fluorophenyl | 4-chloro-2-fluoro-6-propargyloxyphenyl |
| methyl | methyl | —O— | 2-bromo-4-fluorophenyl | 2-chloro-4-fluoro-6-propargyloxyphenyl |
| methyl | methyl | —O— | 2-bromo-4-fluorophenyl | 4-allyloxy-2-fluorophenyl |
| methyl | methyl | —O— | 2-bromo-4-fluorophenyl | 2-fluoro-4-propargyloxyphenyl |
| methyl | methyl | —O— | 2-bromo-4-fluorophenyl | 2-allyloxyphenyl |
| methyl | methyl | —O— | 2-bromo-4-fluorophenyl | 2-propargyloxyphenyl |
| methyl | methyl | —O— | 2-bromo-4-fluorophenyl | 2-allyloxy-5-fluorophenyl |
| methyl | methyl | —O— | 2-bromo-4-fluorophenyl | 5-fluoro-2-propargyloxyphenyl |
| methyl | methyl | —O— | 2-bromo-4-fluorophenyl | 2-allyloxy-4-methylphenyl |
| methyl | methyl | —O— | 2-bromo-4-fluorophenyl | 4-methyl-2-propargyloxyphenyl |
| methyl | methyl | —O— | 2-bromo-4-fluorophenyl | 2-allyloxy-5-cyanophenyl |
| methyl | methyl | —O— | 2-bromo-4-fluorophenyl | 5-cyano-2-propargyloxyphenyl |
| methyl | methyl | —O— | 2-bromo-4-fluorophenyl | 5-allyloxy-2-fluorophenyl |
| methyl | methyl | —O— | 2-bromo-4-fluorophenyl | 2-fluoro-5-propargyloxyphenyl |
| methyl | methyl | —O— | 2-bromo-4-fluorophenyl | 4-allyloxy-2-chlorophenyl |
| methyl | methyl | —O— | 2-bromo-4-fluorophenyl | 2-chloro-4-propargyloxyphenyl |
| methyl | methyl | —O— | 2-bromo-4-fluorophenyl | 4-allyloxy-3-fluorophenyl |
| methyl | methyl | —O— | 2-bromo-4-fluorophenyl | 3-fluoro-4-propargyloxyphenyl |
| methyl | methyl | —O— | 2-bromo-4-fluorophenyl | 4-allyloxyphenyl |
| methyl | methyl | —O— | 2-bromo-4-fluorophenyl | 4-propargyloxyphenyl |
| methyl | methyl | —O— | 2-bromo-4-fluorophenyl | 3-fluoro-5-propargyloxyphenyl |
| methyl | methyl | —O— | 2-bromo-4-fluorophenyl | 3-fluoro-5-allyloxyphenyl |
| methyl | methyl | —O— | 2-bromo-4-fluorophenyl | 2,5-difluoro-4-propargyloxyphenyl |
| methyl | methyl | —O— | 2-bromo-4-fluorophenyl | 2,5-difluoro-4-allyloxyphenyl |
| methyl | methyl | —O— | 2-bromo-4-fluorophenyl | 6-allyloxypyridin-3-yl |
| methyl | methyl | —O— | 2-bromo-4-fluorophenyl | 6-propargyloxypyridin-3-yl |
| methyl | methyl | —O— | 2-bromo-4-fluorophenyl | 2-propargyloxy-6-trifluorophenyl |
| methyl | methyl | —O— | 2-bromo-4-fluorophenyl | 2-allyloxy-6-trifluormethylphenyl |
| methyl | methyl | —O— | 2-bromo-4-fluorophenyl | 2-chloro-6-propargyloxyphenyl |
| methyl | methyl | —O— | 2-bromo-4-fluorophenyl | 2-allyloxy-6-chlorophenyl |
| methyl | methyl | —O— | 2-bromo-4-fluorophenyl | 2,4-dimethyl-6-propargyloxyphenyl |
| methyl | methyl | —O— | 2-bromo-4-fluorophenyl | 2-allyloxy-4,6-dimethylphenyl |
| methyl | methyl | —O— | 2,4,6-trifluorophenyl | 2,6-difluoro-4-propargyloxyphenyl |
| methyl | methyl | —O— | 2,4,6-trifluorophenyl | 4-allyloxy-2,6-difluorophenyl |
| methyl | methyl | —O— | 2,4,6-trifluorophenyl | 2,4-difluoro-6-propargyloxyphenyl |
| methyl | methyl | —O— | 2,4,6-trifluorophenyl | 4-fluoro-2-propargyloxyphenyl |
| methyl | methyl | —O— | 2,4,6-trifluorophenyl | 2-fluoro-6-propargyloxyphenyl |
| methyl | methyl | —O— | 2,4,6-trifluorophenyl | 4-chloro-2-fluoro-6-propargyloxyphenyl |
| methyl | methyl | —O— | 2,4,6-trifluorophenyl | 2-chloro-4-fluoro-6-propargyloxyphenyl |
| methyl | methyl | —O— | 2,4,6-trifluorophenyl | 4-allyloxy-2-fluorophenyl |
| methyl | methyl | —O— | 2,4,6-trifluorophenyl | 2-fluoro-4-propargyloxyphenyl |
| methyl | methyl | —O— | 2,4,6-trifluorophenyl | 2-allyloxyphenyl |

-continued

| R¹ | R² | X | Q¹ | Q² |
|---|---|---|---|---|
| methyl | methyl | —O— | 2,4,6-trifluorophenyl | 2-propargyloxyphenyl |
| methyl | methyl | —O— | 2,4,6-trifluorophenyl | 2-allyloxy-5-fluorophenyl |
| methyl | methyl | —O— | 2,4,6-trifluorophenyl | 5-fluoro-2-propargyloxyphenyl |
| methyl | methyl | —O— | 2,4,6-trifluorophenyl | 2-allyloxy-4-methylphenyl |
| methyl | methyl | —O— | 2,4,6-trifluorophenyl | 4-methyl-2-propargyloxyphenyl |
| methyl | methyl | —O— | 2,4,6-trifluorophenyl | 2-allyloxy-5-cyanophenyl |
| methyl | methyl | —O— | 2,4,6-trifluorophenyl | 5-cyano-2-propargyloxyphenyl |
| methyl | methyl | —O— | 2,4,6-trifluorophenyl | 5-allyloxy-2-fluorophenyl |
| methyl | methyl | —O— | 2,4,6-trifluorophenyl | 2-fluoro-5-propargyloxyphenyl |
| methyl | methyl | —O— | 2,4,6-trifluorophenyl | 4-allyloxy-2-chlorophenyl |
| methyl | methyl | —O— | 2,4,6-trifluorophenyl | 2-chloro-4-propargyloxyphenyl |
| methyl | methyl | —O— | 2,4,6-trifluorophenyl | 4-allyloxy-3-fluorophenyl |
| methyl | methyl | —O— | 2,4,6-trifluorophenyl | 3-fluoro-4-propargyloxyphenyl |
| methyl | methyl | —O— | 2,4,6-trifluorophenyl | 4-allyloxyphenyl |
| methyl | methyl | —O— | 2,4,6-trifluorophenyl | 4-propargyloxyphenyl |
| methyl | methyl | —O— | 2,4,6-trifluorophenyl | 3-fluoro-5-propargyloxyphenyl |
| methyl | methyl | —O— | 2,4,6-trifluorophenyl | 3-fluoro-5-allyloxyphenyl |
| methyl | methyl | —O— | 2,4,6-trifluorophenyl | 2,5-difluoro-4-propargyloxyphenyl |
| methyl | methyl | —O— | 2,4,6-trifluorophenyl | 2,5-difluoro-4-allyloxyphenyl |
| methyl | methyl | —O— | 2,4,6-trifluorophenyl | 6-allyloxypyridin-3-yl |
| methyl | methyl | —O— | 2,4,6-trifluorophenyl | 6-propargyloxypyridin-3-yl |
| methyl | methyl | —O— | 2,4,6-trifluorophenyl | 2-propargyloxy-6-trifluorophenyl |
| methyl | methyl | —O— | 2,4,6-trifluorophenyl | 2-allyloxy-6-trifluormethylphenyl |
| methyl | methyl | —O— | 2,4,6-trifluorophenyl | 2-chloro-6-propargyloxyphenyl |
| methyl | methyl | —O— | 2,4,6-trifluorophenyl | 2-allyloxy-6-chlorophenyl |
| methyl | methyl | —O— | 2,4,6-trifluorophenyl | 2,4-dimethyl-6-propargyloxyphenyl |
| methyl | methyl | —O— | 2,4,6-trifluorophenyl | 2-allyloxy-4,6-dimethylphenyl |
| methyl | methyl | —O— | 4-chloro-2,6-difluorophenyl | 2,6-difluoro-4-propargyloxyphenyl |
| methyl | methyl | —O— | 4-chloro-2,6-difluorophenyl | 4-allyloxy-2,6-difluorophenyl |
| methyl | methyl | —O— | 4-chloro-2,6-difluorophenyl | 2,4-difluoro-6-propargyloxyphenyl |
| methyl | methyl | —O— | 4-chloro-2,6-difluorophenyl | 4-fluoro-2-propargyloxyphenyl |
| methyl | methyl | —O— | 4-chloro-2,6-difluorophenyl | 2-fluoro-6-propargyloxyphenyl |
| methyl | methyl | —O— | 4-chloro-2,6-difluorophenyl | 4-chloro-2-fluoro-6-propargyloxyphenyl |
| methyl | methyl | —O— | 4-chloro-2,6-difluorophenyl | 2-chloro-4-fluoro-6-propargyloxyphenyl |
| methyl | methyl | —O— | 4-chloro-2,6-difluorophenyl | 4-allyloxy-2-fluorophenyl |
| methyl | methyl | —O— | 4-chloro-2,6-difluorophenyl | 2-fluoro-4-propargyloxyphenyl |
| methyl | methyl | —O— | 4-chloro-2,6-difluorophenyl | 2-allyloxyphenyl |
| methyl | methyl | —O— | 4-chloro-2,6-difluorophenyl | 2-propargyloxyphenyl |
| methyl | methyl | —O— | 4-chloro-2,6-difluorophenyl | 2-allyloxy-5-fluorophenyl |
| methyl | methyl | —O— | 4-chloro-2,6-difluorophenyl | 5-fluoro-2-propargyloxyphenyl |
| methyl | methyl | —O— | 4-chloro-2,6-difluorophenyl | 2-allyloxy-4-methylphenyl |
| methyl | methyl | —O— | 4-chloro-2,6-difluorophenyl | 4-methyl-2-propargyloxyphenyl |
| methyl | methyl | —O— | 4-chloro-2,6-difluorophenyl | 2-allyloxy-5-cyanophenyl |
| methyl | methyl | —O— | 4-chloro-2,6-difluorophenyl | 5-cyano-2-propargyloxyphenyl |
| methyl | methyl | —O— | 4-chloro-2,6-difluorophenyl | 5-allyloxy-2-fluorophenyl |
| methyl | methyl | —O— | 4-chloro-2,6-difluorophenyl | 2-fluoro-5-propargyloxyphenyl |
| methyl | methyl | —O— | 4-chloro-2,6-difluorophenyl | 4-allyloxy-2-chlorophenyl |
| methyl | methyl | —O— | 4-chloro-2,6-difluorophenyl | 2-chloro-4-propargyloxyphenyl |
| methyl | methyl | —O— | 4-chloro-2,6-difluorophenyl | 4-allyloxy-3-fluorophenyl |
| methyl | methyl | —O— | 4-chloro-2,6-difluorophenyl | 3-fluoro-4-propargyloxyphenyl |
| methyl | methyl | —O— | 4-chloro-2,6-difluorophenyl | 4-allyloxyphenyl |
| methyl | methyl | —O— | 4-chloro-2,6-difluorophenyl | 4-propargyloxyphenyl |
| methyl | methyl | —O— | 4-chloro-2,6-difluorophenyl | 3-fluoro-5-propargyloxyphenyl |
| methyl | methyl | —O— | 4-chloro-2,6-difluorophenyl | 3-fluoro-5-allyloxyphenyl |
| methyl | methyl | —O— | 4-chloro-2,6-difluorophenyl | 2,5-difluoro-4-propargyloxyphenyl |
| methyl | methyl | —O— | 4-chloro-2,6-difluorophenyl | 2,5-difluoro-4-allyloxyphenyl |
| methyl | methyl | —O— | 4-chloro-2,6-difluorophenyl | 6-allyloxypyridin-3-yl |
| methyl | methyl | —O— | 4-chloro-2,6-difluorophenyl | 6-propargyloxypyridin-3-yl |
| methyl | methyl | —O— | 4-chloro-2,6-difluorophenyl | 2-propargyloxy-6-trifluorophenyl |
| methyl | methyl | —O— | 4-chloro-2,6-difluorophenyl | 2-allyloxy-6-trifluormethylphenyl |
| methyl | methyl | —O— | 4-chloro-2,6-difluorophenyl | 2-chloro-6-propargyloxyphenyl |
| methyl | methyl | —O— | 4-chloro-2,6-difluorophenyl | 2-allyloxy-6-chlorophenyl |
| methyl | methyl | —O— | 4-chloro-2,6-difluorophenyl | 2,4-dimethyl-6-propargyloxyphenyl |
| methyl | methyl | —O— | 4-chloro-2,6-difluorophenyl | 2-allyloxy-4,6-dimethylphenyl |
| methyl | methyl | —O— | 4-chloro-2,6-difluorophenyl | 2,6-difluoro-4-propargyloxyphenyl |
| methyl | methyl | —O— | 4-chloro-2,6-difluorophenyl | 4-allyloxy-2,6-difluorophenyl |
| methyl | methyl | —O— | 4-chloro-2,6-difluorophenyl | 2,4-difluoro-6-propargyloxyphenyl |
| methyl | methyl | —O— | 4-chloro-2,6-difluorophenyl | 4-fluoro-2-propargyloxyphenyl |
| methyl | methyl | —O— | 4-chloro-2,6-difluorophenyl | 2-fluoro-6-propargyloxyphenyl |
| methyl | methyl | —O— | 4-chloro-2,6-difluorophenyl | 4-chloro-2-fluoro-6-propargyloxyphenyl |
| methyl | methyl | —O— | 4-chloro-2,6-difluorophenyl | 2-chloro-4-fluoro-6-propargyloxyphenyl |
| methyl | methyl | —O— | 4-chloro-2,6-difluorophenyl | 4-allyloxy-2-fluorophenyl |
| methyl | methyl | —O— | 4-chloro-2,6-difluorophenyl | 2-fluoro-4-propargyloxyphenyl |

| R¹ | R² | X | Q¹ | Q² |
|---|---|---|---|---|
| methyl | methyl | —O— | 4-chloro-2,6-difluorophenyl | 2-allyloxyphenyl |
| methyl | methyl | —O— | 4-chloro-2,6-difluorophenyl | 2-propargyloxyphenyl |
| methyl | methyl | —O— | 4-chloro-2,6-difluorophenyl | 2-allyloxy-5-fluorophenyl |
| methyl | methyl | —O— | 4-chloro-2,6-difluorophenyl | 5-fluoro-2-propargyloxyphenyl |
| methyl | methyl | —O— | 4-chloro-2,6-difluorophenyl | 2-allyloxy-4-methylphenyl |
| methyl | methyl | —O— | 4-chloro-2,6-difluorophenyl | 4-methyl-2-propargyloxyphenyl |
| methyl | methyl | —O— | 4-chloro-2,6-difluorophenyl | 2-allyloxy-5-cyanophenyl |
| methyl | methyl | —O— | 4-chloro-2,6-difluorophenyl | 5-cyano-2-propargyloxyphenyl |
| methyl | methyl | —O— | 4-chloro-2,6-difluorophenyl | 5-allyloxy-2-fluorophenyl |
| methyl | methyl | —O— | 4-chloro-2,6-difluorophenyl | 2-fluoro-5-propargyloxyphenyl |
| methyl | methyl | —O— | 4-chloro-2,6-difluorophenyl | 4-allyloxy-2-chlorophenyl |
| methyl | methyl | —O— | 4-chloro-2,6-difluorophenyl | 2-chloro-4-propargyloxyphenyl |
| methyl | methyl | —O— | 4-chloro-2,6-difluorophenyl | 4-allyloxy-3-fluorophenyl |
| methyl | methyl | —O— | 4-chloro-2,6-difluorophenyl | 3-fluoro-4-propargyloxyphenyl |
| methyl | methyl | —O— | 4-chloro-2,6-difluorophenyl | 4-allyloxyphenyl |
| methyl | methyl | —O— | 4-chloro-2,6-difluorophenyl | 4-propargyloxyphenyl |
| methyl | methyl | —O— | 4-chloro-2,6-difluorophenyl | 3-fluoro-5-propargyloxyphenyl |
| methyl | methyl | —O— | 4-chloro-2,6-difluorophenyl | 3-fluoro-5-allyloxyphenyl |
| methyl | methyl | —O— | 4-chloro-2,6-difluorophenyl | 2,5-difluoro-4-propargyloxyphenyl |
| methyl | methyl | —O— | 4-chloro-2,6-difluorophenyl | 2,5-difluoro-4-allyloxyphenyl |
| methyl | methyl | —O— | 4-chloro-2,6-difluorophenyl | 6-allyloxypyridin-3-yl |
| methyl | methyl | —O— | 4-chloro-2,6-difluorophenyl | 6-propargyloxypyridin-3-yl |
| methyl | methyl | —O— | 4-chloro-2,6-difluorophenyl | 2-propargyloxy-6-trifluorophenyl |
| methyl | methyl | —O— | 4-chloro-2,6-difluorophenyl | 2-allyloxy-6-trifluormethylphenyl |
| methyl | methyl | —O— | 4-chloro-2,6-difluorophenyl | 2-chloro-6-propargyloxyphenyl |
| methyl | methyl | —O— | 4-chloro-2,6-difluorophenyl | 2-allyloxy-6-chlorophenyl |
| methyl | methyl | —O— | 4-chloro-2,6-difluorophenyl | 2,4-dimethyl-6-propargyloxyphenyl |
| methyl | methyl | —O— | 4-chloro-2,6-difluorophenyl | 2-allyloxy-4,6-dimethylphenyl |
| methyl | methyl | —O— | 3,4-dichlorophenyl | 2,6-difluoro-4-propargyloxyphenyl |
| methyl | methyl | —O— | 3,4-dichlorophenyl | 4-allyloxy-2,6-difluorophenyl |
| methyl | methyl | —O— | 3,4-dichlorophenyl | 2,4-difluoro-6-propargyloxyphenyl |
| methyl | methyl | —O— | 3,4-dichlorophenyl | 4-fluoro-2-propargyloxyphenyl |
| methyl | methyl | —O— | 3,4-dichlorophenyl | 2-fluoro-6-propargyloxyphenyl |
| methyl | methyl | —O— | 3,4-dichlorophenyl | 4-chloro-2-fluoro-6-propargyloxyphenyl |
| methyl | methyl | —O— | 3,4-dichlorophenyl | 2-chloro-4-fluoro-6-propargyloxyphenyl |
| methyl | methyl | —O— | 3,4-dichlorophenyl | 4-allyloxy-2-fluorophenyl |
| methyl | methyl | —O— | 3,4-dichlorophenyl | 2-fluoro-4-propargyloxyphenyl |
| methyl | methyl | —O— | 3,4-dichlorophenyl | 2-allyloxyphenyl |
| methyl | methyl | —O— | 3,4-dichlorophenyl | 2-propargyloxyphenyl |
| methyl | methyl | —O— | 3,4-dichlorophenyl | 2-allyloxy-5-fluorophenyl |
| methyl | methyl | —O— | 3,4-dichlorophenyl | 5-fluoro-2-propargyloxyphenyl |
| methyl | methyl | —O— | 3,4-dichlorophenyl | 2-allyloxy-4-methylphenyl |
| methyl | methyl | —O— | 3,4-dichlorophenyl | 4-methyl-2-propargyloxyphenyl |
| methyl | methyl | —O— | 3,4-dichlorophenyl | 2-allyloxy-5-cyanophenyl |
| methyl | methyl | —O— | 3,4-dichlorophenyl | 5-cyano-2-propargyloxyphenyl |
| methyl | methyl | —O— | 3,4-dichlorophenyl | 5-allyloxy-2-fluorophenyl |
| methyl | methyl | —O— | 3,4-dichlorophenyl | 2-fluoro-5-propargyloxyphenyl |
| methyl | methyl | —O— | 3,4-dichlorophenyl | 4-allyloxy-2-chlorophenyl |
| methyl | methyl | —O— | 3,4-dichlorophenyl | 2-chloro-4-propargyloxyphenyl |
| methyl | methyl | —O— | 3,4-dichlorophenyl | 4-allyloxy-3-fluorophenyl |
| methyl | methyl | —O— | 3,4-dichlorophenyl | 3-fluoro-4-propargyloxyphenyl |
| methyl | methyl | —O— | 3,4-dichlorophenyl | 4-allyloxyphenyl |
| methyl | methyl | —O— | 3,4-dichlorophenyl | 4-propargyloxyphenyl |
| methyl | methyl | —O— | 3,4-dichlorophenyl | 3-fluoro-5-propargyloxyphenyl |
| methyl | methyl | —O— | 3,4-dichlorophenyl | 3-fluoro-5-allyloxyphenyl |
| methyl | methyl | —O— | 3,4-dichlorophenyl | 2,5-difluoro-4-propargyloxyphenyl |
| methyl | methyl | —O— | 3,4-dichlorophenyl | 2,5-difluoro-4-allyloxyphenyl |
| methyl | methyl | —O— | 3,4-dichlorophenyl | 6-allyloxypyridin-3-yl |
| methyl | methyl | —O— | 3,4-dichlorophenyl | 6-propargyloxypyridin-3-yl |
| methyl | methyl | —O— | 3,4-dichlorophenyl | 2-propargyloxy-6-trifluorophenyl |
| methyl | methyl | —O— | 3,4-dichlorophenyl | 2-allyloxy-6-trifluormethylphenyl |
| methyl | methyl | —O— | 3,4-dichlorophenyl | 2-chloro-6-propargyloxyphenyl |
| methyl | methyl | —O— | 3,4-dichlorophenyl | 2-allyloxy-6-chlorophenyl |
| methyl | methyl | —O— | 3,4-dichlorophenyl | 2,4-dimethyl-6-propargyloxyphenyl |
| methyl | methyl | —O— | 3,4-dichlorophenyl | 2-allyloxy-4,6-dimethylphenyl |
| methyl | methyl | —O— | 3,5-dichlorophenyl | 2,6-difluoro-4-propargyloxyphenyl |
| methyl | methyl | —O— | 3,5-dichlorophenyl | 4-allyloxy-2,6-difluorophenyl |
| methyl | methyl | —O— | 3,5-dichlorophenyl | 2,4-difluoro-6-propargyloxyphenyl |
| methyl | methyl | —O— | 3,5-dichlorophenyl | 4-fluoro-2-propargyloxyphenyl |
| methyl | methyl | —O— | 3,5-dichlorophenyl | 2-fluoro-6-propargyloxyphenyl |
| methyl | methyl | —O— | 3,5-dichlorophenyl | 4-chloro-2-fluoro-6-propargyloxyphenyl |
| methyl | methyl | —O— | 3,5-dichlorophenyl | 2-chloro-4-fluoro-6-propargyloxyphenyl |
| methyl | methyl | —O— | 3,5-dichlorophenyl | 4-allyloxy-2-fluorophenyl |

-continued

| R¹ | R² | X | Q¹ | Q² |
|---|---|---|---|---|
| methyl | methyl | —O— | 3,5-dichlorophenyl | 2-fluoro-4-propargyloxyphenyl |
| methyl | methyl | —O— | 3,5-dichlorophenyl | 2-allyloxyphenyl |
| methyl | methyl | —O— | 3,5-dichlorophenyl | 2-propargyloxyphenyl |
| methyl | methyl | —O— | 3,5-dichlorophenyl | 2-allyloxy-5-fluorophenyl |
| methyl | methyl | —O— | 3,5-dichlorophenyl | 5-fluoro-2-propargyloxyphenyl |
| methyl | methyl | —O— | 3,5-dichlorophenyl | 2-allyloxy-4-methylphenyl |
| methyl | methyl | —O— | 3,5-dichlorophenyl | 4-methyl-2-propargyloxyphenyl |
| methyl | methyl | —O— | 3,5-dichlorophenyl | 2-allyloxy-5-cyanophenyl |
| methyl | methyl | —O— | 3,5-dichlorophenyl | 5-cyano-2-propargyloxyphenyl |
| methyl | methyl | —O— | 3,5-dichlorophenyl | 5-allyloxy-2-fluorophenyl |
| methyl | methyl | —O— | 3,5-dichlorophenyl | 2-fluoro-5-propargyloxyphenyl |
| methyl | methyl | —O— | 3,5-dichlorophenyl | 4-allyloxy-2-chlorophenyl |
| methyl | methyl | —O— | 3,5-dichlorophenyl | 2-chloro-4-propargyloxyphenyl |
| methyl | methyl | —O— | 3,5-dichlorophenyl | 4-allyloxy-3-fluorophenyl |
| methyl | methyl | —O— | 3,5-dichlorophenyl | 3-fluoro-4-propargyloxyphenyl |
| methyl | methyl | —O— | 3,5-dichlorophenyl | 4-allyloxyphenyl |
| methyl | methyl | —O— | 3,5-dichlorophenyl | 4-propargyloxyphenyl |
| methyl | methyl | —O— | 3,5-dichlorophenyl | 3-fluoro-5-propargyloxyphenyl |
| methyl | methyl | —O— | 3,5-dichlorophenyl | 3-fluoro-5-allyloxyphenyl |
| methyl | methyl | —O— | 3,5-dichlorophenyl | 2,5-difluoro-4-propargyloxyphenyl |
| methyl | methyl | —O— | 3,5-dichlorophenyl | 2,5-difluoro-4-allyloxyphenyl |
| methyl | methyl | —O— | 3,5-dichlorophenyl | 6-allyloxypyridin-3-yl |
| methyl | methyl | —O— | 3,5-dichlorophenyl | 6-propargyloxypyridin-3-yl |
| methyl | methyl | —O— | 3,5-dichlorophenyl | 2-propargyloxy-6-trifluorophenyl |
| methyl | methyl | —O— | 3,5-dichlorophenyl | 2-allyloxy-6-trifluormethylphenyl |
| methyl | methyl | —O— | 3,5-dichlorophenyl | 2-chloro-6-propargyloxyphenyl |
| methyl | methyl | —O— | 3,5-dichlorophenyl | 2-allyloxy-6-chlorophenyl |
| methyl | methyl | —O— | 3,5-dichlorophenyl | 2,4-dimethyl-6-propargyloxyphenyl |
| methyl | methyl | —O— | 3,5-dichlorophenyl | 2-allyloxy-4,6-dimethylphenyl |
| methyl | methyl | —O— | 4-fluoro-2-propargyloxyphenyl | 2,6-difluoro-4-propargyloxyphenyl |
| methyl | methyl | —O— | 4-fluoro-2-propargyloxyphenyl | 4-allyloxy-2,6-difluorophenyl |
| methyl | methyl | —O— | 4-fluoro-2-propargyloxyphenyl | 2,4-difluoro-6-propargyloxyphenyl |
| methyl | methyl | —O— | 4-fluoro-2-propargyloxyphenyl | 4-fluoro-2-propargyloxyphenyl |
| methyl | methyl | —O— | 4-fluoro-2-propargyloxyphenyl | 2-fluoro-6-propargyloxyphenyl |
| methyl | methyl | —O— | 4-fluoro-2-propargyloxyphenyl | 4-chloro-2-fluoro-6-propargyloxyphenyl |
| methyl | methyl | —O— | 4-fluoro-2-propargyloxyphenyl | 2-chloro-4-fluoro-6-propargyloxyphenyl |
| methyl | methyl | —O— | 4-fluoro-2-propargyloxyphenyl | 4-allyloxy-2-fluorophenyl |
| methyl | methyl | —O— | 4-fluoro-2-propargyloxyphenyl | 2-fluoro-4-propargyloxyphenyl |
| methyl | methyl | —O— | 4-fluoro-2-propargyloxyphenyl | 2-allyloxyphenyl |
| methyl | methyl | —O— | 4-fluoro-2-propargyloxyphenyl | 2-propargyloxyphenyl |
| methyl | methyl | —O— | 4-fluoro-2-propargyloxyphenyl | 2-allyloxy-5-fluorophenyl |
| methyl | methyl | —O— | 4-fluoro-2-propargyloxyphenyl | 5-fluoro-2-propargyloxyphenyl |
| methyl | methyl | —O— | 4-fluoro-2-propargyloxyphenyl | 2-allyloxy-4-methylphenyl |
| methyl | methyl | —O— | 4-fluoro-2-propargyloxyphenyl | 4-methyl-2-propargyloxyphenyl |
| methyl | methyl | —O— | 4-fluoro-2-propargyloxyphenyl | 2-allyloxy-5-cyanophenyl |
| methyl | methyl | —O— | 4-fluoro-2-propargyloxyphenyl | 5-cyano-2-propargyloxyphenyl |
| methyl | methyl | —O— | 4-fluoro-2-propargyloxyphenyl | 5-allyloxy-2-fluorophenyl |
| methyl | methyl | —O— | 4-fluoro-2-propargyloxyphenyl | 2-fluoro-5-propargyloxyphenyl |
| methyl | methyl | —O— | 4-fluoro-2-propargyloxyphenyl | 4-allyloxy-2-chlorophenyl |
| methyl | methyl | —O— | 4-fluoro-2-propargyloxyphenyl | 2-chloro-4-propargyloxyphenyl |
| methyl | methyl | —O— | 4-fluoro-2-propargyloxyphenyl | 4-allyloxy-3-fluorophenyl |
| methyl | methyl | —O— | 4-fluoro-2-propargyloxyphenyl | 3-fluoro-4-propargyloxyphenyl |
| methyl | methyl | —O— | 4-fluoro-2-propargyloxyphenyl | 4-allyloxyphenyl |
| methyl | methyl | —O— | 4-fluoro-2-propargyloxyphenyl | 4-propargyloxyphenyl |
| methyl | methyl | —O— | 4-fluoro-2-propargyloxyphenyl | 3-fluoro-5-propargyloxyphenyl |
| methyl | methyl | —O— | 4-fluoro-2-propargyloxyphenyl | 3-fluoro-5-allyloxyphenyl |
| methyl | methyl | —O— | 4-fluoro-2-propargyloxyphenyl | 2,5-difluoro-4-propargyloxyphenyl |
| methyl | methyl | —O— | 4-fluoro-2-propargyloxyphenyl | 2,5-difluoro-4-allyloxyphenyl |
| methyl | methyl | —O— | 4-fluoro-2-propargyloxyphenyl | 6-allyloxypyridin-3-yl |
| methyl | methyl | —O— | 4-fluoro-2-propargyloxyphenyl | 6-propargyloxypyridin-3-yl |
| methyl | methyl | —O— | 4-fluoro-2-propargyloxyphenyl | 2-propargyloxy-6-trifluorophenyl |
| methyl | methyl | —O— | 4-fluoro-2-propargyloxyphenyl | 2-allyloxy-6-trifluormethylphenyl |
| methyl | methyl | —O— | 4-fluoro-2-propargyloxyphenyl | 2-chloro-6-propargyloxyphenyl |
| methyl | methyl | —O— | 4-fluoro-2-propargyloxyphenyl | 2-allyloxy-6-chlorophenyl |
| methyl | methyl | —O— | 4-fluoro-2-propargyloxyphenyl | 2,4-dimethyl-6-propargyloxyphenyl |
| methyl | methyl | —O— | 4-fluoro-2-propargyloxyphenyl | 2-allyloxy-4,6-dimethylphenyl |
| methyl | methyl | —O— | 2,6-difluoro-4-propargyloxyphenyl | 2,6-difluoro-4-propargyloxyphenyl |
| methyl | methyl | —O— | 2,6-difluoro-4-propargyloxyphenyl | 4-allyloxy-2,6-difluorophenyl |
| methyl | methyl | —O— | 2,6-difluoro-4-propargyloxyphenyl | 2,4-difluoro-6-propargyloxyphenyl |
| methyl | methyl | —O— | 2,6-difluoro-4-propargyloxyphenyl | 4-fluoro-2-propargyloxyphenyl |

| R¹ | R² | X | Q¹ | Q² |
|---|---|---|---|---|
| methyl | methyl | —O— | 2,6-difluoro-4-propargyloxyphenyl | 2-fluoro-6-propargyloxyphenyl |
| methyl | methyl | —O— | 2,6-difluoro-4-propargyloxyphenyl | 4-chloro-2-fluoro-6-propargyloxyphenyl |
| methyl | methyl | —O— | 2,6-difluoro-4-propargyloxyphenyl | 2-chloro-4-fluoro-6-propargyloxyphenyl |
| methyl | methyl | —O— | 2,6-difluoro-4-propargyloxyphenyl | 4-allyloxy-2-fluorophenyl |
| methyl | methyl | —O— | 2,6-difluoro-4-propargyloxyphenyl | 2-fluoro-4-propargyloxyphenyl |
| methyl | methyl | —O— | 2,6-difluoro-4-propargyloxyphenyl | 2-allyloxyphenyl |
| methyl | methyl | —O— | 2,6-difluoro-4-propargyloxyphenyl | 2-propargyloxyphenyl |
| methyl | methyl | —O— | 2,6-difluoro-4-propargyloxyphenyl | 2-allyloxy-5-fluorophenyl |
| methyl | methyl | —O— | 2,6-difluoro-4-propargyloxyphenyl | 5-fluoro-2-propargyloxyphenyl |
| methyl | methyl | —O— | 2,6-difluoro-4-propargyloxyphenyl | 2-allyloxy-4-methylphenyl |
| methyl | methyl | —O— | 2,6-difluoro-4-propargyloxyphenyl | 4-methyl-2-propargyloxyphenyl |
| methyl | methyl | —O— | 2,6-difluoro-4-propargyloxyphenyl | 2-allyloxy-5-cyanophenyl |
| methyl | methyl | —O— | 2,6-difluoro-4-propargyloxyphenyl | 5-cyano-2-propargyloxyphenyl |
| methyl | methyl | —O— | 2,6-difluoro-4-propargyloxyphenyl | 5-allyloxy-2-fluorophenyl |
| methyl | methyl | —O— | 2,6-difluoro-4-propargyloxyphenyl | 2-fluoro-5-propargyloxyphenyl |
| methyl | methyl | —O— | 2,6-difluoro-4-propargyloxyphenyl | 4-allyloxy-2-chlorophenyl |
| methyl | methyl | —O— | 2,6-difluoro-4-propargyloxyphenyl | 2-chloro-4-propargyloxyphenyl |
| methyl | methyl | —O— | 2,6-difluoro-4-propargyloxyphenyl | 4-allyloxy-3-fluorophenyl |
| methyl | methyl | —O— | 2,6-difluoro-4-propargyloxyphenyl | 3-fluoro-4-propargyloxyphenyl |
| methyl | methyl | —O— | 2,6-difluoro-4-propargyloxyphenyl | 4-allyloxyphenyl |
| methyl | methyl | —O— | 2,6-difluoro-4-propargyloxyphenyl | 4-propargyloxyphenyl |
| methyl | methyl | —O— | 2,6-difluoro-4-propargyloxyphenyl | 3-fluoro-5-propargyloxyphenyl |
| methyl | methyl | —O— | 2,6-difluoro-4-propargyloxyphenyl | 3-fluoro-5-allyloxyphenyl |
| methyl | methyl | —O— | 2,6-difluoro-4-propargyloxyphenyl | 2,5-difluoro-4-propargyloxyphenyl |
| methyl | methyl | —O— | 2,6-difluoro-4-propargyloxyphenyl | 2,5-difluoro-4-allyloxyphenyl |
| methyl | methyl | —O— | 2,6-difluoro-4-propargyloxyphenyl | 6-allyloxypyridin-3-yl |
| methyl | methyl | —O— | 2,6-difluoro-4-propargyloxyphenyl | 6-propargyloxypyridin-3-yl |
| methyl | methyl | —O— | 2,6-difluoro-4-propargyloxyphenyl | 2-propargyloxy-6-trifluorophenyl |
| methyl | methyl | —O— | 2,6-difluoro-4-propargyloxyphenyl | 2-allyloxy-6-trifluormethylphenyl |
| methyl | methyl | —O— | 2,6-difluoro-4-propargyloxyphenyl | 2-chloro-6-propargyloxyphenyl |
| methyl | methyl | —O— | 2,6-difluoro-4-propargyloxyphenyl | 2-allyloxy-6-chlorophenyl |
| methyl | methyl | —O— | 2,6-difluoro-4-propargyloxyphenyl | 2,4-dimethyl-6-propargyloxyphenyl |
| methyl | methyl | —O— | 2,6-difluoro-4-propargyloxyphenyl | 2-allyloxy-4,6-dimethylphenyl |
| methyl | methyl | —O— | 2-fluoro-5-(furan-2-yl)phenyl | 2,6-difluoro-4-propargyloxyphenyl |
| methyl | methyl | —O— | 2-fluoro-5-(furan-2-yl)phenyl | 4-allyloxy-2,6-difluorophenyl |
| methyl | methyl | —O— | 2-fluoro-5-(furan-2-yl)phenyl | 2,4-difluoro-6-propargyloxyphenyl |
| methyl | methyl | —O— | 2-fluoro-5-(furan-2-yl)phenyl | 4-fluoro-2-propargyloxyphenyl |
| methyl | methyl | —O— | 2-fluoro-5-(furan-2-yl)phenyl | 2-fluoro-6-propargyloxyphenyl |
| methyl | methyl | —O— | 2-fluoro-5-(furan-2-yl)phenyl | 4-chloro-2-fluoro-6-propargyloxyphenyl |
| methyl | methyl | —O— | 2-fluoro-5-(furan-2-yl)phenyl | 2-chloro-4-fluoro-6-propargyloxyphenyl |
| methyl | methyl | —O— | 2-fluoro-5-(furan-2-yl)phenyl | 4-allyloxy-2-fluorophenyl |
| methyl | methyl | —O— | 2-fluoro-5-(furan-2-yl)phenyl | 2-fluoro-4-propargyloxyphenyl |

-continued

| R¹ | R² | X | Q¹ | Q² |
|---|---|---|---|---|
| methyl | methyl | —O— | 2-fluoro-5-(furan-2-yl)phenyl | 2-allyloxyphenyl |
| methyl | methyl | —O— | 2-fluoro-5-(furan-2-yl)phenyl | 2-propargyloxyphenyl |
| methyl | methyl | —O— | 2-fluoro-5-(furan-2-yl)phenyl | 2-allyloxy-5-fluorophenyl |
| methyl | methyl | —O— | 2-fluoro-5-(furan-2-yl)phenyl | 5-fluoro-2-propargyloxyphenyl |
| methyl | methyl | —O— | 2-fluoro-5-(furan-2-yl)phenyl | 2-allyloxy-4-methylphenyl |
| methyl | methyl | —O— | 2-fluoro-5-(furan-2-yl)phenyl | 4-methyl-2-propargyloxyphenyl |
| methyl | methyl | —O— | 2-fluoro-5-(furan-2-yl)phenyl | 2-allyloxy-5-cyanophenyl |
| methyl | methyl | —O— | 2-fluoro-5-(furan-2-yl)phenyl | 5-cyano-2-propargyloxyphenyl |
| methyl | methyl | —O— | 2-fluoro-5-(furan-2-yl)phenyl | 5-allyloxy-2-fluorophenyl |
| methyl | methyl | —O— | 2-fluoro-5-(furan-2-yl)phenyl | 2-fluoro-5-propargyloxyphenyl |
| methyl | methyl | —O— | 2-fluoro-5-(furan-2-yl)phenyl | 4-allyloxy-2-chlorophenyl |
| methyl | methyl | —O— | 2-fluoro-5-(furan-2-yl)phenyl | 2-chloro-4-propargyloxyphenyl |
| methyl | methyl | —O— | 2-fluoro-5-(furan-2-yl)phenyl | 4-allyloxy-3-fluorophenyl |
| methyl | methyl | —O— | 2-fluoro-5-(furan-2-yl)phenyl | 3-fluoro-4-propargyloxyphenyl |
| methyl | methyl | —O— | 2-fluoro-5-(furan-2-yl)phenyl | 4-allyloxyphenyl |
| methyl | methyl | —O— | 2-fluoro-5-(furan-2-yl)phenyl | 4-propargyloxyphenyl |
| methyl | methyl | —O— | 2-fluoro-5-(furan-2-yl)phenyl | 3-fluoro-5-propargyloxyphenyl |
| methyl | methyl | —O— | 2-fluoro-5-(furan-2-yl)phenyl | 3-fluoro-5-allyloxyphenyl |
| methyl | methyl | —O— | 2-fluoro-5-(furan-2-yl)phenyl | 2,5-difluoro-4-propargyloxyphenyl |
| methyl | methyl | —O— | 2-fluoro-5-(furan-2-yl)phenyl | 2,5-difluoro-4-allyloxyphenyl |
| methyl | methyl | —O— | 2-fluoro-5-(furan-2-yl)phenyl | 6-allyloxypyridin-3-yl |
| methyl | methyl | —O— | 2-fluoro-5-(furan-2-yl)phenyl | 6-propargyloxypyridin-3-yl |
| methyl | methyl | —O— | 2-fluoro-5-(furan-2-yl)phenyl | 2-propargyloxy-6-trifluorophenyl |
| methyl | methyl | —O— | 2-fluoro-5-(furan-2-yl)phenyl | 2-allyloxy-6-trifluormethylphenyl |
| methyl | methyl | —O— | 2-fluoro-5-(furan-2-yl)phenyl | 2-chloro-6-propargyloxyphenyl |
| methyl | methyl | —O— | 2-fluoro-5-(furan-2-yl)phenyl | 2-allyloxy-6-chlorophenyl |
| methyl | methyl | —O— | 2-fluoro-5-(furan-2-yl)phenyl | 2,4-dimethyl-6-propargyloxyphenyl |
| methyl | methyl | —O— | 2-fluoro-5-(furan-2-yl)phenyl | 2-allyloxy-4,6-dimethylphenyl |
| Cl— | methyl | —(NH)— | 2-chloro-4-fluorophenyl | 2,6-difluoro-4-propargyloxyphenyl |
| Cl— | methyl | —(NH)— | 2-chloro-4-fluorophenyl | 4-allyloxy-2,6-difluorophenyl |
| Cl— | methyl | —(NH)— | 2-chloro-4-fluorophenyl | 2,4-difluoro-6-propargyloxyphenyl |
| Cl— | methyl | —(NH)— | 2-chloro-4-fluorophenyl | 4-fluoro-2-propargyloxyphenyl |
| Cl— | methyl | —(NH)— | 2-chloro-4-fluorophenyl | 2-fluoro-6-propargyloxyphenyl |
| Cl— | methyl | —(NH)— | 2-chloro-4-fluorophenyl | 4-chloro-2-fluoro-6-propargyloxyphenyl |
| Cl— | methyl | —(NH)— | 2-chloro-4-fluorophenyl | 2-chloro-4-fluoro-6-propargyloxyphenyl |
| Cl— | methyl | —(NH)— | 2-chloro-4-fluorophenyl | 4-allyloxy-2-fluorophenyl |
| Cl— | methyl | —(NH)— | 2-chloro-4-fluorophenyl | 2-fluoro-4-propargyloxyphenyl |
| Cl— | methyl | —(NH)— | 2-chloro-4-fluorophenyl | 2-allyloxyphenyl |
| Cl— | methyl | —(NH)— | 2-chloro-4-fluorophenyl | 2-propargyloxyphenyl |
| Cl— | methyl | —(NH)— | 2-chloro-4-fluorophenyl | 2-allyloxy-5-fluorophenyl |
| Cl— | methyl | —(NH)— | 2-chloro-4-fluorophenyl | 5-fluoro-2-propargyloxyphenyl |
| Cl— | methyl | —(NH)— | 2-chloro-4-fluorophenyl | 2-allyloxy-4-methylphenyl |
| Cl— | methyl | —(NH)— | 2-chloro-4-fluorophenyl | 4-methyl-2-propargyloxyphenyl |
| Cl— | methyl | —(NH)— | 2-chloro-4-fluorophenyl | 2-allyloxy-5-cyanophenyl |
| Cl— | methyl | —(NH)— | 2-chloro-4-fluorophenyl | 5-cyano-2-propargyloxyphenyl |
| Cl— | methyl | —(NH)— | 2-chloro-4-fluorophenyl | 5-allyloxy-2-fluorophenyl |
| Cl— | methyl | —(NH)— | 2-chloro-4-fluorophenyl | 2-fluoro-5-propargyloxyphenyl |
| Cl— | methyl | —(NH)— | 2-chloro-4-fluorophenyl | 4-allyloxy-2-chlorophenyl |
| Cl— | methyl | —(NH)— | 2-chloro-4-fluorophenyl | 2-chloro-4-propargyloxyphenyl |
| Cl— | methyl | —(NH)— | 2-chloro-4-fluorophenyl | 4-allyloxy-3-fluorophenyl |
| Cl— | methyl | —(NH)— | 2-chloro-4-fluorophenyl | 3-fluoro-4-propargyloxyphenyl |
| Cl— | methyl | —(NH)— | 2-chloro-4-fluorophenyl | 4-allyloxyphenyl |
| Cl— | methyl | —(NH)— | 2-chloro-4-fluorophenyl | 4-propargyloxyphenyl |
| Cl— | methyl | —(NH)— | 2-chloro-4-fluorophenyl | 3-fluoro-5-propargyloxyphenyl |
| Cl— | methyl | —(NH)— | 2-chloro-4-fluorophenyl | 3-fluoro-5-allyloxyphenyl |
| Cl— | methyl | —(NH)— | 2-chloro-4-fluorophenyl | 2,5-difluoro-4-propargyloxyphenyl |
| Cl— | methyl | —(NH)— | 2-chloro-4-fluorophenyl | 2,5-difluoro-4-allyloxyphenyl |
| Cl— | methyl | —(NH)— | 2-chloro-4-fluorophenyl | 6-allyloxypyridin-3-yl |
| Cl— | methyl | —(NH)— | 2-chloro-4-fluorophenyl | 6-propargyloxypyridin-3-yl |
| Cl— | methyl | —(NH)— | 2-chloro-4-fluorophenyl | 2-propargyloxy-6-trifluorophenyl |
| Cl— | methyl | —(NH)— | 2-chloro-4-fluorophenyl | 2-allyloxy-6-trifluormethylphenyl |
| Cl— | methyl | —(NH)— | 2-chloro-4-fluorophenyl | 2-chloro-6-propargyloxyphenyl |
| Cl— | methyl | —(NH)— | 2-chloro-4-fluorophenyl | 2-allyloxy-6-chlorophenyl |
| Cl— | methyl | —(NH)— | 2-chloro-4-fluorophenyl | 2,4-dimethyl-6-propargyloxyphenyl |
| Cl— | methyl | —(NH)— | 2-chloro-4-fluorophenyl | 2-allyloxy-4,6-dimethylphenyl |
| Cl— | methyl | —(NH)— | 2,4-dichlorophenyl | 2,6-difluoro-4-propargyloxyphenyl |
| Cl— | methyl | —(NH)— | 2,4-dichlorophenyl | 4-allyloxy-2,6-difluorophenyl |
| Cl— | methyl | —(NH)— | 2,4-dichlorophenyl | 2,4-difluoro-6-propargyloxyphenyl |
| Cl— | methyl | —(NH)— | 2,4-dichlorophenyl | 4-fluoro-2-propargyloxyphenyl |
| Cl— | methyl | —(NH)— | 2,4-dichlorophenyl | 2-fluoro-6-propargyloxyphenyl |
| Cl— | methyl | —(NH)— | 2,4-dichlorophenyl | 4-chloro-2-fluoro-6-propargyloxyphenyl |
| Cl— | methyl | —(NH)— | 2,4-dichlorophenyl | 2-chloro-4-fluoro-6-propargyloxyphenyl |
| Cl— | methyl | —(NH)— | 2,4-dichlorophenyl | 4-allyloxy-2-fluorophenyl |

-continued

| R¹ | R² | X | Q¹ | Q² |
|---|---|---|---|---|
| Cl— | methyl | —(NH)— | 2,4-dichlorophenyl | 2-fluoro-4-propargyloxyphenyl |
| Cl— | methyl | —(NH)— | 2,4-dichlorophenyl | 2-allyloxyphenyl |
| Cl— | methyl | —(NH)— | 2,4-dichlorophenyl | 2-propargyloxyphenyl |
| Cl— | methyl | —(NH)— | 2,4-dichlorophenyl | 2-allyloxy-5-fluorophenyl |
| Cl— | methyl | —(NH)— | 2,4-dichlorophenyl | 5-fluoro-2-propargyloxyphenyl |
| Cl— | methyl | —(NH)— | 2,4-dichlorophenyl | 2-allyloxy-4-methylphenyl |
| Cl— | methyl | —(NH)— | 2,4-dichlorophenyl | 4-methyl-2-propargyloxyphenyl |
| Cl— | methyl | —(NH)— | 2,4-dichlorophenyl | 2-allyloxy-5-cyanophenyl |
| Cl— | methyl | —(NH)— | 2,4-dichlorophenyl | 5-cyano-2-propargyloxyphenyl |
| Cl— | methyl | —(NH)— | 2,4-dichlorophenyl | 5-allyloxy-2-fluorophenyl |
| Cl— | methyl | —(NH)— | 2,4-dichlorophenyl | 2-fluoro-5-propargyloxyphenyl |
| Cl— | methyl | —(NH)— | 2,4-dichlorophenyl | 4-allyloxy-2-chlorophenyl |
| Cl— | methyl | —(NH)— | 2,4-dichlorophenyl | 2-chloro-4-propargyloxyphenyl |
| Cl— | methyl | —(NH)— | 2,4-dichlorophenyl | 4-allyloxy-3-fluorophenyl |
| Cl— | methyl | —(NH)— | 2,4-dichlorophenyl | 3-fluoro-4-propargyloxyphenyl |
| Cl— | methyl | —(NH)— | 2,4-dichlorophenyl | 4-allyloxyphenyl |
| Cl— | methyl | —(NH)— | 2,4-dichlorophenyl | 4-propargyloxyphenyl |
| Cl— | methyl | —(NH)— | 2,4-dichlorophenyl | 3-fluoro-5-propargyloxyphenyl |
| Cl— | methyl | —(NH)— | 2,4-dichlorophenyl | 3-fluoro-5-allyloxyphenyl |
| Cl— | methyl | —(NH)— | 2,4-dichlorophenyl | 2,5-difluoro-4-propargyloxyphenyl |
| Cl— | methyl | —(NH)— | 2,4-dichlorophenyl | 2,5-difluoro-4-allyloxyphenyl |
| Cl— | methyl | —(NH)— | 2,4-dichlorophenyl | 6-allyloxypyridin-3-yl |
| Cl— | methyl | —(NH)— | 2,4-dichlorophenyl | 6-propargyloxypyridin-3-yl |
| Cl— | methyl | —(NH)— | 2,4-dichlorophenyl | 2-propargyloxy-6-trifluorophenyl |
| Cl— | methyl | —(NH)— | 2,4-dichlorophenyl | 2-allyloxy-6-trifluormethylphenyl |
| Cl— | methyl | —(NH)— | 2,4-dichlorophenyl | 2-chloro-6-propargyloxyphenyl |
| Cl— | methyl | —(NH)— | 2,4-dichlorophenyl | 2-allyloxy-6-chlorophenyl |
| Cl— | methyl | —(NH)— | 2,4-dichlorophenyl | 2,4-dimethyl-6-propargyloxyphenyl |
| Cl— | methyl | —(NH)— | 2,4-dichlorophenyl | 2-allyloxy-4,6-dimethylphenyl |
| Cl— | methyl | —(NH)— | 2-fluorophenyl | 2,6-difluoro-4-propargyloxyphenyl |
| Cl— | methyl | —(NH)— | 2-fluorophenyl | 4-allyloxy-2,6-difluorophenyl |
| Cl— | methyl | —(NH)— | 2-fluorophenyl | 2,4-difluoro-6-propargyloxyphenyl |
| Cl— | methyl | —(NH)— | 2-fluorophenyl | 4-fluoro-2-propargyloxyphenyl |
| Cl— | methyl | —(NH)— | 2-fluorophenyl | 2-fluoro-6-propargyloxyphenyl |
| Cl— | methyl | —(NH)— | 2-fluorophenyl | 4-chloro-2-fluoro-6-propargyloxyphenyl |
| Cl— | methyl | —(NH)— | 2-fluorophenyl | 2-chloro-4-fluoro-6-propargyloxyphenyl |
| Cl— | methyl | —(NH)— | 2-fluorophenyl | 4-allyloxy-2-fluorophenyl |
| Cl— | methyl | —(NH)— | 2-fluorophenyl | 2-fluoro-4-propargyloxyphenyl |
| Cl— | methyl | —(NH)— | 2-fluorophenyl | 2-allyloxyphenyl |
| Cl— | methyl | —(NH)— | 2-fluorophenyl | 2-propargyloxyphenyl |
| Cl— | methyl | —(NH)— | 2-fluorophenyl | 2-allyloxy-5-fluorophenyl |
| Cl— | methyl | —(NH)— | 2-fluorophenyl | 5-fluoro-2-propargyloxyphenyl |
| Cl— | methyl | —(NH)— | 2-fluorophenyl | 2-allyloxy-4-methylphenyl |
| Cl— | methyl | —(NH)— | 2-fluorophenyl | 4-methyl-2-propargyloxyphenyl |
| Cl— | methyl | —(NH)— | 2-fluorophenyl | 2-allyloxy-5-cyanophenyl |
| Cl— | methyl | —(NH)— | 2-fluorophenyl | 5-cyano-2-propargyloxyphenyl |
| Cl— | methyl | —(NH)— | 2-fluorophenyl | 5-allyloxy-2-fluorophenyl |
| Cl— | methyl | —(NH)— | 2-fluorophenyl | 2-fluoro-5-propargyloxyphenyl |
| Cl— | methyl | —(NH)— | 2-fluorophenyl | 4-allyloxy-2-chlorophenyl |
| Cl— | methyl | —(NH)— | 2-fluorophenyl | 2-chloro-4-propargyloxyphenyl |
| Cl— | methyl | —(NH)— | 2-fluorophenyl | 4-allyloxy-3-fluorophenyl |
| Cl— | methyl | —(NH)— | 2-fluorophenyl | 3-fluoro-4-propargyloxyphenyl |
| Cl— | methyl | —(NH)— | 2-fluorophenyl | 4-allyloxyphenyl |
| Cl— | methyl | —(NH)— | 2-fluorophenyl | 4-propargyloxyphenyl |
| Cl— | methyl | —(NH)— | 2-fluorophenyl | 3-fluoro-5-propargyloxyphenyl |
| Cl— | methyl | —(NH)— | 2-fluorophenyl | 3-fluoro-5-allyloxyphenyl |
| Cl— | methyl | —(NH)— | 2-fluorophenyl | 2,5-difluoro-4-propargyloxyphenyl |
| Cl— | methyl | —(NH)— | 2-fluorophenyl | 2,5-difluoro-4-allyloxyphenyl |
| Cl— | methyl | —(NH)— | 2-fluorophenyl | 6-allyloxypyridin-3-yl |
| Cl— | methyl | —(NH)— | 2-fluorophenyl | 6-propargyloxypyridin-3-yl |
| Cl— | methyl | —(NH)— | 2-fluorophenyl | 2-propargyloxy-6-trifluorophenyl |
| Cl— | methyl | —(NH)— | 2-fluorophenyl | 2-allyloxy-6-trifluormethylphenyl |
| Cl— | methyl | —(NH)— | 2-fluorophenyl | 2-chloro-6-propargyloxyphenyl |
| Cl— | methyl | —(NH)— | 2-fluorophenyl | 2-allyloxy-6-chlorophenyl |
| Cl— | methyl | —(NH)— | 2-fluorophenyl | 2,4-dimethyl-6-propargyloxyphenyl |
| Cl— | methyl | —(NH)— | 2-fluorophenyl | 2-allyloxy-4,6-dimethylphenyl |
| Cl— | methyl | —(NH)— | 3,5-dimethoxyphenyl | 2,6-difluoro-4-propargyloxyphenyl |
| Cl— | methyl | —(NH)— | 3,5-dimethoxyphenyl | 4-allyloxy-2,6-difluorophenyl |
| Cl— | methyl | —(NH)— | 3,5-dimethoxyphenyl | 2,4-difluoro-6-propargyloxyphenyl |
| Cl— | methyl | —(NH)— | 3,5-dimethoxyphenyl | 4-fluoro-2-propargyloxyphenyl |
| Cl— | methyl | —(NH)— | 3,5-dimethoxyphenyl | 2-fluoro-6-propargyloxyphenyl |
| Cl— | methyl | —(NH)— | 3,5-dimethoxyphenyl | 4-chloro-2-fluoro-6-propargyloxyphenyl |
| Cl— | methyl | —(NH)— | 3,5-dimethoxyphenyl | 2-chloro-4-fluoro-6-propargyloxyphenyl |

-continued

| R¹ | R² | X | Q¹ | Q² |
|---|---|---|---|---|
| Cl— | methyl | —(NH)— | 3,5-dimethoxyphenyl | 4-allyloxy-2-fluorophenyl |
| Cl— | methyl | —(NH)— | 3,5-dimethoxyphenyl | 2-fluoro-4-propargyloxyphenyl |
| Cl— | methyl | —(NH)— | 3,5-dimethoxyphenyl | 2-allyloxyphenyl |
| Cl— | methyl | —(NH)— | 3,5-dimethoxyphenyl | 2-propargyloxyphenyl |
| Cl— | methyl | —(NH)— | 3,5-dimethoxyphenyl | 2-allyloxy-5-fluorophenyl |
| Cl— | methyl | —(NH)— | 3,5-dimethoxyphenyl | 5-fluoro-2-propargyloxyphenyl |
| Cl— | methyl | —(NH)— | 3,5-dimethoxyphenyl | 2-allyloxy-4-methylphenyl |
| Cl— | methyl | —(NH)— | 3,5-dimethoxyphenyl | 4-methyl-2-propargyloxyphenyl |
| Cl— | methyl | —(NH)— | 3,5-dimethoxyphenyl | 2-allyloxy-5-cyanophenyl |
| Cl— | methyl | —(NH)— | 3,5-dimethoxyphenyl | 5-cyano-2-propargyloxyphenyl |
| Cl— | methyl | —(NH)— | 3,5-dimethoxyphenyl | 5-allyloxy-2-fluorophenyl |
| Cl— | methyl | —(NH)— | 3,5-dimethoxyphenyl | 2-fluoro-5-propargyloxyphenyl |
| Cl— | methyl | —(NH)— | 3,5-dimethoxyphenyl | 4-allyloxy-2-chlorophenyl |
| Cl— | methyl | —(NH)— | 3,5-dimethoxyphenyl | 2-chloro-4-propargyloxyphenyl |
| Cl— | methyl | —(NH)— | 3,5-dimethoxyphenyl | 4-allyloxy-3-fluorophenyl |
| Cl— | methyl | —(NH)— | 3,5-dimethoxyphenyl | 3-fluoro-4-propargyloxyphenyl |
| Cl— | methyl | —(NH)— | 3,5-dimethoxyphenyl | 4-allyloxyphenyl |
| Cl— | methyl | —(NH)— | 3,5-dimethoxyphenyl | 4-propargyloxyphenyl |
| Cl— | methyl | —(NH)— | 3,5-dimethoxyphenyl | 3-fluoro-5-propargyloxyphenyl |
| Cl— | methyl | —(NH)— | 3,5-dimethoxyphenyl | 3-fluoro-5-allyloxyphenyl |
| Cl— | methyl | —(NH)— | 3,5-dimethoxyphenyl | 2,5-difluoro-4-propargyloxyphenyl |
| Cl— | methyl | —(NH)— | 3,5-dimethoxyphenyl | 2,5-difluoro-4-allyloxyphenyl |
| Cl— | methyl | —(NH)— | 3,5-dimethoxyphenyl | 6-allyloxypyridin-3-yl |
| Cl— | methyl | —(NH)— | 3,5-dimethoxyphenyl | 6-propargyloxypyridin-3-yl |
| Cl— | methyl | —(NH)— | 3,5-dimethoxyphenyl | 2-propargyloxy-6-trifluorophenyl |
| Cl— | methyl | —(NH)— | 3,5-dimethoxyphenyl | 2-allyloxy-6-trifluormethylphenyl |
| Cl— | methyl | —(NH)— | 3,5-dimethoxyphenyl | 2-chloro-6-propargyloxyphenyl |
| Cl— | methyl | —(NH)— | 3,5-dimethoxyphenyl | 2-allyloxy-6-chlorophenyl |
| Cl— | methyl | —(NH)— | 3,5-dimethoxyphenyl | 2,4-dimethyl-6-propargyloxyphenyl |
| Cl— | methyl | —(NH)— | 3,5-dimethoxyphenyl | 2-allyloxy-4,6-dimethylphenyl |
| Cl— | methyl | —(NH)— | 2,4-difluorphenyl | 2,6-difluoro-4-propargyloxyphenyl |
| Cl— | methyl | —(NH)— | 2,4-difluorphenyl | 4-allyloxy-2,6-difluorophenyl |
| Cl— | methyl | —(NH)— | 2,4-difluorphenyl | 2,4-difluoro-6-propargyloxyphenyl |
| Cl— | methyl | —(NH)— | 2,4-difluorphenyl | 4-fluoro-2-propargyloxyphenyl |
| Cl— | methyl | —(NH)— | 2,4-difluorphenyl | 2-fluoro-6-propargyloxyphenyl |
| Cl— | methyl | —(NH)— | 2,4-difluorphenyl | 4-chloro-2-fluoro-6-propargyloxyphenyl |
| Cl— | methyl | —(NH)— | 2,4-difluorphenyl | 2-chloro-4-fluoro-6-propargyloxyphenyl |
| Cl— | methyl | —(NH)— | 2,4-difluorphenyl | 4-allyloxy-2-fluorophenyl |
| Cl— | methyl | —(NH)— | 2,4-difluorphenyl | 2-fluoro-4-propargyloxyphenyl |
| Cl— | methyl | —(NH)— | 2,4-difluorphenyl | 2-allyloxyphenyl |
| Cl— | methyl | —(NH)— | 2,4-difluorphenyl | 2-propargyloxyphenyl |
| Cl— | methyl | —(NH)— | 2,4-difluorphenyl | 2-allyloxy-5-fluorophenyl |
| Cl— | methyl | —(NH)— | 2,4-difluorphenyl | 5-fluoro-2-propargyloxyphenyl |
| Cl— | methyl | —(NH)— | 2,4-difluorphenyl | 2-allyloxy-4-methylphenyl |
| Cl— | methyl | —(NH)— | 2,4-difluorphenyl | 4-methyl-2-propargyloxyphenyl |
| Cl— | methyl | —(NH)— | 2,4-difluorphenyl | 2-allyloxy-5-cyanophenyl |
| Cl— | methyl | —(NH)— | 2,4-difluorphenyl | 5-cyano-2-propargyloxyphenyl |
| Cl— | methyl | —(NH)— | 2,4-difluorphenyl | 5-allyloxy-2-fluorophenyl |
| Cl— | methyl | —(NH)— | 2,4-difluorphenyl | 2-fluoro-5-propargyloxyphenyl |
| Cl— | methyl | —(NH)— | 2,4-difluorphenyl | 4-allyloxy-2-chlorophenyl |
| Cl— | methyl | —(NH)— | 2,4-difluorphenyl | 2-chloro-4-propargyloxyphenyl |
| Cl— | methyl | —(NH)— | 2,4-difluorphenyl | 4-allyloxy-3-fluorophenyl |
| Cl— | methyl | —(NH)— | 2,4-difluorphenyl | 3-fluoro-4-propargyloxyphenyl |
| Cl— | methyl | —(NH)— | 2,4-difluorphenyl | 4-allyloxyphenyl |
| Cl— | methyl | —(NH)— | 2,4-difluorphenyl | 4-propargyloxyphenyl |
| Cl— | methyl | —(NH)— | 2,4-difluorphenyl | 3-fluoro-5-propargyloxyphenyl |
| Cl— | methyl | —(NH)— | 2,4-difluorphenyl | 3-fluoro-5-allyloxyphenyl |
| Cl— | methyl | —(NH)— | 2,4-difluorphenyl | 2,5-difluoro-4-propargyloxyphenyl |
| Cl— | methyl | —(NH)— | 2,4-difluorphenyl | 2,5-difluoro-4-allyloxyphenyl |
| Cl— | methyl | —(NH)— | 2,4-difluorphenyl | 6-allyloxypyridin-3-yl |
| Cl— | methyl | —(NH)— | 2,4-difluorphenyl | 6-propargyloxypyridin-3-yl |
| Cl— | methyl | —(NH)— | 2,4-difluorphenyl | 2-propargyloxy-6-trifluorophenyl |
| Cl— | methyl | —(NH)— | 2,4-difluorphenyl | 2-allyloxy-6-trifluormethylphenyl |
| Cl— | methyl | —(NH)— | 2,4-difluorphenyl | 2-chloro-6-propargyloxyphenyl |
| Cl— | methyl | —(NH)— | 2,4-difluorphenyl | 2-allyloxy-6-chlorophenyl |
| Cl— | methyl | —(NH)— | 2,4-difluorphenyl | 2,4-dimethyl-6-propargyloxyphenyl |
| Cl— | methyl | —(NH)— | 2,4-difluorphenyl | 2-allyloxy-4,6-dimethylphenyl |
| Cl— | methyl | —(NH)— | 2-fluoro-4-methoxyphenyl | 2,6-difluoro-4-propargyloxyphenyl |
| Cl— | methyl | —(NH)— | 2-fluoro-4-methoxyphenyl | 4-allyloxy-2,6-difluorophenyl |
| Cl— | methyl | —(NH)— | 2-fluoro-4-methoxyphenyl | 2,4-difluoro-6-propargyloxyphenyl |
| Cl— | methyl | —(NH)— | 2-fluoro-4-methoxyphenyl | 4-fluoro-2-propargyloxyphenyl |
| Cl— | methyl | —(NH)— | 2-fluoro-4-methoxyphenyl | 2-fluoro-6-propargyloxyphenyl |
| Cl— | methyl | —(NH)— | 2-fluoro-4-methoxyphenyl | 4-chloro-2-fluoro-6-propargyloxyphenyl |

-continued

| R¹ | R² | X | Q¹ | Q² |
|---|---|---|---|---|
| Cl— | methyl | —(NH)— | 2-fluoro-4-methoxyphenyl | 2-chloro-4-fluoro-6-propargyloxyphenyl |
| Cl— | methyl | —(NH)— | 2-fluoro-4-methoxyphenyl | 4-allyloxy-2-fluorophenyl |
| Cl— | methyl | —(NH)— | 2-fluoro-4-methoxyphenyl | 2-fluoro-4-propargyloxyphenyl |
| Cl— | methyl | —(NH)— | 2-fluoro-4-methoxyphenyl | 2-allyloxyphenyl |
| Cl— | methyl | —(NH)— | 2-fluoro-4-methoxyphenyl | 2-propargyloxyphenyl |
| Cl— | methyl | —(NH)— | 2-fluoro-4-methoxyphenyl | 2-allyloxy-5-fluorophenyl |
| Cl— | methyl | —(NH)— | 2-fluoro-4-methoxyphenyl | 5-fluoro-2-propargyloxyphenyl |
| Cl— | methyl | —(NH)— | 2-fluoro-4-methoxyphenyl | 2-allyloxy-4-methylphenyl |
| Cl— | methyl | —(NH)— | 2-fluoro-4-methoxyphenyl | 4-methyl-2-propargyloxyphenyl |
| Cl— | methyl | —(NH)— | 2-fluoro-4-methoxyphenyl | 2-allyloxy-5-cyanophenyl |
| Cl— | methyl | —(NH)— | 2-fluoro-4-methoxyphenyl | 5-cyano-2-propargyloxyphenyl |
| Cl— | methyl | —(NH)— | 2-fluoro-4-methoxyphenyl | 5-allyloxy-2-fluorophenyl |
| Cl— | methyl | —(NH)— | 2-fluoro-4-methoxyphenyl | 2-fluoro-5-propargyloxyphenyl |
| Cl— | methyl | —(NH)— | 2-fluoro-4-methoxyphenyl | 4-allyloxy-2-chlorophenyl |
| Cl— | methyl | —(NH)— | 2-fluoro-4-methoxyphenyl | 2-chloro-4-propargyloxyphenyl |
| Cl— | methyl | —(NH)— | 2-fluoro-4-methoxyphenyl | 4-allyloxy-3-fluorophenyl |
| Cl— | methyl | —(NH)— | 2-fluoro-4-methoxyphenyl | 3-fluoro-4-propargyloxyphenyl |
| Cl— | methyl | —(NH)— | 2-fluoro-4-methoxyphenyl | 4-allyloxyphenyl |
| Cl— | methyl | —(NH)— | 2-fluoro-4-methoxyphenyl | 4-propargyloxyphenyl |
| Cl— | methyl | —(NH)— | 2-fluoro-4-methoxyphenyl | 3-fluoro-5-propargyloxyphenyl |
| Cl— | methyl | —(NH)— | 2-fluoro-4-methoxyphenyl | 3-fluoro-5-allyloxyphenyl |
| Cl— | methyl | —(NH)— | 2-fluoro-4-methoxyphenyl | 2,5-difluoro-4-propargyloxyphenyl |
| Cl— | methyl | —(NH)— | 2-fluoro-4-methoxyphenyl | 2,5-difluoro-4-allyloxyphenyl |
| Cl— | methyl | —(NH)— | 2-fluoro-4-methoxyphenyl | 6-allyloxypyridin-3-yl |
| Cl— | methyl | —(NH)— | 2-fluoro-4-methoxyphenyl | 6-propargyloxypyridin-3-yl |
| Cl— | methyl | —(NH)— | 2-fluoro-4-methoxyphenyl | 2-propargyloxy-6-trifluorophenyl |
| Cl— | methyl | —(NH)— | 2-fluoro-4-methoxyphenyl | 2-allyloxy-6-trifluormethylphenyl |
| Cl— | methyl | —(NH)— | 2-fluoro-4-methoxyphenyl | 2-chloro-6-propargyloxyphenyl |
| Cl— | methyl | —(NH)— | 2-fluoro-4-methoxyphenyl | 2-allyloxy-6-chlorophenyl |
| Cl— | methyl | —(NH)— | 2-fluoro-4-methoxyphenyl | 2,4-dimethyl-6-propargyloxyphenyl |
| Cl— | methyl | —(NH)— | 2-fluoro-4-methoxyphenyl | 2-allyloxy-4,6-dimethylphenyl |
| Cl— | methyl | —(NH)— | (2-chloropyridin)-5-yl | 2,6-difluoro-4-propargyloxyphenyl |
| Cl— | methyl | —(NH)— | (2-chloropyridin)-5-yl | 4-allyloxy-2,6-difluorophenyl |
| Cl— | methyl | —(NH)— | (2-chloropyridin)-5-yl | 2,4-difluoro-6-propargyloxyphenyl |
| Cl— | methyl | —(NH)— | (2-chloropyridin)-5-yl | 4-fluoro-2-propargyloxyphenyl |
| Cl— | methyl | —(NH)— | (2-chloropyridin)-5-yl | 2-fluoro-6-propargyloxyphenyl |
| Cl— | methyl | —(NH)— | (2-chloropyridin)-5-yl | 4-chloro-2-fluoro-6-propargyloxyphenyl |
| Cl— | methyl | —(NH)— | (2-chloropyridin)-5-yl | 2-chloro-4-fluoro-6-propargyloxyphenyl |
| Cl— | methyl | —(NH)— | (2-chloropyridin)-5-yl | 4-allyloxy-2-fluorophenyl |
| Cl— | methyl | —(NH)— | (2-chloropyridin)-5-yl | 2-fluoro-4-propargyloxyphenyl |
| Cl— | methyl | —(NH)— | (2-chloropyridin)-5-yl | 2-allyloxyphenyl |
| Cl— | methyl | —(NH)— | (2-chloropyridin)-5-yl | 2-propargyloxyphenyl |
| Cl— | methyl | —(NH)— | (2-chloropyridin)-5-yl | 2-allyloxy-5-fluorophenyl |
| Cl— | methyl | —(NH)— | (2-chloropyridin)-5-yl | 5-fluoro-2-propargyloxyphenyl |
| Cl— | methyl | —(NH)— | (2-chloropyridin)-5-yl | 2-allyloxy-4-methylphenyl |
| Cl— | methyl | —(NH)— | (2-chloropyridin)-5-yl | 4-methyl-2-propargyloxyphenyl |
| Cl— | methyl | —(NH)— | (2-chloropyridin)-5-yl | 2-allyloxy-5-cyanophenyl |
| Cl— | methyl | —(NH)— | (2-chloropyridin)-5-yl | 5-cyano-2-propargyloxyphenyl |
| Cl— | methyl | —(NH)— | (2-chloropyridin)-5-yl | 5-allyloxy-2-fluorophenyl |
| Cl— | methyl | —(NH)— | (2-chloropyridin)-5-yl | 2-fluoro-5-propargyloxyphenyl |
| Cl— | methyl | —(NH)— | (2-chloropyridin)-5-yl | 4-allyloxy-2-chlorophenyl |
| Cl— | methyl | —(NH)— | (2-chloropyridin)-5-yl | 2-chloro-4-propargyloxyphenyl |
| Cl— | methyl | —(NH)— | (2-chloropyridin)-5-yl | 4-allyloxy-3-fluorophenyl |
| Cl— | methyl | —(NH)— | (2-chloropyridin)-5-yl | 3-fluoro-4-propargyloxyphenyl |
| Cl— | methyl | —(NH)— | (2-chloropyridin)-5-yl | 4-allyloxyphenyl |
| Cl— | methyl | —(NH)— | (2-chloropyridin)-5-yl | 4-propargyloxyphenyl |
| Cl— | methyl | —(NH)— | (2-chloropyridin)-5-yl | 3-fluoro-5-propargyloxyphenyl |
| Cl— | methyl | —(NH)— | (2-chloropyridin)-5-yl | 3-fluoro-5-allyloxyphenyl |
| Cl— | methyl | —(NH)— | (2-chloropyridin)-5-yl | 2,5-difluoro-4-propargyloxyphenyl |
| Cl— | methyl | —(NH)— | (2-chloropyridin)-5-yl | 2,5-difluoro-4-allyloxyphenyl |
| Cl— | methyl | —(NH)— | (2-chloropyridin)-5-yl | 6-allyloxypyridin-3-yl |
| Cl— | methyl | —(NH)— | (2-chloropyridin)-5-yl | 6-propargyloxypyridin-3-yl |
| Cl— | methyl | —(NH)— | (2-chloropyridin)-5-yl | 2-propargyloxy-6-trifluorophenyl |
| Cl— | methyl | —(NH)— | (2-chloropyridin)-5-yl | 2-allyloxy-6-trifluormethylphenyl |
| Cl— | methyl | —(NH)— | (2-chloropyridin)-5-yl | 2-chloro-6-propargyloxyphenyl |
| Cl— | methyl | —(NH)— | (2-chloropyridin)-5-yl | 2-allyloxy-6-chlorophenyl |
| Cl— | methyl | —(NH)— | (2-chloropyridin)-5-yl | 2,4-dimethyl-6-propargyloxyphenyl |
| Cl— | methyl | —(NH)— | (2-chloropyridin)-5-yl | 2-allyloxy-4,6-dimethylphenyl |
| Cl— | methyl | —(NH)— | 4-allyloxy-2-fluorophenyl | 2,6-difluoro-4-propargyloxyphenyl |
| Cl— | methyl | —(NH)— | 4-allyloxy-2-fluorophenyl | 4-allyloxy-2,6-difluorophenyl |
| Cl— | methyl | —(NH)— | 4-allyloxy-2-fluorophenyl | 2,4-difluoro-6-propargyloxyphenyl |
| Cl— | methyl | —(NH)— | 4-allyloxy-2-fluorophenyl | 4-fluoro-2-propargyloxyphenyl |
| Cl— | methyl | —(NH)— | 4-allyloxy-2-fluorophenyl | 2-fluoro-6-propargyloxyphenyl |

-continued

| R¹ | R² | X | Q¹ | Q² |
|---|---|---|---|---|
| Cl— | methyl | —(NH)— | 4-allyloxy-2-fluorophenyl | 4-chloro-2-fluoro-6-propargyloxyphenyl |
| Cl— | methyl | —(NH)— | 4-allyloxy-2-fluorophenyl | 2-chloro-4-fluoro-6-propargyloxyphenyl |
| Cl— | methyl | —(NH)— | 4-allyloxy-2-fluorophenyl | 4-allyloxy-2-fluorophenyl |
| Cl— | methyl | —(NH)— | 4-allyloxy-2-fluorophenyl | 2-fluoro-4-propargyloxyphenyl |
| Cl— | methyl | —(NH)— | 4-allyloxy-2-fluorophenyl | 2-allyloxyphenyl |
| Cl— | methyl | —(NH)— | 4-allyloxy-2-fluorophenyl | 2-propargyloxyphenyl |
| Cl— | methyl | —(NH)— | 4-allyloxy-2-fluorophenyl | 2-allyloxy-5-fluorophenyl |
| Cl— | methyl | —(NH)— | 4-allyloxy-2-fluorophenyl | 5-fluoro-2-propargyloxyphenyl |
| Cl— | methyl | —(NH)— | 4-allyloxy-2-fluorophenyl | 2-allyloxy-4-methylphenyl |
| Cl— | methyl | —(NH)— | 4-allyloxy-2-fluorophenyl | 4-methyl-2-propargyloxyphenyl |
| Cl— | methyl | —(NH)— | 4-allyloxy-2-fluorophenyl | 2-allyloxy-5-cyanophenyl |
| Cl— | methyl | —(NH)— | 4-allyloxy-2-fluorophenyl | 5-cyano-2-propargyloxyphenyl |
| Cl— | methyl | —(NH)— | 4-allyloxy-2-fluorophenyl | 5-allyloxy-2-fluorophenyl |
| Cl— | methyl | —(NH)— | 4-allyloxy-2-fluorophenyl | 2-fluoro-5-propargyloxyphenyl |
| Cl— | methyl | —(NH)— | 4-allyloxy-2-fluorophenyl | 4-allyloxy-2-chlorophenyl |
| Cl— | methyl | —(NH)— | 4-allyloxy-2-fluorophenyl | 2-chloro-4-propargyloxyphenyl |
| Cl— | methyl | —(NH)— | 4-allyloxy-2-fluorophenyl | 4-allyloxy-3-fluorophenyl |
| Cl— | methyl | —(NH)— | 4-allyloxy-2-fluorophenyl | 3-fluoro-4-propargyloxyphenyl |
| Cl— | methyl | —(NH)— | 4-allyloxy-2-fluorophenyl | 4-allyloxyphenyl |
| Cl— | methyl | —(NH)— | 4-allyloxy-2-fluorophenyl | 4-propargyloxyphenyl |
| Cl— | methyl | —(NH)— | 4-allyloxy-2-fluorophenyl | 3-fluoro-5-propargyloxyphenyl |
| Cl— | methyl | —(NH)— | 4-allyloxy-2-fluorophenyl | 3-fluoro-5-allyloxyphenyl |
| Cl— | methyl | —(NH)— | 4-allyloxy-2-fluorophenyl | 2,5-difluoro-4-propargyloxyphenyl |
| Cl— | methyl | —(NH)— | 4-allyloxy-2-fluorophenyl | 2,5-difluoro-4-allyloxyphenyl |
| Cl— | methyl | —(NH)— | 4-allyloxy-2-fluorophenyl | 6-allyloxypyridin-3-yl |
| Cl— | methyl | —(NH)— | 4-allyloxy-2-fluorophenyl | 6-propargyloxypyridin-3-yl |
| Cl— | methyl | —(NH)— | 4-allyloxy-2-fluorophenyl | 2-propargyloxy-6-trifluorophenyl |
| Cl— | methyl | —(NH)— | 4-allyloxy-2-fluorophenyl | 2-allyloxy-6-trifluormethylphenyl |
| Cl— | methyl | —(NH)— | 4-allyloxy-2-fluorophenyl | 2-chloro-6-propargyloxyphenyl |
| Cl— | methyl | —(NH)— | 4-allyloxy-2-fluorophenyl | 2-allyloxy-6-chlorophenyl |
| Cl— | methyl | —(NH)— | 4-allyloxy-2-fluorophenyl | 2,4-dimethyl-6-propargyloxyphenyl |
| Cl— | methyl | —(NH)— | 4-allyloxy-2-fluorophenyl | 2-allyloxy-4,6-dimethylphenyl |
| Cl— | methyl | —(NH)— | 2-propargyloxyphenyl | 2,6-difluoro-4-propargyloxyphenyl |
| Cl— | methyl | —(NH)— | 2-propargyloxyphenyl | 4-allyloxy-2,6-difluorophenyl |
| Cl— | methyl | —(NH)— | 2-propargyloxyphenyl | 2,4-difluoro-6-propargyloxyphenyl |
| Cl— | methyl | —(NH)— | 2-propargyloxyphenyl | 4-fluoro-2-propargyloxyphenyl |
| Cl— | methyl | —(NH)— | 2-propargyloxyphenyl | 2-fluoro-6-propargyloxyphenyl |
| Cl— | methyl | —(NH)— | 2-propargyloxyphenyl | 4-chloro-2-fluoro-6-propargyloxyphenyl |
| Cl— | methyl | —(NH)— | 2-propargyloxyphenyl | 2-chloro-4-fluoro-6-propargyloxyphenyl |
| Cl— | methyl | —(NH)— | 2-propargyloxyphenyl | 4-allyloxy-2-fluorophenyl |
| Cl— | methyl | —(NH)— | 2-propargyloxyphenyl | 2-fluoro-4-propargyloxyphenyl |
| Cl— | methyl | —(NH)— | 2-propargyloxyphenyl | 2-allyloxyphenyl |
| Cl— | methyl | —(NH)— | 2-propargyloxyphenyl | 2-propargyloxyphenyl |
| Cl— | methyl | —(NH)— | 2-propargyloxyphenyl | 2-allyloxy-5-fluorophenyl |
| Cl— | methyl | —(NH)— | 2-propargyloxyphenyl | 5-fluoro-2-propargyloxyphenyl |
| Cl— | methyl | —(NH)— | 2-propargyloxyphenyl | 2-allyloxy-4-methylphenyl |
| Cl— | methyl | —(NH)— | 2-propargyloxyphenyl | 4-methyl-2-propargyloxyphenyl |
| Cl— | methyl | —(NH)— | 2-propargyloxyphenyl | 2-allyloxy-5-cyanophenyl |
| Cl— | methyl | —(NH)— | 2-propargyloxyphenyl | 5-cyano-2-propargyloxyphenyl |
| Cl— | methyl | —(NH)— | 2-propargyloxyphenyl | 5-allyloxy-2-fluorophenyl |
| Cl— | methyl | —(NH)— | 2-propargyloxyphenyl | 2-fluoro-5-propargyloxyphenyl |
| Cl— | methyl | —(NH)— | 2-propargyloxyphenyl | 4-allyloxy-2-chlorophenyl |
| Cl— | methyl | —(NH)— | 2-propargyloxyphenyl | 2-chloro-4-propargyloxyphenyl |
| Cl— | methyl | —(NH)— | 2-propargyloxyphenyl | 4-allyloxy-3-fluorophenyl |
| Cl— | methyl | —(NH)— | 2-propargyloxyphenyl | 3-fluoro-4-propargyloxyphenyl |
| Cl— | methyl | —(NH)— | 2-propargyloxyphenyl | 4-allyloxyphenyl |
| Cl— | methyl | —(NH)— | 2-propargyloxyphenyl | 4-propargyloxyphenyl |
| Cl— | methyl | —(NH)— | 2-propargyloxyphenyl | 3-fluoro-5-propargyloxyphenyl |
| Cl— | methyl | —(NH)— | 2-propargyloxyphenyl | 3-fluoro-5-allyloxyphenyl |
| Cl— | methyl | —(NH)— | 2-propargyloxyphenyl | 2,5-difluoro-4-propargyloxyphenyl |
| Cl— | methyl | —(NH)— | 2-propargyloxyphenyl | 2,5-difluoro-4-allyloxyphenyl |
| Cl— | methyl | —(NH)— | 2-propargyloxyphenyl | 6-allyloxypyridin-3-yl |
| Cl— | methyl | —(NH)— | 2-propargyloxyphenyl | 6-propargyloxypyridin-3-yl |
| Cl— | methyl | —(NH)— | 2-propargyloxyphenyl | 2-propargyloxy-6-trifluorophenyl |
| Cl— | methyl | —(NH)— | 2-propargyloxyphenyl | 2-allyloxy-6-trifluormethylphenyl |
| Cl— | methyl | —(NH)— | 2-propargyloxyphenyl | 2-chloro-6-propargyloxyphenyl |
| Cl— | methyl | —(NH)— | 2-propargyloxyphenyl | 2-allyloxy-6-chlorophenyl |
| Cl— | methyl | —(NH)— | 2-propargyloxyphenyl | 2,4-dimethyl-6-propargyloxyphenyl |
| Cl— | methyl | —(NH)— | 2-propargyloxyphenyl | 2-allyloxy-4,6-dimethylphenyl |
| Cl— | methyl | —(NH)— | 2,6-difluoro-4-methoxyphenyl | 2,6-difluoro-4-propargyloxyphenyl |
| Cl— | methyl | —(NH)— | 2,6-difluoro-4-methoxyphenyl | 4-allyloxy-2,6-difluorophenyl |
| Cl— | methyl | —(NH)— | 2,6-difluoro-4-methoxyphenyl | 2,4-difluoro-6-propargyloxyphenyl |
| Cl— | methyl | —(NH)— | 2,6-difluoro-4-methoxyphenyl | 4-fluoro-2-propargyloxyphenyl |

| R¹ | R² | X | Q¹ | Q² |
|---|---|---|---|---|
| Cl— | methyl | —(NH)— | 2,6-difluoro-4-methoxyphenyl | 2-fluoro-6-propargyloxyphenyl |
| Cl— | methyl | —(NH)— | 2,6-difluoro-4-methoxyphenyl | 4-chloro-2-fluoro-6-propargyloxyphenyl |
| Cl— | methyl | —(NH)— | 2,6-difluoro-4-methoxyphenyl | 2-chloro-4-fluoro-6-propargyloxyphenyl |
| Cl— | methyl | —(NH)— | 2,6-difluoro-4-methoxyphenyl | 4-allyloxy-2-fluorophenyl |
| Cl— | methyl | —(NH)— | 2,6-difluoro-4-methoxyphenyl | 2-fluoro-4-propargyloxyphenyl |
| Cl— | methyl | —(NH)— | 2,6-difluoro-4-methoxyphenyl | 2-allyloxyphenyl |
| Cl— | methyl | —(NH)— | 2,6-difluoro-4-methoxyphenyl | 2-propargyloxyphenyl |
| Cl— | methyl | —(NH)— | 2,6-difluoro-4-methoxyphenyl | 2-allyloxy-5-fluorophenyl |
| Cl— | methyl | —(NH)— | 2,6-difluoro-4-methoxyphenyl | 5-fluoro-2-propargyloxyphenyl |
| Cl— | methyl | —(NH)— | 2,6-difluoro-4-methoxyphenyl | 2-allyloxy-4-methylphenyl |
| Cl— | methyl | —(NH)— | 2,6-difluoro-4-methoxyphenyl | 4-methyl-2-propargyloxyphenyl |
| Cl— | methyl | —(NH)— | 2,6-difluoro-4-methoxyphenyl | 2-allyloxy-5-cyanophenyl |
| Cl— | methyl | —(NH)— | 2,6-difluoro-4-methoxyphenyl | 5-cyano-2-propargyloxyphenyl |
| Cl— | methyl | —(NH)— | 2,6-difluoro-4-methoxyphenyl | 5-allyloxy-2-fluorophenyl |
| Cl— | methyl | —(NH)— | 2,6-difluoro-4-methoxyphenyl | 2-fluoro-5-propargyloxyphenyl |
| Cl— | methyl | —(NH)— | 2,6-difluoro-4-methoxyphenyl | 4-allyloxy-2-chlorophenyl |
| Cl— | methyl | —(NH)— | 2,6-difluoro-4-methoxyphenyl | 2-chloro-4-propargyloxyphenyl |
| Cl— | methyl | —(NH)— | 2,6-difluoro-4-methoxyphenyl | 4-allyloxy-3-fluorophenyl |
| Cl— | methyl | —(NH)— | 2,6-difluoro-4-methoxyphenyl | 3-fluoro-4-propargyloxyphenyl |
| Cl— | methyl | —(NH)— | 2,6-difluoro-4-methoxyphenyl | 4-allyloxyphenyl |
| Cl— | methyl | —(NH)— | 2,6-difluoro-4-methoxyphenyl | 4-propargyloxyphenyl |
| Cl— | methyl | —(NH)— | 2,6-difluoro-4-methoxyphenyl | 3-fluoro-5-propargyloxyphenyl |
| Cl— | methyl | —(NH)— | 2,6-difluoro-4-methoxyphenyl | 3-fluoro-5-allyloxyphenyl |
| Cl— | methyl | —(NH)— | 2,6-difluoro-4-methoxyphenyl | 2,5-difluoro-4-propargyloxyphenyl |
| Cl— | methyl | —(NH)— | 2,6-difluoro-4-methoxyphenyl | 2,5-difluoro-4-allyloxyphenyl |
| Cl— | methyl | —(NH)— | 2,6-difluoro-4-methoxyphenyl | 6-allyloxypyridin-3-yl |
| Cl— | methyl | —(NH)— | 2,6-difluoro-4-methoxyphenyl | 6-propargyloxypyridin-3-yl |
| Cl— | methyl | —(NH)— | 2,6-difluoro-4-methoxyphenyl | 2-propargyloxy-6-trifluorophenyl |
| Cl— | methyl | —(NH)— | 2,6-difluoro-4-methoxyphenyl | 2-allyloxy-6-trifluormethylphenyl |
| Cl— | methyl | —(NH)— | 2,6-difluoro-4-methoxyphenyl | 2-chloro-6-propargyloxyphenyl |
| Cl— | methyl | —(NH)— | 2,6-difluoro-4-methoxyphenyl | 2-allyloxy-6-chlorophenyl |
| Cl— | methyl | —(NH)— | 2,6-difluoro-4-methoxyphenyl | 2,4-dimethyl-6-propargyloxyphenyl |
| Cl— | methyl | —(NH)— | 2,6-difluoro-4-methoxyphenyl | 2-allyloxy-4,6-dimethylphenyl |
| Cl— | methyl | —(NH)— | 2-fluoro-4-propargyloxyphenyl | 2,6-difluoro-4-propargyloxyphenyl |
| Cl— | methyl | —(NH)— | 2-fluoro-4-propargyloxyphenyl | 4-allyloxy-2,6-difluorophenyl |
| Cl— | methyl | —(NH)— | 2-fluoro-4-propargyloxyphenyl | 2,4-difluoro-6-propargyloxyphenyl |
| Cl— | methyl | —(NH)— | 2-fluoro-4-propargyloxyphenyl | 4-fluoro-2-propargyloxyphenyl |
| Cl— | methyl | —(NH)— | 2-fluoro-4-propargyloxyphenyl | 2-fluoro-6-propargyloxyphenyl |
| Cl— | methyl | —(NH)— | 2-fluoro-4-propargyloxyphenyl | 4-chloro-2-fluoro-6-propargyloxyphenyl |
| Cl— | methyl | —(NH)— | 2-fluoro-4-propargyloxyphenyl | 2-chloro-4-fluoro-6-propargyloxyphenyl |
| Cl— | methyl | —(NH)— | 2-fluoro-4-propargyloxyphenyl | 4-allyloxy-2-fluorophenyl |
| Cl— | methyl | —(NH)— | 2-fluoro-4-propargyloxyphenyl | 2-fluoro-4-propargyloxyphenyl |
| Cl— | methyl | —(NH)— | 2-fluoro-4-propargyloxyphenyl | 2-allyloxyphenyl |
| Cl— | methyl | —(NH)— | 2-fluoro-4-propargyloxyphenyl | 2-propargyloxyphenyl |
| Cl— | methyl | —(NH)— | 2-fluoro-4-propargyloxyphenyl | 2-allyloxy-5-fluorophenyl |
| Cl— | methyl | —(NH)— | 2-fluoro-4-propargyloxyphenyl | 5-fluoro-2-propargyloxyphenyl |
| Cl— | methyl | —(NH)— | 2-fluoro-4-propargyloxyphenyl | 2-allyloxy-4-methylphenyl |
| Cl— | methyl | —(NH)— | 2-fluoro-4-propargyloxyphenyl | 4-methyl-2-propargyloxyphenyl |
| Cl— | methyl | —(NH)— | 2-fluoro-4-propargyloxyphenyl | 2-allyloxy-5-cyanophenyl |
| Cl— | methyl | —(NH)— | 2-fluoro-4-propargyloxyphenyl | 5-cyano-2-propargyloxyphenyl |
| Cl— | methyl | —(NH)— | 2-fluoro-4-propargyloxyphenyl | 5-allyloxy-2-fluorophenyl |
| Cl— | methyl | —(NH)— | 2-fluoro-4-propargyloxyphenyl | 2-fluoro-5-propargyloxyphenyl |
| Cl— | methyl | —(NH)— | 2-fluoro-4-propargyloxyphenyl | 4-allyloxy-2-chlorophenyl |
| Cl— | methyl | —(NH)— | 2-fluoro-4-propargyloxyphenyl | 2-chloro-4-propargyloxyphenyl |
| Cl— | methyl | —(NH)— | 2-fluoro-4-propargyloxyphenyl | 4-allyloxy-3-fluorophenyl |
| Cl— | methyl | —(NH)— | 2-fluoro-4-propargyloxyphenyl | 3-fluoro-4-propargyloxyphenyl |
| Cl— | methyl | —(NH)— | 2-fluoro-4-propargyloxyphenyl | 4-allyloxyphenyl |
| Cl— | methyl | —(NH)— | 2-fluoro-4-propargyloxyphenyl | 4-propargyloxyphenyl |
| Cl— | methyl | —(NH)— | 2-fluoro-4-propargyloxyphenyl | 3-fluoro-5-propargyloxyphenyl |
| Cl— | methyl | —(NH)— | 2-fluoro-4-propargyloxyphenyl | 3-fluoro-5-allyloxyphenyl |
| Cl— | methyl | —(NH)— | 2-fluoro-4-propargyloxyphenyl | 2,5-difluoro-4-propargyloxyphenyl |
| Cl— | methyl | —(NH)— | 2-fluoro-4-propargyloxyphenyl | 2,5-difluoro-4-allyloxyphenyl |
| Cl— | methyl | —(NH)— | 2-fluoro-4-propargyloxyphenyl | 6-allyloxypyridin-3-yl |
| Cl— | methyl | —(NH)— | 2-fluoro-4-propargyloxyphenyl | 6-propargyloxypyridin-3-yl |
| Cl— | methyl | —(NH)— | 2-fluoro-4-propargyloxyphenyl | 2-propargyloxy-6-trifluorophenyl |
| Cl— | methyl | —(NH)— | 2-fluoro-4-propargyloxyphenyl | 2-allyloxy-6-trifluormethylphenyl |
| Cl— | methyl | —(NH)— | 2-fluoro-4-propargyloxyphenyl | 2-chloro-6-propargyloxyphenyl |
| Cl— | methyl | —(NH)— | 2-fluoro-4-propargyloxyphenyl | 2-allyloxy-6-chlorophenyl |
| Cl— | methyl | —(NH)— | 2-fluoro-4-propargyloxyphenyl | 2,4-dimethyl-6-propargyloxyphenyl |
| Cl— | methyl | —(NH)— | 2-fluoro-4-propargyloxyphenyl | 2-allyloxy-4,6-dimethylphenyl |
| Cl— | methyl | —(NH)— | 4-chloro-2-fluorophenyl | 2,6-difluoro-4-propargyloxyphenyl |
| Cl— | methyl | —(NH)— | 4-chloro-2-fluorophenyl | 4-allyloxy-2,6-difluorophenyl |
| Cl— | methyl | —(NH)— | 4-chloro-2-fluorophenyl | 2,4-difluoro-6-propargyloxyphenyl |

-continued

| R¹ | R² | X | Q¹ | Q² |
|---|---|---|---|---|
| Cl— | methyl | —(NH)— | 4-chloro-2-fluorophenyl | 4-fluoro-2-propargyloxyphenyl |
| Cl— | methyl | —(NH)— | 4-chloro-2-fluorophenyl | 2-fluoro-6-propargyloxyphenyl |
| Cl— | methyl | —(NH)— | 4-chloro-2-fluorophenyl | 4-chloro-2-fluoro-6-propargyloxyphenyl |
| Cl— | methyl | —(NH)— | 4-chloro-2-fluorophenyl | 2-chloro-4-fluoro-6-propargyloxyphenyl |
| Cl— | methyl | —(NH)— | 4-chloro-2-fluorophenyl | 4-allyloxy-2-fluorophenyl |
| Cl— | methyl | —(NH)— | 4-chloro-2-fluorophenyl | 2-fluoro-4-propargyloxyphenyl |
| Cl— | methyl | —(NH)— | 4-chloro-2-fluorophenyl | 2-allyloxyphenyl |
| Cl— | methyl | —(NH)— | 4-chloro-2-fluorophenyl | 2-propargyloxyphenyl |
| Cl— | methyl | —(NH)— | 4-chloro-2-fluorophenyl | 2-allyloxy-5-fluorophenyl |
| Cl— | methyl | —(NH)— | 4-chloro-2-fluorophenyl | 5-fluoro-2-propargyloxyphenyl |
| Cl— | methyl | —(NH)— | 4-chloro-2-fluorophenyl | 2-allyloxy-4-methylphenyl |
| Cl— | methyl | —(NH)— | 4-chloro-2-fluorophenyl | 4-methyl-2-propargyloxyphenyl |
| Cl— | methyl | —(NH)— | 4-chloro-2-fluorophenyl | 2-allyloxy-5-cyanophenyl |
| Cl— | methyl | —(NH)— | 4-chloro-2-fluorophenyl | 5-cyano-2-propargyloxyphenyl |
| Cl— | methyl | —(NH)— | 4-chloro-2-fluorophenyl | 5-allyloxy-2-fluorophenyl |
| Cl— | methyl | —(NH)— | 4-chloro-2-fluorophenyl | 2-fluoro-5-propargyloxyphenyl |
| Cl— | methyl | —(NH)— | 4-chloro-2-fluorophenyl | 4-allyloxy-2-chlorophenyl |
| Cl— | methyl | —(NH)— | 4-chloro-2-fluorophenyl | 2-chloro-4-propargyloxyphenyl |
| Cl— | methyl | —(NH)— | 4-chloro-2-fluorophenyl | 4-allyloxy-3-fluorophenyl |
| Cl— | methyl | —(NH)— | 4-chloro-2-fluorophenyl | 3-fluoro-4-propargyloxyphenyl |
| Cl— | methyl | —(NH)— | 4-chloro-2-fluorophenyl | 4-allyloxyphenyl |
| Cl— | methyl | —(NH)— | 4-chloro-2-fluorophenyl | 4-propargyloxyphenyl |
| Cl— | methyl | —(NH)— | 4-chloro-2-fluorophenyl | 3-fluoro-5-propargyloxyphenyl |
| Cl— | methyl | —(NH)— | 4-chloro-2-fluorophenyl | 3-fluoro-5-allyloxyphenyl |
| Cl— | methyl | —(NH)— | 4-chloro-2-fluorophenyl | 2,5-difluoro-4-propargyloxyphenyl |
| Cl— | methyl | —(NH)— | 4-chloro-2-fluorophenyl | 2,5-difluoro-4-allyloxyphenyl |
| Cl— | methyl | —(NH)— | 4-chloro-2-fluorophenyl | 6-allyloxypyridin-3-yl |
| Cl— | methyl | —(NH)— | 4-chloro-2-fluorophenyl | 6-propargyloxypyridin-3-yl |
| Cl— | methyl | —(NH)— | 4-chloro-2-fluorophenyl | 2-propargyloxy-6-trifluorophenyl |
| Cl— | methyl | —(NH)— | 4-chloro-2-fluorophenyl | 2-allyloxy-6-trifluormethylphenyl |
| Cl— | methyl | —(NH)— | 4-chloro-2-fluorophenyl | 2-chloro-6-propargyloxyphenyl |
| Cl— | methyl | —(NH)— | 4-chloro-2-fluorophenyl | 2-allyloxy-6-chlorophenyl |
| Cl— | methyl | —(NH)— | 4-chloro-2-fluorophenyl | 2,4-dimethyl-6-propargyloxyphenyl |
| Cl— | methyl | —(NH)— | 4-chloro-2-fluorophenyl | 2-allyloxy-4,6-dimethylphenyl |
| Cl— | methyl | —(NH)— | 2-bromo-4-fluorophenyl | 2,6-difluoro-4-propargyloxyphenyl |
| Cl— | methyl | —(NH)— | 2-bromo-4-fluorophenyl | 4-allyloxy-2,6-difluorophenyl |
| Cl— | methyl | —(NH)— | 2-bromo-4-fluorophenyl | 2,4-difluoro-6-propargyloxyphenyl |
| Cl— | methyl | —(NH)— | 2-bromo-4-fluorophenyl | 4-fluoro-2-propargyloxyphenyl |
| Cl— | methyl | —(NH)— | 2-bromo-4-fluorophenyl | 2-fluoro-6-propargyloxyphenyl |
| Cl— | methyl | —(NH)— | 2-bromo-4-fluorophenyl | 4-chloro-2-fluoro-6-propargyloxyphenyl |
| Cl— | methyl | —(NH)— | 2-bromo-4-fluorophenyl | 2-chloro-4-fluoro-6-propargyloxyphenyl |
| Cl— | methyl | —(NH)— | 2-bromo-4-fluorophenyl | 4-allyloxy-2-fluorophenyl |
| Cl— | methyl | —(NH)— | 2-bromo-4-fluorophenyl | 2-fluoro-4-propargyloxyphenyl |
| Cl— | methyl | —(NH)— | 2-bromo-4-fluorophenyl | 2-allyloxyphenyl |
| Cl— | methyl | —(NH)— | 2-bromo-4-fluorophenyl | 2-propargyloxyphenyl |
| Cl— | methyl | —(NH)— | 2-bromo-4-fluorophenyl | 2-allyloxy-5-fluorophenyl |
| Cl— | methyl | —(NH)— | 2-bromo-4-fluorophenyl | 5-fluoro-2-propargyloxyphenyl |
| Cl— | methyl | —(NH)— | 2-bromo-4-fluorophenyl | 2-allyloxy-4-methylphenyl |
| Cl— | methyl | —(NH)— | 2-bromo-4-fluorophenyl | 4-methyl-2-propargyloxyphenyl |
| Cl— | methyl | —(NH)— | 2-bromo-4-fluorophenyl | 2-allyloxy-5-cyanophenyl |
| Cl— | methyl | —(NH)— | 2-bromo-4-fluorophenyl | 5-cyano-2-propargyloxyphenyl |
| Cl— | methyl | —(NH)— | 2-bromo-4-fluorophenyl | 5-allyloxy-2-fluorophenyl |
| Cl— | methyl | —(NH)— | 2-bromo-4-fluorophenyl | 2-fluoro-5-propargyloxyphenyl |
| Cl— | methyl | —(NH)— | 2-bromo-4-fluorophenyl | 4-allyloxy-2-chlorophenyl |
| Cl— | methyl | —(NH)— | 2-bromo-4-fluorophenyl | 2-chloro-4-propargyloxyphenyl |
| Cl— | methyl | —(NH)— | 2-bromo-4-fluorophenyl | 4-allyloxy-3-fluorophenyl |
| Cl— | methyl | —(NH)— | 2-bromo-4-fluorophenyl | 3-fluoro-4-propargyloxyphenyl |
| Cl— | methyl | —(NH)— | 2-bromo-4-fluorophenyl | 4-allyloxyphenyl |
| Cl— | methyl | —(NH)— | 2-bromo-4-fluorophenyl | 4-propargyloxyphenyl |
| Cl— | methyl | —(NH)— | 2-bromo-4-fluorophenyl | 3-fluoro-5-propargyloxyphenyl |
| Cl— | methyl | —(NH)— | 2-bromo-4-fluorophenyl | 3-fluoro-5-allyloxyphenyl |
| Cl— | methyl | —(NH)— | 2-bromo-4-fluorophenyl | 2,5-difluoro-4-propargyloxyphenyl |
| Cl— | methyl | —(NH)— | 2-bromo-4-fluorophenyl | 2,5-difluoro-4-allyloxyphenyl |
| Cl— | methyl | —(NH)— | 2-bromo-4-fluorophenyl | 6-allyloxypyridin-3-yl |
| Cl— | methyl | —(NH)— | 2-bromo-4-fluorophenyl | 6-propargyloxypyridin-3-yl |
| Cl— | methyl | —(NH)— | 2-bromo-4-fluorophenyl | 2-propargyloxy-6-trifluorophenyl |
| Cl— | methyl | —(NH)— | 2-bromo-4-fluorophenyl | 2-allyloxy-6-trifluormethylphenyl |
| Cl— | methyl | —(NH)— | 2-bromo-4-fluorophenyl | 2-chloro-6-propargyloxyphenyl |
| Cl— | methyl | —(NH)— | 2-bromo-4-fluorophenyl | 2-allyloxy-6-chlorophenyl |
| Cl— | methyl | —(NH)— | 2-bromo-4-fluorophenyl | 2,4-dimethyl-6-propargyloxyphenyl |
| Cl— | methyl | —(NH)— | 2-bromo-4-fluorophenyl | 2-allyloxy-4,6-dimethylphenyl |
| Cl— | methyl | —(NH)— | 2,4,6-trifluorophenyl | 2,6-difluoro-4-propargyloxyphenyl |
| Cl— | methyl | —(NH)— | 2,4,6-trifluorophenyl | 4-allyloxy-2,6-difluorophenyl |

-continued

| R¹ | R² | X | Q¹ | Q² |
|---|---|---|---|---|
| Cl— | methyl | —(NH)— | 2,4,6-trifluorophenyl | 2,4-difluoro-6-propargyloxyphenyl |
| Cl— | methyl | —(NH)— | 2,4,6-trifluorophenyl | 4-fluoro-2-propargyloxyphenyl |
| Cl— | methyl | —(NH)— | 2,4,6-trifluorophenyl | 2-fluoro-6-propargyloxyphenyl |
| Cl— | methyl | —(NH)— | 2,4,6-trifluorophenyl | 4-chloro-2-fluoro-6-propargyloxyphenyl |
| Cl— | methyl | —(NH)— | 2,4,6-trifluorophenyl | 2-chloro-4-fluoro-6-propargyloxyphenyl |
| Cl— | methyl | —(NH)— | 2,4,6-trifluorophenyl | 4-allyloxy-2-fluorophenyl |
| Cl— | methyl | —(NH)— | 2,4,6-trifluorophenyl | 2-fluoro-4-propargyloxyphenyl |
| Cl— | methyl | —(NH)— | 2,4,6-trifluorophenyl | 2-allyloxyphenyl |
| Cl— | methyl | —(NH)— | 2,4,6-trifluorophenyl | 2-propargyloxyphenyl |
| Cl— | methyl | —(NH)— | 2,4,6-trifluorophenyl | 2-allyloxy-5-fluorophenyl |
| Cl— | methyl | —(NH)— | 2,4,6-trifluorophenyl | 5-fluoro-2-propargyloxyphenyl |
| Cl— | methyl | —(NH)— | 2,4,6-trifluorophenyl | 2-allyloxy-4-methylphenyl |
| Cl— | methyl | —(NH)— | 2,4,6-trifluorophenyl | 4-methyl-2-propargyloxyphenyl |
| Cl— | methyl | —(NH)— | 2,4,6-trifluorophenyl | 2-allyloxy-5-cyanophenyl |
| Cl— | methyl | —(NH)— | 2,4,6-trifluorophenyl | 5-cyano-2-propargyloxyphenyl |
| Cl— | methyl | —(NH)— | 2,4,6-trifluorophenyl | 5-allyloxy-2-fluorophenyl |
| Cl— | methyl | —(NH)— | 2,4,6-trifluorophenyl | 2-fluoro-5-propargyloxyphenyl |
| Cl— | methyl | —(NH)— | 2,4,6-trifluorophenyl | 4-allyloxy-2-chlorophenyl |
| Cl— | methyl | —(NH)— | 2,4,6-trifluorophenyl | 2-chloro-4-propargyloxyphenyl |
| Cl— | methyl | —(NH)— | 2,4,6-trifluorophenyl | 4-allyloxy-3-fluorophenyl |
| Cl— | methyl | —(NH)— | 2,4,6-trifluorophenyl | 3-fluoro-4-propargyloxyphenyl |
| Cl— | methyl | —(NH)— | 2,4,6-trifluorophenyl | 4-allyloxyphenyl |
| Cl— | methyl | —(NH)— | 2,4,6-trifluorophenyl | 4-propargyloxyphenyl |
| Cl— | methyl | —(NH)— | 2,4,6-trifluorophenyl | 3-fluoro-5-propargyloxyphenyl |
| Cl— | methyl | —(NH)— | 2,4,6-trifluorophenyl | 3-fluoro-5-allyloxyphenyl |
| Cl— | methyl | —(NH)— | 2,4,6-trifluorophenyl | 2,5-difluoro-4-propargyloxyphenyl |
| Cl— | methyl | —(NH)— | 2,4,6-trifluorophenyl | 2,5-difluoro-4-allyloxyphenyl |
| Cl— | methyl | —(NH)— | 2,4,6-trifluorophenyl | 6-allyloxypyridin-3-yl |
| Cl— | methyl | —(NH)— | 2,4,6-trifluorophenyl | 6-propargyloxypyridin-3-yl |
| Cl— | methyl | —(NH)— | 2,4,6-trifluorophenyl | 2-propargyloxy-6-trifluorophenyl |
| Cl— | methyl | —(NH)— | 2,4,6-trifluorophenyl | 2-allyloxy-6-trifluormethylphenyl |
| Cl— | methyl | —(NH)— | 2,4,6-trifluorophenyl | 2-chloro-6-propargyloxyphenyl |
| Cl— | methyl | —(NH)— | 2,4,6-trifluorophenyl | 2-allyloxy-6-chlorophenyl |
| Cl— | methyl | —(NH)— | 2,4,6-trifluorophenyl | 2,4-dimethyl-6-propargyloxyphenyl |
| Cl— | methyl | —(NH)— | 2,4,6-trifluorophenyl | 2-allyloxy-4,6-dimethylphenyl |
| Cl— | methyl | —(NH)— | 4-chloro-2,6-difluorophenyl | 2,6-difluoro-4-propargyloxyphenyl |
| Cl— | methyl | —(NH)— | 4-chloro-2,6-difluorophenyl | 4-allyloxy-2,6-difluorophenyl |
| Cl— | methyl | —(NH)— | 4-chloro-2,6-difluorophenyl | 2,4-difluoro-6-propargyloxyphenyl |
| Cl— | methyl | —(NH)— | 4-chloro-2,6-difluorophenyl | 4-fluoro-2-propargyloxyphenyl |
| Cl— | methyl | —(NH)— | 4-chloro-2,6-difluorophenyl | 2-fluoro-6-propargyloxyphenyl |
| Cl— | methyl | —(NH)— | 4-chloro-2,6-difluorophenyl | 4-chloro-2-fluoro-6-propargyloxyphenyl |
| Cl— | methyl | —(NH)— | 4-chloro-2,6-difluorophenyl | 2-chloro-4-fluoro-6-propargyloxyphenyl |
| Cl— | methyl | —(NH)— | 4-chloro-2,6-difluorophenyl | 4-allyloxy-2-fluorophenyl |
| Cl— | methyl | —(NH)— | 4-chloro-2,6-difluorophenyl | 2-fluoro-4-propargyloxyphenyl |
| Cl— | methyl | —(NH)— | 4-chloro-2,6-difluorophenyl | 2-allyloxyphenyl |
| Cl— | methyl | —(NH)— | 4-chloro-2,6-difluorophenyl | 2-propargyloxyphenyl |
| Cl— | methyl | —(NH)— | 4-chloro-2,6-difluorophenyl | 2-allyloxy-5-fluorophenyl |
| Cl— | methyl | —(NH)— | 4-chloro-2,6-difluorophenyl | 5-fluoro-2-propargyloxyphenyl |
| Cl— | methyl | —(NH)— | 4-chloro-2,6-difluorophenyl | 2-allyloxy-4-methylphenyl |
| Cl— | methyl | —(NH)— | 4-chloro-2,6-difluorophenyl | 4-methyl-2-propargyloxyphenyl |
| Cl— | methyl | —(NH)— | 4-chloro-2,6-difluorophenyl | 2-allyloxy-5-cyanophenyl |
| Cl— | methyl | —(NH)— | 4-chloro-2,6-difluorophenyl | 5-cyano-2-propargyloxyphenyl |
| Cl— | methyl | —(NH)— | 4-chloro-2,6-difluorophenyl | 5-allyloxy-2-fluorophenyl |
| Cl— | methyl | —(NH)— | 4-chloro-2,6-difluorophenyl | 2-fluoro-5-propargyloxyphenyl |
| Cl— | methyl | —(NH)— | 4-chloro-2,6-difluorophenyl | 4-allyloxy-2-chlorophenyl |
| Cl— | methyl | —(NH)— | 4-chloro-2,6-difluorophenyl | 2-chloro-4-propargyloxyphenyl |
| Cl— | methyl | —(NH)— | 4-chloro-2,6-difluorophenyl | 4-allyloxy-3-fluorophenyl |
| Cl— | methyl | —(NH)— | 4-chloro-2,6-difluorophenyl | 3-fluoro-4-propargyloxyphenyl |
| Cl— | methyl | —(NH)— | 4-chloro-2,6-difluorophenyl | 4-allyloxyphenyl |
| Cl— | methyl | —(NH)— | 4-chloro-2,6-difluorophenyl | 4-propargyloxyphenyl |
| Cl— | methyl | —(NH)— | 4-chloro-2,6-difluorophenyl | 3-fluoro-5-propargyloxyphenyl |
| Cl— | methyl | —(NH)— | 4-chloro-2,6-difluorophenyl | 3-fluoro-5-allyloxyphenyl |
| Cl— | methyl | —(NH)— | 4-chloro-2,6-difluorophenyl | 2,5-difluoro-4-propargyloxyphenyl |
| Cl— | methyl | —(NH)— | 4-chloro-2,6-difluorophenyl | 2,5-difluoro-4-allyloxyphenyl |
| Cl— | methyl | —(NH)— | 4-chloro-2,6-difluorophenyl | 6-allyloxypyridin-3-yl |
| Cl— | methyl | —(NH)— | 4-chloro-2,6-difluorophenyl | 6-propargyloxypyridin-3-yl |
| Cl— | methyl | —(NH)— | 4-chloro-2,6-difluorophenyl | 2-propargyloxy-6-trifluorophenyl |
| Cl— | methyl | —(NH)— | 4-chloro-2,6-difluorophenyl | 2-allyloxy-6-trifluormethylphenyl |
| Cl— | methyl | —(NH)— | 4-chloro-2,6-difluorophenyl | 2-chloro-6-propargyloxyphenyl |
| Cl— | methyl | —(NH)— | 4-chloro-2,6-difluorophenyl | 2-allyloxy-6-chlorophenyl |
| Cl— | methyl | —(NH)— | 4-chloro-2,6-difluorophenyl | 2,4-dimethyl-6-propargyloxyphenyl |
| Cl— | methyl | —(NH)— | 4-chloro-2,6-difluorophenyl | 2-allyloxy-4,6-dimethylphenyl |
| Cl— | methyl | —(NH)— | 4-chloro-2,6-difluorophenyl | 2,6-difluoro-4-propargyloxyphenyl |

-continued

| R¹ | R² | X | Q¹ | Q² |
|---|---|---|---|---|
| Cl— | methyl | —(NH)— | 4-chloro-2,6-difluorophenyl | 4-allyloxy-2,6-difluorophenyl |
| Cl— | methyl | —(NH)— | 4-chloro-2,6-difluorophenyl | 2,4-difluoro-6-propargyloxyphenyl |
| Cl— | methyl | —(NH)— | 4-chloro-2,6-difluorophenyl | 4-fluoro-2-propargyloxyphenyl |
| Cl— | methyl | —(NH)— | 4-chloro-2,6-difluorophenyl | 2-fluoro-6-propargyloxyphenyl |
| Cl— | methyl | —(NH)— | 4-chloro-2,6-difluorophenyl | 4-chloro-2-fluoro-6-propargyloxyphenyl |
| Cl— | methyl | —(NH)— | 4-chloro-2,6-difluorophenyl | 2-chloro-4-fluoro-6-propargyloxyphenyl |
| Cl— | methyl | —(NH)— | 4-chloro-2,6-difluorophenyl | 4-allyloxy-2-fluorophenyl |
| Cl— | methyl | —(NH)— | 4-chloro-2,6-difluorophenyl | 2-fluoro-4-propargyloxyphenyl |
| Cl— | methyl | —(NH)— | 4-chloro-2,6-difluorophenyl | 2-allyloxyphenyl |
| Cl— | methyl | —(NH)— | 4-chloro-2,6-difluorophenyl | 2-propargyloxyphenyl |
| Cl— | methyl | —(NH)— | 4-chloro-2,6-difluorophenyl | 2-allyloxy-5-fluorophenyl |
| Cl— | methyl | —(NH)— | 4-chloro-2,6-difluorophenyl | 5-fluoro-2-propargyloxyphenyl |
| Cl— | methyl | —(NH)— | 4-chloro-2,6-difluorophenyl | 2-allyloxy-4-methylphenyl |
| Cl— | methyl | —(NH)— | 4-chloro-2,6-difluorophenyl | 4-methyl-2-propargyloxyphenyl |
| Cl— | methyl | —(NH)— | 4-chloro-2,6-difluorophenyl | 2-allyloxy-5-cyanophenyl |
| Cl— | methyl | —(NH)— | 4-chloro-2,6-difluorophenyl | 5-cyano-2-propargyloxyphenyl |
| Cl— | methyl | —(NH)— | 4-chloro-2,6-difluorophenyl | 5-allyloxy-2-fluorophenyl |
| Cl— | methyl | —(NH)— | 4-chloro-2,6-difluorophenyl | 2-fluoro-5-propargyloxyphenyl |
| Cl— | methyl | —(NH)— | 4-chloro-2,6-difluorophenyl | 4-allyloxy-2-chlorophenyl |
| Cl— | methyl | —(NH)— | 4-chloro-2,6-difluorophenyl | 2-chloro-4-propargyloxyphenyl |
| Cl— | methyl | —(NH)— | 4-chloro-2,6-difluorophenyl | 4-allyloxy-3-fluorophenyl |
| Cl— | methyl | —(NH)— | 4-chloro-2,6-difluorophenyl | 3-fluoro-4-propargyloxyphenyl |
| Cl— | methyl | —(NH)— | 4-chloro-2,6-difluorophenyl | 4-allyloxyphenyl |
| Cl— | methyl | —(NH)— | 4-chloro-2,6-difluorophenyl | 4-propargyloxyphenyl |
| Cl— | methyl | —(NH)— | 4-chloro-2,6-difluorophenyl | 3-fluoro-5-propargyloxyphenyl |
| Cl— | methyl | —(NH)— | 4-chloro-2,6-difluorophenyl | 3-fluoro-5-allyloxyphenyl |
| Cl— | methyl | —(NH)— | 4-chloro-2,6-difluorophenyl | 2,5-difluoro-4-propargyloxyphenyl |
| Cl— | methyl | —(NH)— | 4-chloro-2,6-difluorophenyl | 2,5-difluoro-4-allyloxyphenyl |
| Cl— | methyl | —(NH)— | 4-chloro-2,6-difluorophenyl | 6-allyloxypyridin-3-yl |
| Cl— | methyl | —(NH)— | 4-chloro-2,6-difluorophenyl | 6-propargyloxypyridin-3-yl |
| Cl— | methyl | —(NH)— | 4-chloro-2,6-difluorophenyl | 2-propargyloxy-6-trifluorophenyl |
| Cl— | methyl | —(NH)— | 4-chloro-2,6-difluorophenyl | 2-allyloxy-6-trifluormethylphenyl |
| Cl— | methyl | —(NH)— | 4-chloro-2,6-difluorophenyl | 2-chloro-6-propargyloxyphenyl |
| Cl— | methyl | —(NH)— | 4-chloro-2,6-difluorophenyl | 2-allyloxy-6-chlorophenyl |
| Cl— | methyl | —(NH)— | 4-chloro-2,6-difluorophenyl | 2,4-dimethyl-6-propargyloxyphenyl |
| Cl— | methyl | —(NH)— | 4-chloro-2,6-difluorophenyl | 2-allyloxy-4,6-dimethylphenyl |
| Cl— | methyl | —(NH)— | 3,4-dichlorophenyl | 2,6-difluoro-4-propargyloxyphenyl |
| Cl— | methyl | —(NH)— | 3,4-dichlorophenyl | 4-allyloxy-2,6-difluorophenyl |
| Cl— | methyl | —(NH)— | 3,4-dichlorophenyl | 2,4-difluoro-6-propargyloxyphenyl |
| Cl— | methyl | —(NH)— | 3,4-dichlorophenyl | 4-fluoro-2-propargyloxyphenyl |
| Cl— | methyl | —(NH)— | 3,4-dichlorophenyl | 2-fluoro-6-propargyloxyphenyl |
| Cl— | methyl | —(NH)— | 3,4-dichlorophenyl | 4-chloro-2-fluoro-6-propargyloxyphenyl |
| Cl— | methyl | —(NH)— | 3,4-dichlorophenyl | 2-chloro-4-fluoro-6-propargyloxyphenyl |
| Cl— | methyl | —(NH)— | 3,4-dichlorophenyl | 4-allyloxy-2-fluorophenyl |
| Cl— | methyl | —(NH)— | 3,4-dichlorophenyl | 2-fluoro-4-propargyloxyphenyl |
| Cl— | methyl | —(NH)— | 3,4-dichlorophenyl | 2-allyloxyphenyl |
| Cl— | methyl | —(NH)— | 3,4-dichlorophenyl | 2-propargyloxyphenyl |
| Cl— | methyl | —(NH)— | 3,4-dichlorophenyl | 2-allyloxy-5-fluorophenyl |
| Cl— | methyl | —(NH)— | 3,4-dichlorophenyl | 5-fluoro-2-propargyloxyphenyl |
| Cl— | methyl | —(NH)— | 3,4-dichlorophenyl | 2-allyloxy-4-methylphenyl |
| Cl— | methyl | —(NH)— | 3,4-dichlorophenyl | 4-methyl-2-propargyloxyphenyl |
| Cl— | methyl | —(NH)— | 3,4-dichlorophenyl | 2-allyloxy-5-cyanophenyl |
| Cl— | methyl | —(NH)— | 3,4-dichlorophenyl | 5-cyano-2-propargyloxyphenyl |
| Cl— | methyl | —(NH)— | 3,4-dichlorophenyl | 5-allyloxy-2-fluorophenyl |
| Cl— | methyl | —(NH)— | 3,4-dichlorophenyl | 2-fluoro-5-propargyloxyphenyl |
| Cl— | methyl | —(NH)— | 3,4-dichlorophenyl | 4-allyloxy-2-chlorophenyl |
| Cl— | methyl | —(NH)— | 3,4-dichlorophenyl | 2-chloro-4-propargyloxyphenyl |
| Cl— | methyl | —(NH)— | 3,4-dichlorophenyl | 4-allyloxy-3-fluorophenyl |
| Cl— | methyl | —(NH)— | 3,4-dichlorophenyl | 3-fluoro-4-propargyloxyphenyl |
| Cl— | methyl | —(NH)— | 3,4-dichlorophenyl | 4-allyloxyphenyl |
| Cl— | methyl | —(NH)— | 3,4-dichlorophenyl | 4-propargyloxyphenyl |
| Cl— | methyl | —(NH)— | 3,4-dichlorophenyl | 3-fluoro-5-propargyloxyphenyl |
| Cl— | methyl | —(NH)— | 3,4-dichlorophenyl | 3-fluoro-5-allyloxyphenyl |
| Cl— | methyl | —(NH)— | 3,4-dichlorophenyl | 2,5-difluoro-4-propargyloxyphenyl |
| Cl— | methyl | —(NH)— | 3,4-dichlorophenyl | 2,5-difluoro-4-allyloxyphenyl |
| Cl— | methyl | —(NH)— | 3,4-dichlorophenyl | 6-allyloxypyridin-3-yl |
| Cl— | methyl | —(NH)— | 3,4-dichlorophenyl | 6-propargyloxypyridin-3-yl |
| Cl— | methyl | —(NH)— | 3,4-dichlorophenyl | 2-propargyloxy-6-trifluorophenyl |
| Cl— | methyl | —(NH)— | 3,4-dichlorophenyl | 2-allyloxy-6-trifluormethylphenyl |
| Cl— | methyl | —(NH)— | 3,4-dichlorophenyl | 2-chloro-6-propargyloxyphenyl |
| Cl— | methyl | —(NH)— | 3,4-dichlorophenyl | 2-allyloxy-6-chlorophenyl |
| Cl— | methyl | —(NH)— | 3,4-dichlorophenyl | 2,4-dimethyl-6-propargyloxyphenyl |
| Cl— | methyl | —(NH)— | 3,4-dichlorophenyl | 2-allyloxy-4,6-dimethylphenyl |

-continued

| R¹ | R² | X | Q¹ | Q² |
|---|---|---|---|---|
| Cl— | methyl | —(NH)— | 3,5-dichlorophenyl | 2,6-difluoro-4-propargyloxyphenyl |
| Cl— | methyl | —(NH)— | 3,5-dichlorophenyl | 4-allyloxy-2,6-difluorophenyl |
| Cl— | methyl | —(NH)— | 3,5-dichlorophenyl | 2,4-difluoro-6-propargyloxyphenyl |
| Cl— | methyl | —(NH)— | 3,5-dichlorophenyl | 4-fluoro-2-propargyloxyphenyl |
| Cl— | methyl | —(NH)— | 3,5-dichlorophenyl | 2-fluoro-6-propargyloxyphenyl |
| Cl— | methyl | —(NH)— | 3,5-dichlorophenyl | 4-chloro-2-fluoro-6-propargyloxyphenyl |
| Cl— | methyl | —(NH)— | 3,5-dichlorophenyl | 2-chloro-4-fluoro-6-propargyloxyphenyl |
| Cl— | methyl | —(NH)— | 3,5-dichlorophenyl | 4-allyloxy-2-fluorophenyl |
| Cl— | methyl | —(NH)— | 3,5-dichlorophenyl | 2-fluoro-4-propargyloxyphenyl |
| Cl— | methyl | —(NH)— | 3,5-dichlorophenyl | 2-allyloxyphenyl |
| Cl— | methyl | —(NH)— | 3,5-dichlorophenyl | 2-propargyloxyphenyl |
| Cl— | methyl | —(NH)— | 3,5-dichlorophenyl | 2-allyloxy-5-fluorophenyl |
| Cl— | methyl | —(NH)— | 3,5-dichlorophenyl | 5-fluoro-2-propargyloxyphenyl |
| Cl— | methyl | —(NH)— | 3,5-dichlorophenyl | 2-allyloxy-4-methylphenyl |
| Cl— | methyl | —(NH)— | 3,5-dichlorophenyl | 4-methyl-2-propargyloxyphenyl |
| Cl— | methyl | —(NH)— | 3,5-dichlorophenyl | 2-allyloxy-5-cyanophenyl |
| Cl— | methyl | —(NH)— | 3,5-dichlorophenyl | 5-cyano-2-propargyloxyphenyl |
| Cl— | methyl | —(NH)— | 3,5-dichlorophenyl | 5-allyloxy-2-fluorophenyl |
| Cl— | methyl | —(NH)— | 3,5-dichlorophenyl | 2-fluoro-5-propargyloxyphenyl |
| Cl— | methyl | —(NH)— | 3,5-dichlorophenyl | 4-allyloxy-2-chlorophenyl |
| Cl— | methyl | —(NH)— | 3,5-dichlorophenyl | 2-chloro-4-propargyloxyphenyl |
| Cl— | methyl | —(NH)— | 3,5-dichlorophenyl | 4-allyloxy-3-fluorophenyl |
| Cl— | methyl | —(NH)— | 3,5-dichlorophenyl | 3-fluoro-4-propargyloxyphenyl |
| Cl— | methyl | —(NH)— | 3,5-dichlorophenyl | 4-allyloxyphenyl |
| Cl— | methyl | —(NH)— | 3,5-dichlorophenyl | 4-propargyloxyphenyl |
| Cl— | methyl | —(NH)— | 3,5-dichlorophenyl | 3-fluoro-5-propargyloxyphenyl |
| Cl— | methyl | —(NH)— | 3,5-dichlorophenyl | 3-fluoro-5-allyloxyphenyl |
| Cl— | methyl | —(NH)— | 3,5-dichlorophenyl | 2,5-difluoro-4-propargyloxyphenyl |
| Cl— | methyl | —(NH)— | 3,5-dichlorophenyl | 2,5-difluoro-4-allyloxyphenyl |
| Cl— | methyl | —(NH)— | 3,5-dichlorophenyl | 6-allyloxypyridin-3-yl |
| Cl— | methyl | —(NH)— | 3,5-dichlorophenyl | 6-propargyloxypyridin-3-yl |
| Cl— | methyl | —(NH)— | 3,5-dichlorophenyl | 2-propargyloxy-6-trifluorophenyl |
| Cl— | methyl | —(NH)— | 3,5-dichlorophenyl | 2-allyloxy-6-trifluormethylphenyl |
| Cl— | methyl | —(NH)— | 3,5-dichlorophenyl | 2-chloro-6-propargyloxyphenyl |
| Cl— | methyl | —(NH)— | 3,5-dichlorophenyl | 2-allyloxy-6-chlorophenyl |
| Cl— | methyl | —(NH)— | 3,5-dichlorophenyl | 2,4-dimethyl-6-propargyloxyphenyl |
| Cl— | methyl | —(NH)— | 3,5-dichlorophenyl | 2-allyloxy-4,6-dimethylphenyl |
| Cl— | methyl | —(NH)— | 4-fluoro-2-propargyloxyphenyl | 2,6-difluoro-4-propargyloxyphenyl |
| Cl— | methyl | —(NH)— | 4-fluoro-2-propargyloxyphenyl | 4-allyloxy-2,6-difluorophenyl |
| Cl— | methyl | —(NH)— | 4-fluoro-2-propargyloxyphenyl | 2,4-difluoro-6-propargyloxyphenyl |
| Cl— | methyl | —(NH)— | 4-fluoro-2-propargyloxyphenyl | 4-fluoro-2-propargyloxyphenyl |
| Cl— | methyl | —(NH)— | 4-fluoro-2-propargyloxyphenyl | 2-fluoro-6-propargyloxyphenyl |
| Cl— | methyl | —(NH)— | 4-fluoro-2-propargyloxyphenyl | 4-chloro-2-fluoro-6-propargyloxyphenyl |
| Cl— | methyl | —(NH)— | 4-fluoro-2-propargyloxyphenyl | 2-chloro-4-fluoro-6-propargyloxyphenyl |
| Cl— | methyl | —(NH)— | 4-fluoro-2-propargyloxyphenyl | 4-allyloxy-2-fluorophenyl |
| Cl— | methyl | —(NH)— | 4-fluoro-2-propargyloxyphenyl | 2-fluoro-4-propargyloxyphenyl |
| Cl— | methyl | —(NH)— | 4-fluoro-2-propargyloxyphenyl | 2-allyloxyphenyl |
| Cl— | methyl | —(NH)— | 4-fluoro-2-propargyloxyphenyl | 2-propargyloxyphenyl |
| Cl— | methyl | —(NH)— | 4-fluoro-2-propargyloxyphenyl | 2-allyloxy-5-fluorophenyl |
| Cl— | methyl | —(NH)— | 4-fluoro-2-propargyloxyphenyl | 5-fluoro-2-propargyloxyphenyl |
| Cl— | methyl | —(NH)— | 4-fluoro-2-propargyloxyphenyl | 2-allyloxy-4-methylphenyl |
| Cl— | methyl | —(NH)— | 4-fluoro-2-propargyloxyphenyl | 4-methyl-2-propargyloxyphenyl |
| Cl— | methyl | —(NH)— | 4-fluoro-2-propargyloxyphenyl | 2-allyloxy-5-cyanophenyl |
| Cl— | methyl | —(NH)— | 4-fluoro-2-propargyloxyphenyl | 5-cyano-2-propargyloxyphenyl |
| Cl— | methyl | —(NH)— | 4-fluoro-2-propargyloxyphenyl | 5-allyloxy-2-fluorophenyl |
| Cl— | methyl | —(NH)— | 4-fluoro-2-propargyloxyphenyl | 2-fluoro-5-propargyloxyphenyl |
| Cl— | methyl | —(NH)— | 4-fluoro-2-propargyloxyphenyl | 4-allyloxy-2-chlorophenyl |
| Cl— | methyl | —(NH)— | 4-fluoro-2-propargyloxyphenyl | 2-chloro-4-propargyloxyphenyl |
| Cl— | methyl | —(NH)— | 4-fluoro-2-propargyloxyphenyl | 4-allyloxy-3-fluorophenyl |
| Cl— | methyl | —(NH)— | 4-fluoro-2-propargyloxyphenyl | 3-fluoro-4-propargyloxyphenyl |
| Cl— | methyl | —(NH)— | 4-fluoro-2-propargyloxyphenyl | 4-allyloxyphenyl |
| Cl— | methyl | —(NH)— | 4-fluoro-2-propargyloxyphenyl | 4-propargyloxyphenyl |
| Cl— | methyl | —(NH)— | 4-fluoro-2-propargyloxyphenyl | 3-fluoro-5-propargyloxyphenyl |
| Cl— | methyl | —(NH)— | 4-fluoro-2-propargyloxyphenyl | 3-fluoro-5-allyloxyphenyl |
| Cl— | methyl | —(NH)— | 4-fluoro-2-propargyloxyphenyl | 2,5-difluoro-4-propargyloxyphenyl |
| Cl— | methyl | —(NH)— | 4-fluoro-2-propargyloxyphenyl | 2,5-difluoro-4-allyloxyphenyl |
| Cl— | methyl | —(NH)— | 4-fluoro-2-propargyloxyphenyl | 6-allyloxypyridin-3-yl |
| Cl— | methyl | —(NH)— | 4-fluoro-2-propargyloxyphenyl | 6-propargyloxypyridin-3-yl |
| Cl— | methyl | —(NH)— | 4-fluoro-2-propargyloxyphenyl | 2-propargyloxy-6-trifluorophenyl |
| Cl— | methyl | —(NH)— | 4-fluoro-2-propargyloxyphenyl | 2-allyloxy-6-trifluormethylphenyl |
| Cl— | methyl | —(NH)— | 4-fluoro-2-propargyloxyphenyl | 2-chloro-6-propargyloxyphenyl |
| Cl— | methyl | —(NH)— | 4-fluoro-2-propargyloxyphenyl | 2-allyloxy-6-chlorophenyl |
| Cl— | methyl | —(NH)— | 4-fluoro-2-propargyloxyphenyl | 2,4-dimethyl-6-propargyloxyphenyl |

-continued

| R¹ | R² | X | Q¹ | Q² |
|---|---|---|---|---|
| Cl— | methyl | —(NH)— | 4-fluoro-2-propargyloxyphenyl | 2-allyloxy-4,6-dimethylphenyl |
| Cl— | methyl | —(NH)— | 2,6-difluoro-4-propargyloxyphenyl | 2,6-difluoro-4-propargyloxyphenyl |
| Cl— | methyl | —(NH)— | 2,6-difluoro-4-propargyloxyphenyl | 4-allyloxy-2,6-difluorophenyl |
| Cl— | methyl | —(NH)— | 2,6-difluoro-4-propargyloxyphenyl | 2,4-difluoro-6-propargyloxyphenyl |
| Cl— | methyl | —(NH)— | 2,6-difluoro-4-propargyloxyphenyl | 4-fluoro-2-propargyloxyphenyl |
| Cl— | methyl | —(NH)— | 2,6-difluoro-4-propargyloxyphenyl | 2-fluoro-6-propargyloxyphenyl |
| Cl— | methyl | —(NH)— | 2,6-difluoro-4-propargyloxyphenyl | 4-chloro-2-fluoro-6-propargyloxyphenyl |
| Cl— | methyl | —(NH)— | 2,6-difluoro-4-propargyloxyphenyl | 2-chloro-4-fluoro-6-propargyloxyphenyl |
| Cl— | methyl | —(NH)— | 2,6-difluoro-4-propargyloxyphenyl | 4-allyloxy-2-fluorophenyl |
| Cl— | methyl | —(NH)— | 2,6-difluoro-4-propargyloxyphenyl | 2-fluoro-4-propargyloxyphenyl |
| Cl— | methyl | —(NH)— | 2,6-difluoro-4-propargyloxyphenyl | 2-allyloxyphenyl |
| Cl— | methyl | —(NH)— | 2,6-difluoro-4-propargyloxyphenyl | 2-propargyloxyphenyl |
| Cl— | methyl | —(NH)— | 2,6-difluoro-4-propargyloxyphenyl | 2-allyloxy-5-fluorophenyl |
| Cl— | methyl | —(NH)— | 2,6-difluoro-4-propargyloxyphenyl | 5-fluoro-2-propargyloxyphenyl |
| Cl— | methyl | —(NH)— | 2,6-difluoro-4-propargyloxyphenyl | 2-allyloxy-4-methylphenyl |
| Cl— | methyl | —(NH)— | 2,6-difluoro-4-propargyloxyphenyl | 4-methyl-2-propargyloxyphenyl |
| Cl— | methyl | —(NH)— | 2,6-difluoro-4-propargyloxyphenyl | 2-allyloxy-5-cyanophenyl |
| Cl— | methyl | —(NH)— | 2,6-difluoro-4-propargyloxyphenyl | 5-cyano-2-propargyloxyphenyl |
| Cl— | methyl | —(NH)— | 2,6-difluoro-4-propargyloxyphenyl | 5-allyloxy-2-fluorophenyl |
| Cl— | methyl | —(NH)— | 2,6-difluoro-4-propargyloxyphenyl | 2-fluoro-5-propargyloxyphenyl |
| Cl— | methyl | —(NH)— | 2,6-difluoro-4-propargyloxyphenyl | 4-allyloxy-2-chlorophenyl |
| Cl— | methyl | —(NH)— | 2,6-difluoro-4-propargyloxyphenyl | 2-chloro-4-propargyloxyphenyl |
| Cl— | methyl | —(NH)— | 2,6-difluoro-4-propargyloxyphenyl | 4-allyloxy-3-fluorophenyl |
| Cl— | methyl | —(NH)— | 2,6-difluoro-4-propargyloxyphenyl | 3-fluoro-4-propargyloxyphenyl |
| Cl— | methyl | —(NH)— | 2,6-difluoro-4-propargyloxyphenyl | 4-allyloxyphenyl |
| Cl— | methyl | —(NH)— | 2,6-difluoro-4-propargyloxyphenyl | 4-propargyloxyphenyl |
| Cl— | methyl | —(NH)— | 2,6-difluoro-4-propargyloxyphenyl | 3-fluoro-5-propargyloxyphenyl |
| Cl— | methyl | —(NH)— | 2,6-difluoro-4-propargyloxyphenyl | 3-fluoro-5-allyloxyphenyl |
| Cl— | methyl | —(NH)— | 2,6-difluoro-4-propargyloxyphenyl | 2,5-difluoro-4-propargyloxyphenyl |
| Cl— | methyl | —(NH)— | 2,6-difluoro-4-propargyloxyphenyl | 2,5-difluoro-4-allyloxyphenyl |
| Cl— | methyl | —(NH)— | 2,6-difluoro-4-propargyloxyphenyl | 6-allyloxypyridin-3-yl |
| Cl— | methyl | —(NH)— | 2,6-difluoro-4-propargyloxyphenyl | 6-propargyloxypyridin-3-yl |
| Cl— | methyl | —(NH)— | 2,6-difluoro-4-propargyloxyphenyl | 2-propargyloxy-6-trifluorophenyl |
| Cl— | methyl | —(NH)— | 2,6-difluoro-4-propargyloxyphenyl | 2-allyloxy-6-trifluormethylphenyl |
| Cl— | methyl | —(NH)— | 2,6-difluoro-4-propargyloxyphenyl | 2-chloro-6-propargyloxyphenyl |
| Cl— | methyl | —(NH)— | 2,6-difluoro-4-propargyloxyphenyl | 2-allyloxy-6-chlorophenyl |
| Cl— | methyl | —(NH)— | 2,6-difluoro-4-propargyloxyphenyl | 2,4-dimethyl-6-propargyloxyphenyl |
| Cl— | methyl | —(NH)— | 2,6-difluoro-4-propargyloxyphenyl | 2-allyloxy-4,6-dimethylphenyl |
| Cl— | methyl | —(NH)— | 2-fluoro-5-(furan-2-yl)phenyl | 2,6-difluoro-4-propargyloxyphenyl |
| Cl— | methyl | —(NH)— | 2-fluoro-5-(furan-2-yl)phenyl | 4-allyloxy-2,6-difluorophenyl |

-continued

| R¹ | R² | X | Q¹ | Q² |
|---|---|---|---|---|
| Cl— | methyl | —(NH)— | 2-fluoro-5-(furan-2-yl)phenyl | 2,4-difluoro-6-propargyloxyphenyl |
| Cl— | methyl | —(NH)— | 2-fluoro-5-(furan-2-yl)phenyl | 4-fluoro-2-propargyloxyphenyl |
| Cl— | methyl | —(NH)— | 2-fluoro-5-(furan-2-yl)phenyl | 2-fluoro-6-propargyloxyphenyl |
| Cl— | methyl | —(NH)— | 2-fluoro-5-(furan-2-yl)phenyl | 4-chloro-2-fluoro-6-propargyloxyphenyl |
| Cl— | methyl | —(NH)— | 2-fluoro-5-(furan-2-yl)phenyl | 2-chloro-4-fluoro-6-propargyloxyphenyl |
| Cl— | methyl | —(NH)— | 2-fluoro-5-(furan-2-yl)phenyl | 4-allyloxy-2-fluorophenyl |
| Cl— | methyl | —(NH)— | 2-fluoro-5-(furan-2-yl)phenyl | 2-fluoro-4-propargyloxyphenyl |
| Cl— | methyl | —(NH)— | 2-fluoro-5-(furan-2-yl)phenyl | 2-allyloxyphenyl |
| Cl— | methyl | —(NH)— | 2-fluoro-5-(furan-2-yl)phenyl | 2-propargyloxyphenyl |
| Cl— | methyl | —(NH)— | 2-fluoro-5-(furan-2-yl)phenyl | 2-allyloxy-5-fluorophenyl |
| Cl— | methyl | —(NH)— | 2-fluoro-5-(furan-2-yl)phenyl | 5-fluoro-2-propargyloxyphenyl |
| Cl— | methyl | —(NH)— | 2-fluoro-5-(furan-2-yl)phenyl | 2-allyloxy-4-methylphenyl |
| Cl— | methyl | —(NH)— | 2-fluoro-5-(furan-2-yl)phenyl | 4-methyl-2-propargyloxyphenyl |
| Cl— | methyl | —(NH)— | 2-fluoro-5-(furan-2-yl)phenyl | 2-allyloxy-5-cyanophenyl |
| Cl— | methyl | —(NH)— | 2-fluoro-5-(furan-2-yl)phenyl | 5-cyano-2-propargyloxyphenyl |
| Cl— | methyl | —(NH)— | 2-fluoro-5-(furan-2-yl)phenyl | 5-allyloxy-2-fluorophenyl |
| Cl— | methyl | —(NH)— | 2-fluoro-5-(furan-2-yl)phenyl | 2-fluoro-5-propargyloxyphenyl |
| Cl— | methyl | —(NH)— | 2-fluoro-5-(furan-2-yl)phenyl | 4-allyloxy-2-chlorophenyl |
| Cl— | methyl | —(NH)— | 2-fluoro-5-(furan-2-yl)phenyl | 2-chloro-4-propargyloxyphenyl |
| Cl— | methyl | —(NH)— | 2-fluoro-5-(furan-2-yl)phenyl | 4-allyloxy-3-fluorophenyl |
| Cl— | methyl | —(NH)— | 2-fluoro-5-(furan-2-yl)phenyl | 3-fluoro-4-propargyloxyphenyl |
| Cl— | methyl | —(NH)— | 2-fluoro-5-(furan-2-yl)phenyl | 4-allyloxyphenyl |
| Cl— | methyl | —(NH)— | 2-fluoro-5-(furan-2-yl)phenyl | 4-propargyloxyphenyl |
| Cl— | methyl | —(NH)— | 2-fluoro-5-(furan-2-yl)phenyl | 3-fluoro-5-propargyloxyphenyl |
| Cl— | methyl | —(NH)— | 2-fluoro-5-(furan-2-yl)phenyl | 3-fluoro-5-allyloxyphenyl |
| Cl— | methyl | —(NH)— | 2-fluoro-5-(furan-2-yl)phenyl | 2,5-difluoro-4-propargyloxyphenyl |
| Cl— | methyl | —(NH)— | 2-fluoro-5-(furan-2-yl)phenyl | 2,5-difluoro-4-allyloxyphenyl |
| Cl— | methyl | —(NH)— | 2-fluoro-5-(furan-2-yl)phenyl | 6-allyloxypyridin-3-yl |
| Cl— | methyl | —(NH)— | 2-fluoro-5-(furan-2-yl)phenyl | 6-propargyloxypyridin-3-yl |
| Cl— | methyl | —(NH)— | 2-fluoro-5-(furan-2-yl)phenyl | 2-propargyloxy-6-trifluorophenyl |
| Cl— | methyl | —(NH)— | 2-fluoro-5-(furan-2-yl)phenyl | 2-allyloxy-6-trifluormethylphenyl |
| Cl— | methyl | —(NH)— | 2-fluoro-5-(furan-2-yl)phenyl | 2-chloro-6-propargyloxyphenyl |
| Cl— | methyl | —(NH)— | 2-fluoro-5-(furan-2-yl)phenyl | 2-allyloxy-6-chlorophenyl |
| Cl— | methyl | —(NH)— | 2-fluoro-5-(furan-2-yl)phenyl | 2,4-dimethyl-6-propargyloxyphenyl |
| Cl— | methyl | —(NH)— | 2-fluoro-5-(furan-2-yl)phenyl | 2-allyloxy-4,6-dimethylphenyl |
| methyl | methyl | —(NH)— | 4-methylpiperidin-1-yl | 2,6-difluoro-4-propargyloxyphenyl |
| methyl | methyl | —(NH)— | 4-methylpiperidin-1-yl | 4-allyloxy-2,6-difluorophenyl |
| methyl | methyl | —(NH)— | 4-methylpiperidin-1-yl | 2,4-difluoro-6-propargyloxyphenyl |
| methyl | methyl | —(NH)— | 4-methylpiperidin-1-yl | 4-fluoro-2-propargyloxyphenyl |
| methyl | methyl | —(NH)— | 4-methylpiperidin-1-yl | 2-fluoro-6-propargyloxyphenyl |
| methyl | methyl | —(NH)— | 4-methylpiperidin-1-yl | 4-chloro-2-fluoro-6-propargyloxyphenyl |
| methyl | methyl | —(NH)— | 4-methylpiperidin-1-yl | 2-chloro-4-fluoro-6-propargyloxyphenyl |
| methyl | methyl | —(NH)— | 4-methylpiperidin-1-yl | 4-allyloxy-2-fluorophenyl |
| methyl | methyl | —(NH)— | 4-methylpiperidin-1-yl | 2-fluoro-4-propargyloxyphenyl |
| methyl | methyl | —(NH)— | 4-methylpiperidin-1-yl | 2-allyloxyphenyl |
| methyl | methyl | —(NH)— | 4-methylpiperidin-1-yl | 2-propargyloxyphenyl |
| methyl | methyl | —(NH)— | 4-methylpiperidin-1-yl | 2-allyloxy-5-fluorophenyl |
| methyl | methyl | —(NH)— | 4-methylpiperidin-1-yl | 5-fluoro-2-propargyloxyphenyl |
| methyl | methyl | —(NH)— | 4-methylpiperidin-1-yl | 2-allyloxy-4-methylphenyl |
| methyl | methyl | —(NH)— | 4-methylpiperidin-1-yl | 4-methyl-2-propargyloxyphenyl |
| methyl | methyl | —(NH)— | 4-methylpiperidin-1-yl | 2-allyloxy-5-cyanophenyl |
| methyl | methyl | —(NH)— | 4-methylpiperidin-1-yl | 5-cyano-2-propargyloxyphenyl |
| methyl | methyl | —(NH)— | 4-methylpiperidin-1-yl | 5-allyloxy-2-fluorophenyl |
| methyl | methyl | —(NH)— | 4-methylpiperidin-1-yl | 2-fluoro-5-propargyloxyphenyl |
| methyl | methyl | —(NH)— | 4-methylpiperidin-1-yl | 4-allyloxy-2-chlorophenyl |
| methyl | methyl | —(NH)— | 4-methylpiperidin-1-yl | 2-chloro-4-propargyloxyphenyl |
| methyl | methyl | —(NH)— | 4-methylpiperidin-1-yl | 4-allyloxy-3-fluorophenyl |
| methyl | methyl | —(NH)— | 4-methylpiperidin-1-yl | 3-fluoro-4-propargyloxyphenyl |
| methyl | methyl | —(NH)— | 4-methylpiperidin-1-yl | 4-allyloxyphenyl |
| methyl | methyl | —(NH)— | 4-methylpiperidin-1-yl | 4-propargyloxyphenyl |
| methyl | methyl | —(NH)— | 4-methylpiperidin-1-yl | 3-fluoro-5-propargyloxyphenyl |
| methyl | methyl | —(NH)— | 4-methylpiperidin-1-yl | 3-fluoro-5-allyloxyphenyl |
| methyl | methyl | —(NH)— | 4-methylpiperidin-1-yl | 2,5-difluoro-4-propargyloxyphenyl |
| methyl | methyl | —(NH)— | 4-methylpiperidin-1-yl | 2,5-difluoro-4-allyloxyphenyl |
| methyl | methyl | —(NH)— | 4-methylpiperidin-1-yl | 6-allyloxypyridin-3-yl |
| methyl | methyl | —(NH)— | 4-methylpiperidin-1-yl | 6-propargyloxypyridin-3-yl |
| methyl | methyl | —(NH)— | 4-methylpiperidin-1-yl | 2-propargyloxy-6-trifluorophenyl |
| methyl | methyl | —(NH)— | 4-methylpiperidin-1-yl | 2-allyloxy-6-trifluormethylphenyl |
| methyl | methyl | —(NH)— | 4-methylpiperidin-1-yl | 2-chloro-6-propargyloxyphenyl |
| methyl | methyl | —(NH)— | 4-methylpiperidin-1-yl | 2-allyloxy-6-chlorophenyl |
| methyl | methyl | —(NH)— | 4-methylpiperidin-1-yl | 2,4-dimethyl-6-propargyloxyphenyl |
| methyl | methyl | —(NH)— | 4-methylpiperidin-1-yl | 2-allyloxy-4,6-dimethylphenyl |
| methyl | methyl | —(NH)— | 4-methylpiperidin-1-yl | 2,6-difluoro-4-propargyloxyphenyl |

-continued

| R¹ | R² | X | Q¹ | Q² |
|---|---|---|---|---|
| methyl | methyl | —(NH)— | azepan-1-yl | 4-allyloxy-2,6-difluorophenyl |
| methyl | methyl | —(NH)— | azepan-1-yl | 2,4-difluoro-6-propargyloxyphenyl |
| methyl | methyl | —(NH)— | azepan-1-yl | 4-fluoro-2-propargyloxyphenyl |
| methyl | methyl | —(NH)— | azepan-1-yl | 2-fluoro-6-propargyloxyphenyl |
| methyl | methyl | —(NH)— | azepan-1-yl | 4-chloro-2-fluoro-6-propargyloxyphenyl |
| methyl | methyl | —(NH)— | azepan-1-yl | 2-chloro-4-fluoro-6-propargyloxyphenyl |
| methyl | methyl | —(NH)— | azepan-1-yl | 4-allyloxy-2-fluorophenyl |
| methyl | methyl | —(NH)— | azepan-1-yl | 2-fluoro-4-propargyloxyphenyl |
| methyl | methyl | —(NH)— | azepan-1-yl | 2-allyloxyphenyl |
| methyl | methyl | —(NH)— | azepan-1-yl | 2-propargyloxyphenyl |
| methyl | methyl | —(NH)— | azepan-1-yl | 2-allyloxy-5-fluorophenyl |
| methyl | methyl | —(NH)— | azepan-1-yl | 5-fluoro-2-propargyloxyphenyl |
| methyl | methyl | —(NH)— | azepan-1-yl | 2-allyloxy-4-methylphenyl |
| methyl | methyl | —(NH)— | azepan-1-yl | 4-methyl-2-propargyloxyphenyl |
| methyl | methyl | —(NH)— | azepan-1-yl | 2-allyloxy-5-cyanophenyl |
| methyl | methyl | —(NH)— | azepan-1-yl | 5-cyano-2-propargyloxyphenyl |
| methyl | methyl | —(NH)— | azepan-1-yl | 5-allyloxy-2-fluorophenyl |
| methyl | methyl | —(NH)— | azepan-1-yl | 2-fluoro-5-propargyloxyphenyl |
| methyl | methyl | —(NH)— | azepan-1-yl | 4-allyloxy-2-chlorophenyl |
| methyl | methyl | —(NH)— | azepan-1-yl | 2-chloro-4-propargyloxyphenyl |
| methyl | methyl | —(NH)— | azepan-1-yl | 4-allyloxy-3-fluorophenyl |
| methyl | methyl | —(NH)— | azepan-1-yl | 3-fluoro-4-propargyloxyphenyl |
| methyl | methyl | —(NH)— | azepan-1-yl | 4-allyloxyphenyl |
| methyl | methyl | —(NH)— | azepan-1-yl | 4-propargyloxyphenyl |
| methyl | methyl | —(NH)— | azepan-1-yl | 3-fluoro-5-propargyloxyphenyl |
| methyl | methyl | —(NH)— | azepan-1-yl | 3-fluoro-5-allyloxyphenyl |
| methyl | methyl | —(NH)— | azepan-1-yl | 2,5-difluoro-4-propargyloxyphenyl |
| methyl | methyl | —(NH)— | azepan-1-yl | 2,5-difluoro-4-allyloxyphenyl |
| methyl | methyl | —(NH)— | azepan-1-yl | 6-allyloxypyridin-3-yl |
| methyl | methyl | —(NH)— | azepan-1-yl | 6-propargyloxypyridin-3-yl |
| methyl | methyl | —(NH)— | azepan-1-yl | 2-propargyloxy-6-trifluorophenyl |
| methyl | methyl | —(NH)— | azepan-1-yl | 2-allyloxy-6-trifluoromethylphenyl |
| methyl | methyl | —(NH)— | azepan-1-yl | 2-chloro-6-propargyloxyphenyl |
| methyl | methyl | —(NH)— | azepan-1-yl | 2-allyloxy-6-chlorophenyl |
| methyl | methyl | —(NH)— | azepan-1-yl | 2,4-dimethyl-6-propargyloxyphenyl |
| methyl | methyl | —(NH)— | azepan-1-yl | 2-allyloxy-4,6-dimethylphenyl |
| methyl | methyl | —(NH)— | 4-morpholinyl | 2,6-difluoro-4-propargyloxyphenyl |
| methyl | methyl | —(NH)— | 4-morpholinyl | 4-allyloxy-2,6-difluorophenyl |
| methyl | methyl | —(NH)— | 4-morpholinyl | 2,4-difluoro-6-propargyloxyphenyl |
| methyl | methyl | —(NH)— | 4-morpholinyl | 4-fluoro-2-propargyloxyphenyl |
| methyl | methyl | —(NH)— | 4-morpholinyl | 2-fluoro-6-propargyloxyphenyl |
| methyl | methyl | —(NH)— | 4-morpholinyl | 4-chloro-2-fluoro-6-propargyloxyphenyl |
| methyl | methyl | —(NH)— | 4-morpholinyl | 2-chloro-4-fluoro-6-propargyloxyphenyl |
| methyl | methyl | —(NH)— | 4-morpholinyl | 4-allyloxy-2-fluorophenyl |
| methyl | methyl | —(NH)— | 4-morpholinyl | 2-fluoro-4-propargyloxyphenyl |
| methyl | methyl | —(NH)— | 4-morpholinyl | 2-allyloxyphenyl |
| methyl | methyl | —(NH)— | 4-morpholinyl | 2-propargyloxyphenyl |
| methyl | methyl | —(NH)— | 4-morpholinyl | 2-allyloxy-5-fluorophenyl |
| methyl | methyl | —(NH)— | 4-morpholinyl | 5-fluoro-2-propargyloxyphenyl |
| methyl | methyl | —(NH)— | 4-morpholinyl | 2-allyloxy-4-methylphenyl |
| methyl | methyl | —(NH)— | 4-morpholinyl | 4-methyl-2-propargyloxyphenyl |
| methyl | methyl | —(NH)— | 4-morpholinyl | 2-allyloxy-5-cyanophenyl |
| methyl | methyl | —(NH)— | 4-morpholinyl | 5-cyano-2-propargyloxyphenyl |
| methyl | methyl | —(NH)— | 4-morpholinyl | 5-allyloxy-2-fluorophenyl |
| methyl | methyl | —(NH)— | 4-morpholinyl | 2-fluoro-5-propargyloxyphenyl |
| methyl | methyl | —(NH)— | 4-morpholinyl | 4-allyloxy-2-chlorophenyl |
| methyl | methyl | —(NH)— | 4-morpholinyl | 2-chloro-4-propargyloxyphenyl |
| methyl | methyl | —(NH)— | 4-morpholinyl | 4-allyloxy-3-fluorophenyl |
| methyl | methyl | —(NH)— | 4-morpholinyl | 3-fluoro-4-propargyloxyphenyl |
| methyl | methyl | —(NH)— | 4-morpholinyl | 4-allyloxyphenyl |
| methyl | methyl | —(NH)— | 4-morpholinyl | 4-propargyloxyphenyl |
| methyl | methyl | —(NH)— | 4-morpholinyl | 3-fluoro-5-propargyloxyphenyl |
| methyl | methyl | —(NH)— | 4-morpholinyl | 3-fluoro-5-allyloxyphenyl |
| methyl | methyl | —(NH)— | 4-morpholinyl | 2,5-difluoro-4-propargyloxyphenyl |
| methyl | methyl | —(NH)— | 4-morpholinyl | 2,5-difluoro-4-allyloxyphenyl |
| methyl | methyl | —(NH)— | 4-morpholinyl | 6-allyloxypyridin-3-yl |
| methyl | methyl | —(NH)— | 4-morpholinyl | 6-propargyloxypyridin-3-yl |
| methyl | methyl | —(NH)— | 4-morpholinyl | 2-propargyloxy-6-trifluorophenyl |
| methyl | methyl | —(NH)— | 4-morpholinyl | 2-allyloxy-6-trifluoromethylphenyl |
| methyl | methyl | —(NH)— | 4-morpholinyl | 2-chloro-6-propargyloxyphenyl |
| methyl | methyl | —(NH)— | 4-morpholinyl | 2-allyloxy-6-chlorophenyl |
| methyl | methyl | —(NH)— | 4-morpholinyl | 2,4-dimethyl-6-propargyloxyphenyl |
| methyl | methyl | —(NH)— | 4-morpholinyl | 2-allyloxy-4,6-dimethylphenyl |

-continued

| R¹ | R² | X | Q¹ | Q² |
|---|---|---|---|---|
| Cl— | methyl | —(NH)— | 4-methylpiperidin-1-yl | 2,6-difluoro-4-propargyloxyphenyl |
| Cl— | methyl | —(NH)— | 4-methylpiperidin-1-yl | 4-allyloxy-2,6-difluorophenyl |
| Cl— | methyl | —(NH)— | 4-methylpiperidin-1-yl | 2,4-difluoro-6-propargyloxyphenyl |
| Cl— | methyl | —(NH)— | 4-methylpiperidin-1-yl | 4-fluoro-2-propargyloxyphenyl |
| Cl— | methyl | —(NH)— | 4-methylpiperidin-1-yl | 2-fluoro-6-propargyloxyphenyl |
| Cl— | methyl | —(NH)— | 4-methylpiperidin-1-yl | 4-chloro-2-fluoro-6-propargyloxyphenyl |
| Cl— | methyl | —(NH)— | 4-methylpiperidin-1-yl | 2-chloro-4-fluoro-6-propargyloxyphenyl |
| Cl— | methyl | —(NH)— | 4-methylpiperidin-1-yl | 4-allyloxy-2-fluorophenyl |
| Cl— | methyl | —(NH)— | 4-methylpiperidin-1-yl | 2-fluoro-4-propargyloxyphenyl |
| Cl— | methyl | —(NH)— | 4-methylpiperidin-1-yl | 2-allyloxyphenyl |
| Cl— | methyl | —(NH)— | 4-methylpiperidin-1-yl | 2-propargyloxyphenyl |
| Cl— | methyl | —(NH)— | 4-methylpiperidin-1-yl | 2-allyloxy-5-fluorophenyl |
| Cl— | methyl | —(NH)— | 4-methylpiperidin-1-yl | 5-fluoro-2-propargyloxyphenyl |
| Cl— | methyl | —(NH)— | 4-methylpiperidin-1-yl | 2-allyloxy-4-methylphenyl |
| Cl— | methyl | —(NH)— | 4-methylpiperidin-1-yl | 4-methyl-2-propargyloxyphenyl |
| Cl— | methyl | —(NH)— | 4-methylpiperidin-1-yl | 2-allyloxy-5-cyanophenyl |
| Cl— | methyl | —(NH)— | 4-methylpiperidin-1-yl | 5-cyano-2-propargyloxyphenyl |
| Cl— | methyl | —(NH)— | 4-methylpiperidin-1-yl | 5-allyloxy-2-fluorophenyl |
| Cl— | methyl | —(NH)— | 4-methylpiperidin-1-yl | 2-fluoro-5-propargyloxyphenyl |
| Cl— | methyl | —(NH)— | 4-methylpiperidin-1-yl | 4-allyloxy-2-chlorophenyl |
| Cl— | methyl | —(NH)— | 4-methylpiperidin-1-yl | 2-chloro-4-propargyloxyphenyl |
| Cl— | methyl | —(NH)— | 4-methylpiperidin-1-yl | 4-allyloxy-3-fluorophenyl |
| Cl— | methyl | —(NH)— | 4-methylpiperidin-1-yl | 3-fluoro-4-propargyloxyphenyl |
| Cl— | methyl | —(NH)— | 4-methylpiperidin-1-yl | 4-allyloxyphenyl |
| Cl— | methyl | —(NH)— | 4-methylpiperidin-1-yl | 4-propargyloxyphenyl |
| Cl— | methyl | —(NH)— | 4-methylpiperidin-1-yl | 3-fluoro-5-propargyloxyphenyl |
| Cl— | methyl | —(NH)— | 4-methylpiperidin-1-yl | 3-fluoro-5-allyloxyphenyl |
| Cl— | methyl | —(NH)— | 4-methylpiperidin-1-yl | 2,5-difluoro-4-propargyloxyphenyl |
| Cl— | methyl | —(NH)— | 4-methylpiperidin-1-yl | 2,5-difluoro-4-allyloxyphenyl |
| Cl— | methyl | —(NH)— | 4-methylpiperidin-1-yl | 6-allyloxypyridin-3-yl |
| Cl— | methyl | —(NH)— | 4-methylpiperidin-1-yl | 6-propargyloxypyridin-3-yl |
| Cl— | methyl | —(NH)— | 4-methylpiperidin-1-yl | 2-propargyloxy-6-trifluorphenyl |
| Cl— | methyl | —(NH)— | 4-methylpiperidin-1-yl | 2-allyloxy-6-trifluormethylphenyl |
| Cl— | methyl | —(NH)— | 4-methylpiperidin-1-yl | 2-chloro-6-propargyloxyphenyl |
| Cl— | methyl | —(NH)— | 4-methylpiperidin-1-yl | 2-allyloxy-6-chlorophenyl |
| Cl— | methyl | —(NH)— | 4-methylpiperidin-1-yl | 2,4-dimethyl-6-propargyloxyphenyl |
| Cl— | methyl | —(NH)— | 4-methylpiperidin-1-yl | 2-allyloxy-4,6-dimethylphenyl |
| Cl— | methyl | —(NH)— | 4-methylpiperidin-1-yl | 2,6-difluoro-4-propargyloxyphenyl |
| Cl— | methyl | —(NH)— | azepan-1-yl | 4-allyloxy-2,6-difluorophenyl |
| Cl— | methyl | —(NH)— | azepan-1-yl | 2,4-difluoro-6-propargyloxyphenyl |
| Cl— | methyl | —(NH)— | azepan-1-yl | 4-fluoro-2-propargyloxyphenyl |
| Cl— | methyl | —(NH)— | azepan-1-yl | 2-fluoro-6-propargyloxyphenyl |
| Cl— | methyl | —(NH)— | azepan-1-yl | 4-chloro-2-fluoro-6-propargyloxyphenyl |
| Cl— | methyl | —(NH)— | azepan-1-yl | 2-chloro-4-fluoro-6-propargyloxyphenyl |
| Cl— | methyl | —(NH)— | azepan-1-yl | 4-allyloxy-2-fluorophenyl |
| Cl— | methyl | —(NH)— | azepan-1-yl | 2-fluoro-4-propargyloxyphenyl |
| Cl— | methyl | —(NH)— | azepan-1-yl | 2-allyloxyphenyl |
| Cl— | methyl | —(NH)— | azepan-1-yl | 2-propargyloxyphenyl |
| Cl— | methyl | —(NH)— | azepan-1-yl | 2-allyloxy-5-fluorophenyl |
| Cl— | methyl | —(NH)— | azepan-1-yl | 5-fluoro-2-propargyloxyphenyl |
| Cl— | methyl | —(NH)— | azepan-1-yl | 2-allyloxy-4-methylphenyl |
| Cl— | methyl | —(NH)— | azepan-1-yl | 4-methyl-2-propargyloxyphenyl |
| Cl— | methyl | —(NH)— | azepan-1-yl | 2-allyloxy-5-cyanophenyl |
| Cl— | methyl | —(NH)— | azepan-1-yl | 5-cyano-2-propargyloxyphenyl |
| Cl— | methyl | —(NH)— | azepan-1-yl | 5-allyloxy-2-fluorophenyl |
| Cl— | methyl | —(NH)— | azepan-1-yl | 2-fluoro-5-propargyloxyphenyl |
| Cl— | methyl | —(NH)— | azepan-1-yl | 4-allyloxy-2-chlorophenyl |
| Cl— | methyl | —(NH)— | azepan-1-yl | 2-chloro-4-propargyloxyphenyl |
| Cl— | methyl | —(NH)— | azepan-1-yl | 4-allyloxy-3-fluorophenyl |
| Cl— | methyl | —(NH)— | azepan-1-yl | 3-fluoro-4-propargyloxyphenyl |
| Cl— | methyl | —(NH)— | azepan-1-yl | 4-allyloxyphenyl |
| Cl— | methyl | —(NH)— | azepan-1-yl | 4-propargyloxyphenyl |
| Cl— | methyl | —(NH)— | azepan-1-yl | 3-fluoro-5-propargyloxyphenyl |
| Cl— | methyl | —(NH)— | azepan-1-yl | 3-fluoro-5-allyloxyphenyl |
| Cl— | methyl | —(NH)— | azepan-1-yl | 2,5-difluoro-4-propargyloxyphenyl |
| Cl— | methyl | —(NH)— | azepan-1-yl | 2,5-difluoro-4-allyloxyphenyl |
| Cl— | methyl | —(NH)— | azepan-1-yl | 6-allyloxypyridin-3-yl |
| Cl— | methyl | —(NH)— | azepan-1-yl | 6-propargyloxypyridin-3-yl |
| Cl— | methyl | —(NH)— | azepan-1-yl | 2-propargyloxy-6-trifluorophenyl |
| Cl— | methyl | —(NH)— | azepan-1-yl | 2-allyloxy-6-trifluormethylphenyl |
| Cl— | methyl | —(NH)— | azepan-1-yl | 2-chloro-6-propargyloxyphenyl |
| Cl— | methyl | —(NH)— | azepan-1-yl | 2-allyloxy-6-chlorophenyl |
| Cl— | methyl | —(NH)— | azepan-1-yl | 2,4-dimethyl-6-propargyloxyphenyl |

| R¹ | R² | X | Q¹ | Q² |
|---|---|---|---|---|
| Cl— | methyl | —(NH)— | azepan-1-yl | 2-allyloxy-4,6-dimethylphenyl |
| Cl— | methyl | —(NH)— | 4-morpholinyl | 2,6-difluoro-4-propargyloxyphenyl |
| Cl— | methyl | —(NH)— | 4-morpholinyl | 4-allyloxy-2,6-difluorophenyl |
| Cl— | methyl | —(NH)— | 4-morpholinyl | 2,4-difluoro-6-propargyloxyphenyl |
| Cl— | methyl | —(NH)— | 4-morpholinyl | 4-fluoro-2-propargyloxyphenyl |
| Cl— | methyl | —(NH)— | 4-morpholinyl | 2-fluoro-6-propargyloxyphenyl |
| Cl— | methyl | —(NH)— | 4-morpholinyl | 4-chloro-2-fluoro-6-propargyloxyphenyl |
| Cl— | methyl | —(NH)— | 4-morpholinyl | 2-chloro-4-fluoro-6-propargyloxyphenyl |
| Cl— | methyl | —(NH)— | 4-morpholinyl | 4-allyloxy-2-fluorophenyl |
| Cl— | methyl | —(NH)— | 4-morpholinyl | 2-fluoro-4-propargyloxyphenyl |
| Cl— | methyl | —(NH)— | 4-morpholinyl | 2-allyloxyphenyl |
| Cl— | methyl | —(NH)— | 4-morpholinyl | 2-propargyloxyphenyl |
| Cl— | methyl | —(NH)— | 4-morpholinyl | 2-allyloxy-5-fluorophenyl |
| Cl— | methyl | —(NH)— | 4-morpholinyl | 5-fluoro-2-propargyloxyphenyl |
| Cl— | methyl | —(NH)— | 4-morpholinyl | 2-allyloxy-4-methylphenyl |
| Cl— | methyl | —(NH)— | 4-morpholinyl | 4-methyl-2-propargyloxyphenyl |
| Cl— | methyl | —(NH)— | 4-morpholinyl | 2-allyloxy-5-cyanophenyl |
| Cl— | methyl | —(NH)— | 4-morpholinyl | 5-cyano-2-propargyloxyphenyl |
| Cl— | methyl | —(NH)— | 4-morpholinyl | 5-allyloxy-2-fluorophenyl |
| Cl— | methyl | —(NH)— | 4-morpholinyl | 2-fluoro-5-propargyloxyphenyl |
| Cl— | methyl | —(NH)— | 4-morpholinyl | 4-allyloxy-2-chlorophenyl |
| Cl— | methyl | —(NH)— | 4-morpholinyl | 2-chloro-4-propargyloxyphenyl |
| Cl— | methyl | —(NH)— | 4-morpholinyl | 4-allyloxy-3-fluorophenyl |
| Cl— | methyl | —(NH)— | 4-morpholinyl | 3-fluoro-4-propargyloxyphenyl |
| Cl— | methyl | —(NH)— | 4-morpholinyl | 4-allyloxyphenyl |
| Cl— | methyl | —(NH)— | 4-morpholinyl | 4-propargyloxyphenyl |
| Cl— | methyl | —(NH)— | 4-morpholinyl | 3-fluoro-5-propargyloxyphenyl |
| Cl— | methyl | —(NH)— | 4-morpholinyl | 3-fluoro-5-allyloxyphenyl |
| Cl— | methyl | —(NH)— | 4-morpholinyl | 2,5-difluoro-4-propargyloxyphenyl |
| Cl— | methyl | —(NH)— | 4-morpholinyl | 2,5-difluoro-4-allyloxyphenyl |
| Cl— | methyl | —(NH)— | 4-morpholinyl | 6-allyloxypyridin-3-yl |
| Cl— | methyl | —(NH)— | 4-morpholinyl | 6-propargyloxypyridin-3-yl |
| Cl— | methyl | —(NH)— | 4-morpholinyl | 2-propargyloxy-6-trifluorophenyl |
| Cl— | methyl | —(NH)— | 4-morpholinyl | 2-allyloxy-6-trifluormethylphenyl |
| Cl— | methyl | —(NH)— | 4-morpholinyl | 2-chloro-6-propargyloxyphenyl |
| Cl— | methyl | —(NH)— | 4-morpholinyl | 2-allyloxy-6-chlorophenyl |
| Cl— | methyl | —(NH)— | 4-morpholinyl | 2,4-dimethyl-6-propargyloxyphenyl |
| Cl— | methyl | —(NH)— | 4-morpholinyl | 2-allyloxy-4,6-dimethylphenyl |
| methyl | methyl | —O— | 4-methylpiperidin-1-yl | 2,6-difluoro-4-propargyloxyphenyl |
| methyl | methyl | —O— | 4-methylpiperidin-1-yl | 4-allyloxy-2,6-difluorophenyl |
| methyl | methyl | —O— | 4-methylpiperidin-1-yl | 2,4-difluoro-6-propargyloxyphenyl |
| methyl | methyl | —O— | 4-methylpiperidin-1-yl | 4-fluoro-2-propargyloxyphenyl |
| methyl | methyl | —O— | 4-methylpiperidin-1-yl | 2-fluoro-6-propargyloxyphenyl |
| methyl | methyl | —O— | 4-methylpiperidin-1-yl | 4-chloro-2-fluoro-6-propargyloxyphenyl |
| methyl | methyl | —O— | 4-methylpiperidin-1-yl | 2-chloro-4-fluoro-6-propargyloxyphenyl |
| methyl | methyl | —O— | 4-methylpiperidin-1-yl | 4-allyloxy-2-fluorophenyl |
| methyl | methyl | —O— | 4-methylpiperidin-1-yl | 2-fluoro-4-propargyloxyphenyl |
| methyl | methyl | —O— | 4-methylpiperidin-1-yl | 2-allyloxyphenyl |
| methyl | methyl | —O— | 4-methylpiperidin-1-yl | 2-propargyloxyphenyl |
| methyl | methyl | —O— | 4-methylpiperidin-1-yl | 2-allyloxy-5-fluorophenyl |
| methyl | methyl | —O— | 4-methylpiperidin-1-yl | 5-fluoro-2-propargyloxyphenyl |
| methyl | methyl | —O— | 4-methylpiperidin-1-yl | 2-allyloxy-4-methylphenyl |
| methyl | methyl | —O— | 4-methylpiperidin-1-yl | 4-methyl-2-propargyloxyphenyl |
| methyl | methyl | —O— | 4-methylpiperidin-1-yl | 2-allyloxy-5-cyanophenyl |
| methyl | methyl | —O— | 4-methylpiperidin-1-yl | 5-cyano-2-propargyloxyphenyl |
| methyl | methyl | —O— | 4-methylpiperidin-1-yl | 5-allyloxy-2-fluorophenyl |
| methyl | methyl | —O— | 4-methylpiperidin-1-yl | 2-fluoro-5-propargyloxyphenyl |
| methyl | methyl | —O— | 4-methylpiperidin-1-yl | 4-allyloxy-2-chlorophenyl |
| methyl | methyl | —O— | 4-methylpiperidin-1-yl | 2-chloro-4-propargyloxyphenyl |
| methyl | methyl | —O— | 4-methylpiperidin-1-yl | 4-allyloxy-3-fluorophenyl |
| methyl | methyl | —O— | 4-methylpiperidin-1-yl | 3-fluoro-4-propargyloxyphenyl |
| methyl | methyl | —O— | 4-methylpiperidin-1-yl | 4-allyloxyphenyl |
| methyl | methyl | —O— | 4-methylpiperidin-1-yl | 4-propargyloxyphenyl |
| methyl | methyl | —O— | 4-methylpiperidin-1-yl | 3-fluoro-5-propargyloxyphenyl |
| methyl | methyl | —O— | 4-methylpiperidin-1-yl | 3-fluoro-5-allyloxyphenyl |
| methyl | methyl | —O— | 4-methylpiperidin-1-yl | 2,5-difluoro-4-propargyloxyphenyl |
| methyl | methyl | —O— | 4-methylpiperidin-1-yl | 2,5-difluoro-4-allyloxyphenyl |
| methyl | methyl | —O— | 4-methylpiperidin-1-yl | 6-allyloxypyridin-3-yl |
| methyl | methyl | —O— | 4-methylpiperidin-1-yl | 6-propargyloxypyridin-3-yl |
| methyl | methyl | —O— | 4-methylpiperidin-1-yl | 2-propargyloxy-6-trifluorophenyl |
| methyl | methyl | —O— | 4-methylpiperidin-1-yl | 2-allyloxy-6-trifluormethylphenyl |
| methyl | methyl | —O— | 4-methylpiperidin-1-yl | 2-chloro-6-propargyloxyphenyl |
| methyl | methyl | —O— | 4-methylpiperidin-1-yl | 2-allyloxy-6-chlorophenyl |

-continued

| R¹ | R² | X | Q¹ | Q² |
|---|---|---|---|---|
| methyl | methyl | —O— | 4-methylpiperidin-1-yl | 2,4-dimethyl-6-propargyloxyphenyl |
| methyl | methyl | —O— | 4-methylpiperidin-1-yl | 2-allyloxy-4,6-dimethylphenyl |
| methyl | methyl | —O— | 4-methylpiperidin-1-yl | 2,6-difluoro-4-propargyloxyphenyl |
| methyl | methyl | —O— | azepan-1-yl | 4-allyloxy-2,6-difluorophenyl |
| methyl | methyl | —O— | azepan-1-yl | 2,4-difluoro-6-propargyloxyphenyl |
| methyl | methyl | —O— | azepan-1-yl | 4-fluoro-2-propargyloxyphenyl |
| methyl | methyl | —O— | azepan-1-yl | 2-fluoro-6-propargyloxyphenyl |
| methyl | methyl | —O— | azepan-1-yl | 4-chloro-2-fluoro-6-propargyloxyphenyl |
| methyl | methyl | —O— | azepan-1-yl | 2-chloro-4-fluoro-6-propargyloxyphenyl |
| methyl | methyl | —O— | azepan-1-yl | 4-allyloxy-2-fluorophenyl |
| methyl | methyl | —O— | azepan-1-yl | 2-fluoro-4-propargyloxyphenyl |
| methyl | methyl | —O— | azepan-1-yl | 2-allyloxyphenyl |
| methyl | methyl | —O— | azepan-1-yl | 2-propargyloxyphenyl |
| methyl | methyl | —O— | azepan-1-yl | 2-allyloxy-5-fluorophenyl |
| methyl | methyl | —O— | azepan-1-yl | 5-fluoro-2-propargyloxyphenyl |
| methyl | methyl | —O— | azepan-1-yl | 2-allyloxy-4-methylphenyl |
| methyl | methyl | —O— | azepan-1-yl | 4-methyl-2-propargyloxyphenyl |
| methyl | methyl | —O— | azepan-1-yl | 2-allyloxy-5-cyanophenyl |
| methyl | methyl | —O— | azepan-1-yl | 5-cyano-2-propargyloxyphenyl |
| methyl | methyl | —O— | azepan-1-yl | 5-allyloxy-2-fluorophenyl |
| methyl | methyl | —O— | azepan-1-yl | 2-fluoro-5-propargyloxyphenyl |
| methyl | methyl | —O— | azepan-1-yl | 4-allyloxy-2-chlorophenyl |
| methyl | methyl | —O— | azepan-1-yl | 2-chloro-4-propargyloxyphenyl |
| methyl | methyl | —O— | azepan-1-yl | 4-allyloxy-3-fluorophenyl |
| methyl | methyl | —O— | azepan-1-yl | 3-fluoro-4-propargyloxyphenyl |
| methyl | methyl | —O— | azepan-1-yl | 4-allyloxyphenyl |
| methyl | methyl | —O— | azepan-1-yl | 4-propargyloxyphenyl |
| methyl | methyl | —O— | azepan-1-yl | 3-fluoro-5-propargyloxyphenyl |
| methyl | methyl | —O— | azepan-1-yl | 3-fluoro-5-allyloxyphenyl |
| methyl | methyl | —O— | azepan-1-yl | 2,5-difluoro-4-propargyloxyphenyl |
| methyl | methyl | —O— | azepan-1-yl | 2,5-difluoro-4-allyloxyphenyl |
| methyl | methyl | —O— | azepan-1-yl | 6-allyloxypyridin-3-yl |
| methyl | methyl | —O— | azepan-1-yl | 6-propargyloxypyridin-3-yl |
| methyl | methyl | —O— | azepan-1-yl | 2-propargyloxy-6-trifluorophenyl |
| methyl | methyl | —O— | azepan-1-yl | 2-allyloxy-6-trifluormethylphenyl |
| methyl | methyl | —O— | azepan-1-yl | 2-chloro-6-propargyloxyphenyl |
| methyl | methyl | —O— | azepan-1-yl | 2-allyloxy-6-chlorophenyl |
| methyl | methyl | —O— | azepan-1-yl | 2,4-dimethyl-6-propargyloxyphenyl |
| methyl | methyl | —O— | azepan-1-yl | 2-allyloxy-4,6-dimethylphenyl |
| methyl | methyl | —O— | 4-morpholinyl | 2,6-difluoro-4-propargyloxyphenyl |
| methyl | methyl | —O— | 4-morpholinyl | 4-allyloxy-2,6-difluorophenyl |
| methyl | methyl | —O— | 4-morpholinyl | 2,4-difluoro-6-propargyloxyphenyl |
| methyl | methyl | —O— | 4-morpholinyl | 4-fluoro-2-propargyloxyphenyl |
| methyl | methyl | —O— | 4-morpholinyl | 2-fluoro-6-propargyloxyphenyl |
| methyl | methyl | —O— | 4-morpholinyl | 4-chloro-2-fluoro-6-propargyloxyphenyl |
| methyl | methyl | —O— | 4-morpholinyl | 2-chloro-4-fluoro-6-propargyloxyphenyl |
| methyl | methyl | —O— | 4-morpholinyl | 4-allyloxy-2-fluorophenyl |
| methyl | methyl | —O— | 4-morpholinyl | 2-fluoro-4-propargyloxyphenyl |
| methyl | methyl | —O— | 4-morpholinyl | 2-allyloxyphenyl |
| methyl | methyl | —O— | 4-morpholinyl | 2-propargyloxyphenyl |
| methyl | methyl | —O— | 4-morpholinyl | 2-allyloxy-5-fluorophenyl |
| methyl | methyl | —O— | 4-morpholinyl | 5-fluoro-2-propargyloxyphenyl |
| methyl | methyl | —O— | 4-morpholinyl | 2-allyloxy-4-methylphenyl |
| methyl | methyl | —O— | 4-morpholinyl | 4-methyl-2-propargyloxyphenyl |
| methyl | methyl | —O— | 4-morpholinyl | 2-allyloxy-5-cyanophenyl |
| methyl | methyl | —O— | 4-morpholinyl | 5-cyano-2-propargyloxyphenyl |
| methyl | methyl | —O— | 4-morpholinyl | 5-allyloxy-2-fluorophenyl |
| methyl | methyl | —O— | 4-morpholinyl | 2-fluoro-5-propargyloxyphenyl |
| methyl | methyl | —O— | 4-morpholinyl | 4-allyloxy-2-chlorophenyl |
| methyl | methyl | —O— | 4-morpholinyl | 2-chloro-4-propargyloxyphenyl |
| methyl | methyl | —O— | 4-morpholinyl | 4-allyloxy-3-fluorophenyl |
| methyl | methyl | —O— | 4-morpholinyl | 3-fluoro-4-propargyloxyphenyl |
| methyl | methyl | —O— | 4-morpholinyl | 4-allyloxyphenyl |
| methyl | methyl | —O— | 4-morpholinyl | 4-propargyloxyphenyl |
| methyl | methyl | —O— | 4-morpholinyl | 3-fluoro-5-propargyloxyphenyl |
| methyl | methyl | —O— | 4-morpholinyl | 3-fluoro-5-allyloxyphenyl |
| methyl | methyl | —O— | 4-morpholinyl | 2,5-difluoro-4-propargyloxyphenyl |
| methyl | methyl | —O— | 4-morpholinyl | 2,5-difluoro-4-allyloxyphenyl |
| methyl | methyl | —O— | 4-morpholinyl | 6-allyloxypyridin-3-yl |
| methyl | methyl | —O— | 4-morpholinyl | 6-propargyloxypyridin-3-yl |
| methyl | methyl | —O— | 4-morpholinyl | 2-propargyloxy-6-trifluorophenyl |
| methyl | methyl | —O— | 4-morpholinyl | 2-allyloxy-6-trifluormethylphenyl |
| methyl | methyl | —O— | 4-morpholinyl | 2-chloro-6-propargyloxyphenyl |

-continued

| R¹ | R² | X | Q¹ | Q² |
|---|---|---|---|---|
| methyl | methyl | —O— | 4-morpholinyl | 2-allyloxy-6-chlorophenyl |
| methyl | methyl | —O— | 4-morpholinyl | 2,4-dimethyl-6-propargyloxyphenyl |
| methyl | methyl | —O— | 4-morpholinyl | 2-allyloxy-4,6-dimethylphenyl |

In a further aspect, the present invention relates to a composition comprising
(a) a fungicidally effective amount of a compound of the formula (I) according to the present invention as defined herein,
and one or more further constituents selected from the group consisting of groups (b) and (c):
(b) agrochemically acceptable adjuvants, preferably selected from the group consisting of surfactants, liquid diluents and solid diluents, and
(c) other pesticidally active ingredients (i.e. pesticidally active ingredients not corresponding to compounds of the formula (I), tautomers and/or salts thereof according to the present invention as defined herein).

In a further aspect, the present invention preferably relates to a composition according to the present invention as defined herein, comprising
(c) one or more further fungicidally active ingredients (i.e. fungicidally active ingredients not corresponding to compounds of the formula (I), tautomers and/or salts thereof according to the present invention as defined herein).

In a further aspect, the present invention relates to a method for controlling one or more plant diseases caused by fungal plant pathogens, comprising the steps of
(i) providing a compound of the formula (I) according to the present invention as defined herein or a composition according to the present invention as defined herein, and
(ii) applying to the plant, to a portion of the plant or to plant seeds a fungicidally effective amount the compound provided in step (i).

In the context of the present invention, "control" or "controlling" of harmful microorganisms such as phytopathogenic fungi means a reduction in infestation by harmful microorganisms, in particular phytopathogenic fungi, compared with the untreated plant measured as fungicidal efficacy. Preferably, a reduction of at least 25% (i.e. 25% or more), and more preferably a reduction of at least 50% (i.e. 50% or more) is achieved, in each case compared to the untreated plant. Even more preferably, the infestation by harmful microorganisms, in particular phytopathogenic fungi, is suppressed by 70-100% compared to the untreated plant. The infestation of the untreated plant in each case is defined as 100% infestation.

In the context of the present invention, the "control" or "controlling" of harmful microorganisms, in particular phytopathogenic fungi, may be curative, i.e. for treatment of already infected plants, or protective, i.e. for protection of plants which have not yet been infected.

More specifically, the present invention preferably relates to a method for controlling phytopathogenic harmful fungi, characterized in that one or more compounds of the formula (I) according to the present invention are applied to the phytopathogenic harmful fungi and/or their habitat.

In a further aspect, the present invention relates to the use of one or more compounds of the formula (I) according to the present invention or of compositions according to the present invention for controlling fungi, preferably for controlling fungi in plants or plant seeds.

In a further aspect, the present invention preferably relates to the use of one or more compounds of the formula (I) according to the present invention or of compositions according to the present invention for control of phytopathogenic harmful fungi.

The compounds of the formula (I) according to the invention showed remarkable efficacy against various phytopathogenic harmful fungi, inter alia against species selected from the group consisting of *Botiytis* spp., *Puccinia* spp., *Septoria* spp., *Sphaerotheca* spp., *Uromyces* spp., *Alternaria* spp., *Phakopsora* spp. and *Venturia* spp.

The compounds of the formula (I) according to the invention showed remarkable efficacy against various phytopathogenic harmful fungi, inter alia against species selected from the group consisting of *Puccinia* spp., *Septoria* spp., *Sphaerotheca* spp., *Uromyces* spp. and *Venturia* spp., in particular against *Septoria* spp. and *Venturia* spp.

The compounds of the formula (I) according to the invention allowed remarkable control of species selected from the group of *Botrytis cinerea, Puccinia recondita, Septoria tritici, Sphaerotheca fuliginea, Uromyces appendiculatus, Alternaria solani, Phakopsora pachyrhizi,* and *Venturia inaequalis.*

The compounds of the formula (I) according to the invention allowed remarkable control of species selected from the group of *Puccinia recondita, Septoria tritici, Sphaerotheca fuliginea, Uromyces appendiculatus,* and *Venturia inaequalis.*

As described in more detail in the biological examples below, the compounds of the formula (I) according to the invention showed remarkable efficacy in controlling *Puccinia recondita* (brown rust) on wheat, *Septoria tritici* (leaf spot) on wheat, *Sphaerotheca fuliginea* (powdery mildew) on cucurbits, *Uromyces appendiculatus* (bean rust) on beans, *Alternaria solani* (early blight) on tomatoes, *Phakopsora pachyrhizi* (soybean rust) on soybeans, and *Venturia inaequalis* (apple scab) on apples.

As described in more detail in the biological examples below, the compounds of the formula (I) according to the invention showed remarkable efficacy in controlling *Puccinia recondita* (brown rust) on wheat, *Septoria tritici* (leaf spot) on wheat, *Sphaerotheca fuliginea* (powdery mildew) on cucurbits, *Uromyces appendiculatus* (bean rust) on beans, and *Venturia inaequalis* (apple scab) on apples.

The compounds of the formula (I) according to the invention showed remarkable efficacy against various phytopathogenic harmful fungi, in particular the species mentioned above, typically in concentrations of 50 ppm, 100 ppm, 250 ppm or 500 ppm (see also the biological examples below).

In a further aspect, the present invention preferably relates to the use of one or more compounds of the formula (I) according to the present invention or of compositions according to the present invention for treatment of transgenic plants, of seeds and of seed of transgenic plants.

The compounds of the formula (I) according to the present invention can be obtained via different synthetis pathways and methods.

In the following several synthetic methods are described that may be used to obtain the compounds of the formula (I) according to the present invention. The different synthetic methods are also summarized in the following schemes. In said schemes $R^1$, $R^2$, $Q^1$ and $Q^2$ correspond to $R^1$, $R^2$, $Q^1$ and $Q^2$ as defined herein for the compounds of the formula (I) according to the present invention.

Depending on the linker X in the compounds of the formula (I) according to the present invention, different synthetic methods may be used to obtain these compounds.

In a final synthetic transformation, the compounds of the formula (I) of the present invention are obtained by heating compounds of the formula (Z-ix) together with a hydrazine derivative of the formula (Z-x) or a solvate, a salt or a solvate of a salt of (Z-x) in a solvent, preferably a polar solvent, more preferably a mixture of ethanol or methanol with acetic acid.

These different synthetic steps and pathways are shown in the following Scheme 1.

Scheme 1:

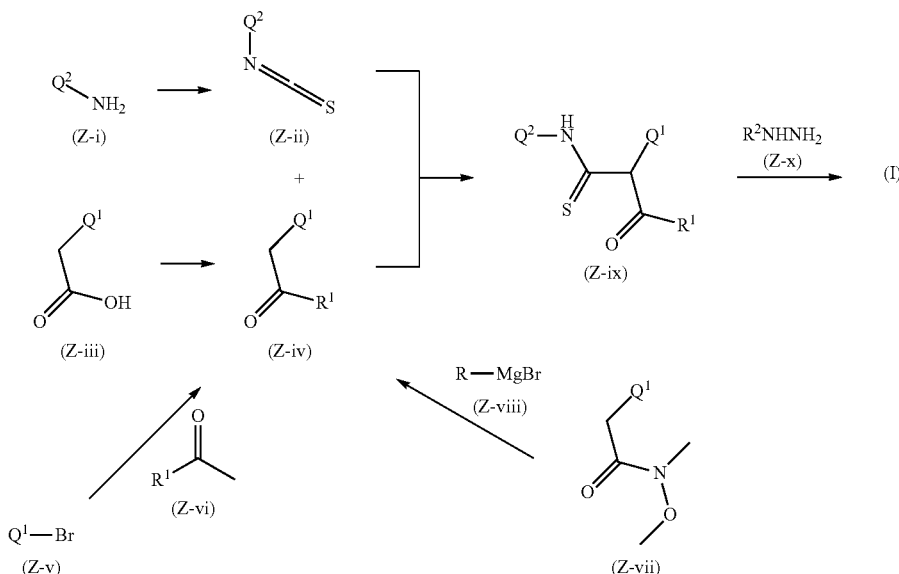

The synthetic methods illustrated in the following schemes exemplify to the skilled person which synthetic pathways and methodologies may be used to synthesize the compounds of the formula (I) according to the present invention.

Compounds of the formula (I) can be synthesized starting from amines of the formula (Z-i). These are converted into the corresponding isothiocyanates of formula (Z-ii) by reacting them with thiophosgene (S=CCl$_2$) in the presence of a base, preferably sodium hydrogen carbonate, in an inert solvent, such as dichloromethane.

Ketones of the formula (Z-iv) either are commercially available or may be prepared starting from commercial precursors, for example from carboxylic acids of formula (Z-iii) by a Dakin West reaction using acetic acid anhydride and a base, preferably pyridine or N-methyl imidazole (for a review Chem. Soc. Rev. 1988, 17, 91-109). Another method to synthesize compounds (Z-iv) is reacting the bromide of formula (Z-v) with a ketone of formula (Z-vi) in the presence of a palladium catalyst and a base by enolate-Heck reaction as described for example in J. Am. Chem. Soc. 2011, 133, 5194-5197. Still another methodology is based on the reaction of a Weinreb amide of formula (Z-vii) with a Grignard reagent (Z-viii).

The reaction of (Z-iv) with a base, preferably sodium hydride, in a solvent, followed by the addition of isothiocyanate of formula (Z-ii) gives the intermediates of the formula (Z-ix) (see WO 2010/101973). This reaction is usually carried out in a solvent, preferably a polar aprotic solvent, more preferably DMF, DMSO, THF or diethyl ether.

An alternative methodology to produce compounds of the formula (I) is outlined in Scheme 2 below. In this method, aminopyrazoles of the formula (Z-xii) [that can be obtained by condensation of cyano-ketones of the formula (Z-xi) with a hydrazine derivative of the formula (Z-x) (see for example Russian Journal of Organic Chemistry 1999, 35, 119-123)] are coupled with aryl bromides of the formula (Z-xiii) to give compounds of the formula (I) under Buchwald-Hartwig conditions. An overview of useful reagents and reaction conditions for transformations of this type can be found in Adv. Synth. Catal. 2004, 346, 1599-1626. A preferred reaction variant comprises the use of a palladium salt, for instance palladium (II) acetate or Pd(dba)$_2$, a phosphine ligand, for example tri-tert-butylphosphine or BINAP and an inorganic base, for example sodium tert-butylate, potassium phosphate or cesium carbonate, in an organic solvent such as toluene or diglyme.

Scheme 2:

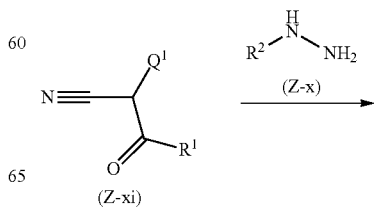

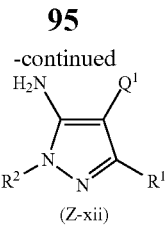

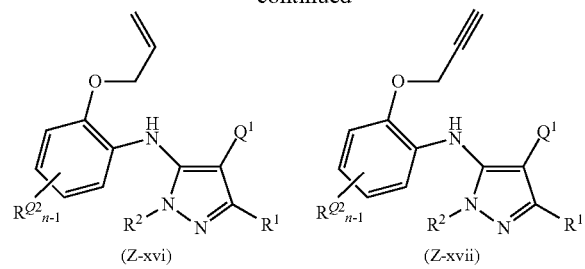

Since certain ether groups as substituents R$^{Q1}$ and/or R$^{Q2}$, like allyl and propargyl ethers, are prone to cleavage in the presence of palladium reagents to some extent, a protecting group (PG) may be needed. Such a protecting group would mask a hydroxyl group on Q$^1$ and/or Q$^2$ that eventually will be converted into the corresponding ether groups as substituents R$^{Q1}$ and/or R$^{Q2}$, like allyl and propargyl ether groups. After the Buchwald-Hartwig coupling reaction (see Scheme 2), this protecting group is removed and the final product is obtained by reacting the free phenol with the corresponding halide, for example allyl or propargyl halogenide (e.g. allyl bromide or propargyl bromide). This methodology is illustrated in Scheme 3 below.

Appropriate protecting groups can be silyl ethers, methyl ethers, MOM, MEM, SEM or other groups known to be useful for the protection of phenolic hydroxyl groups and known to be stable under the conditions of Buchwald-Hartwig coupling. A preferred protecting group strategy uses a methoxy group that can be cleaved with boron tribromide or by the action of aqueous hydrobromic acid in acetic acid. It is understood that this methodology not only applies to compounds having an ether group in the ortho position, but also may be used for derivatives of the formula (Z-xvi) or (Z-xvii) (which both are compounds according to the formula (I)) carrying the respective ether group in meta and/or para position.

Still another method to synthesise compounds of the formula (I) is outlined in Scheme 4 below. This method is especially suitable for cases where R$^1$ is halogen or alkoxy. The intermediate of the formula (Z-xviii) is submitted to the action of an appropriate halogenating agent (referred to as "HalA" in Scheme 4) such as sulfonyl chloride, phosphorous trichloride, phosphorous pentachloride or phosphorous tribromide to give the corresponding halogenides corresponding to the formula (I) of the present invention. In a further alternative method, alkylating agents (referred to as "AlkylA" in Scheme 4) such as C$_1$-C$_4$ alkyl bromides, C$_1$-C$_4$ alkyl iodides, C$_1$-C$_4$ alkyl chlorides, or sulfates or sulfonic esters of aliphatic C$_1$-C$_4$ alcohols are reacted with the intermediate of the formula (Z-xviii) to give the corresponding C$_1$-C$_4$ alkoxy derivatives corresponding to the formula (I) of the present invention.

Scheme 3:

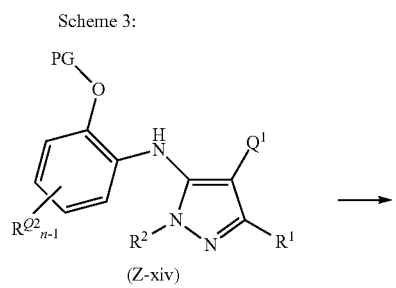

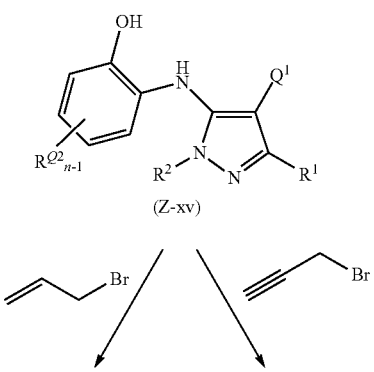

Scheme 4:

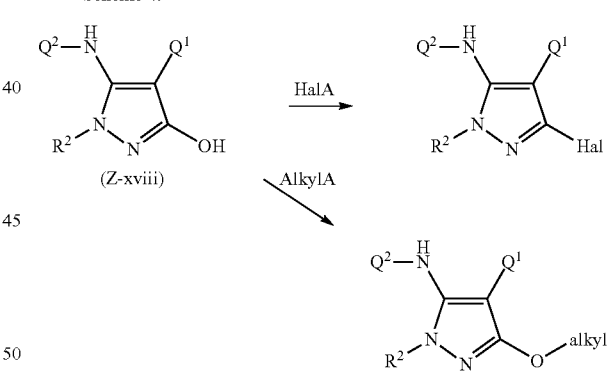

Scheme 5 illustrates the synthesis of compounds of the formula (I) wherein the linker X is a hydroxymethylene (X=CH(OH)) or a methylene (CH$_2$) group.

Scheme 5:

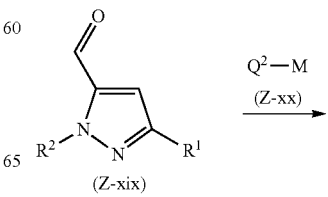

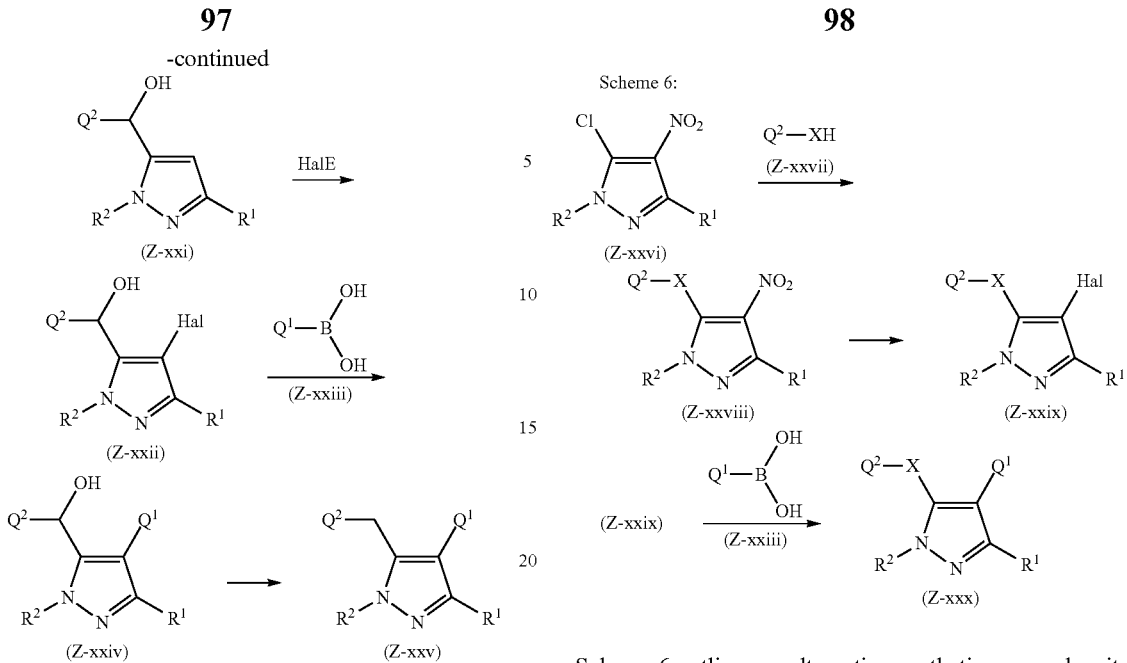

The (preferably aromatic) moiety Q$^1$ is introduced via an organometallic species (Z-xx) which is reacted with the aldehyde of the formula (Z-xix). The organometallic species (Z-xx) may be an organolithium or a Grignard reagent, an organocopper species, an organozinc species or any other organometal reagent that is able to undergo an addition to a carbonyl group. It is understood that the organometallic reagent may be monomeric, dimeric, oligomeric and may be stabilized by ligands. An example for an organometallic reagent is a Grignard reagent where different organomagnesium species are present in the Schlenk equilibrium and where the solvent—usually THF or diethyl ether—serves also as a complexing agent. The resulting compound of the formula (Z-xxi) is then converted via a halogenation reaction into a compound of the formula (Z-xxii). Said halogenation reaction may be carried out with an electrophilic halogenating agent (referred to as "HalE" in Scheme 5) known in the art, for example N-iodo succinimide, N-bromo succinimide or iodine. The compound of the formula (Z-xxii) is then converted into the compound of formula (Z-xxiv) (which is a compound according to the formula (I)) by means of a modified Suzuki coupling reaction, preferably in the presence of a copper catalyst and a base. Suitable conditions are described for example in Angew. Chem. 2014, 126, 3543-3547.

From the compound of the formula (Z-xxiv) a dehydroxylation step gives the corresponding compound of formula (Z-xxv) (which is a compound according to the formula (I)), thereby converting the hydroxymethylene linker (X═CH(OH)) into a methylene linker (X═CH$_2$). This dehydroxylation can be achieved for example by a hydrogenation reaction, preferably using hydrogen and a suitable catalyst such as Raney nickel, a platinum catalyst, or a palladium catalyst. Alternatively, a radical dehydroxylation methodology may be used, for example as described in J. Chem. Soc. Perkin Trans. 1 1975, 1574-1585, or Eur. J. Org. Chem. 2013, 6496-6500 and literature cited therein.

Scheme 6 outlines an alternative synthetic approach suitable for the synthesis of compounds of the formula (I) with amine, ether or thioether linkers (X═NH, O or S).

Different linkers (X═NH, O or S) can be introduced into the compound of the formula (Z-xxvi) via a nucleophilic substitution reaction with a compound of the formula (Z-xxvii) to give a compound of the formula (Z-xxviii) (see for example Chem. Ber. 1930, 63, 2510-2519 or EP 0627423A1). While compounds of the formula (Z-xxvii) wherein X═NH may be used in form of the amines directly, a base may be needed to convert the intermediate of the formula (Z-xxvii) with X═O or X═S into a more nucleophilic species before being reacted with the compound of the formula (Z-xxvi). For example, phenols of the formula (Z-xxvii) may be used in the form of sodium phenolates, and thiophenols of the formula (Z-xxvii) may be used in the form of sodium thiophenolates. These may be obtained by reacting the intermediate of the formula (Z-xxvii) with a suitable base like sodium hydride.

The subsequent reduction of the nitro group in the compound of the formula (Z-xxviii) can be achieved e.g. with tin(II) chloride, iron powder in an acidic medium or any other method known in the art, which is then followed by a Sandmeyer reaction to yield a compound of the formula (Z-xxix). The halogenated intermediate of the formula (Z-xxix) is subsequently converted into the compound of the formula (Z-xxx) (which is a compound according to the formula (I)) by means of a modified Suzuki coupling reaction with a compound of the formula (Z-xxiii), analogously to the methods described in the above Scheme 5.

Compounds of formula (I) wherein Q$^1$ is a fully or partially saturated heterocyclic ring as defined above may also be prepared by the synthesis described in Scheme 7.

Scheme 7:

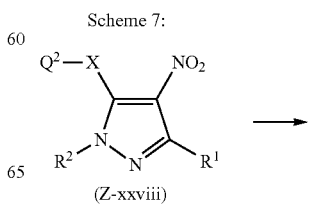

-continued

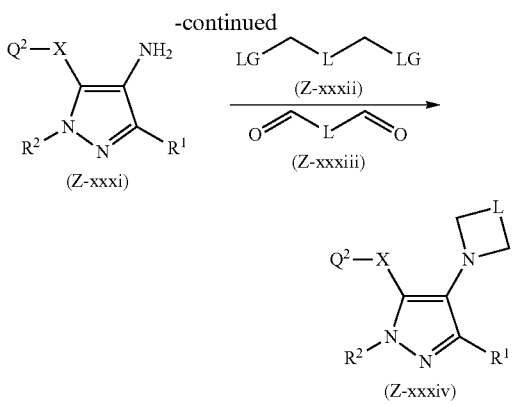

The intermediate of the formula (Z-xxviii) (as described in Scheme 6) is reduced e.g. with tin(II) chloride, iron powder in an acidic medium or any other method known in the art. The resulting compound of the formula (Z-xxxi) is then submitted to a cyclization reaction to give the compound of the formula (Z-xxxiv) (which is a compound according to the formula (I)). For the cyclization, preferably a double nucleophilic substitution reaction is used where the reagent of the formula (Z-xxxii) is reacted at elevated temperature with compound (Z-xxxi) in a solvent, preferably DMF, in the presence of a base, preferably sodium hydride. The leaving group LG in the compound of the formula (Z-xxxii) may be a halogen, such as bromine or chlorine, or it may be a sulfonic ester, e.g. mesylate, triflate, or tosylate. Alternatively, the cyclization is achieved via a double reductive amination reaction with the compound of the formula (Z-xxxiii) in the presence of a solvent, preferably a mixture of ethanol or methanol with acetic acid in the presence of a reducing agent, preferably sodium cyanoborohydride, thereby obtaining the compound of the formula (Z-xxxiv). The group L in the compounds of formulae (Z-xxxii) and (Z-xxxiii) may be alkylene, e.g. ethylene (—CH$_2$CH$_2$—), it may contain an unsaturated moiety, e.g. —CH═CH—, it may carry substituents R$^{Q1}$ as defined above and it may also contain heteroatoms, overall as defined for Q$^1$ in the context of the formula (I) of the present invention.

The present invention also relates to a process for the preparation of compounds of formula (I) of the present invention and to several intermediates which are particularly useful in for the preparation of compounds of formula (I) of the present invention, in particular for obtaining the preferred compounds of formula (I) of the present invention.

Thus, according to a further aspect of the present invention, the present invention relates to a method for producing a compound of formula (I) as defined herein, characterized by the following steps:
(i) providing a compound of formula (Z-ix)

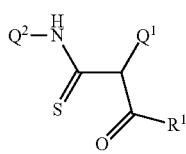

(Z-ix)

wherein Q$^1$, Q$^2$, and R$^1$ each have the meaning as defined herein, (ii) providing a compound of formula (Z-x)

R$^2$NH—NH$_2$ (Z-x)

wherein R$^2$ has the meaning as defined herein,
(iii) reacting compounds (Z-ix) and (Z-x), thereby obtaining a compound of formula (I) as defined herein.

According to a further aspect, the present invention relates to a compound of formula (Z-i)

Q$^2$-NH$_2$ (Z-i)

wherein Q$^2$ has the meaning as defined herein.

According to a further aspect, the present invention relates to a compound of formula (Z-ii)

Q$^2$-N═C═S (Z-ii)

wherein Q$^2$ has the meaning as defined herein.

Particularly preferred compounds of formula (Z-ii) are the compounds Z-ii-01 to Z-ii-20 as described in the examples below.

In a further aspect of the present invention, the invention relates to a process for producing a compound of formula (Z-ii) as defined herein, characterized by the following steps:
(i) providing a compound of the formula (Z-i)

Q$^2$-NH$_2$ (Z-i)

wherein Q$^2$ has the meaning as defined herein,
(ii) reacting said compound of the formula (Z-i) with thiophosgene (S═CCl$_2$) in the presence of a base, preferably sodium hydrogen carbonate,
thereby obtaining a compound of formula (Z-ii) as defined herein.

According to a further aspect, the present invention relates to a compound of formula (Z-ix)

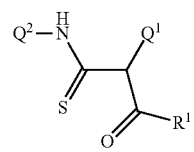

(Z-ix)

tautomers, solvates and/or salts thereof,
wherein Q$^1$, Q$^2$ and R$^1$ each have the meaning as defined herein.

Particularly preferred compounds of formula (Z-ix) are the compounds Z-ix-01, Z-ix-02 and Z-ix-03 as described in the examples below.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to a method for controlling unwanted microorganisms, characterized in that the compounds of the formula (I) are applied to the microorganisms and/or in their habitat.

The invention further relates to seed which has been treated with at least one compound of the formula (I).

The invention also provides a method for protecting seed against unwanted microorganisms by using seed treated with at least one compound of the formula (I).

The compounds of the formula (I) have potent microbicidal activity and can be used for control of unwanted microorganisms, such as fungi and bacteria, in crop protection and in the protection of materials.

The compounds of the formula (I) have very good fungicidal properties and can be used in crop protection, for example for control of Plasmodiophoromycetes, Oomycetes, Chytridiomycetes, Zygomycetes, Ascomycetes, Basidiomycetes and Deuteromycetes.

Bactericides can be used in crop protection, for example, for control of Pseudomonadaceae, Rhizobiaceae, Enterobacteriaceae, Corynebacteriaceae and Streptomycetaceae.

The compounds of the formula (I) can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

Plants

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

Pathogens

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita, Puccinia graminis* oder *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthianum*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola, Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Stagonospora* species, for example *Stagonospora nodorum*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cla-

*dosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Stagnospora* species, for example *Stagnospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

seed- and soil-borne rot and wilt diseases, and also diseases of seedlings, caused, for example, by *Alternaria* species, for example *Alternaria brassicicola*; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidial form: *Drechslera, Bipolaris* Syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella nivalis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium rolfsii*; *Septoria* species, for example *Septoria nodorum*; *Typhula* species, for example *Typhula incamata*; *Verticillium* species, for example *Verticillium dahliae*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Exobasidium* species, for example *Exobasidium vexans*; *Taphrina* species, for example *Taphrina deformans*;

degenerative diseases in woody plants, caused, for example, by *Esca* species, for example *Phaeomoniella chlamydospora, Phaeoacremonium aleophilum* or *Fomitiporia mediterranea*; *Ganoderma* species, for example *Ganoderma boninense*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soya beans:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Mycotoxins

In addition, the compounds of the formula (I) can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The compounds of the formula (I) can also be used in the protection of materials, for protection of industrial materials against attack and destruction by phytopathogenic fungi.

In addition, the compounds of the formula (I) can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compounds of the formula (I) may prevent adverse effects, such as rotting, decay, discoloration, decoloration or formation of mould.

In the case of treatment of wood the compounds of the formula (I) may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

In addition, the compounds of the formula (I) can be used to protect objects which come into contact with saltwater or brackish water, especially hulls, screens, nets, buildings, moorings and signalling systems, from fouling.

The compounds of the formula (I) can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive compositions may prevent adverse effects, such as rotting, decay, discoloration, decoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

Formulations

The present invention further relates to a composition for controlling unwanted microorganisms, comprising at least one of the compounds of the formula (I). These are preferably fungicidal compositions which comprise agriculturally suitable auxiliaries, solvents, carriers, surfactants or extenders.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid carriers include: for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural products impregnated with active ingredient, synthetic substances impregnated with active ingredient, fertilizers and also microencapsulations in polymeric substances.

The active ingredients can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, broadcasting, dusting, foaming, spreadingon and the like. It is also possible to deploy the active ingredients by the ultra-low volume method or to inject the active ingredient preparation/the active ingredient itself into the soil. It is also possible to treat the seed of the plants.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The compounds of the formula (I) may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Compositions comprising compounds of the formula (I) may additionally comprise further components, for example surfactants. Suitable surfactants are emulsifiers and/or foam formers, dispersants or wetting agents having ionic or nonionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers.

In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70 percent by weight.

The formulations described above can be used for controlling unwanted microorganisms, in which the compositions comprising compounds of the formula (I) are applied to the microorganisms and/or in their habitat.

Mixtures

Compounds of the formula (I) can be used as such or in formulations thereof and can be mixed with known fungicides, bactericides, acaricides, nematicides or insecticides, in order thus to broaden, for example, the activity spectrum or to prevent development of resistance.

Useful mixing partners include, for example, known fungicides, insecticides, acaricides, nematicides or else bactericides (see also "The Pesticide Manual", 16th edition, November 2012, The British Crop Protection Council and the Royal Soc. of Chemistry).

A mixture with other known active ingredients, such as herbicides, or with fertilizers and growth regulators, safeners and/or semiochemicals, is also possible.

Seed Treatment

The invention furthermore includes a method for treating seed.

A further aspect of the present invention relates in particular to seeds (dormant, primed, pregerminated or even with emerged roots and leaves) treated with at least one of the compounds of the formula (I). The inventive seeds are used in methods for protection of seeds and emerged plants from the seeds from phytopathogenic harmful fungi. In these methods, seed treated with at least one inventive active ingredient is used.

The compounds of the formula (I) are also suitable for the treatment of seeds and young seedlings. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which have been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests. Surprisingly, a further synergistic effect can be observed in this case, which additionally increases the effectiveness for protection against attack by pests, microorganisms, weeds or abiotic stress.

The compounds of the formula (I) are suitable for protection of seed of any plant variety which is used in agriculture, in the greenhouse, in forests or in horticulture. More particularly, the seed is that of cereals (such as wheat, barley, rye, millet and oats), oilseed rape, maize, cotton, soybean, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described below, the treatment of transgenic seed with the inventive active ingredients or compositions is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originate from *Bacillus* sp., in which case the gene product is effective against the European corn borer and/or the Western corn rootworm. Particularly preferably, the heterologous genes originate from *Bacillus thuringiensis*.

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The compounds of the formula (I) can be applied directly, i.e. without containing any other components and without having been diluted. In general, it is preferable to apply the compositions to the seed in the form of a suitable formulation. Suitable formulations and methods for seed treatment are known to those skilled in the art. The compounds of the formula (I) can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds. The application rate of each single active ingredient is generally between 0.001 and 15 g per kilogram of seed, preferably between 0.01 and 5 g per kilogram of seed.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as Tobacco plants, with altered post-translational protein modification patterns.

Application Rates

When using the compounds of the formula (I) as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);

in the case of seed treatment: from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The invention is illustrated by the examples below. However, the invention is not limited to the examples.

EXAMPLES

Log P Values

Measurement of Log P values was performed according to EEC directive 79/831 Annex V.A8 by HPLC (High Performance Liquid Chromatography) on reversed phase columns with the following methods:

[$^a$] Log P value is determined by measurement of LC-UV, in an acidic range, with 0.1% formic acid in water and acetonitrile as eluent (linear gradient from 10% acetonitrile to 95% acetonitrile).

[$^b$] Log P value is determined by measurement of LC-UV, in a neutral range, with 0.001 molar ammonium acetate solution in water and acetonitrile as eluent (linear gradient from 10% acetonitrile to 95% acetonitrile).

[$^c$] Log P value is determined by measurement of LC-UV, in an acidic range, with 0.1% phosphoric acid and acetonitrile as eluent (linear gradient from 10% acetonitrile to 95% acetonitrile).

Calibration was done with straight-chain alkan-2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

NMR-Peak Lists $^1$H-NMR data of selected examples are written in form of $^1$H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

Synthesis Example 1

Preparation of 4-[4-(Allyloxy)-2-fluorophenyl]-N-[2,4-difluoro-6-(prop-2-yn-1-yloxy)phenyl]-1,3-dimethyl-1H-pyrazol-5-amine (compound I-22)

Example 1.1—Step 1

1-(2-fluoro-4-methoxyphenyl)acetone (Z-iv-2)

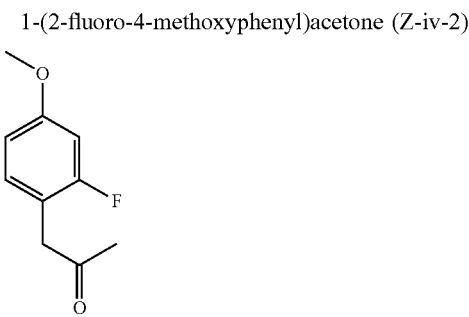

1-Bromo-2-fluoro-4-methoxybenzene (3.00 g, 14.6 mmol) was dissolved in acetone (30.0 mL) in a dry reaction tube. Cesium carbonate (9.54 g, 29.2 mmol) was added. The mixture was degassed with argon for 5 minutes, then [Pd (cinnamyl)Cl$_2$]$_2$ (CAS-RN 12131-44-11, 114 mg, 0.21 mmol) and MorDalPhos (CAS-RN 1237588-12-3, 0.41 g, 0.87 mmol) were added, the tube was sealed and the mixture was heated to 90° C. in a stirring block for 18 h. After that, the mixture was diluted with conc ammonium chloride, extracted with ethyl acetate and the organic phase was dried over sodium sulphate, filtered and eventually evaporated. The crude product was purified by flash chromatography over silica gel. Yield: 2.28 g (81% of theory).

Example 1.2—Step 2

1-(2-fluoro-4-hydroxyphenyl)acetone

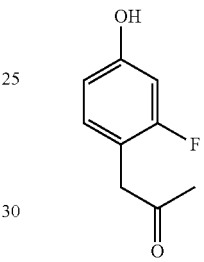

The product from Step 1 (2.34 g, 12.8 mmol) was dissolved in acetic acid (47 mL). Conc hydrobromic acid (14.5 mL) was added and the mixture was stirred under reflux for 5 h. The reaction was then cooled to room temperature, diluted with ice-water and extracted with ethyl acetate. The organic phase was washed with water and brine, dried over sodium sulfate, filtered and evaporated. The crude product was purified by flash chromatography over silica gel to give 1.80 g (82% of theory) of 1-(2-fluoro-4-hydroxyphenyl)acetone.

log P[$^a$]=1.13.

Example 1.3—Step 3

1-[4-(allyloxy)-2-fluorophenyl]acetone (Z-iv-1)

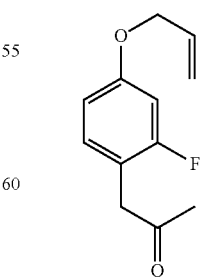

The product from Step 2 (1.80 g, 10.7 mmol) was dissolved in DMF (20.0 mL), potassium carbonate (2.22 g, 16.0 mmol) was added and then allyl bromide (1.11 mL, 12.8 mmol) were added slowly under stirring. The reaction mixture was stirred for 16 h at ambient temperature. Water was then added, the mixture was extracted with ethyl acetate. The organic phase was washed with water and brine, dried over sodium sulfate, filtered and evaporated. The crude product was purified by flash chromatography over silica gel to give 1.61 g (72% of theory) of the desired product.

Example 1.4—Step 4

3,5-difluoro-2-isothiocyanatophenyl prop-2-yn-1-yl ether (Z-ii-03)

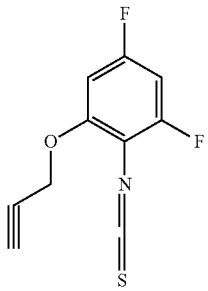 [SMILES: C#CCOc1cc(F)cc(F)c1N=CC=S]

2,4-Difluoro-6-(prop-2-yn-1-yloxy)aniline (1.00 g, 5.46 mmol) was dissolved in dichloromethane (10.0 mL), sodium hydrogen carbonate (1.61 g, 19.1 mmol) was added and the mixture was cooled to 0° C. Thiophosgene (0.55 mL, 5.46 mmol) was added dropwise, the reaction was then stirred for 2 h and finally partitioned between water and dichloromethane. The organic phase was dried over sodium sulfate, filtered and evaporated. Yield: 1.23 g (quant.).

log P (pH 2.3)=3.72

Example 1.5—Step 5

4-[4-(Allyloxy)-2-fluorophenyl]-N-[2,4-difluoro-6-(prop-2-yn-1-yloxy)phenyl]-1,3-dimethyl-1H-pyrazol-5-amine (compound I-22)

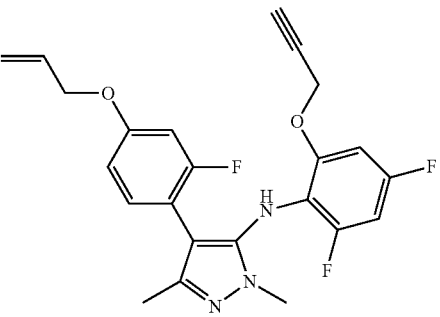 [SMILES: C#CCOc1cc(F)cc(F)c1Nc1c(-c2ccc(OCC=C)cc2F)c(C)nn1C]

Sodium hydride (60% in paraffine, 0.05 g, 1.24 mmol) was suspended under argon in THF (2.0 mL). The product from Example 1.3—Step 3 (0.24 g, 1.15 mmol) was dissolved in THF (3.0 mL) and was then added dropwise at 0° C. to the suspension of sodium hydride. Stirring was maintained for 1 h at 0° C., then a solution of the product from Example 1.4—Step 4 (0.20 g, 0.88 mmol) in THF (3.0 mL) was added and the reaction was stirred for further 1 h at 0° C. After that, acetic acid (0.18 mL, 3.10 mmol) and methyl hydrazine (0.06 mL, 1.10 mmol) were added and the reaction was stirred at reflux for 2 h. Conc. ammonium chloride was added followed by extraction with ethyl acetate. The combined organic phases were washed with water and brine, dried, concentrated and purified via companion to afford the product in a yield of 0.22 g (54% of theory).

Preparation Examples

The compounds according to formula (I) of the invention listed in the following table were obtained in analogy to the examples above and to the general description of the processes of preparing the compounds of the formula (I).

The following compounds I-01 to I-67 of the formula (I) ($R^1$=methyl, $R^2$=methyl) were synthesised, and are preferred compounds of formula (I) according to the present invention:

| Ex N° | X | $Q^1$ | $Q^2$ | LogP |
|---|---|---|---|---|
| I-01 | NH | 2-chloro-4-fluorophenyl | 2,4-difluoro-6-(prop-2-yn-1-yloxy)phenyl | 3.26[a]; 3.10[c] |
| I-02 | NH | 2-chloro-4-fluorophenyl | 4-(allyloxy)-2,6-difluorophenyl | 3.54[a]; 3.40[c] |
| I-03 | NH | 2-chloro-4-fluorophenyl | 2,6-difluoro-4-(prop-2-yn-1-yloxy)phenyl | 3.09[a]; 2.90[c] |
| I-04 | N(CH₃) | 2-chloro-4-fluorophenyl | 4-(allyloxy)-2,6-difluorophenyl | 4.40[a] |
| I-05 | NH | 2,4-dichlorophenyl | 2,4-difluoro-6-(prop-2-yn-1-yloxy)phenyl | 3.69[a] |
| I-06 | NH | 2-fluorophenyl | 2,6-difluoro-4-(prop-2-yn-1-yloxy)phenyl | 2.78[a] |
| I-07 | NH | 2-fluorophenyl | 2,4-difluoro-6-(prop-2-yn-1-yloxy)phenyl | 2.96[a] |
| I-08 | NH | 2,4-dichlorophenyl | 4-(allyloxy)-2,6-difluorophenyl | 3.97[a] |
| I-09 | NH | 2,4-dichlorophenyl | 2,6-difluoro-4-(prop-2-yn-1-yloxy)phenyl | 3.44[a] |
| I-10 | NH | 3,5-dimethoxyphenyl | 2,6-difluoro-4-(prop-2-yn-1-yloxy)phenyl | 2.73[a] |
| I-11 | NH | 3,5-dimethoxyphenyl | 4-(allyloxy)-2,6-difluorophenyl | 3.11[a] |
| I-12 | NH | 3,5-dimethoxyphenyl | 2,4-difluoro-6-(prop-2-yn-1-yloxy)phenyl | 2.85[a] |
| I-13 | NH | 2-fluorophenyl | 4-(allyloxy)-2,6-difluorophenyl | 3.22[a] |

-continued

| Ex N° | X | Q¹ | Q² | LogP |
|---|---|---|---|---|
| I-14 | NH | 2,4-difluorophenyl | 2,6-difluoro-4-(prop-2-yn-1-yloxy)phenyl | 2.90[a] |
| I-15 | NH | 2,4-difluorophenyl | 4-(allyloxy)-2,6-difluorophenyl | 3.33[a] |
| I-16 | NH | 2,4-difluorophenyl | 2,4-difluoro-6-(prop-2-yn-1-yloxy)phenyl | 3.07[a] |
| I-17 | NH | 2-fluoro-4-methoxyphenyl | 2,6-difluoro-4-(prop-2-yn-1-yloxy)phenyl | 2.74[a] |
| I-18 | NH | 2-fluoro-4-methoxyphenyl | 4-(allyloxy)-2,6-difluorophenyl | 3.11[a] |
| I-19 | NH | 2-fluoro-4-methoxyphenyl | 2,4-difluoro-6-(prop-2-yn-1-yloxy)phenyl | 2.86[a] |
| I-20 | NH | 6-chloropyridin-3-yl | 2,6-difluoro-4-(prop-2-yn-1-yloxy)phenyl | 2.56[a]; 2.54[b] |
| I-21 | NH | 6-chloropyridin-3-yl | 4-(allyloxy)-2,6-difluorophenyl | 2.95[a]; 2.92[b] |
| I-22 | NH | 4-(allyloxy)-2-fluorophenyl | 2,4-difluoro-6-(prop-2-yn-1-yloxy)phenyl | 3.30[a] |
| I-23 | NH | 4-(allyloxy)-2-fluorophenyl | 4-(allyloxy)-2,6-difluorophenyl | 3.62[a] |
| I-24 | NH | 4-(allyloxy)-2-fluorophenyl | 2,6-difluoro-4-(prop-2-yn-1-yloxy)phenyl | 3.17[a] |
| I-25 | NH | 6-chloropyridin-3-yl | 2,4-difluoro-6-(prop-2-yn-1-yloxy)phenyl | 2.69[a]; 2.63[b] |
| I-26 | NH | 2-fluoro-4-(prop-2-yn-1-yloxy)phenyl | 2,4-difluoro-6-(prop-2-yn-1-yloxy)phenyl | 2.88[a] |
| I-27 | NH | 2-fluoro-4-(prop-2-yn-1-yloxy)phenyl | 2,6-difluoro-4-(prop-2-yn-1-yloxy)phenyl | 2.77[a] |
| I-28 | NH | 2-fluoro-4-(prop-2-yn-1-yloxy)phenyl | 4-(allyloxy)-2,6-difluorophenyl | 3.13[a] |
| I-29 | NH | 2-chloro-4-fluorophenyl | 2-fluoro-4-(prop-2-yn-1-yloxy)phenyl | 3.25[a]; 3.22[b] |
| I-30 | NH | 2-chloro-4-fluorophenyl | 4-(allyloxy)phenyl | 3.51[a]; 3.52[b] |
| I-31 | NH | 2-chloro-4-fluorophenyl | 4-(prop-2-yn-1-yloxy)phenyl | 3.09[a]; 3.06[b] |
| I-32 | NH | 2-chloro-4-fluorophenyl | 2-chloro-4-(prop-2-yn-1-yloxy)phenyl | 3.65[a]; 3.59[b] |
| I-33 | NH | 2-chloro-4-fluorophenyl | 2,5-difluoro-4-(prop-2-yn-1-yloxy)phenyl | 3.33[a]; 3.23[b]; 3.20[c] |
| I-34 | NH | 2-chloro-4-fluorophenyl | 4-(allyloxy)-2,5-difluorophenyl | 3.74[a]; 3.66[b]; 3.60[c] |
| I-35 | NH | 2-chloro-4-fluorophenyl | 4-(allyloxy)-3-fluorophenyl | 3.61[a]; 3.56[b]; 3.50[c] |
| I-36 | NH | 2-chloro-4-fluorophenyl | 3-fluoro-4-(prop-2-yn-1-yloxy)phenyl | 3.17[a]; 3.14[b]; 3.10[c] |
| I-37 | NH | 2-chloro-4-fluorophenyl | 5-(allyloxy)-2-fluorophenyl | 3.78[a]; 3.73[b]; 3.70[c] |
| I-38 | NH | 2-chloro-4-fluorophenyl | 2-fluoro-5-(prop-2-yn-1-yloxy)phenyl | 3.33[a]; 3.27[b]; 3.20[c] |
| I-39 | NH | 2,4-dichlorophenyl | 2,5-difluoro-4-(prop-2-yn-1-yloxy)phenyl | 3.70[a]; 3.62[b]; 3.60[c] |
| I-40 | NH | 2,4-dichlorophenyl | 2-chloro-4-(prop-2-yn-1-yloxy)phenyl | 4.13[a]; 4.06[b]; 4.00[c] |
| I-41 | NH | 2-chloro-4-fluorophenyl | 4-(allyloxy)-2-chlorophenyl | 4.23[a]; 4.20[b] |
| I-42 | NH | 2-bromo-4-fluorophenyl | 2,4-difluoro-6-(prop-2-yn-1-yloxy)phenyl | 3.33[a]; 3.32[b] |
| I-43 | NH | 2-bromo-4-fluorophenyl | 2-(prop-2-yn-1-yloxy)phenyl | 3.60[a] |
| I-44 | NH | 2-bromo-4-fluorophenyl | 2-(allyloxy)-5-fluorophenyl | 4.08[a] |
| I-45 | NH | 2-bromo-4-fluorophenyl | 5-fluoro-2-(prop-2-yn-1-yloxy)phenyl | 3.64[a] |
| I-46 | NH | 2-bromo-4-fluorophenyl | 2-(allyloxy)-4-methylphenyl | 4.39[a] |
| I-47 | NH | 2-bromo-4-fluorophenyl | 4-methyl-2-(prop-2-yn-1-yloxy)phenyl | 3.87[a] |
| I-48 | NH | 2-chloro-4-fluorophenyl | 2-(allyloxy)phenyl | 3.99[a] |
| I-49 | NH | 2-chloro-4-fluorophenyl | 2-(prop-2-yn-1-yloxy)phenyl | 3.53[a] |
| I-50 | NH | 2-chloro-4-fluorophenyl | 2-(allyloxy)-5-fluorophenyl | 4.01[a] |
| I-51 | NH | 2-chloro-4-fluorophenyl | 5-fluoro-2-(prop-2-yn-1-yloxy)phenyl | 3.58[a] |

-continued

| Ex N° | X | Q¹ | Q² | LogP |
|---|---|---|---|---|
| I-52 | NH | 2-chloro-4-fluorophenyl | 2-(allyloxy)-4-methylphenyl | 4.32[a] |
| I-53 | NH | 2-chloro-4-fluorophenyl | 4-methyl-2-(prop-2-yn-1-yloxy)phenyl | 3.83[a] |
| I-54 | NH | 2,4-dichlorophenyl | 2-(allyloxy)phenyl | 4.49[a] |
| I-55 | NH | 2,4-dichlorophenyl | 2-(prop-2-yn-1-yloxy)phenyl | 3.96[a] |
| I-56 | NH | 2,4-dichlorophenyl | 2-(allyloxy)-5-fluorophenyl | 4.49[a] |
| I-57 | NH | 2,4-dichlorophenyl | 2-(allyloxy)-4-methylphenyl | 4.85[a] |
| I-58 | NH | 2,4-dichlorophenyl | 4-methyl-2-(prop-2-yn-1-yloxy)phenyl | 4.30[a] |
| I-59 | NH | 2,4,6-trifluorophenyl | 2,4-difluoro-6-(prop-2-yn-1-yloxy)phenyl | 3.10[a] |
| I-60 | NH | 4-chloro-2,6-difluorophenyl | 2,4-difluoro-6-(prop-2-yn-1-yloxy)phenyl | 3.49[a] |
| I-61 | NH | 2,6-difluoro-4-methoxyphenyl | 2,4-difluoro-6-(prop-2-yn-1-yloxy)phenyl | 3.00[a] |
| I-62 | NH | 2,6-difluoro-4-methoxyphenyl | 2,6-difluoro-4-(prop-2-yn-1-yloxy)phenyl | 2.85[a] |
| I-63 | NH | 2,6-difluoro-4-(prop-2-yn-1-yloxy)phenyl | 2,4-difluoro-6-(prop-2-yn-1-yloxy)phenyl | 2.99[a] |
| I-64 | NH | 2-chloro-4-fluorophenyl | 2-chloro-6-(prop-2-yn-1-yloxy)phenyl | 3.56[a] |
| I-65 | NH | 2-chloro-4-fluorophenyl | 2-(allyloxy)-6-chlorophenyl | 4.06[a] |
| I-66 | NH | 2,4-dichlorophenyl | 2-chloro-6-(prop-2-yn-1-yloxy)phenyl | 3.99[a] |
| I-67 | NH | 2,4-difluorophenyl | 2-chloro-6-(prop-2-yn-1-yloxy)phenyl | 3.26[a] |

NMR Peak Lists for Active Ingredients According to Formula (I)

Example I-01

$^1$H-NMR (601.6 MHz, $d_6$-DMSO):
δ=7.208 (1.4); 7.203 (1.4); 7.193 (1.5); 7.188 (1.4); 7.060 (1.1); 7.049 (1.2); 7.046 (1.6); 7.035 (1.6); 7.028 (2.4); 6.984 (0.9); 6.979 (0.8); 6.970 (1.5); 6.965 (1.4); 6.956 (0.7); 6.951 (0.6); 6.595 (0.9); 6.578 (0.9); 6.527 (0.5); 6.522 (0.5); 6.508 (0.9); 6.493 (0.6); 6.489 (0.5); 4.730 (1.8); 4.727 (2.0); 4.719 (1.9); 4.715 (1.9); 3.660 (1.6); 3.656 (3.9); 3.652 (16.0); 3.636 (0.5); 3.330 (16.6); 2.524 (0.4); 2.521 (0.5); 2.518 (0.5); 2.509 (12.5); 2.506 (28.6); 2.503 (41.1); 2.500 (31.7); 2.497 (16.2); 1.883 (14.5); 1.872 (0.7); 0.005 (1.8); 0.000 (62.3); −0.006 (3.0)

Example I-02

$^1$H-NMR (400.0 MHz, $d_6$-DMSO):
δ=7.375 (2.4); 7.192 (1.5); 7.186 (1.6); 7.170 (1.6); 7.163 (1.6); 7.081 (0.9); 7.065 (1.1); 7.060 (1.7); 7.044 (1.6); 7.016 (1.2); 7.009 (1.0); 6.995 (1.8); 6.988 (1.6); 6.973 (0.7); 6.967 (0.6); 6.432 (0.5); 6.421 (3.7); 6.395 (3.6); 6.384 (0.5); 5.953 (0.4); 5.940 (0.7); 5.926 (0.7); 5.913 (0.9); 5.909 (0.5); 5.900 (0.5); 5.896 (0.9); 5.883 (0.8); 5.870 (0.9); 5.857 (0.4); 5.301 (1.5); 5.297 (1.6); 5.293 (0.6); 5.258 (1.8); 5.254 (2.9); 5.250 (2.0); 5.227 (1.5); 5.223 (1.4); 4.431 (2.4); 4.427 (2.5); 4.422 (1.9); 4.418 (2.4); 4.414 (2.3); 3.659 (16.0); 3.326 (24.0); 2.525 (0.8); 2.511 (17.0); 2.507 (34.1); 2.502 (45.0); 2.498 (33.3); 2.493 (16.5); 1.879 (15.6); 0.008 (2.6); 0.000 (68.9); −0.009 (2.8)

Example I-03

$^1$H-NMR (400.0 MHz, $d_6$-DMSO):
δ=7.417 (2.4); 7.197 (1.6); 7.191 (1.7); 7.175 (1.7); 7.169 (1.6); 7.086 (0.9); 7.069 (1.1); 7.064 (1.7); 7.048 (1.6); 7.019 (1.2); 7.012 (1.0); 6.998 (1.8); 6.991 (1.6); 6.977 (0.7); 6.970 (0.6); 6.490 (0.5); 6.479 (3.7); 6.453 (3.7); 6.442 (0.5); 4.663 (5.2); 4.657 (5.3); 3.662 (16.0); 3.580 (1.5); 3.574 (3.4); 3.569 (1.5); 3.327 (24.5); 2.713 (0.4); 2.701 (0.4); 2.525 (0.6); 2.511 (14.0); 2.507 (28.7); 2.502 (38.2); 2.498 (28.2); 2.493 (13.9); 1.989 (0.4); 1.888 (15.6); 1.596 (0.6); 0.008 (2.0); 0.000 (57.6); −0.009 (2.2)

Example I-04

$^1$H-NMR (400.0 MHz, $d_6$-DMSO):
δ=7.369 (1.4); 7.363 (1.5); 7.347 (1.4); 7.341 (1.4); 7.123 (0.5); 7.117 (0.4); 7.102 (1.6); 7.096 (1.5); 7.080 (2.7); 7.075 (1.6); 7.063 (2.1); 7.059 (0.8); 7.042 (0.6); 6.553 (0.6); 6.543 (3.3); 6.516 (3.3); 6.507 (0.6); 6.000 (0.3); 5.987 (0.8); 5.974 (0.7); 5.960 (0.9); 5.957 (0.5); 5.947 (0.4); 5.944 (1.0); 5.930 (0.8); 5.917 (0.9); 5.904 (0.4); 5.363 (0.5); 5.359 (1.5); 5.355 (1.6); 5.351 (0.6); 5.320 (0.5); 5.316 (1.3); 5.311 (1.4); 5.307 (0.6); 5.275 (1.5); 5.271 (1.5); 5.249 (1.4); 5.245 (1.4); 4.499 (1.9); 4.496 (3.3); 4.492 (2.1); 4.486 (2.0); 4.483 (3.2); 4.479 (1.9); 3.645 (15.5); 3.326 (35.9); 3.099 (8.6); 2.671 (0.4); 2.667 (0.3); 2.524 (1.0); 2.511 (24.3); 2.507 (51.0); 2.502 (68.5); 2.497 (50.0); 2.493 (24.2); 2.329 (0.4); 2.300 (0.4); 1.839 (16.0); 0.000 (4.8)

Example I-05

$^1$H-NMR (400.0 MHz, $d_6$-DMSO):
δ=11.852 (0.5); 7.577 (0.5); 7.572 (0.5); 7.388 (0.3); 7.379 (3.3); 7.374 (3.5); 7.368 (0.4); 7.273 (0.4); 7.183 (1.7); 7.178 (1.6); 7.163 (2.2); 7.157 (2.2); 7.082 (2.4); 7.036 (3.6); 7.015 (2.7); 6.619 (0.7); 6.613 (1.1); 6.608 (0.9); 6.592 (0.8); 6.586 (1.1); 6.546 (0.7); 6.539 (0.6); 6.523 (0.8); 6.517 (1.1); 6.512 (0.7); 6.495 (0.7); 6.489 (0.6); 4.734 (2.4); 4.728 (4.2); 4.722 (2.4); 3.819 (1.6); 3.664 (1.5); 3.659 (3.2); 3.652 (2.2); 3.646 (16.0); 3.509 (0.9); 3.338 (42.4); 3.336 (41.4); 3.331 (49.7); 2.707 (0.8); 2.695 (0.8); 2.676 (0.4); 2.671 (0.6); 2.667 (0.4); 2.525 (1.6); 2.511 (31.0); 2.507 (62.8); 2.502 (82.6); 2.498 (60.2); 2.493 (29.7); 2.334 (0.4); 2.329 (0.5); 2.325 (0.4); 1.909

(0.4); 1.891 (15.7); 1.604 (1.8); 1.397 (14.7); 1.235 (0.4); 1.040 (1.2); 0.008 (2.2); 0.000 (61.5); −0.009 (2.3)

Example I-06

$^1$H-NMR (400.0 MHz, d$_6$-DMSO):

δ=7.469 (2.2); 7.146 (0.3); 7.142 (0.4); 7.133 (0.4); 7.128 (0.9); 7.123 (0.7); 7.108 (1.0); 7.103 (0.6); 7.095 (0.5); 7.090 (0.5); 7.057 (0.5); 7.053 (0.6); 7.038 (1.4); 7.034 (1.3); 7.019 (1.0); 7.015 (0.8); 6.986 (1.3); 6.983 (1.5); 6.967 (1.7); 6.965 (1.9); 6.953 (1.2); 6.950 (1.2); 6.946 (0.9); 6.928 (1.3); 6.907 (0.8); 6.482 (0.5); 6.470 (3.6); 6.444 (3.6); 6.432 (0.5); 4.639 (5.6); 4.633 (5.7); 3.653 (16.0); 3.600 (1.5); 3.594 (3.4); 3.588 (1.5); 3.339 (34.7); 3.336 (39.0); 3.332 (44.8); 2.671 (0.4); 2.525 (1.0); 2.511 (22.4); 2.507 (45.3); 2.502 (59.7); 2.498 (43.8); 2.493 (21.7); 2.329 (0.4); 1.962 (11.2); 1.235 (0.5); 0.008 (2.0); 0.000 (60.1); −0.009 (2.3)

Example I-07

$^1$H-NMR (400.0 MHz, d$_6$-DMSO):

δ=7.150 (0.6); 7.145 (0.6); 7.131 (1.3); 7.128 (1.2); 7.126 (1.2); 7.112 (3.8); 7.098 (0.8); 7.094 (0.7); 7.045 (0.7); 7.042 (0.7); 7.027 (1.6); 7.023 (1.6); 7.007 (1.2); 6.974 (1.4); 6.963 (1.8); 6.945 (2.8); 6.927 (1.8); 6.614 (1.3); 6.588 (1.3); 6.506 (0.8); 6.500 (0.7); 6.483 (0.9); 6.478 (1.4); 6.472 (0.8); 6.455 (0.8); 6.449 (0.7); 4.743 (5.8); 4.738 (5.8); 3.805 (0.9); 3.665 (1.7); 3.659 (3.5); 3.653 (2.0); 3.642 (16.0); 3.425 (0.3); 3.338 (12.8); 3.334 (15.1); 2.932 (0.3); 2.507 (16.1); 2.503 (19.9); 1.958 (12.2); 1.587 (0.7); 1.068 (0.6); 0.008 (1.0); 0.000 (19.6); −0.008 (1.0)

Example I-08

$^1$H-NMR (400.0 MHz, d$_6$-DMSO):

δ=7.437 (2.7); 7.348 (3.5); 7.342 (3.7); 7.202 (1.8); 7.197 (1.7); 7.181 (2.3); 7.176 (2.3); 7.045 (3.2); 7.025 (2.5); 6.433 (0.5); 6.422 (3.8); 6.396 (3.7); 6.386 (0.6); 5.966 (0.4); 5.953 (0.8); 5.940 (0.8); 5.927 (0.9); 5.923 (0.5); 5.914 (0.5); 5.910 (1.0); 5.897 (0.9); 5.883 (1.0); 5.870 (0.5); 5.318 (1.6); 5.314 (1.7); 5.310 (0.7); 5.274 (2.0); 5.270 (3.1); 5.267 (2.1); 5.244 (1.5); 5.240 (1.4); 4.433 (1.7); 4.429 (1.9); 4.425 (2.2); 4.420 (2.2); 4.416 (1.9); 4.413 (1.7); 3.659 (16.0); 3.332 (16.0); 2.525 (0.4); 2.512 (9.5); 2.507 (19.1); 2.503 (25.0); 2.498 (18.2); 2.494 (8.9); 1.886 (15.8); 1.397 (2.4); 0.008 (0.7); 0.000 (22.0); −0.009 (0.9)

Example I-09

$^1$H-NMR (400.0 MHz, d$_6$-DMSO):

δ=7.576 (0.5); 7.571 (0.5); 7.465 (2.6); 7.388 (0.3); 7.382 (0.3); 7.366 (3.5); 7.361 (3.8); 7.273 (0.6); 7.252 (0.4); 7.213 (1.7); 7.207 (1.6); 7.192 (2.2); 7.187 (2.2); 7.055 (3.2); 7.034 (2.5); 6.498 (0.5); 6.486 (3.7); 6.461 (3.7); 6.450 (0.5); 4.659 (5.1); 4.653 (5.3); 3.658 (16.0); 3.595 (1.5); 3.589 (3.5); 3.583 (1.6); 3.510 (1.5); 3.331 (28.4); 2.708 (1.1); 2.696 (1.1); 2.525 (0.7); 2.520 (1.1); 2.511 (15.5); 2.507 (31.9); 2.503 (42.5); 2.498 (31.2); 2.494 (15.6); 1.989 (1.3); 1.896 (15.7); 1.604 (3.0); 1.585 (0.5); 1.397 (6.1); 1.193 (0.4); 1.175 (0.7); 1.157 (0.3); 0.008 (1.0); 0.000 (31.5); −0.009 (1.2)

Example I-10

$^1$H-NMR (400.0 MHz, d$_6$-DMSO):

δ=7.400 (1.1); 6.614 (1.6); 6.588 (1.6); 6.329 (2.9); 6.323 (3.1); 6.234 (0.9); 6.229 (1.5); 6.223 (0.8); 4.678 (2.6); 4.673 (2.6); 3.635 (16.0); 3.626 (7.5); 3.602 (0.4); 3.568 (0.7); 3.562 (1.5); 3.557 (0.7); 3.325 (7.9); 2.506 (12.6); 2.502 (15.8); 2.497 (11.7); 2.131 (6.4); 1.989 (1.1); 1.909 (0.8); 1.175 (0.6); 0.008 (0.7); 0.000 (13.7); −0.008 (0.8)

Example I-11

$^1$H-NMR (400.0 MHz, d$_6$-DMSO):

δ=7.352 (1.0); 6.549 (1.5); 6.523 (1.5); 6.309 (2.7); 6.303 (3.1); 6.224 (0.9); 6.219 (1.5); 6.213 (0.7); 5.966 (0.3); 5.939 (0.4); 5.922 (0.4); 5.909 (0.4); 5.896 (0.4); 5.334 (0.7); 5.330 (0.7); 5.291 (0.6); 5.287 (0.6); 5.239 (0.7); 5.235 (0.7); 5.213 (0.6); 5.209 (0.6); 4.435 (0.9); 4.432 (1.5); 4.428 (1.0); 4.422 (0.9); 4.419 (1.5); 4.415 (0.9); 3.638 (16.0); 3.623 (6.7); 3.325 (8.9); 2.511 (5.7); 2.506 (11.7); 2.502 (15.6); 2.497 (11.6); 2.493 (5.8); 2.116 (6.5); 1.989 (1.2); 1.909 (0.6); 1.398 (1.0); 1.193 (0.3); 1.175 (0.7); 1.157 (0.3); 0.008 (0.5); 0.000 (14.8); −0.009 (0.6)

Example I-12

$^1$H-NMR (400.0 MHz, d$_6$-DMSO):

δ=7.100 (0.9); 7.094 (0.9); 6.742 (0.4); 6.737 (0.4); 6.721 (0.3); 6.716 (0.4); 6.710 (0.4); 6.619 (0.3); 6.613 (0.6); 6.313 (2.9); 6.307 (3.2); 6.216 (0.9); 6.210 (1.5); 6.204 (0.7); 5.756 (0.4); 4.756 (2.2); 4.750 (2.3); 3.637 (0.9); 3.631 (2.4); 3.625 (16.0); 3.601 (6.4); 3.327 (2.3); 2.511 (3.5); 2.506 (7.3); 2.502 (9.8); 2.497 (7.2); 2.493 (3.6); 2.127 (6.3); 1.909 (0.4); 0.008 (0.4); 0.000 (11.5); −0.009 (0.4)

Example I-13

$^1$H-NMR (400.0 MHz, d$_6$-DMSO):

δ=7.422 (2.4); 7.149 (0.4); 7.144 (0.4); 7.135 (0.4); 7.130 (0.9); 7.125 (0.8); 7.110 (1.1); 7.105 (0.6); 7.097 (0.5); 7.092 (0.5); 7.055 (0.6); 7.051 (0.6); 7.036 (1.4); 7.032 (1.4); 7.017 (1.1); 7.013 (0.9); 6.980 (1.6); 6.961 (2.0); 6.951 (1.2); 6.945 (0.9); 6.943 (0.9); 6.927 (1.4); 6.905 (0.9); 6.429 (0.5); 6.417 (3.7); 6.391 (3.7); 6.380 (0.5); 5.952 (0.3); 5.939 (0.7); 5.926 (0.7); 5.913 (0.8); 5.900 (0.5); 5.896 (0.9); 5.883 (0.8); 5.870 (0.9); 5.857 (0.4); 5.308 (1.5); 5.304 (1.6); 5.265 (1.3); 5.261 (1.4); 5.245 (1.6); 5.241 (1.5); 5.219 (1.4); 5.215 (1.4); 4.397 (3.5); 4.384 (3.4); 3.650 (16.0); 3.329 (57.1); 2.676 (0.4); 2.671 (0.5); 2.667 (0.4); 2.506 (59.7); 2.502 (76.7); 2.498 (56.3); 2.333 (0.4); 2.329 (0.5); 2.325 (0.4); 1.954 (12.0); 0.146 (0.3); 0.008 (3.0); 0.000 (72.5); −0.008 (2.9); −0.150 (0.3)

Example I-14

$^1$H-NMR (400.0 MHz, d$_6$-DMSO):

δ=7.502 (1.6); 7.083 (0.4); 7.062 (0.9); 7.045 (0.9); 7.041 (0.6); 7.023 (0.5); 6.972 (0.5); 6.966 (0.5); 6.948 (0.8); 6.941 (0.8); 6.923 (0.5); 6.917 (0.5); 6.886 (0.5); 6.880 (0.4); 6.865 (0.9); 6.859 (0.7); 6.843 (0.4); 6.837 (0.3); 6.503 (2.5); 6.478 (2.5); 6.466 (0.3); 4.667 (3.8); 4.661 (3.8); 3.652 (10.5); 3.573 (1.0); 3.567 (2.2); 3.561 (1.0); 3.327 (17.2); 2.525 (0.4); 2.520 (0.6); 2.511 (8.9); 2.507 (18.3); 2.502 (24.7); 2.498 (18.5); 2.493 (9.3); 1.989 (0.5); 1.943 (7.9); 1.398 (16.0); 0.008 (0.7); 0.000 (22.0); −0.009 (0.8)

Example I-15

$^1$H-NMR (400.0 MHz, d$_6$-DMSO):
δ=7.463 (2.8); 7.074 (0.6); 7.053 (1.4); 7.036 (1.4); 7.014 (0.7); 6.970 (0.7); 6.964 (0.8); 6.946 (1.3); 6.939 (1.4); 6.922 (0.7); 6.915 (0.8); 6.880 (0.8); 6.874 (0.7); 6.859 (1.4); 6.853 (1.2); 6.838 (0.7); 6.832 (0.6); 6.458 (0.6); 6.446 (3.9); 6.420 (3.8); 6.409 (0.6); 5.954 (0.3); 5.941 (0.7); 5.928 (0.7); 5.915 (0.8); 5.911 (0.5); 5.898 (0.9); 5.885 (0.8); 5.872 (0.9); 5.859 (0.4); 5.304 (1.5); 5.300 (1.7); 5.261 (1.4); 5.257 (1.6); 5.252 (1.4); 5.249 (1.8); 5.245 (1.6); 5.223 (1.5); 5.219 (1.5); 4.430 (3.7); 4.417 (3.7); 3.650 (16.0); 3.328 (26.3); 2.507 (30.2); 2.502 (39.7); 2.498 (30.6); 1.934 (13.2); 0.008 (1.4); 0.000 (30.9)

Example I-16

$^1$H-NMR (400.0 MHz, d$_6$-DMSO):
δ=7.155 (2.3); 7.151 (2.3); 7.056 (0.6); 7.038 (0.8); 7.034 (1.4); 7.017 (1.4); 7.013 (0.9); 6.996 (1.3); 6.990 (0.8); 6.972 (1.2); 6.966 (1.3); 6.948 (0.7); 6.941 (0.7); 6.855 (0.7); 6.849 (0.7); 6.833 (1.2); 6.827 (1.2); 6.812 (0.6); 6.806 (0.5); 6.654 (0.7); 6.649 (1.1); 6.644 (0.9); 6.627 (0.8); 6.623 (1.1); 6.617 (0.8); 6.543 (0.7); 6.536 (0.6); 6.520 (0.8); 6.514 (1.2); 6.508 (0.7); 6.492 (0.7); 6.485 (0.6); 4.762 (5.3); 4.756 (5.5); 4.038 (0.9); 4.020 (0.9); 3.676 (1.5); 3.670 (3.4); 3.664 (1.5); 3.639 (16.0); 3.506 (0.7); 3.327 (30.9); 2.671 (0.3); 2.525 (0.8); 2.520 (1.2); 2.511 (17.9); 2.507 (36.6); 2.502 (49.3); 2.498 (36.8); 2.493 (18.4); 2.329 (0.3); 1.989 (4.1); 1.937 (10.8); 1.908 (2.8); 1.398 (3.8); 1.193 (1.1); 1.175 (2.2); 1.157 (1.1); 0.008 (1.3); 0.000 (41.3); −0.009 (1.5)

Example I-17

$^1$H-NMR (400.0 MHz, d$_6$-DMSO):
δ=7.387 (2.2); 6.941 (0.9); 6.920 (1.8); 6.899 (1.0); 6.580 (3.0); 6.555 (3.1); 6.510 (0.4); 6.497 (3.2); 6.472 (3.2); 6.459 (0.4); 4.652 (4.9); 4.646 (5.0); 3.678 (16.0); 3.636 (13.0); 3.577 (1.3); 3.571 (2.7); 3.565 (1.2); 3.329 (9.1); 2.507 (13.1); 2.502 (17.4); 2.498 (13.1); 1.939 (10.4); 0.008 (0.6); 0.000 (15.4); −0.008 (0.6)

Example I-18

$^1$H-NMR (400.0 MHz, d$_6$-DMSO):
δ=7.355 (2.3); 6.925 (0.9); 6.904 (1.8); 6.883 (1.1); 6.566 (3.5); 6.541 (2.6); 6.535 (0.9); 6.445 (0.4); 6.433 (3.3); 6.407 (3.2); 6.395 (0.5); 5.950 (0.6); 5.937 (0.6); 5.924 (0.7); 5.920 (0.5); 5.907 (0.8); 5.894 (0.7); 5.881 (0.8); 5.868 (0.4); 5.315 (1.3); 5.311 (1.4); 5.271 (1.2); 5.267 (1.3); 5.245 (1.3); 5.241 (1.3); 5.218 (1.3); 5.215 (1.3); 4.411 (3.1); 4.398 (3.0); 3.673 (16.0); 3.637 (13.0); 3.329 (9.9); 2.524 (0.3); 2.507 (13.8); 2.502 (18.4); 2.498 (14.1); 1.928 (10.6); 1.909 (0.5); 0.008 (0.6); 0.000 (16.5); −0.008 (0.7)

Example I-19

$^1$H-NMR (400.0 MHz, d$_6$-DMSO):
δ=7.020 (2.3); 7.016 (2.3); 6.932 (1.1); 6.910 (2.2); 6.889 (1.3); 6.649 (0.8); 6.644 (1.1); 6.622 (0.8); 6.617 (1.1); 6.612 (1.0); 6.606 (1.4); 6.600 (1.6); 6.577 (1.1); 6.571 (1.6); 6.555 (1.7); 6.549 (1.5); 6.534 (2.0); 6.528 (1.8); 6.512 (0.8); 6.506 (1.2); 6.500 (0.6); 6.484 (0.7); 6.477 (0.6); 5.757 (0.5); 4.753 (4.9); 4.747 (5.0); 3.683 (16.0); 3.668 (1.9); 3.662 (3.2); 3.656 (1.7); 3.624 (12.9); 3.330 (14.0); 2.507 (15.3); 2.502 (19.9); 2.498 (15.6); 1.935 (9.7); 1.910 (0.8); 0.008 (0.8); 0.000 (15.0)

Example I-20

$^1$H-NMR (400.0 MHz, d$_6$-DMSO):
δ=8.176 (2.6); 8.170 (2.8); 7.595 (2.5); 7.588 (2.5); 7.582 (1.7); 7.567 (1.9); 7.561 (1.9); 7.341 (3.1); 7.320 (2.6); 6.634 (0.5); 6.621 (3.8); 6.595 (3.8); 6.582 (0.5); 5.757 (3.4); 4.692 (5.8); 4.686 (6.0); 3.633 (16.0); 3.571 (1.5); 3.565 (3.4); 3.559 (1.5); 3.328 (52.1); 2.671 (0.4); 2.667 (0.3); 2.524 (1.0); 2.507 (48.9); 2.502 (64.6); 2.498 (48.9); 2.329 (0.4); 2.325 (0.3); 2.116 (15.5); 1.989 (0.6); 1.909 (0.4); 0.008 (2.2); 0.000 (60.1); −0.008 (2.6)

Example I-21

$^1$H-NMR (400.0 MHz, d$_6$-DMSO):
δ=8.135 (2.5); 8.129 (2.6); 7.559 (2.4); 7.555 (3.0); 7.548 (1.8); 7.534 (2.0); 7.528 (2.0); 7.321 (2.9); 7.319 (2.9); 7.300 (2.5); 7.299 (2.5); 6.568 (0.5); 6.556 (3.8); 6.530 (3.7); 6.518 (0.5); 5.979 (0.4); 5.966 (0.8); 5.953 (0.7); 5.940 (0.9); 5.936 (0.5); 5.926 (0.5); 5.923 (1.0); 5.910 (0.8); 5.896 (0.9); 5.883 (0.5); 5.757 (2.3); 5.334 (0.5); 5.330 (1.5); 5.326 (1.7); 5.322 (0.6); 5.291 (0.5); 5.287 (1.4); 5.283 (1.5); 5.279 (0.6); 5.257 (0.7); 5.254 (1.6); 5.250 (1.5); 5.228 (1.4); 5.224 (1.4); 4.451 (2.0); 4.448 (3.4); 4.444 (2.2); 4.438 (2.1); 4.435 (3.4); 4.431 (2.0); 3.636 (16.0); 3.327 (60.3); 2.676 (0.4); 2.671 (0.5); 2.667 (0.4); 2.525 (1.2); 2.520 (1.8); 2.511 (27.5); 2.507 (56.3); 2.502 (75.0); 2.498 (55.5); 2.493 (27.6); 2.334 (0.4); 2.329 (0.5); 2.325 (0.4); 2.098 (15.6); 1.909 (0.4); 0.146 (0.4); 0.008 (2.8); 0.000 (83.2); −0.009 (2.9); −0.150 (0.4)

Example I-22

$^1$H-NMR (400.0 MHz, d$_6$-DMSO):
δ=7.035 (2.8); 7.032 (2.7); 6.915 (1.4); 6.893 (2.8); 6.872 (1.6); 6.641 (1.0); 6.637 (1.3); 6.610 (2.8); 6.604 (2.7); 6.580 (1.4); 6.574 (2.0); 6.562 (2.2); 6.555 (1.5); 6.541 (1.7); 6.534 (1.5); 6.521 (0.8); 6.515 (0.7); 6.498 (1.0); 6.493 (1.4); 6.487 (0.9); 6.470 (0.8); 6.464 (0.7); 6.027 (0.4); 6.014 (0.8); 6.000 (0.8); 5.987 (1.0); 5.984 (0.6); 5.974 (0.6); 5.970 (1.0); 5.957 (0.9); 5.944 (1.0); 5.931 (0.5); 5.359 (1.7); 5.355 (1.8); 5.316 (1.5); 5.312 (1.6); 5.265 (1.8); 5.261 (1.7); 5.238 (1.7); 5.235 (1.6); 4.749 (6.0); 4.743 (6.0); 4.505 (4.0); 4.492 (3.9); 3.670 (1.7); 3.664 (3.5); 3.658 (1.7); 3.626 (16.0); 3.332 (22.9); 2.507 (20.7); 2.503 (26.6); 2.498 (20.0); 2.142 (0.6); 1.933 (12.4); 1.909 (0.5); 0.008 (2.1); 0.000 (44.2)

Example I-23

$^1$H-NMR (400.0 MHz, d$_6$-DMSO):
δ=7.372 (2.6); 6.915 (1.0); 6.892 (2.2); 6.878 (0.5); 6.871 (1.4); 6.580 (2.2); 6.573 (4.9); 6.556 (1.9); 6.552 (2.1); 6.545 (2.1); 6.539 (1.1); 6.448 (0.5); 6.426 (4.0); 6.400 (3.7); 6.388 (0.5); 6.021 (0.5); 6.008 (0.9); 5.995 (0.9); 5.990 (0.4); 5.982 (1.1); 5.978 (0.7); 5.969 (0.8); 5.965 (1.2); 5.961 (0.7); 5.952 (1.1); 5.948 (1.1); 5.939 (1.3); 5.935 (1.0); 5.930 (0.5); 5.926 (0.8); 5.922 (1.1); 5.918 (0.7); 5.913 (0.4); 5.909 (0.7); 5.905 (1.1); 5.900 (0.3); 5.892 (0.9); 5.887 (0.3); 5.878 (1.0); 5.866 (0.5); 5.761 (0.6); 5.754 (2.2); 5.365 (1.2); 5.361 (2.0); 5.357 (1.8); 5.353 (1.2); 5.322 (2.2); 5.318 (3.6); 5.314 (3.3); 5.310 (1.2); 5.279 (1.2); 5.275 (2.0); 5.270 (2.0); 5.266 (1.4); 5.264 (1.5); 5.260 (2.2); 5.256 (2.0); 5.252 (1.2); 5.246

(1.6); 5.242 (2.6); 5.238 (2.6); 5.234 (2.3); 5.229 (1.8); 5.226 (1.1); 5.219 (1.2); 5.216 (1.9); 5.212 (1.5); 5.208 (0.6); 4.486 (3.3); 4.482 (4.3); 4.478 (3.2); 4.473 (3.1); 4.469 (3.7); 4.407 (3.3); 4.403 (4.4); 4.399 (3.3); 4.394 (3.1); 4.390 (3.7); 4.387 (2.0); 3.648 (5.0); 3.640 (16.0); 3.385 (40.0); 3.366 (35.4); 3.357 (45.4); 2.514 (14.9); 2.509 (21.5); 2.505 (23.9); 2.500 (15.8); 2.496 (7.1); 1.929 (12.8); 1.920 (2.0); 1.911 (6.4); 0.008 (7.9); 0.000 (31.5); −0.009 (1.2)

Example I-24

$^1$H-NMR (400.0 MHz, $d_6$-DMSO):

δ=7.399 (2.7); 6.930 (1.0); 6.908 (2.2); 6.887 (1.4); 6.588 (4.4); 6.562 (3.0); 6.556 (1.1); 6.504 (0.5); 6.492 (4.0); 6.466 (4.0); 6.454 (0.5); 6.029 (0.4); 6.016 (0.8); 6.003 (0.8); 5.989 (0.9); 5.976 (0.5); 5.973 (0.9); 5.959 (0.9); 5.946 (0.9); 5.933 (0.5); 5.369 (1.6); 5.365 (1.7); 5.326 (1.4); 5.322 (1.4); 5.266 (1.7); 5.263 (1.6); 5.240 (1.6); 5.236 (1.5); 4.643 (6.1); 4.637 (6.2); 4.491 (3.7); 4.478 (3.7); 3.637 (16.0); 3.573 (1.6); 3.568 (3.5); 3.562 (1.6); 3.331 (37.2); 2.525 (0.6); 2.507 (25.9); 2.503 (33.8); 2.498 (25.2); 1.989 (0.5); 1.939 (13.1); 1.398 (2.5); 0.008 (2.0); 0.000 (48.9); −0.008 (2.0)

Example I-25

$^1$H-NMR (400.0 MHz, $d_6$-DMSO):

δ=8.369 (2.8); 8.364 (2.8); 7.819 (1.8); 7.812 (1.8); 7.798 (2.0); 7.792 (2.0); 7.484 (3.0); 7.464 (2.7); 6.836 (0.8); 6.829 (1.1); 6.826 (1.0); 6.809 (0.8); 6.802 (1.2); 6.786 (0.8); 6.780 (0.6); 6.763 (1.1); 6.760 (1.2); 6.737 (0.8); 6.730 (0.6); 6.590 (3.6); 5.756 (6.4); 4.800 (5.5); 4.794 (5.7); 3.639 (1.5); 3.633 (3.3); 3.628 (1.5); 3.569 (16.0); 3.328 (27.9); 2.506 (30.4); 2.502 (39.9); 2.498 (30.2); 2.206 (15.5); 1.989 (0.9); 1.909 (0.7); 1.175 (0.5); 0.008 (1.8); 0.000 (44.3); −0.008 (2.0)

Example I-26

$^1$H-NMR (400.0 MHz, $d_6$-DMSO):

δ=7.037 (2.5); 7.033 (2.5); 6.953 (1.4); 6.932 (2.8); 6.910 (1.6); 6.669 (1.5); 6.663 (1.7); 6.640 (2.2); 6.634 (2.7); 6.616 (0.9); 6.607 (2.8); 6.601 (1.7); 6.586 (1.6); 6.579 (1.4); 6.530 (0.8); 6.524 (0.7); 6.508 (0.9); 6.502 (1.3); 6.495 (0.8); 6.479 (0.8); 6.473 (0.7); 5.757 (1.0); 4.749 (5.9); 4.743 (6.0); 4.733 (6.4); 4.727 (6.3); 3.665 (1.7); 3.659 (3.7); 3.653 (1.7); 3.623 (16.0); 3.584 (1.7); 3.578 (3.7); 3.572 (1.6); 3.338 (20.5); 2.520 (0.5); 2.512 (7.3); 2.507 (14.9); 2.503 (19.7); 2.498 (14.2); 2.494 (6.9); 1.940 (11.3); 0.000 (3.1)

Example I-27

$^1$H-NMR (400.0 MHz, $d_6$-DMSO):

δ=7.396 (2.6); 6.973 (1.3); 6.952 (2.5); 6.940 (0.4); 6.929 (1.3); 6.658 (1.2); 6.652 (1.9); 6.637 (1.6); 6.634 (1.8); 6.628 (1.8); 6.622 (1.8); 6.617 (2.3); 6.611 (1.1); 6.516 (0.5); 6.503 (4.0); 6.478 (3.9); 6.465 (0.5); 4.721 (6.1); 4.715 (6.2); 4.650 (6.1); 4.644 (6.3); 3.631 (16.0); 3.579 (1.7); 3.573 (4.2); 3.565 (4.1); 3.559 (1.7); 3.329 (43.4); 2.671 (0.4); 2.525 (0.8); 2.511 (20.2); 2.507 (41.1); 2.502 (54.2); 2.498 (39.8); 2.493 (19.8); 2.329 (0.4); 1.989 (0.7); 1.947 (12.5); 1.908 (0.5); 1.398 (9.1); 1.175 (0.4); 0.000 (6.6)

Example I-28

$^1$H-NMR (400.0 MHz, $d_6$-DMSO):

δ=7.365 (2.5); 6.952 (1.2); 6.931 (2.3); 6.915 (0.4); 6.908 (1.1); 6.639 (1.2); 6.633 (1.9); 6.622 (1.6); 6.619 (1.7); 6.609 (1.5); 6.602 (3.4); 6.595 (1.1); 6.447 (0.5); 6.435 (3.9); 6.409 (3.9); 6.397 (0.5); 5.969 (0.4); 5.956 (0.8); 5.943 (0.8); 5.930 (1.0); 5.926 (0.6); 5.917 (0.5); 5.913 (1.0); 5.900 (0.9); 5.887 (1.0); 5.873 (0.5); 5.330 (0.6); 5.326 (1.7); 5.322 (1.8); 5.318 (0.7); 5.287 (0.5); 5.283 (1.5); 5.279 (1.6); 5.275 (0.7); 5.253 (0.7); 5.250 (1.7); 5.246 (1.7); 5.227 (0.7); 5.224 (1.6); 5.220 (1.6); 4.712 (6.0); 4.706 (6.2); 4.412 (2.2); 4.408 (3.8); 4.405 (2.4); 4.399 (2.3); 4.395 (3.6); 4.392 (2.2); 3.632 (16.0); 3.585 (1.7); 3.579 (3.8); 3.573 (1.7); 3.330 (45.5); 2.671 (0.4); 2.524 (0.8); 2.520 (1.3); 2.511 (19.4); 2.507 (40.0); 2.502 (53.3); 2.498 (39.2); 2.493 (19.4); 2.329 (0.4); 2.183 (0.4); 1.989 (0.9); 1.935 (12.6); 1.909 (2.5); 1.355 (3.3); 1.193 (0.4); 1.175 (0.6); 1.169 (1.1); 0.008 (0.4); 0.000 (13.4); −0.009 (0.5)

Example I-29

$^1$H-NMR (400.0 MHz, $d_6$-DMSO):

δ=7.451 (2.6); 7.449 (2.6); 7.367 (1.6); 7.361 (1.7); 7.345 (1.7); 7.338 (1.7); 7.229 (1.2); 7.213 (1.4); 7.208 (2.0); 7.192 (1.8); 7.142 (1.1); 7.135 (1.0); 7.121 (1.8); 7.114 (1.6); 7.099 (0.7); 7.093 (0.7); 6.767 (1.5); 6.760 (1.5); 6.734 (1.5); 6.727 (1.5); 6.492 (1.0); 6.487 (0.9); 6.470 (1.3); 6.464 (1.3); 6.371 (1.6); 6.347 (2.0); 6.324 (1.2); 5.757 (1.7); 4.640 (6.1); 4.634 (6.2); 3.582 (16.0); 3.526 (1.6); 3.521 (3.6); 3.515 (1.6); 3.331 (46.3); 2.525 (0.6); 2.511 (15.6); 2.507 (31.1); 2.503 (40.8); 2.498 (30.2); 2.494 (15.3); 2.006 (15.5); 0.008 (0.5); 0.000 (15.1); −0.008 (0.6)

Example I-30

$^1$H-NMR (400.0 MHz, $d_6$-DMSO):

δ=8.317 (0.4); 7.489 (3.7); 7.463 (0.4); 7.408 (1.5); 7.402 (1.6); 7.386 (1.6); 7.379 (1.5); 7.199 (0.9); 7.182 (1.2); 7.177 (2.2); 7.161 (2.0); 7.149 (1.3); 7.142 (1.2); 7.128 (1.8); 7.121 (1.6); 7.106 (0.6); 7.100 (0.6); 6.675 (0.4); 6.666 (3.9); 6.661 (1.5); 6.649 (1.4); 6.644 (4.8); 6.635 (0.9); 6.612 (0.5); 6.446 (0.5); 6.437 (4.8); 6.420 (1.3); 6.415 (4.2); 6.017 (0.3); 6.004 (0.7); 5.991 (0.7); 5.978 (0.8); 5.974 (0.5); 5.965 (0.5); 5.961 (0.9); 5.948 (0.8); 5.935 (0.9); 5.922 (0.4); 5.757 (0.5); 5.344 (0.5); 5.340 (1.4); 5.336 (1.6); 5.332 (0.7); 5.297 (1.3); 5.293 (1.4); 5.288 (0.6); 5.212 (1.4); 5.208 (1.4); 5.186 (1.3); 5.182 (1.3); 4.392 (3.5); 4.389 (2.3); 4.383 (2.2); 4.379 (3.4); 3.853 (0.4); 3.836 (0.4); 3.536 (15.5); 3.329 (61.0); 2.675 (0.3); 2.671 (0.5); 2.667 (0.4); 2.524 (1.5); 2.511 (28.5); 2.507 (57.1); 2.502 (75.3); 2.498 (56.6); 2.333 (0.4); 2.329 (0.5); 2.325 (0.4); 2.044 (0.4); 2.008 (16.0); 1.252 (0.5); 1.235 (1.2); 1.218 (0.5); 0.146 (0.5); 0.008 (4.4); 0.000 (113.6); −0.008 (5.4); −0.020 (0.4); −0.150 (0.5)

Example I-31

$^1$H-NMR (400.0 MHz, $d_6$-DMSO):

δ=7.541 (4.0); 7.415 (1.6); 7.409 (1.7); 7.393 (1.6); 7.386 (1.6); 7.208 (1.0); 7.191 (1.2); 7.186 (2.2); 7.170 (2.1); 7.156 (1.3); 7.150 (1.2); 7.135 (1.8); 7.128 (1.6); 7.114 (0.6); 7.107 (0.6); 6.719 (0.4); 6.710 (4.3); 6.705 (1.5); 6.693 (1.6); 6.688 (5.1); 6.679 (0.5); 6.458 (0.5); 6.450 (5.1); 6.444 (1.7); 6.433 (1.5); 6.427 (4.4); 6.419 (0.5); 5.757 (3.3); 4.605 (6.4); 4.600 (6.5); 3.920 (0.4); 3.818 (0.5); 3.539 (16.0); 3.491 (1.6); 3.485 (3.4); 3.479 (1.6); 3.332 (74.2); 2.672 (0.3); 2.525 (0.9); 2.511 (19.3); 2.507 (38.3);

Example I-32

¹H-NMR (400.0 MHz, d₆-DMSO):
δ=7.397 (1.6); 7.391 (1.7); 7.375 (1.7); 7.368 (1.6); 7.283 (1.3); 7.266 (1.5); 7.261 (1.9); 7.245 (1.8); 7.203 (4.1); 7.160 (1.1); 7.154 (1.0); 7.139 (1.8); 7.133 (1.6); 7.118 (0.8); 7.111 (0.7); 6.936 (3.4); 6.929 (3.6); 6.669 (1.6); 6.662 (1.5); 6.647 (1.8); 6.640 (1.7); 6.312 (3.5); 6.290 (3.2); 5.756 (2.3); 4.659 (6.2); 4.653 (6.2); 3.571 (16.0); 3.529 (1.7); 3.523 (3.6); 3.518 (1.6); 3.331 (51.8); 2.525 (0.9); 2.511 (18.5); 2.507 (36.7); 2.503 (47.7); 2.498 (34.9); 2.494 (17.3); 2.028 (15.6); 0.008 (0.3); 0.000 (9.1); −0.008 (0.3)

Example I-33

¹H-NMR (400.0 MHz, d₆-DMSO):
δ=7.754 (2.5); 7.403 (1.6); 7.396 (1.6); 7.381 (1.7); 7.374 (1.6); 7.259 (1.2); 7.243 (1.4); 7.237 (1.9); 7.221 (1.8); 7.171 (1.1); 7.164 (1.0); 7.149 (1.7); 7.143 (1.6); 7.128 (0.7); 7.122 (0.7); 7.073 (1.2); 7.054 (1.2); 7.042 (1.2); 7.022 (1.2); 6.240 (1.2); 6.220 (1.3); 6.209 (1.3); 6.188 (1.3); 5.757 (4.3); 4.713 (6.0); 4.707 (6.1); 3.627 (0.4); 3.614 (16.0); 3.573 (1.6); 3.567 (3.4); 3.561 (1.6); 3.344 (0.9); 3.332 (46.4); 3.315 (0.4); 2.525 (0.9); 2.512 (16.6); 2.507 (33.0); 2.503 (43.3); 2.498 (32.0); 2.494 (16.3); 2.021 (15.5); 1.397 (0.5); 0.000 (1.6)

Example I-34

¹H-NMR (400.0 MHz, d₆-DMSO):
δ=7.688 (2.4); 7.394 (1.6); 7.387 (1.7); 7.372 (1.7); 7.365 (1.7); 7.249 (1.2); 7.233 (1.3); 7.227 (2.0); 7.211 (1.8); 7.162 (1.1); 7.156 (1.0); 7.141 (1.7); 7.134 (1.6); 7.120 (0.7); 7.113 (0.7); 6.998 (1.2); 6.979 (1.2); 6.967 (1.2); 6.947 (1.2); 6.242 (1.2); 6.221 (1.3); 6.210 (1.3); 6.190 (1.3); 5.986 (0.4); 5.972 (0.8); 5.959 (0.7); 5.946 (0.9); 5.943 (0.6); 5.932 (0.5); 5.929 (1.0); 5.916 (0.8); 5.903 (0.9); 5.889 (0.5); 5.758 (3.2); 5.336 (0.5); 5.332 (1.5); 5.328 (1.7); 5.324 (0.7); 5.293 (0.5); 5.289 (1.3); 5.285 (1.5); 5.281 (0.6); 5.241 (1.5); 5.237 (1.5); 5.215 (1.4); 5.211 (1.4); 4.472 (3.4); 4.459 (3.4); 3.648 (0.3); 3.612 (16.0); 3.367 (0.7); 3.331 (33.0); 2.548 (0.5); 2.543 (0.8); 2.539 (0.8); 2.534 (0.5); 2.512 (15.4); 2.507 (31.6); 2.503 (42.2); 2.498 (31.5); 2.494 (16.3); 2.050 (0.3); 2.014 (15.5); 1.235 (0.7); 0.000 (1.6)

Example I-35

¹H-NMR (400.0 MHz, d₆-DMSO):
δ=7.760 (3.5); 7.429 (1.5); 7.422 (1.6); 7.406 (1.6); 7.400 (1.5); 7.220 (0.9); 7.203 (1.1); 7.198 (2.2); 7.182 (2.0); 7.170 (1.3); 7.164 (1.1); 7.149 (1.7); 7.143 (1.5); 7.128 (0.6); 7.121 (0.5); 6.874 (1.3); 6.851 (2.2); 6.828 (1.4); 6.317 (1.4); 6.311 (1.6); 6.284 (1.3); 6.277 (1.7); 6.239 (1.1); 6.237 (1.3); 6.233 (1.1); 6.217 (1.1); 6.215 (1.2); 6.211 (1.0); 6.008 (0.4); 5.995 (0.8); 5.982 (0.7); 5.968 (0.9); 5.965 (0.6); 5.955 (0.5); 5.952 (1.0); 5.938 (0.8); 5.925 (0.9); 5.912 (0.4); 5.757 (2.5); 5.340 (0.6); 5.336 (1.6); 5.332 (1.7); 5.328 (0.7); 5.297 (0.5); 5.293 (1.4); 5.289 (1.4); 5.285 (0.6); 5.225 (1.5); 5.221 (1.5); 5.199 (1.4); 5.195 (1.4); 4.441 (3.6); 4.427 (3.6); 3.561 (16.0); 3.331 (40.5); 2.525 (0.7); 2.511 (15.3); 2.507 (30.5); 2.503 (40.0); 2.498 (29.7); 2.018 (15.6); 1.397 (0.4); 0.146 (0.7); 0.008 (6.2); 0.000 (129.2); −0.009 (6.7); −0.150 (0.7)

Example I-36

¹H-NMR (400.0 MHz, d₆-DMSO):
δ=7.818 (3.6); 7.435 (1.5); 7.428 (1.6); 7.413 (1.6); 7.406 (1.6); 7.228 (0.9); 7.212 (1.2); 7.207 (2.1); 7.191 (2.0); 7.177 (1.3); 7.170 (1.1); 7.155 (1.7); 7.149 (1.5); 7.134 (0.6); 7.128 (0.5); 6.947 (1.3); 6.924 (2.3); 6.901 (1.4); 6.322 (1.3); 6.315 (1.6); 6.289 (1.2); 6.282 (1.7); 6.260 (1.3); 6.254 (1.0); 6.238 (1.2); 6.234 (1.0); 5.757 (4.0); 4.661 (6.2); 4.655 (6.4); 3.564 (16.0); 3.535 (1.6); 3.529 (3.3); 3.523 (1.6); 3.332 (69.8); 2.672 (0.3); 2.525 (0.9); 2.511 (20.5); 2.507 (40.8); 2.503 (53.7); 2.498 (39.8); 2.329 (0.3); 2.021 (15.4); 1.398 (0.4); 0.146 (0.9); 0.022 (0.5); 0.008 (7.8); 0.000 (164.2); −0.009 (8.6); −0.150 (0.9)

Example I-37

¹H-NMR (400.0 MHz, d₆-DMSO):
δ=7.743 (2.4); 7.740 (2.4); 7.426 (1.6); 7.420 (1.7); 7.404 (1.7); 7.397 (1.7); 7.293 (1.3); 7.278 (1.4); 7.272 (1.9); 7.256 (1.8); 7.189 (1.1); 7.182 (1.0); 7.168 (1.8); 7.161 (1.6); 7.146 (0.8); 7.140 (0.7); 6.945 (1.5); 6.923 (1.6); 6.917 (1.6); 6.895 (1.6); 6.187 (0.8); 6.179 (1.5); 6.171 (0.9); 6.164 (0.8); 6.157 (1.3); 6.148 (0.8); 5.967 (0.4); 5.954 (0.8); 5.941 (0.7); 5.927 (0.9); 5.924 (0.5); 5.915 (0.5); 5.911 (1.0); 5.897 (0.8); 5.884 (1.0); 5.871 (0.5); 5.856 (1.5); 5.849 (1.5); 5.838 (1.5); 5.830 (1.4); 5.757 (2.6); 5.298 (0.6); 5.294 (1.6); 5.290 (1.7); 5.286 (0.7); 5.251 (1.4); 5.247 (1.5); 5.243 (0.6); 5.201 (1.6); 5.197 (1.5); 5.174 (1.5); 5.170 (1.4); 4.321 (3.5); 4.317 (2.4); 4.311 (2.3); 4.308 (3.5); 3.593 (16.0); 3.330 (46.4); 2.525 (0.7); 2.511 (17.8); 2.507 (35.9); 2.503 (47.1); 2.498 (34.9); 2.494 (17.6); 2.047 (15.9); 1.235 (0.4); 0.146 (0.4); 0.008 (3.5); 0.000 (89.7); −0.009 (4.0); −0.150 (0.4)

Example I-38

¹H-NMR (400.0 MHz, d₆-DMSO):
δ=7.767 (2.4); 7.763 (2.4); 7.424 (1.6); 7.418 (1.7); 7.402 (1.7); 7.396 (1.6); 7.296 (1.3); 7.280 (1.4); 7.275 (1.9); 7.259 (1.8); 7.189 (1.1); 7.183 (1.0); 7.168 (1.7); 7.161 (1.6); 7.147 (0.7); 7.140 (0.7); 6.982 (1.5); 6.960 (1.6); 6.954 (1.6); 6.932 (1.6); 6.246 (0.8); 6.238 (1.5); 6.230 (0.9); 6.224 (0.8); 6.216 (1.3); 6.208 (0.7); 5.893 (1.5); 5.885 (1.5); 5.874 (1.5); 5.867 (1.4); 5.757 (3.7); 4.559 (4.2); 3.590 (16.0); 3.520 (1.6); 3.515 (3.4); 3.509 (1.6); 3.332 (66.9); 2.525 (0.9); 2.512 (17.8); 2.507 (36.2); 2.503 (47.7); 2.498 (34.9); 2.494 (17.2); 2.044 (15.8); 1.398 (0.5); 0.146 (0.5); 0.008 (3.4); 0.000 (92.0); −0.008 (3.7); −0.150 (0.5)

Example I-39

¹H-NMR (400.0 MHz, d₆-DMSO):
δ=7.783 (2.8); 7.570 (3.3); 7.564 (3.5); 7.362 (1.7); 7.356 (1.6); 7.341 (2.2); 7.335 (2.2); 7.230 (3.9); 7.210 (2.9); 7.083 (1.2); 7.063 (1.3); 7.052 (1.3); 7.032 (1.2); 6.239 (1.3); 6.218 (1.3); 6.207 (1.3); 6.187 (1.3); 5.758 (4.3); 4.715 (6.0); 4.710 (6.2); 3.613 (16.0); 3.578 (1.6); 3.572 (3.2); 3.567 (1.6); 3.332 (39.1); 2.508 (31.7); 2.503 (41.5); 2.499 (31.5); 2.027 (15.6); 1.397 (0.4); 0.008 (1.2); 0.000 (32.9)

Example I-40

¹H-NMR (400.0 MHz, d₆-DMSO):
δ=7.566 (3.3); 7.560 (3.6); 7.351 (1.6); 7.346 (1.5); 7.330 (2.3); 7.325 (2.3); 7.253 (4.1); 7.237 (4.7); 7.233 (4.0); 6.944 (3.3); 6.937 (3.5); 6.673 (1.6); 6.666 (1.5); 6.651 (1.8); 6.644 (1.7); 6.307 (3.3); 6.284 (3.0); 5.757 (2.2); 4.661 (6.2); 4.655 (6.4); 3.569 (16.0); 3.533 (1.7); 3.528 (3.4); 3.522 (1.7); 3.333 (96.3); 2.672 (0.5); 2.507 (57.5); 2.503 (73.6); 2.499 (56.2); 2.330 (0.5); 2.035 (15.7); 1.397 (0.9); 1.235 (0.5); 0.008 (0.9); 0.000 (20.6)

Example I-41

¹H-NMR (400.0 MHz, d₆-DMSO):
δ=7.389 (1.5); 7.383 (1.6); 7.367 (1.6); 7.361 (1.5); 7.273 (1.3); 7.257 (1.5); 7.252 (2.0); 7.236 (1.8); 7.155 (4.6); 7.147 (1.3); 7.132 (2.1); 7.126 (1.7); 7.111 (0.8); 7.104 (0.7); 6.870 (3.0); 6.863 (3.2); 6.833 (0.4); 6.826 (0.4); 6.632 (1.4); 6.625 (1.4); 6.610 (1.6); 6.603 (1.7); 6.312 (3.2); 6.290 (2.9); 5.993 (0.3); 5.980 (0.7); 5.967 (0.7); 5.954 (0.8); 5.951 (0.5); 5.937 (0.8); 5.924 (0.7); 5.911 (0.8); 5.898 (0.4); 5.757 (1.8); 5.331 (1.4); 5.327 (1.5); 5.288 (1.3); 5.284 (1.3); 5.223 (1.5); 5.220 (1.4); 5.197 (1.4); 5.193 (1.4); 4.427 (3.4); 4.414 (3.3); 3.878 (0.5); 3.860 (0.5); 3.570 (15.3); 3.330 (23.9); 2.507 (28.6); 2.503 (36.6); 2.498 (27.5); 2.022 (16.0); 1.245 (0.5); 1.227 (1.1); 1.210 (0.5); 0.007 (2.0); 0.000 (43.0)

Example I-42

¹H-NMR (400.0 MHz, d₆-DMSO):
δ=7.370 (1.3); 7.364 (1.4); 7.349 (1.4); 7.343 (1.4); 7.067 (0.5); 7.046 (2.0); 7.035 (1.4); 7.029 (2.9); 7.014 (1.5); 7.008 (1.4); 6.993 (0.4); 6.987 (0.4); 6.957 (2.4); 6.596 (1.0); 6.569 (1.0); 6.542 (0.7); 6.536 (0.6); 6.519 (0.8); 6.515 (1.0); 6.509 (0.7); 6.493 (0.7); 6.486 (0.6); 5.757 (0.9); 4.724 (2.4); 4.718 (4.4); 4.712 (2.6); 3.825 (0.4); 3.653 (16.0); 3.510 (0.7); 3.330 (38.5); 2.715 (0.5); 2.704 (0.5); 2.672 (0.4); 2.525 (0.9); 2.507 (42.3); 2.502 (56.7); 2.498 (43.6); 2.329 (0.4); 2.183 (0.4); 1.877 (13.8); 1.601 (1.4); 1.235 (0.7); 0.000 (2.2)

Example I-43

¹H-NMR (400.1 MHz, CDCl₃):
δ=7.341 (1.5); 7.334 (1.6); 7.320 (1.6); 7.313 (1.5); 7.259 (9.6); 7.110 (1.3); 7.095 (1.4); 7.089 (1.8); 7.074 (1.7); 6.955 (1.0); 6.949 (0.9); 6.935 (1.4); 6.928 (1.3); 6.913 (1.7); 6.908 (1.7); 6.893 (1.7); 6.889 (1.7); 6.812 (0.5); 6.808 (0.5); 6.793 (1.4); 6.789 (1.3); 6.774 (1.2); 6.770 (1.0); 6.757 (1.2); 6.752 (1.4); 6.737 (1.4); 6.733 (1.5); 6.718 (0.6); 6.714 (0.5); 6.383 (1.6); 6.379 (1.7); 6.364 (1.4); 6.359 (1.4); 5.702 (1.8); 5.296 (1.6); 4.704 (6.1); 4.698 (6.1); 3.681 (16.0); 2.492 (1.7); 2.486 (3.4); 2.480 (1.6); 2.170 (15.9); 2.001 (2.9); 1.595 (1.1); 0.000 (0.3)

Example I-44

¹H-NMR (400.1 MHz, CDCl₃):
δ=7.351 (1.5); 7.344 (1.5); 7.330 (1.5); 7.323 (1.5); 7.260 (13.6); 7.134 (1.3); 7.119 (1.4); 7.112 (1.7); 7.097 (1.7); 6.985 (0.9); 6.979 (0.9); 6.965 (1.3); 6.958 (1.3); 6.944 (0.7); 6.937 (0.7); 6.691 (1.3); 6.678 (1.3); 6.668 (1.4); 6.656 (1.4); 6.388 (1.6); 6.380 (1.7); 6.366 (1.4); 6.359 (1.3); 6.345 (0.7); 6.337 (0.7); 6.091 (1.5); 6.084 (1.4); 6.066 (1.5); 6.058 (1.4); 6.046 (0.4); 6.032 (0.7); 6.019 (0.7); 6.006 (0.8); 6.003 (0.5); 5.993 (0.5); 5.989 (0.8); 5.976 (0.8); 5.963 (0.8); 5.950 (0.4); 5.832 (1.6); 5.368 (0.5); 5.364 (1.3); 5.360 (1.4); 5.356 (0.6); 5.324 (0.5); 5.321 (1.2); 5.317 (1.2); 5.313 (0.5); 5.297 (0.5); 5.279 (1.4); 5.276 (1.4); 5.253 (1.3); 5.249 (1.3); 4.512 (2.2); 4.508 (2.2); 4.503 (1.4); 4.499 (2.2); 4.495 (2.1); 3.706 (16.0); 2.172 (16.0); 2.003 (0.4); 1.567 (4.9); 0.000 (0.5)

Example I-45

¹H-NMR (400.1 MHz, CDCl₃):
δ=7.352 (1.5); 7.346 (1.6); 7.332 (1.6); 7.325 (1.5); 7.261 (6.7); 7.133 (1.3); 7.118 (1.4); 7.111 (1.8); 7.096 (1.7); 6.985 (1.0); 6.979 (1.0); 6.965 (1.3); 6.959 (1.3); 6.944 (0.8); 6.937 (0.7); 6.835 (1.3); 6.823 (1.4); 6.813 (1.5); 6.801 (1.4); 6.417 (0.8); 6.410 (0.9); 6.397 (1.1); 6.395 (1.0); 6.389 (1.1); 6.375 (0.8); 6.367 (0.8); 6.114 (1.5); 6.107 (1.4); 6.089 (1.6); 6.082 (1.4); 5.794 (1.5); 5.296 (1.3); 4.666 (5.2); 4.660 (5.1); 3.699 (16.0); 2.480 (1.7); 2.474 (3.5); 2.468 (1.7); 2.170 (15.9); 2.001 (3.1); 1.615 (0.6)

Example I-46

¹H-NMR (400.1 MHz, CDCl₃):
δ=7.339 (1.6); 7.332 (1.6); 7.318 (1.6); 7.311 (1.5); 7.259 (7.5); 7.107 (1.3); 7.092 (1.4); 7.086 (1.8); 7.071 (1.7); 6.953 (1.0); 6.947 (1.0); 6.933 (1.4); 6.926 (1.3); 6.912 (0.8); 6.905 (0.7); 6.602 (2.0); 6.599 (2.2); 6.559 (1.0); 6.538 (1.1); 6.249 (2.7); 6.229 (2.4); 6.067 (0.4); 6.054 (0.8); 6.041 (0.7); 6.027 (0.9); 6.024 (0.5); 6.014 (0.5); 6.011 (0.9); 5.997 (0.8); 5.984 (0.9); 5.971 (0.4); 5.623 (1.9); 5.376 (0.5); 5.372 (1.4); 5.368 (1.4); 5.364 (0.5); 5.333 (0.5); 5.329 (1.2); 5.325 (1.2); 5.321 (0.5); 5.295 (1.5); 5.276 (0.6); 5.273 (1.5); 5.269 (1.5); 5.266 (0.6); 5.250 (0.5); 5.246 (1.4); 5.243 (1.4); 5.239 (0.5); 4.537 (0.8); 4.533 (1.5); 4.530 (1.5); 4.526 (1.6); 4.523 (1.5); 4.520 (1.6); 4.517 (1.5); 4.513 (1.4); 4.510 (0.8); 3.676 (16.0); 2.218 (11.4); 2.165 (15.8); 2.000 (1.7); 1.641 (0.5)

Example I-47

¹H-NMR (400.1 MHz, CDCl₃):
δ=7.341 (1.5); 7.335 (1.6); 7.321 (1.5); 7.314 (1.5); 7.259 (7.8); 7.106 (1.3); 7.091 (1.4); 7.085 (1.7); 7.070 (1.7); 6.955 (1.0); 6.948 (0.9); 6.934 (1.4); 6.928 (1.3); 6.913 (0.7); 6.907 (0.7); 6.717 (2.2); 6.713 (2.2); 6.606 (1.0); 6.586 (1.2); 6.274 (2.8); 6.254 (2.5); 5.569 (1.7); 5.296 (1.7); 4.681 (6.1); 4.675 (6.1); 3.665 (16.0); 2.487 (1.7); 2.481 (3.4); 2.475 (1.6); 2.327 (0.4); 2.237 (11.7); 2.163 (15.8); 2.001 (2.2); 1.611 (1.0)

Example I-48

¹H-NMR (400.1 MHz, CDCl₃):
δ=7.259 (11.5); 7.155 (1.5); 7.148 (1.5); 7.133 (1.5); 7.127 (1.5); 7.117 (1.4); 7.101 (1.4); 7.095 (1.7); 7.080 (1.6); 6.911 (1.0); 6.904 (0.9); 6.891 (1.3); 6.884 (1.2); 6.869 (0.8); 6.863 (0.8); 6.794 (1.0); 6.789 (0.8); 6.776 (1.5); 6.770 (1.9); 6.765 (0.4); 6.760 (0.5); 6.746 (1.4); 6.741 (1.2); 6.729 (2.6); 6.724 (2.5); 6.711 (1.4); 6.706 (1.1); 6.692 (0.4); 6.345 (1.6); 6.340 (1.6); 6.328 (0.9); 6.326 (1.0); 6.322 (1.4); 6.070 (0.4); 6.057 (0.7); 6.044 (0.7); 6.031 (0.8); 6.027 (0.5); 6.018 (0.5); 6.014 (0.9); 6.001 (0.8); 5.988 (0.9); 5.974 (0.4); 5.759 (1.8); 5.381 (0.5); 5.377 (1.4); 5.373 (1.4); 5.369 (0.5); 5.338 (0.5); 5.334 (1.2); 5.330 (1.2); 5.326 (0.5); 5.296 (0.4); 5.286 (0.6); 5.283 (1.5); 5.280 (1.5); 5.276 (0.5); 5.260 (0.5); 5.257 (1.4); 5.253

(1.3); 5.250 (0.5); 4.556 (1.7); 4.545 (1.7); 3.690 (16.0); 2.181 (15.9); 2.001 (0.4); 1.584 (1.7); 0.000 (0.4)

Example I-49

¹H-NMR (400.1 MHz, CDCl₃):
δ=7.259 (4.3); 7.156 (1.5); 7.149 (1.6); 7.134 (1.5); 7.128 (1.6); 7.114 (1.4); 7.098 (1.4); 7.092 (1.7); 7.077 (1.6); 6.916 (1.3); 6.912 (1.5); 6.910 (1.3); 6.903 (1.0); 6.897 (1.8); 6.893 (1.9); 6.889 (1.6); 6.883 (1.3); 6.868 (0.8); 6.861 (0.8); 6.810 (0.5); 6.807 (0.5); 6.791 (1.4); 6.788 (1.4); 6.773 (1.2); 6.769 (1.0); 6.758 (1.3); 6.753 (1.5); 6.739 (1.4); 6.734 (1.5); 6.720 (0.6); 6.715 (0.5); 6.367 (1.6); 6.362 (1.7); 6.347 (1.4); 6.343 (1.5); 5.706 (1.9); 5.293 (1.1); 4.707 (6.2); 4.701 (6.2); 3.680 (16.0); 2.494 (1.7); 2.488 (3.6); 2.482 (1.7); 2.178 (15.9); 1.998 (2.7)

Example I-50

¹H-NMR (400.1 MHz, CDCl₃):
δ=7.260 (6.4); 7.167 (1.5); 7.160 (1.6); 7.145 (1.5); 7.138 (2.1); 7.122 (1.4); 7.116 (1.7); 7.100 (1.6); 6.940 (1.0); 6.933 (0.9); 6.920 (1.3); 6.913 (1.2); 6.899 (0.8); 6.892 (0.7); 6.695 (1.3); 6.683 (1.3); 6.673 (1.4); 6.661 (1.4); 6.389 (0.9); 6.382 (0.9); 6.368 (1.2); 6.361 (1.2); 6.347 (0.8); 6.339 (0.8); 6.075 (1.5); 6.068 (1.5); 6.050 (1.6); 6.046 (0.6); 6.043 (1.5); 6.033 (0.8); 6.020 (0.7); 6.007 (0.8); 6.003 (0.5); 5.993 (0.5); 5.990 (0.9); 5.977 (0.8); 5.963 (0.9); 5.950 (0.4); 5.834 (1.5); 5.367 (0.5); 5.364 (1.3); 5.360 (1.4); 5.356 (0.6); 5.324 (0.5); 5.320 (1.2); 5.317 (1.2); 5.313 (0.5); 5.296 (0.3); 5.285 (0.6); 5.282 (1.5); 5.279 (1.4); 5.275 (0.5); 5.259 (0.6); 5.256 (1.4); 5.252 (1.3); 5.249 (0.5); 4.514 (1.8); 4.502 (1.8); 3.705 (16.0); 2.182 (15.9); 2.001 (0.4); 1.615 (0.6)

Example I-51

¹H-NMR (400.1 MHz, CDCl₃):
δ=7.260 (9.0); 7.169 (1.5); 7.163 (1.5); 7.148 (1.5); 7.141 (1.5); 7.135 (1.4); 7.120 (1.4); 7.114 (1.7); 7.098 (1.6); 6.940 (1.0); 6.933 (0.9); 6.920 (1.3); 6.913 (1.2); 6.898 (0.8); 6.892 (0.7); 6.839 (1.3); 6.826 (1.4); 6.817 (1.5); 6.804 (1.4); 6.419 (0.9); 6.412 (0.9); 6.399 (1.1); 6.397 (1.1); 6.391 (1.1); 6.390 (1.1); 6.377 (0.8); 6.369 (0.8); 6.095 (1.5); 6.087 (1.4); 6.070 (1.6); 6.062 (1.4); 5.793 (1.4); 5.297 (1.1); 4.670 (5.6); 4.664 (5.6); 3.699 (16.0); 2.484 (1.7); 2.478 (3.6); 2.472 (1.7); 2.179 (15.9); 1.592 (1.0); 1.256 (1.8); 0.000 (0.3)

Example I-52

¹H-NMR (400.1 MHz, CDCl₃):
δ=7.258 (4.9); 7.154 (1.5); 7.147 (1.6); 7.132 (1.5); 7.126 (1.6); 7.112 (1.4); 7.097 (1.5); 7.091 (1.7); 7.075 (1.6); 6.909 (1.0); 6.902 (1.0); 6.888 (1.3); 6.882 (1.2); 6.867 (0.9); 6.860 (0.8); 6.607 (1.9); 6.604 (2.2); 6.558 (1.0); 6.556 (1.0); 6.538 (1.1); 6.536 (1.1); 6.236 (2.7); 6.216 (2.4); 6.066 (0.4); 6.053 (0.8); 6.040 (0.8); 6.027 (0.9); 6.023 (0.5); 6.014 (0.5); 6.010 (0.9); 5.997 (0.9); 5.984 (0.9); 5.971 (0.5); 5.628 (1.9); 5.375 (0.5); 5.371 (1.4); 5.368 (1.5); 5.364 (0.6); 5.332 (0.5); 5.328 (1.2); 5.324 (1.3); 5.320 (0.5); 5.292 (1.3); 5.278 (0.6); 5.275 (1.5); 5.271 (1.6); 5.268 (0.7); 5.252 (0.6); 5.248 (1.4); 5.245 (1.4); 5.241 (0.6); 4.532 (1.6); 4.522 (1.5); 3.675 (16.0); 2.220 (11.3); 2.175 (15.8)

Example I-53

¹H-NMR (400.1 MHz, CDCl₃):
δ=7.259 (6.0); 7.157 (1.5); 7.150 (1.5); 7.135 (1.5); 7.129 (1.5); 7.110 (1.3); 7.094 (1.4); 7.088 (1.7); 7.073 (1.6); 6.910 (0.9); 6.903 (0.9); 6.889 (1.4); 6.883 (1.3); 6.868 (0.8); 6.862 (0.7); 6.721 (2.3); 6.718 (2.4); 6.605 (1.1); 6.585 (1.3); 6.257 (2.8); 6.237 (2.5); 5.571 (2.2); 5.295 (2.2); 4.685 (6.2); 4.679 (6.1); 3.665 (15.9); 2.489 (1.6); 2.483 (3.3); 2.477 (1.6); 2.238 (12.4); 2.172 (16.0); 2.000 (1.3); 1.627 (0.4)

Example I-54

¹H-NMR (400.1 MHz, CDCl₃):
δ=7.411 (3.0); 7.405 (3.1); 7.258 (7.2); 7.157 (1.4); 7.152 (1.3); 7.137 (2.3); 7.131 (2.2); 7.074 (3.8); 7.054 (2.3); 6.798 (1.0); 6.793 (0.8); 6.791 (0.8); 6.780 (1.4); 6.774 (1.9); 6.759 (0.6); 6.746 (1.4); 6.741 (1.2); 6.733 (1.8); 6.729 (2.2); 6.727 (2.4); 6.722 (1.2); 6.715 (1.3); 6.710 (1.1); 6.696 (0.4); 6.331 (1.6); 6.325 (1.4); 6.314 (0.8); 6.312 (1.0); 6.307 (1.4); 6.074 (0.4); 6.061 (0.7); 6.048 (0.7); 6.035 (0.8); 6.031 (0.7); 6.021 (0.5); 6.018 (0.9); 6.005 (0.8); 5.991 (0.9); 5.978 (0.4); 5.768 (2.0); 5.386 (0.5); 5.382 (1.4); 5.378 (1.4); 5.374 (0.6); 5.342 (0.5); 5.339 (1.2); 5.335 (1.3); 5.331 (0.5); 5.295 (1.1); 5.292 (0.7); 5.288 (1.5); 5.285 (1.5); 5.281 (0.6); 5.265 (0.5); 5.262 (1.4); 5.258 (1.3); 5.255 (0.5); 4.561 (2.0); 4.548 (1.9); 3.686 (16.0); 2.185 (16.0); 1.604 (0.5)

Example I-55

¹H-NMR (400.1 MHz, CDCl₃):
δ=7.412 (3.0); 7.407 (3.1); 7.259 (8.6); 7.157 (1.6); 7.151 (1.5); 7.136 (2.4); 7.131 (2.4); 7.070 (3.8); 7.050 (2.3); 6.920 (1.3); 6.916 (1.2); 6.900 (1.7); 6.896 (1.7); 6.810 (0.4); 6.807 (0.5); 6.792 (1.4); 6.788 (1.3); 6.773 (1.3); 6.769 (1.1); 6.763 (1.4); 6.758 (1.5); 6.744 (1.4); 6.739 (1.6); 6.725 (0.6); 6.720 (0.5); 6.353 (1.6); 6.348 (1.7); 6.333 (1.3); 6.329 (1.5); 5.713 (1.9); 5.295 (2.1); 4.714 (6.1); 4.708 (6.1); 4.337 (0.3); 3.678 (15.9); 2.496 (1.8); 2.490 (3.8); 2.485 (1.7); 2.182 (16.0); 2.000 (0.8); 1.601 (0.5)

Example I-56

¹H-NMR (400.1 MHz, CDCl₃):
δ=7.423 (3.1); 7.418 (3.2); 7.259 (7.8); 7.188 (1.5); 7.182 (1.4); 7.167 (2.3); 7.162 (2.2); 7.094 (3.7); 7.074 (2.4); 6.700 (1.3); 6.687 (1.3); 6.678 (1.4); 6.665 (1.4); 6.395 (0.9); 6.388 (0.9); 6.374 (1.2); 6.367 (1.2); 6.352 (0.8); 6.345 (0.8); 6.061 (1.6); 6.053 (1.5); 6.036 (1.9); 6.028 (1.5); 6.024 (0.8); 6.011 (0.8); 6.007 (0.5); 5.997 (0.5); 5.994 (0.9); 5.981 (0.8); 5.967 (0.9); 5.954 (0.5); 5.842 (1.6); 5.372 (0.5); 5.369 (1.4); 5.365 (1.4); 5.361 (0.6); 5.329 (0.5); 5.326 (1.2); 5.322 (1.3); 5.318 (0.5); 5.296 (1.8); 5.290 (0.6); 5.287 (1.5); 5.284 (1.5); 5.281 (0.6); 5.264 (0.6); 5.261 (1.4); 5.258 (1.4); 5.254 (0.5); 4.519 (2.1); 4.506 (2.0); 3.701 (16.0); 2.186 (16.0); 2.001 (0.5); 1.589 (0.8)

Example I-57

¹H-NMR (400.1 MHz, CDCl₃):
δ=7.409 (3.1); 7.404 (3.2); 7.258 (7.8); 7.155 (1.4); 7.150 (1.4); 7.135 (2.3); 7.129 (2.2); 7.069 (3.8); 7.048 (2.4); 6.611 (2.1); 6.607 (2.3); 6.556 (1.1); 6.536 (1.2); 6.221 (2.8); 6.201 (2.5); 6.071 (0.4); 6.058 (0.7); 6.045 (0.7); 6.032 (0.8); 6.028 (0.5); 6.018 (0.5); 6.015 (0.9); 6.002 (0.9); 5.989 (0.9); 5.975 (0.5); 5.634 (2.2); 5.381 (0.5); 5.377

(1.4); 5.373 (1.4); 5.369 (0.6); 5.338 (0.5); 5.334 (1.2); 5.330 (1.3); 5.326 (0.6); 5.295 (1.7); 5.284 (0.6); 5.281 (1.5); 5.277 (1.5); 5.274 (0.7); 5.258 (0.6); 5.255 (1.4); 5.251 (1.4); 5.248 (0.6); 4.539 (1.9); 4.526 (1.9); 4.330 (0.6); 3.672 (16.0); 2.309 (0.8); 2.222 (11.8); 2.193 (0.5); 2.179 (16.0); 2.130 (0.3); 2.000 (0.4); 1.609 (0.5)

Example I-58

$^1$H-NMR (400.1 MHz, CDCl$_3$):
δ=7.412 (3.1); 7.406 (3.2); 7.259 (8.0); 7.155 (1.5); 7.150 (1.4); 7.135 (2.3); 7.129 (2.3); 7.066 (3.8); 7.045 (2.4); 6.724 (2.1); 6.720 (2.2); 6.603 (1.0); 6.583 (1.1); 6.243 (2.8); 6.223 (2.5); 5.581 (2.1); 5.295 (3.0); 4.691 (6.2); 4.685 (6.2); 4.628 (0.4); 4.622 (0.4); 4.321 (0.6); 3.663 (16.0); 2.492 (1.7); 2.486 (3.6); 2.480 (1.7); 2.329 (0.7); 2.240 (11.6); 2.176 (15.9); 2.000 (1.6); 1.603 (0.6)

Example I-59

$^1$H-NMR (400.0 MHz, d$_6$-DMSO):
δ=7.279 (2.6); 6.900 (2.0); 6.881 (2.3); 6.877 (2.3); 6.858 (1.9); 6.633 (0.8); 6.627 (1.1); 6.622 (0.9); 6.606 (0.8); 6.600 (1.1); 6.595 (0.9); 6.568 (0.7); 6.561 (0.6); 6.545 (0.9); 6.540 (1.1); 6.534 (0.7); 6.518 (0.7); 6.511 (0.6); 4.727 (5.2); 4.721 (5.3); 3.665 (16.0); 3.648 (1.7); 3.642 (3.6); 3.636 (1.6); 3.331 (19.4); 2.525 (0.7); 2.512 (15.2); 2.507 (30.8); 2.503 (40.4); 2.498 (29.4); 2.494 (14.3); 1.899 (0.4); 1.874 (12.6); 1.859 (0.4); 1.235 (0.3); 0.008 (0.9); 0.000 (25.0); −0.008 (1.0)

Example I-60

$^1$H-NMR (400.0 MHz, d$_6$-DMSO):
δ=7.329 (2.7); 7.182 (0.3); 7.071 (0.4); 7.059 (4.4); 7.042 (4.2); 7.030 (0.5); 6.633 (0.7); 6.627 (1.1); 6.623 (0.9); 6.606 (0.8); 6.601 (1.1); 6.567 (0.7); 6.560 (0.6); 6.544 (0.9); 6.539 (1.1); 6.533 (0.7); 6.517 (0.8); 6.510 (0.6); 4.729 (5.2); 4.723 (5.3); 3.661 (16.0); 3.649 (1.9); 3.643 (3.8); 3.637 (1.6); 3.327 (36.9); 2.676 (0.4); 2.671 (0.6); 2.667 (0.4); 2.541 (0.4); 2.525 (1.6); 2.520 (2.4); 2.511 (33.9); 2.507 (68.3); 2.502 (89.8); 2.498 (66.2); 2.493 (32.8); 2.333 (0.4); 2.329 (0.6); 2.324 (0.4); 2.300 (1.3); 1.881 (12.5); 1.235 (0.4); 0.008 (2.0); 0.000 (59.5); −0.009 (2.2)

Example I-61

$^1$H-NMR (400.0 MHz, d$_6$-DMSO):
δ=7.124 (2.0); 7.121 (2.0); 6.607 (0.6); 6.601 (0.8); 6.597 (0.7); 6.580 (0.6); 6.575 (0.8); 6.570 (0.7); 6.535 (0.6); 6.529 (0.5); 6.512 (0.7); 6.507 (0.9); 6.501 (0.6); 6.485 (0.6); 6.478 (0.6); 6.467 (0.4); 6.456 (3.1); 6.433 (3.1); 6.422 (0.4); 5.757 (1.8); 4.711 (4.2); 4.706 (4.3); 3.686 (16.0); 3.651 (12.6); 3.642 (1.6); 3.636 (3.0); 3.630 (1.3); 3.326 (44.3); 2.676 (0.5); 2.671 (0.7); 2.667 (0.5); 2.541 (1.0); 2.524 (1.6); 2.520 (2.4); 2.511 (34.5); 2.507 (71.5); 2.502 (95.7); 2.497 (71.0); 2.493 (35.4); 2.333 (0.5); 2.329 (0.6); 2.324 (0.5); 1.868 (10.1); 0.008 (2.1); 0.000 (67.8); −0.009 (2.6)

Example I-62

$^1$H-NMR (400.0 MHz, d$_6$-DMSO):
δ=7.555 (2.9); 6.481 (3.9); 6.457 (6.7); 6.436 (4.0); 5.757 (0.3); 4.653 (5.6); 4.647 (5.6); 3.766 (0.4); 3.677 (16.0); 3.662 (14.1); 3.598 (1.7); 3.593 (3.0); 3.377 (14.1); 2.540 (1.7); 2.502 (48.5); 1.876 (12.2); 0.000 (15.1)

Example I-63

$^1$H-NMR (400.0 MHz, d$_6$-DMSO):
δ=11.650 (0.6); 7.144 (2.9); 6.795 (0.5); 6.772 (0.5); 6.753 (0.4); 6.729 (0.4); 6.594 (1.3); 6.572 (0.9); 6.567 (1.3); 6.536 (0.4); 6.525 (1.3); 6.516 (4.6); 6.494 (4.9); 6.483 (0.7); 6.474 (1.1); 6.468 (0.7); 5.757 (1.1); 4.854 (0.9); 4.848 (1.0); 4.844 (0.7); 4.837 (0.7); 4.754 (5.9); 4.749 (6.0); 4.707 (5.7); 4.701 (5.7); 3.783 (0.7); 3.761 (1.5); 3.706 (0.5); 3.653 (16.0); 3.640 (2.9); 3.634 (4.6); 3.630 (3.3); 3.624 (4.2); 3.619 (1.9); 3.571 (0.4); 3.561 (0.4); 3.331 (10.9); 2.507 (25.2); 2.503 (32.7); 2.498 (24.3); 2.211 (1.8); 1.873 (13.7); 1.235 (0.4); 1.192 (0.9); 0.008 (1.7); 0.000 (43.7); −0.008 (2.0)

Example I-64

$^1$H-NMR (400.0 MHz, d$_6$-DMSO):
δ=7.183 (1.6); 7.177 (1.6); 7.161 (1.6); 7.154 (1.6); 7.096 (1.4); 7.080 (1.5); 7.074 (1.9); 7.058 (1.7); 7.025 (3.8); 6.943 (1.0); 6.936 (1.0); 6.922 (1.8); 6.915 (1.6); 6.900 (0.8); 6.894 (0.7); 6.763 (0.8); 6.754 (1.0); 6.747 (1.3); 6.738 (2.8); 6.732 (1.3); 6.720 (7.8); 6.712 (2.1); 6.704 (1.7); 4.668 (2.2); 4.662 (2.5); 4.656 (2.5); 4.650 (2.2); 3.664 (16.0); 3.620 (1.6); 3.614 (3.2); 3.608 (1.5); 3.331 (29.7); 2.525 (0.9); 2.507 (35.8); 2.502 (46.9); 2.498 (34.3); 2.494 (17.0); 1.905 (16.0); 1.234 (0.5); 0.000 (0.7)

Example I-65

$^1$H-NMR (400.0 MHz, d$_6$-DMSO):
δ=7.179 (1.6); 7.173 (1.7); 7.157 (1.6); 7.150 (1.6); 7.087 (1.4); 7.071 (1.5); 7.065 (1.9); 7.049 (1.7); 6.954 (3.8); 6.947 (1.5); 6.940 (1.1); 6.925 (1.8); 6.918 (1.6); 6.904 (0.8); 6.897 (0.7); 6.714 (0.7); 6.709 (0.9); 6.695 (2.7); 6.690 (4.5); 6.671 (3.6); 6.661 (0.5); 6.652 (1.6); 6.643 (2.3); 6.637 (2.0); 6.624 (1.0); 6.618 (0.9); 5.935 (0.6); 5.922 (0.6); 5.909 (0.7); 5.905 (0.5); 5.896 (0.4); 5.892 (0.8); 5.879 (0.6); 5.865 (0.8); 5.853 (0.4); 5.758 (0.7); 5.303 (1.4); 5.299 (1.5); 5.260 (1.2); 5.256 (1.3); 5.226 (1.5); 5.222 (1.5); 5.199 (1.4); 5.195 (1.4); 4.376 (3.0); 4.364 (3.0); 3.688 (0.7); 3.673 (15.9); 3.638 (0.5); 3.332 (19.2); 2.525 (0.6); 2.512 (12.4); 2.507 (25.2); 2.503 (33.2); 2.499 (24.6); 2.494 (12.6); 1.944 (0.3); 1.933 (0.6); 1.921 (1.4); 1.906 (16.0); 1.234 (0.4); 1.190 (0.5); 0.000 (0.5)

Example I-66

$^1$H-NMR (400.0 MHz, d$_6$-DMSO):
δ=7.353 (3.3); 7.348 (3.5); 7.138 (1.4); 7.133 (1.3); 7.117 (2.6); 7.112 (2.6); 7.073 (7.1); 7.053 (2.4); 6.775 (0.8); 6.765 (1.1); 6.760 (1.4); 6.750 (2.7); 6.739 (1.6); 6.729 (8.2); 6.720 (2.3); 6.714 (2.0); 5.757 (1.0); 4.671 (2.1); 4.665 (2.5); 4.659 (2.4); 4.654 (2.2); 3.777 (0.4); 3.657 (15.9); 3.631 (0.4); 3.617 (1.5); 3.611 (3.2); 3.605 (1.5); 3.331 (23.8); 2.525 (0.7); 2.507 (32.0); 2.503 (41.9); 2.498 (30.8); 1.989 (1.3); 1.914 (16.0); 1.298 (0.3); 1.259 (0.5); 1.235 (0.6); 1.193 (0.4); 1.175 (0.7); 1.157 (0.3); 0.000 (0.5)

Example I-67

$^1$H-NMR (400.0 MHz, d$_6$-DMSO):
δ=7.195 (3.7); 7.075 (0.7); 7.058 (0.9); 7.054 (1.5); 7.037 (1.5); 7.033 (1.0); 7.015 (0.8); 6.975 (0.8); 6.968 (0.8);

6.950 (1.3); 6.944 (1.3); 6.926 (0.8); 6.919 (0.8); 6.818 (1.3); 6.806 (2.5); 6.794 (2.5); 6.784 (0.6); 6.777 (1.3); 6.771 (1.2); 6.755 (0.6); 6.750 (0.6); 6.728 (0.3); 6.715 (0.4); 6.707 (4.9); 6.706 (4.9); 6.695 (4.9); 4.712 (5.5); 4.706 (5.5); 3.794 (0.3); 3.686 (0.5); 3.647 (16.0); 3.638 (2.1); 3.632 (3.4); 3.626 (1.6); 3.443 (0.3); 3.331 (23.1); 2.525 (0.7); 2.511 (15.5); 2.507 (31.3); 2.503 (41.2); 2.498 (30.3); 1.951 (10.4); 1.846 (0.5); 1.259 (0.4); 1.235 (0.7)

The following intermediates were synthesised according to the examples and methods described above
Intermediates According to the Formula (Z-ix):

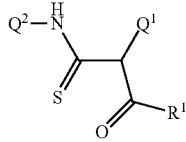

(Z-ix)

| Ex N° | R¹ | Q¹ | Q² | LogP |
|---|---|---|---|---|
| Z-ix-01 | methyl | 2-chloro-4-fluorophenyl | 4-(allyloxy)-2,6-difluorophenyl | 4.55[a] |
| Z-ix-01 | methyl | 2-chloro-4-fluorophenyl | 2,6-difluoro-4-(prop-2-yn-1-yloxy)phenyl | 4.13[a] |
| Z-ix-03 | methyl | 2-chloro-4-fluorophenyl | 2,4-difluoro-6-(prop-2-yn-1-yloxy)phenyl | 3.65[a] |

NMR Peak Lists of Intermediates According to the Formula (Z-ix)

Example Z-ix-01

¹H-NMR (400.0 MHz, $d_6$-DMSO):
δ=14.097 (3.6); 8.545 (0.4); 8.317 (3.0); 7.736 (0.4); 7.679 (0.3); 7.664 (0.4); 7.658 (0.4); 7.643 (0.4); 7.594 (0.3); 7.578 (0.8); 7.571 (0.8); 7.551 (1.1); 7.534 (1.2); 7.528 (1.2); 7.512 (1.2); 7.471 (0.4); 7.465 (0.4); 7.436 (1.4); 7.429 (1.3); 7.414 (1.3); 7.407 (1.3); 7.380 (1.3); 7.370 (1.8); 7.364 (1.6); 7.358 (1.9); 7.353 (3.3); 7.349 (2.8); 7.331 (2.8); 7.323 (1.7); 7.317 (1.5); 7.300 (1.6); 7.296 (1.8); 7.279 (1.6); 7.244 (0.6); 7.217 (3.0); 7.211 (2.7); 7.195 (3.8); 7.189 (3.5); 7.179 (3.0); 7.164 (1.5); 7.158 (1.5); 7.137 (1.1); 7.129 (2.5); 7.122 (2.2); 7.115 (1.7); 7.106 (2.2); 7.099 (2.3); 7.088 (0.9); 7.061 (0.8); 7.051 (2.6); 7.045 (2.6); 7.041 (1.4); 7.033 (1.1); 7.023 (1.1); 7.013 (1.8); 7.007 (1.4); 7.002 (2.1); 6.992 (2.4); 6.985 (2.1); 6.980 (1.3); 6.971 (1.2); 6.964 (1.1); 6.870 (0.6); 6.669 (3.2); 6.646 (3.3); 6.582 (1.3); 6.576 (1.2); 6.550 (1.3); 6.544 (1.2); 6.069 (0.7); 6.057 (1.3); 6.044 (1.4); 6.030 (1.3); 6.014 (1.4); 6.001 (1.4); 5.988 (1.2); 5.975 (0.5); 5.450 (0.5); 5.436 (1.6); 5.432 (1.6); 5.415 (1.6); 5.411 (1.7); 5.393 (1.5); 5.389 (1.4); 5.372 (1.3); 5.289 (1.8); 5.285 (1.7); 5.263 (1.7); 5.259 (1.6); 5.252 (1.5); 5.248 (1.5); 5.225 (1.1); 4.733 (0.4); 4.721 (0.4); 4.655 (0.7); 4.641 (0.8); 4.629 (0.4); 4.572 (3.4); 4.559 (3.4); 4.532 (2.9); 4.519 (2.8); 3.920 (7.4); 3.492 (0.4); 3.474 (0.4); 3.325 (181.2); 3.211 (0.4); 2.942 (1.3); 2.696 (0.5); 2.675 (5.9); 2.671 (7.8); 2.666 (5.7); 2.603 (0.8); 2.506 (898.8); 2.502 (1142.4); 2.497 (846.3); 2.392 (0.4); 2.378 (0.4); 2.359 (0.4); 2.333 (5.7); 2.328 (7.5); 2.324 (5.6); 2.282 (0.6); 2.267 (0.4); 2.225 (2.9); 2.182 (15.5); 2.073 (0.9); 2.061 (1.0); 2.021 (0.4); 1.621 (15.6); 1.603 (1.7); 1.589 (11.6); 1.491 (13.3); 1.486 (16.0); 1.457 (0.4); 1.388 (0.4); 1.355 (5.6); 1.330 (0.5); 1.262 (2.7); 1.235 (6.8); 1.169 (0.9); 1.148 (1.0); 1.117 (0.4); 1.102 (0.4); 1.080 (0.4); 1.065 (0.4); 1.036 (0.4); 0.980 (0.5); 0.931 (0.3); 0.915 (0.3); 0.854 (2.2); 0.837 (1.8); 0.817 (1.0); 0.146 (6.2); 0.036 (0.9); 0.008 (66.4); 0.000 (1332.6); −0.008 (81.7); −0.056 (1.2); −0.095 (0.5); −0.120 (0.4); −0.132 (0.4); −0.150 (6.5)

Example Z-ix-02

¹H-NMR (400.0 MHz, $d_6$-DMSO):
δ=14.136 (3.6); 8.316 (3.5); 7.641 (0.4); 7.619 (0.5); 7.615 (0.5); 7.579 (0.4); 7.534 (0.4); 7.497 (0.4); 7.476 (0.3); 7.470 (0.4); 7.426 (0.4); 7.414 (0.3); 7.407 (0.4); 7.358 (1.3); 7.337 (1.5); 7.331 (1.4); 7.310 (1.6); 7.299 (1.4); 7.293 (1.3); 7.263 (0.4); 7.246 (0.4); 7.220 (3.2); 7.213 (2.0); 7.202 (2.0); 7.198 (3.5); 7.190 (2.1); 7.181 (2.0); 7.175 (0.7); 7.169 (0.7); 7.161 (0.6); 7.150 (1.0); 7.144 (1.2); 7.129 (1.6); 7.123 (1.6); 7.107 (2.4); 7.064 (0.3); 7.039 (0.5); 7.025 (1.2); 7.018 (1.3); 7.011 (0.5); 7.003 (2.1); 6.997 (2.1); 6.982 (1.0); 6.975 (1.0); 6.869 (0.6); 6.713 (3.5); 6.690 (3.5); 6.659 (0.4); 6.643 (1.0); 6.609 (0.7); 4.983 (0.5); 4.977 (0.6); 4.935 (0.4); 4.903 (1.1); 4.897 (1.2); 4.871 (0.6); 4.855 (0.4); 4.819 (5.9); 4.813 (6.0); 4.785 (0.4); 4.751 (6.3); 4.745 (6.3); 4.707 (0.4); 4.695 (0.5); 4.688 (0.5); 3.919 (0.9); 3.692 (0.5); 3.647 (0.5); 3.635 (0.8); 3.624 (1.7); 3.618 (3.7); 3.612 (1.7); 3.602 (0.4); 3.595 (0.4); 3.586 (0.4); 3.559 (0.4); 3.553 (0.4); 3.539 (1.9); 3.534 (3.9); 3.528 (1.9); 3.477 (0.4); 3.458 (0.3); 3.447 (0.4); 3.440 (0.4); 3.433 (0.4); 3.403 (0.5); 3.323 (567.6); 2.875 (0.3); 2.843 (0.4); 2.760 (0.5); 2.750 (0.4); 2.729 (0.5); 2.718 (0.6); 2.701 (0.6); 2.680 (3.2); 2.675 (6.4); 2.671 (8.7); 2.666 (6.6); 2.662 (3.3); 2.647 (0.7); 2.641 (0.8); 2.604 (1.1); 2.524 (23.0); 2.519 (34.3); 2.511 (447.5); 2.506 (925.7); 2.502 (1237.3); 2.497 (900.2); 2.493 (434.2); 2.338 (2.2); 2.333 (5.3); 2.328 (7.5); 2.324 (5.5); 2.319 (2.4); 2.245 (0.5); 2.227 (2.5); 2.182 (2.2); 2.090 (0.3); 2.073 (0.4); 2.061 (0.4); 1.902 (10.4); 1.606 (8.8); 1.489 (16.0); 1.475 (0.7); 1.355 (6.0); 1.296 (0.3); 1.262 (1.4); 1.235 (5.1); 1.207 (1.9); 1.192 (2.0); 1.169 (1.4); 1.165 (1.2); 1.150 (1.1); 1.126 (0.5); 1.111 (0.3); 0.980 (0.5); 0.935 (0.4); 0.868 (0.6); 0.853 (1.7); 0.835 (1.2); 0.810 (0.7); 0.146 (7.9); 0.138 (0.5); 0.063 (0.5); 0.054 (0.7); 0.035 (1.0); 0.026 (1.3); 0.008 (60.4); 0.000 (1802.7); −0.009 (64.8); −0.025 (1.8); −0.032 (0.8); −0.041 (0.5); −0.049 (0.4); −0.150 (7.7)

Example Z-ix-03

¹H-NMR (400.0 MHz, $d_6$-DMSO):
δ=8.317 (9.5); 7.609 (0.4); 7.594 (0.4); 7.426 (0.3); 7.413 (0.4); 7.409 (0.4); 7.379 (0.4); 7.367 (2.1); 7.349 (2.5); 7.345 (2.6); 7.328 (2.5); 7.310 (0.4); 7.288 (0.5); 7.245 (0.4); 7.223 (0.4); 7.201 (0.5); 7.179 (0.8); 7.172 (0.7); 7.146 (0.8); 7.126 (2.3); 7.120 (2.7); 7.103 (2.2); 7.096 (2.4); 7.045 (0.4); 7.011 (1.4); 7.005 (1.3); 6.990 (2.4); 6.983 (2.2); 6.968 (1.2); 6.962 (1.1); 6.762 (0.4); 6.737 (0.5); 5.030 (2.7); 5.024 (2.7); 4.893 (0.4); 4.863 (0.7); 4.858 (0.7); 4.849 (0.9); 4.844 (1.0); 4.826 (0.4); 4.484 (0.4); 3.919 (0.6); 3.756 (0.6); 3.750 (1.2); 3.744 (0.6); 3.629 (0.4); 3.460 (0.4); 3.324 (120.9); 2.675 (3.9); 2.671 (5.2); 2.666 (3.9); 2.506 (599.2); 2.502 (767.2); 2.497 (568.3); 2.332 (3.7); 2.328 (5.1); 2.324 (3.8); 2.309 (0.5); 2.267 (0.4); 2.222 (0.4); 2.182 (1.5); 2.001 (0.8); 1.602 (1.7); 1.574 (16.0); 1.511 (0.4); 1.489 (0.6); 1.482 (0.7); 1.355 (2.6); 1.283 (1.4); 1.262 (3.1); 1.235 (5.3); 1.194 (1.1);

1.168 (1.0); 1.147 (0.7); 1.101 (0.6); 1.080 (0.4); 0.911 (0.4); 0.898 (0.4); 0.853 (2.0); 0.836 (1.4); 0.813 (0.8); 0.146 (4.3); 0.034 (0.4); 0.008 (41.5); 0.000 (912.8); −0.008 (44.1); −0.066 (0.4); −0.150 (4.4)

Intermediates According to the Formula (Z-iv):

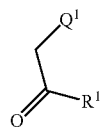

(Z-iv)

| Ex N° | R¹ | Q¹ | LogP |
|---|---|---|---|
| Z-iv-01 | methyl | 4-(allyloxy)-2-fluorophenyl | 2.60[a] |
| Z-iv-02 | methyl | 2-fluoro-4-methoxyphenyl | 1.95[a] |
| Z-iv-03 | methyl | 2-fluoro-4-(prop-2-yn-1-yloxy)phenyl | 2.16[a] |
| Z-iv-04 | methyl | 2,6-difluoro-4-(prop-2-yn-1-yloxy)phenyl | 2.39[a] |

The compounds Z-iv-01 to Z-iv-04 are preferred compounds of formula (Z-iv) in the context of the present invention.

NMR Peak Lists of Intermediates According to the Formula (Z-iv)

Example Z-iv-01

¹H-NMR (400.0 MHz, d₆-DMSO):

δ=7.157 (1.0); 7.135 (2.0); 7.113 (1.1); 6.825 (1.1); 6.819 (1.3); 6.795 (1.1); 6.789 (1.4); 6.760 (1.3); 6.754 (1.1); 6.739 (1.1); 6.733 (1.0); 6.060 (0.6); 6.046 (0.7); 6.033 (0.7); 6.030 (0.4); 6.020 (0.4); 6.016 (0.8); 6.003 (0.7); 5.990 (0.8); 5.977 (0.4); 5.422 (0.4); 5.418 (1.3); 5.414 (1.4); 5.410 (0.5); 5.379 (0.4); 5.375 (1.2); 5.371 (1.2); 5.366 (0.5); 5.283 (0.5); 5.279 (1.2); 5.275 (1.2); 5.256 (0.5); 5.253 (1.1); 5.249 (1.2); 4.576 (1.7); 4.572 (3.1); 4.569 (1.9); 4.563 (1.8); 4.559 (3.0); 4.555 (1.8); 3.729 (5.5); 3.327 (82.5); 2.675 (0.4); 2.671 (0.6); 2.666 (0.4); 2.524 (1.4); 2.519 (2.2); 2.511 (30.8); 2.506 (63.0); 2.502 (83.8); 2.497 (61.9); 2.493 (30.9); 2.333 (0.4); 2.329 (0.5); 2.324 (0.4); 2.141 (16.0); 0.146 (0.5); 0.008 (3.8); 0.000 (110.0); −0.009 (4.6); −0.150 (0.5)

Example Z-iv-02

¹H-NMR (400.0 MHz, d₆-DMSO):

δ=7.165 (1.1); 7.144 (2.2); 7.122 (1.2); 6.810 (1.3); 6.804 (1.5); 6.780 (1.3); 6.774 (1.5); 6.746 (1.6); 6.740 (1.3); 6.725 (1.4); 6.719 (1.2); 3.821 (0.4); 3.751 (16.0); 3.731 (6.9); 3.331 (6.4); 2.506 (8.2); 2.503 (9.6); 2.140 (14.0); 1.989 (0.4); 0.002 (6.1); 0.000 (8.8)

Example Z-iv-03

¹H-NMR (400.0 MHz, d₆-DMSO):

δ=7.184 (1.0); 7.163 (2.0); 7.141 (1.1); 6.870 (1.2); 6.864 (1.3); 6.840 (1.1); 6.834 (1.4); 6.794 (1.3); 6.788 (1.1); 6.773 (1.1); 6.767 (1.0); 4.812 (5.6); 4.806 (5.7); 3.748 (5.4); 3.602 (1.3); 3.596 (3.0); 3.590 (1.3); 3.328 (59.4); 2.671 (0.3); 2.524 (0.8); 2.519 (1.3); 2.511 (19.3); 2.506 (39.7); 2.502 (52.8); 2.497 (38.8); 2.493 (19.0); 2.329 (0.3); 2.150 (16.0); 0.008 (1.0); 0.000 (31.9); −0.009 (1.1)

Example Z-iv-04

¹H-NMR (400.0 MHz, d₆-DMSO):

δ=6.804 (0.6); 6.795 (3.6); 6.771 (3.6); 6.762 (0.6); 4.853 (5.7); 4.847 (5.8); 3.782 (6.3); 3.645 (1.5); 3.639 (3.1); 3.633 (1.5); 3.332 (55.0); 2.507 (30.0); 2.502 (38.4); 2.498 (28.9); 2.210 (16.0); 0.007 (2.6); 0.000 (50.4)

Intermediates According to the Formula (Z-ii):

(Z-ii)

| Ex N° | Q² | LogP |
|---|---|---|
| Z-ii-01 | 4-(allyloxy)-2,6-difluorophenyl | 4.54[a] |
| Z-ii-02 | 2,6-difluoro-4-(prop-2-yn-1-yloxy)phenyl | 3.86[a] |
| Z-ii-03 | 2,4-difluoro-6-(prop-2-yn-1-yloxy)phenyl | 3.68[a] |
| Z-ii-04 | 4-(prop-2-yn-1-yloxy)phenyl | 3.42[a]; 3.41[b] |
| Z-ii-05 | 4-(allyloxy)phenyl | 4.06[a]; 4.09[b] |
| Z-ii-06 | 4-(allyloxy)-3-fluorophenyl | 4.06[a] |
| Z-ii-07 | 5-(allyloxy)-2-fluorophenyl | 4.30[a] |
| Z-ii-08 | 2-fluoro-5-(prop-2-yn-1-yloxy)phenyl | 3.62[a] |
| Z-ii-09 | 2,5-difluoro-4-(prop-2-yn-1-yloxy)phenyl | 3.64[a] |
| Z-ii-10 | 4-(allyloxy)-2,5-difluorophenyl | 4.24[a] |
| Z-ii-11 | 3-fluoro-4-(prop-2-yn-1-yloxy)phenyl | 3.47[a] |
| Z-ii-12 | 2-chloro-4-(prop-2-yn-1-yloxy)phenyl | 3.99[a]; 3.96[b] |
| Z-ii-13 | 4-(allyloxy)-2-chlorophenyl | 4.72[a]; 4.72[b] |
| Z-ii-14 | 2-chloro-6-(prop-2-yn-1-yloxy)phenyl | 3.86[a] |
| Z-ii-15 | 2-(allyloxy)-6-chlorophenyl | |
| Z-ii-16 | 2-(allyloxy)-5-fluorophenyl | 4.24[a] |
| Z-ii-17 | 5-fluoro-2-(prop-2-yn-1-yloxy)phenyl | 3.62[a] |
| Z-ii-18 | 4-methyl-2-(prop-2-yn-1-yloxy)phenyl | 3.82[a] |
| Z-ii-19 | 2-(allyloxy)-5-cyanophenyl | 3.71[a] |
| Z-ii-20 | 5-cyano-2-(prop-2-yn-1-yloxy)phenyl | 3.13[a] |

NMR Peak Lists of Intermediates According to the Formula (Z-ii)

Example Z-ii-01

¹H-NMR (400.0 MHz, d₆-DMSO):

δ=7.060 (0.4); 7.036 (2.0); 7.028 (6.6); 7.023 (16.0); 6.999 (15.5); 6.994 (6.9); 6.986 (1.9); 6.054 (1.3); 6.040 (2.8); 6.027 (2.7); 6.014 (3.2); 6.011 (2.0); 6.000 (1.7); 5.997 (3.4); 5.984 (3.0); 5.971 (3.4); 5.957 (1.6); 5.756 (4.0); 5.436 (1.9); 5.432 (5.5); 5.428 (5.9); 5.424 (2.4); 5.393 (1.7); 5.389 (4.8); 5.385 (5.1); 5.381 (2.1); 5.313 (2.1); 5.310 (5.4); 5.306 (5.5); 5.287 (2.0); 5.284 (5.0); 5.280 (5.2); 4.750 (0.3); 4.737 (0.3); 4.638 (7.2); 4.634 (12.9); 4.631 (8.3); 4.624 (7.5); 4.621 (12.6); 4.617 (7.9); 3.563 (1.7); 2.676 (0.5); 2.671 (0.7); 2.667 (0.5); 2.525 (1.8); 2.511 (39.8); 2.507 (82.3); 2.502 (110.5); 2.498 (82.2); 2.494 (41.5); 2.334 (0.5); 2.329 (0.7); 2.325 (0.5); 0.146 (0.7); 0.008 (5.2); 0.000 (152.9); −0.009 (6.6); −0.150 (0.7)

Example Z-ii-02

¹H-NMR (400.0 MHz, d₆-DMSO):

δ=7.074 (1.3); 7.066 (4.4); 7.062 (10.3); 7.037 (10.0); 7.033 (4.6); 7.025 (1.2); 5.030 (0.4); 5.024 (0.4); 4.902 (15.8); 4.896 (16.0); 3.689 (3.7); 3.683 (7.6); 3.677 (3.7); 3.638 (0.5); 3.635 (0.5); 3.619 (0.5); 2.525 (0.6); 2.521 (1.0); 2.512 (15.2); 2.508 (31.2); 2.503 (41.5); 2.499 (30.5); 2.494 (15.1); 1.209 (1.3); 1.193 (1.5); 1.172 (0.7); 1.156 (0.5); 0.008 (2.2); 0.000 (63.2); −0.009 (2.5)

Example Z-ii-03

¹H-NMR (400.0 MHz, d₆-DMSO):
δ=7.177 (1.7); 7.171 (2.1); 7.154 (2.1); 7.152 (2.2); 7.148 (2.7); 7.145 (2.8); 7.129 (1.7); 7.121 (3.4); 7.116 (2.9); 7.109 (1.9); 7.094 (2.5); 7.089 (2.9); 7.083 (1.9); 5.756 (0.9); 5.030 (15.7); 5.024 (16.0); 3.756 (3.7); 3.750 (8.0); 3.744 (3.7); 3.500 (2.0); 2.676 (0.4); 2.671 (0.6); 2.667 (0.4); 2.525 (1.5); 2.520 (2.3); 2.511 (32.5); 2.507 (67.8); 2.502 (91.0); 2.498 (67.3); 2.493 (33.5); 2.333 (0.4); 2.329 (0.6); 2.324 (0.4); 0.146 (0.6); 0.008 (4.6); 0.000 (135.1); −0.009 (5.5); −0.150 (0.6)

Example Z-ii-04

¹H-NMR (400.0 MHz, d₆-DMSO):
δ=7.439 (1.1); 7.431 (11.3); 7.425 (3.7); 7.413 (3.9); 7.408 (12.5); 7.400 (1.2); 7.062 (1.3); 7.054 (12.6); 7.048 (4.0); 7.037 (3.7); 7.031 (11.1); 7.023 (1.0); 4.846 (15.9); 4.840 (16.0); 3.615 (3.8); 3.609 (7.7); 3.603 (3.7); 3.395 (13.0); 2.672 (0.4); 2.525 (1.1); 2.507 (50.6); 2.502 (65.5); 2.498 (48.7); 2.333 (0.3); 2.329 (0.4); 0.000 (0.6)

Example Z-ii-05

¹H-NMR (400.0 MHz, d₆-DMSO):
δ=7.407 (1.3); 7.398 (14.1); 7.393 (4.6); 7.388 (1.9); 7.381 (4.8); 7.375 (16.0); 7.367 (2.3); 7.024 (1.6); 7.016 (16.0); 7.010 (4.9); 6.999 (4.4); 6.993 (14.2); 6.984 (1.6); 6.982 (1.6); 6.976 (0.5); 6.965 (0.4); 6.959 (1.1); 6.072 (1.1); 6.059 (2.3); 6.046 (2.3); 6.033 (2.6); 6.029 (1.5); 6.019 (1.4); 6.016 (2.8); 6.003 (2.6); 5.989 (2.8); 5.976 (1.4); 5.419 (1.7); 5.414 (4.8); 5.410 (5.0); 5.406 (1.9); 5.375 (1.5); 5.371 (4.2); 5.367 (4.3); 5.363 (1.7); 5.288 (1.8); 5.284 (4.5); 5.281 (4.5); 5.277 (1.9); 5.262 (1.7); 5.258 (4.2); 5.254 (4.2); 5.251 (1.8); 4.605 (6.3); 4.601 (11.0); 4.598 (6.8); 4.592 (6.6); 4.588 (10.8); 4.584 (6.5); 4.067 (0.3); 4.049 (1.1); 4.032 (1.1); 4.014 (0.4); 3.332 (38.3); 2.526 (0.7); 2.521 (1.0); 2.512 (14.5); 2.508 (29.6); 2.503 (39.3); 2.499 (29.2); 2.494 (14.7); 1.397 (2.5); 1.337 (1.2); 1.319 (2.4); 1.302 (1.1); 0.008 (0.8); 0.000 (23.5); −0.009 (0.9)

Example Z-ii-06

¹H-NMR (400.0 MHz, d₆-DMSO):
δ=7.511 (6.3); 7.506 (6.7); 7.482 (6.5); 7.476 (7.0); 7.283 (3.1); 7.281 (3.1); 7.277 (3.2); 7.259 (8.4); 7.254 (9.0); 7.240 (9.5); 7.218 (10.8); 7.196 (4.2); 6.975 (0.4); 6.966 (0.6); 6.960 (0.5); 6.954 (0.4); 6.081 (1.5); 6.067 (3.1); 6.054 (3.1); 6.041 (3.6); 6.038 (2.6); 6.024 (4.0); 6.011 (3.6); 5.998 (3.8); 5.985 (1.8); 5.432 (6.6); 5.428 (7.2); 5.389 (5.8); 5.385 (6.3); 5.309 (6.6); 5.306 (6.9); 5.283 (6.4); 5.280 (6.5); 4.685 (16.0); 4.671 (15.8); 4.594 (0.5); 4.580 (0.5); 4.111 (0.5); 4.093 (0.5); 3.422 (10.6); 2.677 (0.3); 2.673 (0.5); 2.668 (0.4); 2.508 (53.9); 2.504 (71.0); 2.499 (54.5); 2.330 (0.5); 1.384 (0.5); 1.366 (1.1); 1.359 (0.4); 1.349 (0.6); 1.341 (0.7); 1.335 (0.4); 1.324 (0.4); 1.316 (0.5); 1.299 (1.3); 1.259 (1.5); 1.233 (2.1); 0.146 (0.4); 0.007 (3.1); 0.000 (81.0); −0.008 (4.4); −0.150 (0.4)

Example Z-ii-07

¹H-NMR (400.0 MHz, d₆-DMSO):
δ=7.368 (7.0); 7.355 (0.4); 7.345 (13.2); 7.321 (7.8); 7.115 (6.5); 7.107 (7.5); 7.099 (6.9); 7.091 (7.5); 6.995 (4.4); 6.985 (5.8); 6.977 (4.2); 6.972 (4.3); 6.962 (5.0); 6.954 (3.5); 6.057 (1.5); 6.044 (3.2); 6.031 (3.3); 6.018 (3.7); 6.014 (2.3); 6.004 (2.1); 6.001 (4.1); 5.988 (3.7); 5.974 (4.0); 5.961 (2.0); 5.417 (2.4); 5.413 (6.8); 5.408 (7.3); 5.404 (3.2); 5.374 (2.1); 5.369 (5.9); 5.365 (6.4); 5.361 (2.7); 5.287 (2.7); 5.284 (6.6); 5.280 (6.7); 5.276 (3.2); 5.261 (2.6); 5.257 (6.2); 5.253 (6.4); 5.250 (3.0); 4.571 (9.2); 4.567 (16.0); 4.563 (10.5); 4.557 (10.0); 4.554 (16.0); 4.550 (10.2); 4.528 (0.3); 4.524 (0.4); 3.749 (0.4); 3.745 (0.4); 3.701 (2.3); 2.527 (0.6); 2.513 (15.6); 2.509 (32.1); 2.505 (43.3); 2.500 (33.6); 2.496 (17.9)

Example Z-ii-08

¹H-NMR (400.0 MHz, d₆-DMSO):
δ=7.406 (3.8); 7.383 (7.2); 7.359 (4.2); 7.157 (3.6); 7.149 (4.1); 7.142 (3.7); 7.134 (4.0); 7.036 (2.5); 7.028 (2.8); 7.026 (3.2); 7.018 (2.3); 7.013 (2.2); 7.005 (2.5); 7.003 (2.7); 6.995 (1.9); 5.757 (0.4); 4.820 (15.8); 4.814 (16.0); 3.662 (1.5); 3.638 (0.6); 3.622 (3.8); 3.616 (8.0); 3.610 (3.8); 2.526 (0.4); 2.522 (0.6); 2.513 (8.9); 2.508 (18.3); 2.504 (24.5); 2.499 (18.2); 2.495 (9.0)

Example Z-ii-09

¹H-NMR (400.0 MHz, d₆-DMSO):
δ=7.633 (3.5); 7.614 (3.6); 7.605 (3.6); 7.586 (3.5); 7.477 (3.4); 7.458 (3.5); 7.448 (3.5); 7.429 (3.4); 4.972 (15.9); 4.966 (16.0); 3.720 (4.0); 3.714 (8.4); 3.708 (3.9); 3.328 (25.1); 2.526 (0.7); 2.512 (14.2); 2.508 (28.6); 2.503 (37.8); 2.499 (28.1); 2.495 (14.1); 1.398 (1.5); 0.008 (1.6); 0.000 (44.2); −0.009 (1.8)

Example Z-ii-10

¹H-NMR (400.0 MHz, d₆-DMSO):
δ=7.601 (6.5); 7.582 (6.6); 7.572 (6.6); 7.554 (6.5); 7.436 (6.1); 7.417 (6.3); 7.407 (6.2); 7.388 (6.1); 6.077 (1.6); 6.063 (3.4); 6.050 (3.2); 6.037 (3.9); 6.034 (2.4); 6.023 (2.3); 6.020 (4.3); 6.007 (3.7); 5.994 (4.2); 5.980 (2.1); 5.452 (2.6); 5.448 (7.1); 5.444 (7.4); 5.440 (2.9); 5.409 (2.3); 5.405 (6.2); 5.401 (6.4); 5.397 (2.5); 5.327 (6.9); 5.324 (6.9); 5.301 (6.4); 5.298 (6.5); 4.701 (9.6); 4.698 (16.0); 4.695 (10.2); 4.688 (9.9); 4.685 (15.7); 4.682 (9.8); 3.329 (39.8); 2.673 (0.4); 2.526 (1.0); 2.513 (22.1); 2.508 (44.8); 2.504 (59.2); 2.499 (43.9); 2.495 (22.0); 2.331 (0.4); 1.398 (1.3); 1.341 (0.3); 0.008 (2.4); 0.000 (67.0); −0.009 (2.7)

Example Z-ii-11

¹H-NMR (400.0 MHz, d₆-DMSO):
δ=7.535 (3.3); 7.530 (3.5); 7.506 (3.7); 7.500 (3.9); 7.328 (1.7); 7.322 (1.4); 7.305 (6.9); 7.299 (11.2); 7.278 (5.5); 7.256 (2.0); 4.945 (15.7); 4.939 (16.0); 3.676 (3.7); 3.670 (7.6); 3.664 (3.7); 3.532 (1.6); 2.526 (0.4); 2.508 (19.4); 2.504 (25.9); 2.499 (19.7); 0.008 (1.3); 0.000 (33.1); −0.008 (1.6)

Example Z-ii-12

¹H-NMR (400.0 MHz, d6-DMSO):
δ=7.539 (8.4); 7.516 (9.3); 7.307 (8.3); 7.300 (8.7); 7.050 (5.0); 7.043 (4.7); 7.028 (4.6); 7.021 (4.4); 4.895 (15.8); 4.889 (16.0); 3.657 (3.7); 3.651 (7.9); 3.645 (3.7); 3.330 (28.0); 2.526 (0.6); 2.521 (0.9); 2.512 (13.4); 2.508 (27.6);

2.503 (36.7); 2.499 (27.0); 2.494 (13.4); 1.397 (1.0); 0.008 (2.2); 0.000 (59.6); −0.009 (2.4)

Example Z-ii-13

$^1$H-NMR (400.0 MHz, d$_6$-DMSO):
δ=7.506 (14.6); 7.495 (2.5); 7.484 (15.9); 7.473 (2.5); 7.273 (0.4); 7.261 (14.2); 7.254 (15.1); 7.222 (2.0); 7.215 (2.2); 7.014 (8.5); 7.007 (8.1); 6.991 (7.8); 6.984 (7.6); 6.979 (1.8); 6.972 (1.3); 6.957 (1.1); 6.950 (1.1); 6.061 (1.6); 6.048 (3.2); 6.035 (3.2); 6.022 (3.6); 6.018 (2.3); 6.008 (2.1); 6.005 (4.0); 5.992 (3.7); 5.978 (3.9); 5.965 (1.9); 5.424 (2.4); 5.420 (6.6); 5.416 (7.0); 5.412 (2.9); 5.381 (2.1); 5.377 (5.8); 5.373 (6.1); 5.369 (2.5); 5.297 (6.7); 5.294 (6.8); 5.271 (6.2); 5.267 (6.4); 4.641 (9.0); 4.638 (16.0); 4.635 (10.3); 4.628 (9.5); 4.625 (15.8); 4.621 (9.7); 4.609 (0.4); 4.099 (0.9); 4.082 (3.0); 4.064 (3.0); 4.047 (0.9); 3.330 (57.6); 2.677 (0.5); 2.672 (0.6); 2.668 (0.5); 2.526 (1.5); 2.512 (34.5); 2.508 (70.6); 2.503 (94.1); 2.499 (70.3); 2.495 (35.9); 2.335 (0.4); 2.330 (0.6); 2.326 (0.5); 1.398 (1.7); 1.333 (3.0); 1.316 (6.2); 1.299 (3.0); 0.146 (0.7); 0.008 (5.4); 0.000 (148.3); −0.008 (6.7); −0.150 (0.7)

Example Z-ii-14

$^1$H-NMR (400.0 MHz, d$_6$-DMSO):
δ=7.386 (3.4); 7.366 (7.2); 7.345 (6.1); 7.240 (7.1); 7.229 (7.4); 7.227 (4.9); 7.220 (4.3); 7.218 (4.6); 7.209 (5.0); 7.206 (4.1); 5.008 (15.9); 5.002 (16.0); 3.713 (4.2); 3.707 (8.9); 3.702 (4.0); 3.331 (23.3); 2.672 (0.4); 2.525 (1.0); 2.512 (20.9); 2.508 (41.7); 2.503 (54.2); 2.499 (39.4); 2.495 (19.5); 2.330 (0.3); 1.397 (1.0); 0.146 (0.4); 0.008 (3.8); 0.000 (89.9); −0.009 (3.6); −0.150 (0.4)

Example Z-ii-16

$^1$H-NMR (300.2 MHz, CDCl$_3$):
δ=7.260 (3.6); 6.946 (2.3); 6.936 (2.8); 6.920 (2.8); 6.915 (5.2); 6.910 (3.6); 6.906 (6.6); 6.890 (4.9); 6.880 (6.6); 6.861 (9.0); 6.845 (14.8); 6.836 (7.1); 6.830 (5.3); 6.818 (8.6); 6.808 (6.3); 6.123 (1.6); 6.106 (3.2); 6.088 (2.9); 6.070 (3.8); 6.065 (2.3); 6.054 (2.2); 6.048 (4.2); 6.031 (3.6); 6.013 (4.4); 5.996 (2.3); 5.541 (2.6); 5.536 (6.4); 5.531 (6.8); 5.526 (3.1); 5.483 (2.2); 5.478 (5.3); 5.473 (5.6); 5.468 (2.5); 5.359 (2.8); 5.354 (7.0); 5.350 (7.1); 5.345 (3.1); 5.323 (2.6); 5.319 (6.4); 5.314 (6.6); 5.310 (2.9); 4.600 (9.0); 4.595 (16.0); 4.590 (10.0); 4.584 (9.8); 4.578 (16.0); 4.573 (9.4); 1.561 (7.2); 1.264 (1.1); 0.903 (0.4); 0.881 (1.2); 0.858 (0.5); 0.000 (3.4)

Example Z-ii-17

$^1$H-NMR (300.2 MHz, CDCl$_3$):
δ=7.262 (2.8); 7.048 (2.0); 7.032 (2.2); 7.018 (4.4); 7.002 (4.3); 6.974 (2.5); 6.964 (2.9); 6.948 (2.6); 6.944 (1.5); 6.938 (3.0); 6.934 (1.8); 6.918 (1.1); 6.908 (1.6); 6.875 (3.5); 6.865 (2.9); 6.847 (3.6); 6.837 (2.9); 5.300 (0.6); 4.774 (15.7); 4.766 (16.0); 2.576 (3.8); 2.568 (7.7); 2.560 (3.9); 1.559 (5.4); 0.000 (2.6)

Example Z-ii-18

$^1$H-NMR (300.2 MHz, CDCl$_3$):
δ=7.259 (1.2); 7.027 (2.8); 7.000 (3.4); 6.861 (3.1); 6.757 (1.7); 6.754 (1.7); 6.730 (1.4); 6.727 (1.4); 5.298 (0.5); 4.774 (8.1); 4.766 (8.2); 2.569 (2.1); 2.561 (4.2); 2.553 (2.1); 2.354 (16.0); 1.562 (2.5); 0.000 (1.0)

Example Z-ii-19

$^1$H-NMR (300.2 MHz, CDCl$_3$):
δ=7.522 (7.5); 7.515 (8.2); 7.493 (8.4); 7.486 (9.2); 7.358 (15.3); 7.351 (14.1); 7.266 (6.7); 6.986 (14.1); 6.957 (12.7); 6.128 (1.5); 6.111 (3.2); 6.093 (3.0); 6.076 (3.8); 6.071 (2.3); 6.059 (2.3); 6.054 (4.2); 6.036 (3.7); 6.018 (4.4); 6.001 (2.3); 5.567 (2.9); 5.562 (6.4); 5.558 (6.6); 5.553 (3.2); 5.510 (2.4); 5.505 (5.3); 5.501 (5.3); 5.496 (2.6); 5.417 (3.1); 5.413 (7.1); 5.409 (6.9); 5.405 (3.1); 5.382 (2.8); 5.378 (6.4); 5.373 (6.3); 5.369 (2.8); 4.713 (9.3); 4.708 (16.0); 4.703 (9.9); 4.696 (10.1); 4.691 (15.8); 4.686 (9.1); 1.588 (3.5); 0.000 (5.8)

Example Z-ii-20

$^1$H-NMR (300.2 MHz, CDCl$_3$):
δ=7.557 (3.9); 7.551 (4.2); 7.529 (4.5); 7.522 (4.9); 7.385 (7.7); 7.378 (7.2); 7.270 (1.9); 7.165 (7.6); 7.136 (6.6); 4.889 (15.9); 4.881 (16.0); 2.647 (4.1); 2.639 (8.4); 2.631 (4.1); 1.609 (4.3); 0.000 (1.5)

Biological Examples

Biological Example 1: In Vivo Preventive Test on *Puccinia recondita* (Brown Rust on Wheat)

| Solvent: | 5% | by volume of Dimethyl sulfoxide |
| | 10% | by volume of Acetone |
| Emulsifier: | 1 μl | of Tween ® 80 per mg of active ingredient |

The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test, the following compounds according to the invention showed efficacy of at least 70% at a concentration of 500 ppm of active ingredient: I-01; I-02; I-03; I-04.

Biological Example 2: In Vivo Preventive Test on *Septoria tritici* (Leaf Spot on Wheat)

| Solvent: | 5% | by volume of Dimethyl sulfoxide |
| | 10% | by volume of Acetone |
| Emulsifier: | 1 μl | of Tween ® 80 per mg of active ingredient |

The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test, the following compounds according to the invention showed efficacy of at least 70% at a concentration of 500 ppm of active ingredient: I-01; I-02; I-03; I-04.

Biological Example 3: In Vivo Preventive Test on *Sphaerotheca Fuliginea* (Powdery Mildew on Cucurbits)

| Solvent: | 5% | by volume of Dimethyl sulfoxide |
| --- | --- | --- |
|  | 10% | by volume of Acetone |
| Emulsifier: | 1 µl | of Tween ® 80 per mg of active ingredient |

The active ingredients are made soluble and homogenized in a mixture of Dimethyl sulfoxide/Acetone/Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Sphaerotheca fuliginea* spores. The contaminated gherkin plants are incubated for 72 hours at 18° C. and at 100% relative humidity and then for 12 days at 20° C. and at 70-80% relative humidity.

The test is evaluated 15 days after the inoculation. 0% means an efficacy which corresponds to that of the control plants while an efficacy of 100% means that no disease is observed.

In this test, the following compounds according to the invention showed efficacy of at least 70% at a concentration of 500 ppm of active ingredient: I-01; I-02; I-03.

Biological Example 4: In Vivo Preventive Test on *Uromyces Appendiculatus* (Bean Rust)

| Solvent: | 5% | by volume of Dimethyl sulfoxide |
| --- | --- | --- |
|  | 10% | by volume of Acetone |
| Emulsifier: | 1 µl | of Tween ® 80 per mg of active ingredient |

The active ingredients are made soluble and homogenized in a mixture of Dimethyl sulfoxide/Acetone/Tween® 80 and then diluted in water to the desired concentration.

The young plants of bean are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test, the following compounds according to the invention showed efficacy of at least 70% at a concentration of 500 ppm of active ingredient: I-01; I-02; I-03.

Biological Example 5: In Vivo Preventive Test on *Venturia inaequalis* (Apples)

| Solvent: | 24.5 | parts by weight of acetone |
| --- | --- | --- |
|  | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test, the following compounds according to the invention showed efficacy of at least 70% at a concentration of 250 ppm of active ingredient: I-01; I-02; I-03.

Biological Example B1: In Vivo Preventive Test on *Botrytis Cinerea* (Grey Mould)

| Solvent: | 5% | by volume of Dimethyl sulfoxide |
| --- | --- | --- |
|  | 10% | by volume of Acetone |
| Emulsifier: | 1 µl | of Tween ® 80 per mg of active ingredient |

The active ingredients are made soluble and homogenized in a mixture of Dimethyl sulfoxide/Acetone/Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-03; I-42

In this test the following compounds according to the invention showed efficacy between 80% and 89% at a concentration of 500 ppm of active ingredient: I-05

In this test the following compounds according to the invention showed efficacy between 90% and 100% at a concentration of 500 ppm of active ingredient: I-07; I-19; I-26; I-64

Biological Example B2: In Vivo Preventive Test on *Puccinia recondita* (Brown Rust on Wheat)

| | | |
|---|---|---|
| Solvent: | 5% | by volume of Dimethyl sulfoxide |
| | 10% | by volume of Acetone |
| Emulsifier: | 1 µl | of Tween ® 80 per mg of active ingredient |

The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-14; I-19; I-31; I-52; I-56; I-62; I-63; I-65

In this test the following compounds according to the invention showed efficacy between 80% and 89% at a concentration of 500 ppm of active ingredient: I-02; I-03; I-04; I-06; I-08; I-09; I-16; I-29; I-30; I-41; I-45; I-47; I-49; I-50; I-51; I-53; I-57; I-58; I-64; I-66; I-67

In this test the following compounds according to the invention showed efficacy between 90% and 100% at a concentration of 500 ppm of active ingredient: I-01; I-05; I-32; I-42; I-59; I-60; I-61

Biological Example B3: In Vivo Preventive Test on *Septoria tritici* (Leaf Spot on Wheat)

| | | |
|---|---|---|
| Solvent: | 5% | by volume of Dimethyl sulfoxide |
| | 10% | by volume of Acetone |
| Emulsifier: | 1 µl | of Tween ® 80 per mg of active ingredient |

The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test the following compounds according to the invention showed efficacy between 80% and 89% at a concentration of 500 ppm of active ingredient: I-17; I-18; I-24; I-25; I-28; I-44; I-45; I-46; I-50; I-55; I-56

In this test the following compounds according to the invention showed efficacy between 90% and 100% at a concentration of 500 ppm of active ingredient: I-01; I-02; I-03; I-04; I-05; I-06; I-07; I-08; I-09; I-13; I-14; I-15; I-16; I-19; I-22; I-23; I-26; I-29; I-30; I-31; I-32; I-33; I-34; I-35; I-36; I-37; I-38; I-39; I-40; I-41; I-42; I-43; I-47; I-48; I-49; I-51; I-52; I-53; I-54; I-57; I-58; I-59; I-60; I-61; I-62; I-63; I-64; I-65; I-66; I-67

Biological Example B4: In Vivo Preventive Test on *Sphaerotheca fuliginea* (Powdery Mildew on Cucurbits)

| | | |
|---|---|---|
| Solvent: | 5% | by volume of Dimethyl sulfoxide |
| | 10% | by volume of Acetone |
| Emulsifier: | 1 µl | of Tween ® 80 per mg of active ingredient |

The active ingredients are made soluble and homogenized in a mixture of Dimethyl sulfoxide/Acetone/Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Sphaerotheca fuliginea* spores. The contaminated gherkin plants are incubated for 72 hours at 18° C. and at 100% relative humidity and then for 12 days at 20° C. and at 70-80% relative humidity.

The test is evaluated 15 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-38; I-47

In this test the following compounds according to the invention showed efficacy between 80% and 89% at a concentration of 500 ppm of active ingredient: I-09; I-17; I-33; I-43; I-46; I-57

In this test the following compounds according to the invention showed efficacy between 90% and 100% at a concentration of 500 ppm of active ingredient: I-01; I-02; I-03; I-05; I-07; I-16; I-18; I-19; I-29; I-31; I-32; I-34; I-41; I-42; I-44; I-45; I-48; I-49; I-50; I-51; I-52; I-53; I-54; I-59; I-60; I-61; I-62; I-63; I-64; I-65; I-66; I-67

Biological Example B5: In Vivo Preventive Test on *Uromyces appendiculatus* (Bean Rust)

| Solvent: | 5% | by volume of Dimethyl sulfoxide |
|---|---|---|
| | 10% | by volume of Acetone |
| Emulsifier: | 1 µl | of Tween® 80 per mg of active ingredient |

The active ingredients are made soluble and homogenized in a mixture of Dimethyl sulfoxide/Acetone/Tween® 80 and then diluted in water to the desired concentration.

The young plants of bean are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-16; I-65; I-67

In this test the following compounds according to the invention showed efficacy between 80% and 89% at a concentration of 500 ppm of active ingredient: I-01; I-02; I-03; I-60; I-64

In this test the following compounds according to the invention showed efficacy between 90% and 100% at a concentration of 500 ppm of active ingredient: I-59

Biological Example B6: In Vivo Preventive Test on *Alternaria solani* (Tomatoes)

| Solvent: | 24.5 | parts by weight of acetone |
|---|---|---|
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Alternaria solani*. The plants are then placed in an incubation cabinet at approximately 20° C. and a relative atmospheric humidity of 100%.

The test is evaluated 3 days after the inoculation. 0% means an efficacy which corresponds to that of the untreated control while an efficacy of 100% means that no disease is observed.

In this test the following compounds according to the invention showed efficacy between 70% and 79% at a concentration of 50 ppm of active ingredient: I-16

In this test the following compounds according to the invention showed efficacy between 90% and 100% at a concentration of 50 ppm of active ingredient: I-01; I-02; I-03; I-19; I-59; I-60; I-61; I-64

Biological Example B7: In Vivo Preventive Test on *Phakopsora pachyrhizi* (Soybeans)

| Solvent: | 24.5 | parts by weight of acetone |
|---|---|---|
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

In this test the following compounds according to the invention showed efficacy between 90% and 100% at a concentration of 250 ppm of active ingredient: I-01; I-02; I-03; I-59

Biological Example B8: In Vivo Preventive Test on *Sphaerotheca fuliginea* (Cucumbers)

| Solvent: | 24.5 | parts by weight of acetone |
|---|---|---|
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

In this test the following compounds according to the invention showed efficacy between 90% and 100% at a concentration of 50 ppm of active ingredient: I-01; I-02; I-64

Biological Example B9: In Vivo Preventive Test on *Venturia inaequalis* (Apples)

| | | |
|---|---|---|
| Solvent: | 24.5 | parts by weight of acetone |
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test the following compounds according to the invention showed efficacy between 90% and 100% at a concentration of 250 ppm of active ingredient: I-01; I-02; I-03; I-05; I-16; I-19; I-59; I-60; I-61; I-64

Biological Examples C1 to C3: Comparative Examples

Biological Example C1: In Vivo Preventive Test on *Alternaria solani* (Tomatoes)

| | | |
|---|---|---|
| Solvent: | 24.5 | parts by weight of acetone |
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Alternaria solani*. The plants are then placed in an incubation cabinet at approximately 20° C. and a relative atmospheric humidity of 100%.

The test is evaluated 3 days after the inoculation. 0% means an efficacy which corresponds to that of the untreated control while an efficacy of 100% means that no disease is observed.

EFFICACY TABLE C1 in vivo preventive test on *Alternaria solani* (tomatoes)

| Active compound | Rate of application of active compound in ppm | Efficacy in % |
|---|---|---|
| Known from WO 2010/101973: | | |
| [structure] | 50 | 40 |
| According to the invention: | | |
| Ex. I-01 [structure] | 50 | 96 |

Biological Example C2: In Vivo Preventive Test on *Phakopsora pachyrhizi* (Soybeans)

| | | |
|---|---|---|
| Solvent: | 24.5 | parts by weight of acetone |
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%. The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

EFFICACY TABLE C2 in vivo preventive test on *Phakopsora pachyrhizi* (soybeans)

| Active compound | Rate of application of active compound in ppm | Efficacy in % |
|---|---|---|
| Known from WO 2010/101973: | | |
| 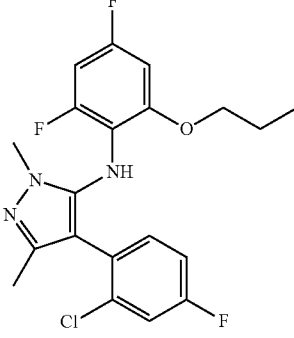 | 250 | 53 |
| According to the invention: | | |
| Ex. I-01 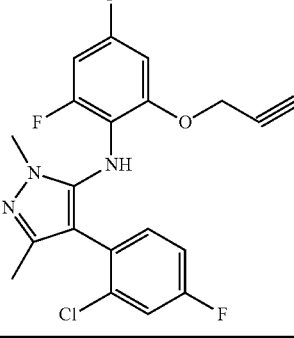 | 250 | 94 |

Biological Example C3: In Vivo Preventive Test on *Sphaerotheca fuliginea* (Cucumbers)

| Solvent: | 24.5 | parts by weight of acetone |
|---|---|---|
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

EFFICACY TABLE C3 in vivo preventive test on *Sphaerotheca fuliginea* (cucumbers)

| Active compound | Rate of application of active compound in ppm | Efficacy in % |
|---|---|---|
| Known from WO 2010/101973: | | |
| 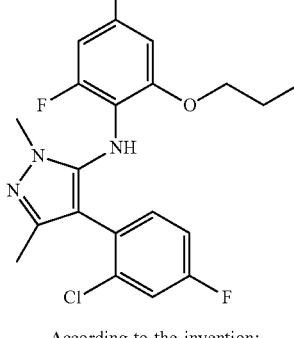 | 50 | 10 |
| According to the invention: | | |
| Ex. I-01 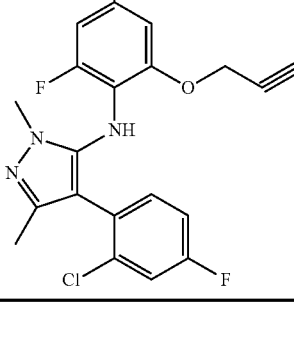 | 50 | 98 |

The invention claimed is:
1. A compound of formula (I)

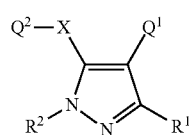

and/or one or more tautomers and/or salts thereof, wherein

R$^1$ is H, CH$_3$, F, Cl, Br, or C$_1$-C$_4$ alkoxy,

R$^2$ is methyl or ethyl,

X is a structure element selected from the group consisting of NH, N(CH$_3$), O, S, CH$_2$, CH(OH), and CH(CH$_3$), Q$^1$ is a 5- to 7-membered carbocyclic ring, optionally substituted with up to 5 independently selected substituents R$^{Q1}$;

or a 5- to 7-membered heterocyclic ring containing ring members selected from the group consisting of C, N, O and S, and containing up to 3 heteroatom ring members independently selected from the group O, S, and N, wherein the heterocyclic ring contains as heteroatom ring members up to 1 O atom, up to 1 S atom, and up to 3 N atoms, wherein optionally up to 3 carbon ring members are independently selected from C(=O) and C(=S), and, if present, the sulfur atom ring members are independently selected from S, S(O), or S(O)$_2$, wherein the heterocyclic ring is optionally substituted with up to 5 substituents $R^{Q1}$ on carbon atom heterocyclic ring members and optionally substituted with substituents $R^N$ on nitrogen atom heterocyclic ring members, if present, each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, SCF$_3$, SF$_5$, SCN, isonitrile, $CR^C$=NO—$C_1$-$C_4$ alkyl, —NR$^{1N}$R$^{2N}$ and optionally substituted phenyl, $Q^2$ is a 5- or 6-membered carbocyclic ring, [optionally] substituted with 1 [up] to 5 substituents $R^{Q2}$;

or a 5- to 7-membered heterocyclic ring containing ring members selected from the group consisting of C, N, O and S, and containing up to 3 heteroatom ring members independently selected from the group O, S, and N, wherein the heterocyclic ring contains as heteroatom ring members up to 1 O atom, up to 1 S atom, and up to 3 N atoms, wherein optionally up to 3 carbon ring members are independently selected from C(=O) and C(=S), and, if present, the sulfur atom ring members are independently selected from S, S(O), or S(O)$_2$, wherein the heterocyclic ring is [optionally] substituted with [up] 1 to 5 substituents $R^{Q2}$ on carbon atom heterocyclic ring members and optionally substituted with substituents $R^N$ on nitrogen atom heterocyclic ring members, if present, each $R^{Q2}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, SCF$_3$, SF$_5$, SCN, isonitrile, $CR^C$=NO—$C_1$-$C_4$ alkyl, —NR$^{1N}$R$^{2N}$ and optionally substituted phenyl, wherein each $R^N$ is independently selected from the group consisting of cyano, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl, $C_1$-$C_6$ aminoalkyl, benzyl, and SO$_2$R$^S$, wherein each $R^C$ is independently selected from the group consisting of H and $C_1$-$C_4$ alkyl, wherein $R^{1N}$ and $R^{2N}$ each are independently selected from $C_1$-$C_4$ alkyl and $C_3$-$C_6$ cycloalkyl, wherein each $R^S$ is independently selected from $C_1$-$C_4$ alkyl, $C_1$-$C_4$ haloalkyl, and $C_3$-$C_6$ cycloalkyl, wherein each optionally substituted phenyl is independently selected from phenyl substituted with up to 5 radicals selected from the group consisting of halogen, cyano, $C_1$-$C_4$ alkyl, $C_1$-$C_4$ haloalkyl, ($C_1$-$C_4$)-alkoxy-($C_1$-$C_4$)-alkyl, $C_1$-$C_4$ alkoxy, $C_1$-$C_4$ haloalkoxy, ($C_1$-$C_4$)-alkoxy-($C_1$-$C_4$)-alkoxy, ($C_1$-$C_4$) alkylthio and nitro, provided that at least one substituent $R^{Q2}$ that is present is $C_3$-$C_7$ alkenylalkoxy or $C_3$-$C_7$ alkynylalkoxy.

2. A compound of formula (I) according to claim 1, and/or one or more tautomers and/or salts thereof, wherein $R^1$ is H, CH$_3$, F, Cl, Br, or OCH$_3$, $R^2$ is methyl or ethyl, X is a structure element selected from the group consisting of NH, N(CH$_3$), O, S, CH$_2$, CH(OH), and CH(CH$_3$), $Q^1$ is a 5- to 7-membered fully saturated carbocyclic ring or a fully unsaturated 6-membered carbocyclic ring, optionally substituted with up to 5 substituents $R^{Q1}$; or a 5- to 7-membered fully saturated heterocyclic ring or a fully unsaturated 5- or 6-membered heterocyclic ring containing ring members selected from the group consisting of C, N, O and S, and containing up to 3 heteroatom ring members independently selected from the group O, S, and N, wherein the heterocyclic ring contains as heteroatom ring members up to 1 O atom, up to 1 S atom, and up to 3 N atoms, wherein the heterocyclic ring is optionally substituted with up to 3 substituents $R^{Q1}$ on carbon atom heterocyclic ring members and optionally substituted with substituents $R^N$ on nitrogen atom heterocyclic ring members, if present, each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, SCF$_3$, SF$_5$, SCN, isonitrile, CH=NO—$C_1$-$C_4$ alkyl, —NR$^{1N}$R$^{2N}$ and optionally substituted phenyl, $Q^2$ is a fully unsaturated or a fully saturated 5- or 6-membered carbocyclic ring, [optionally] substituted with [up] 1 to 5 substituents $R^{Q2}$;

or is a fully unsaturated or a fully saturated 5- or 6-membered heterocyclic ring, wherein the heterocyclic ring is [optionally] substituted with [up] 1 to 5 substituents $R^{Q2}$ on carbon atom heterocyclic ring members and optionally substituted with substituents $R^N$ on nitrogen atom heterocyclic ring members, if present, each $R^{Q2}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, CH=NO—$C_1$-$C_4$ alkyl, —$NR^{1N}R^{2N}$ and optionally substituted phenyl, wherein each $R^N$ is independently selected from the group consisting of cyano, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl, $C_1$-$C_6$ aminoalkyl, benzyl, $SO_2R^S$, wherein $R^{1N}$ and $R^{2N}$ each are independently selected from $C_1$-$C_4$ alkyl and $C_3$-$C_6$ cycloalkyl, wherein each $R^S$ is independently selected from $C_1$-$C_4$ alkyl, $C_1$-$C_4$ haloalkyl, and $C_3$-$C_6$ cycloalkyl, wherein each optionally substituted phenyl is independently selected from phenyl substituted with up to 5 radicals selected from the group consisting of halogen, cyano, $C_1$-$C_4$ alkyl, $C_1$-$C_4$ haloalkyl, ($C_1$-$C_4$)-alkoxy-($C_1$-$C_4$)-alkyl, $C_1$-$C_4$ alkoxy, $C_1$-$C_4$ haloalkoxy, ($C_1$-$C_4$)-alkoxy-($C_1$-$C_4$)-alkoxy, ($C_1$-$C_4$) alkylthio and nitro provided that at least one substituent $R^{Q2}$ is $C_3$-$C_7$ alkenylalkoxy or $C_3$-$C_7$ alkynylalkoxy.

3. A compound of formula (I) according to claim 1, and/or one or more tautomers and/or salts thereof, wherein $R^1$ is H, $CH_3$, F, Cl or Br, $R^2$ is $CH_3$, X is a structure element selected from the group consisting of NH, N($CH_3$), O, S, $CH_2$, CH(OH), and CH($CH_3$), $Q^1$ is a ring selected from the group consisting of phenyl, 5- or 6-membered heteroaromatic rings, 5- to 7-membered fully saturated heterocyclic rings, and 5- to 7-membered fully saturated carbocyclic rings, wherein $Q^1$ is optionally substituted with up to 5 substituents $R^{Q1}$;

wherein each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, CH=NO—$C_1$-$C_4$ alkyl, —$NR^{1N}R^{2N}$ and optionally substituted phenyl, $Q^2$ is a fully unsaturated or a fully saturated 5- or 6-membered carbocyclic or heterocyclic ring, [optionally] substituted with [up] 1 to 5 substituents $R^{Q2}$; wherein each $R^{Q2}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_3$-$C_6$ heterocyclyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkenyloxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_3$-$C_6$ heterocyclyloxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_4$-$C_7$ alkylcycloalkyl, $C_4$-$C_6$ cycloalkylalkyl, $C_2$-$C_3$ alkylcarbonyl, $C_2$-$C_3$ alkylcarbonyloxy, $C_1$-$C_4$ alkanoylamino, $C_2$-$C_3$ alkylcarbonylamino, ($C_1$-$C_6$ alkoxy)iminocarbonyl, tri($C_1$-$C_4$-alkyl)silyl, $SCF_3$, $SF_5$, SCN, isonitrile, CH=NO—$C_1$-$C_4$ alkyl, —$NR^{1N}R^{2N}$ and optionally substituted phenyl, wherein $R^{1N}$ and $R^{2N}$ are independently selected from $C_1$-$C_4$ alkyl and $C_3$-$C_6$ cycloalkyl, wherein each optionally substituted phenyl is independently selected from phenyl substituted with up to 5 radicals selected from the group consisting of halogen, cyano, $C_1$-$C_4$ alkyl, $C_1$-$C_4$ haloalkyl, ($C_1$-$C_4$)-alkoxy-($C_1$-$C_4$)-alkyl, $C_1$-$C_4$ alkoxy, $C_1$-$C_4$ haloalkoxy, ($C_1$-$C_4$)-alkoxy-($C_1$-$C_4$)-alkoxy, ($C_1$-$C_4$) alkylthio and nitro, provided that at least one substituent $R^{Q2}$ is $C_3$-$C_7$ alkenylalkoxy or $C_3$-$C_7$ alkynylalkoxy.

4. A compound of formula (I) according to claim 1, and/or one or more tautomers and/or salts thereof, wherein $R^1$ is $CH_3$ or $C_1$, $R^2$ is $CH_3$, X is a structure element selected from the group consisting of NH, N($CH_3$), O, S, $CH_2$, CH(OH), and CH($CH_3$), $Q^1$ is a ring selected from the group consisting of phenyl, 5- or 6-membered heteroaromatic rings, 5- to 7-membered fully saturated heterocyclic rings, and 5- or 6-membered fully saturated carbocyclic rings, wherein $Q^1$ is optionally substituted with up to 5 substituents $R^{Q1}$;

wherein each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_4$-$C_7$ alkylcycloalkyl, $C_4$-$C_6$ cycloalkylalkyl, $C_1$-$C_4$ alkanoylamino, $SF_5$, SCN, isonitrile, CH=NO—$C_1$-$C_4$ alkyl, —$NR^{1N}R^{2N}$ and optionally substituted phenyl, $Q^2$ is a ring selected from the group consisting of phenyl, 5-membered heteroaromatic rings and 6-membered heteroaromatic rings, wherein $Q^2$ is [optionally] substituted with [up] 1 to 5 substituents $R^{Q2}$;

wherein each $R^{Q2}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_1$-$C_6$ alkoxy, $C_1$-$C_6$ haloalkoxy, $C_2$-$C_6$ alkenyl, $C_3$-$C_4$ alkenylalkoxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_4$-$C_7$ alkylcycloalkyl, $C_4$-$C_6$ cycloalkylalkyl, $C_1$-$C_4$ alkanoylamino, $SF_5$, SCN, isonitrile, CH=NO—$C_1$-$C_4$ alkyl, —$NR^{1N}R^{2N}$ and optionally substituted phenyl,
wherein $R^{1N}$ and $R^{2N}$ are independently selected from $C_1$-$C_4$ alkyl and $C_3$-$C_6$ cycloalkyl,
wherein each optionally substituted phenyl is independently selected from phenyl substituted with up to 5 radicals selected from the group consisting of halogen, cyano, $C_1$-$C_4$ alkyl, $C_1$-$C_4$ haloalkyl, $(C_1$-$C_4)$-alkoxy-$(C_1$-$C_4)$-alkyl, $C_1$-$C_4$ alkoxy, $C_1$-$C_4$ haloalkoxy, $(C_1$-$C_4)$-alkoxy-$(C_1$-$C_4)$-alkoxy, $(C_1$-$C_4)$ alkylthio and nitro,
provided that at least one substituent $R^{Q2}$ is $C_3$-$C_7$ alkenylalkoxy or $C_3$-$C_7$ alkynylalkoxy.

5. A compound of formula (I) according to claim 1, and/or one or more tautomers and/or salts thereof, wherein
$R^1$ is $CH_3$ or $C_1$,
$R^2$ is $CH_3$,
X is a structure element selected from the group consisting of NH, $N(CH_3)$, O, S, $CH_2$, CH(OH), and $CH(CH_3)$,
$Q^1$ is a ring selected from the group consisting of phenyl, 5- or 6-membered heteroaromatic rings, 5- to 7-membered fully saturated heterocyclic rings, and 5- or 6-membered fully saturated carbocyclic rings, wherein $Q^1$ is optionally substituted with up to 5 substituents $R^{Q1}$;
wherein each $R^{Q1}$ is independently selected from the group consisting of halogen, cyano, nitro, amino, hydroxy, formyl, $C_1$-$C_6$ alkyl, $C_1$-$C_6$ haloalkyl, $C_3$-$C_6$ cycloalkyl, $C_3$-$C_7$ halocycloalkyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_4$-$C_7$ alkylcycloalkyl, $C_4$-$C_6$ cycloalkylalkyl, $C_1$-$C_4$ alkanoylamino, $SF_5$, SCN, isonitrile, CH=NO—$C_1$-$C_4$ alkyl, —$NR^{1N}R^{2N}$ and optionally substituted phenyl,
wherein $R^{1N}$ and $R^{2N}$ are independently selected from $C_1$-$C_4$ alkyl and $C_3$-$C_6$ cycloalkyl,
wherein optionally substituted phenyl is phenyl substituted with up to 5 radicals selected from the group consisting of halogen, cyano, $C_1$-$C_4$ alkyl, $C_1$-$C_4$ haloalkyl, $(C_1$-$C_4)$-alkoxy-$(C_1$-$C_4)$-alkyl, $C_1$-$C_4$ alkoxy, $C_1$-$C_4$ haloalkoxy, $(C_1$-$C_4)$-alkoxy-$(C_1$-$C_4)$-alkoxy, $(C_1$-$C_4)$ alkylthio and nitro,
$Q^2$ is a ring selected from the group consisting of phenyl or pyridinyl, wherein $Q^2$ is [optionally] substituted with one or more substituents $R^{Q2}$;
wherein each $R^{Q2}$ is independently selected from the group consisting of halogen, cyano, nitro, amino, hydroxy, $C_1$-$C_6$ alkyl, $C_1$-$C_6$ haloalkyl, $C_1$-$C_6$ alkoxy, $C_1$-$C_6$ haloalkoxy, $C_3$-$C_7$ alkenylalkoxy, $C_2$-$C_6$ alkynyl, $C_3$-$C_7$ alkynylalkoxy, and $C_3$-$C_7$ alkynyloxy,
provided that at least one substituent $R^{Q2}$ is propargyloxy or allyloxy.

6. A compound of formula (I) according to claim 1, and/or one or more tautomers and/or salts thereof, wherein
$R^1$ is $CH_3$ or $C_1$,
$R^2$ is $CH_3$,
X is a structure element selected from the group consisting of NH, $N(CH_3)$, O, S, $CH_2$, CH(OH), and $CH(CH_3)$,
$Q^1$ is a ring selected from the group consisting of phenyl, furanyl, pyridinyl, piperidinyl, azepanyl and morpholinyl, wherein $Q^1$ is optionally substituted with up to 5 substituents $R^{Q1}$;
wherein each $R^{Q1}$ is independently selected from the group consisting of halogen, cyano, nitro, amino, hydroxy, formyl, $C_1$-$C_6$ alkyl, $C_1$-$C_6$haloalkyl, $C_3$-$C_6$ cycloalkyl, $C_3$-$C_7$ halocycloalkyl, $C_1$-$C_6$ alkoxy, $C_1$-$C_6$ haloalkoxy, $C_2$-$C_6$ alkenyl, $C_3$-$C_7$ alkenylalkoxy, $C_2$-$C_6$ alkynyl, $C_3$-$C_7$ alkynylalkoxy, $C_3$-$C_7$ alkynyloxy, $C_3$-$C_7$ cycloalkoxy, $C_3$-$C_6$ halocycloalkoxy, $C_4$-$C_7$ alkylcycloalkyl, $C_4$-$C_6$ cycloalkylalkyl, $C_1$-$C_4$ alkanoylamino, $SF_5$, SCN, isonitrile, and —$NR^{1N}R^{2N}$, wherein
$R^{1N}$ and $R^{2N}$ are independently selected from $C_1$-$C_4$ alkyl and $C_3$-$C_6$ cycloalkyl, provided that at least one of the substituents $R^{Q1}$ is selected from the group consisting of halogen, cyano, nitro, amino, hydroxy, $C_1$-$C_6$ alkyl, $C_1$-$C_6$ haloalkyl, $C_1$-$C_6$ alkoxy, $C_1$-$C_6$ haloalkoxy, $C_2$-$C_6$ alkynyl, $C_3$-$C_7$ alkynylalkoxy, and $C_3$-$C_7$ alkynyloxy,
$Q^2$ is a phenyl ring substituted with one, two, three or four substituents $R^{Q2}$; wherein each $R^{Q2}$ is independently selected from the group consisting of halogen, cyano, nitro, amino, hydroxy, $C_1$-$C_6$ alkyl, $C_1$-$C_6$ haloalkyl, $C_1$-$C_6$ alkoxy, $C_1$-$C_6$ haloalkoxy, $C_3$-$C_7$ alkenylalkoxy, $C_2$-$C_6$ alkynyl, $C_3$-$C_7$ alkynylalkoxy, and $C_3$-$C_7$ alkynyloxy,
provided that one, two or three substituents $R^{Q2}$ are propargyloxy or allyloxy.

7. A compound of formula (I) according to claim 1, and/or one or more tautomers and/or salts thereof, wherein
$R^1$ is $CH_3$ or $C_1$,
$R^2$ is $CH_3$,
X is NH or O,
$Q^1$ is a phenyl or a furanyl ring, wherein $Q^1$ is optionally substituted with one or more substituents $R^{Q1}$ selected from the group consisting of F, Cl, Br, I, cyano, nitro, amino, hydroxy, $C_1$-$C_6$ alkyl, $C_1$-$C_6$haloalkyl, $C_1$-$C_6$ alkoxy, $C_1$-$C_6$ haloalkoxy, $C_3$-$C_6$ alkenylalkoxy, $C_2$-$C_6$ alkynyl, $C_3$-$C_7$ alkynylalkoxy, and $C_3$-$C_7$ alkynyloxy,
$Q^2$ is a phenyl ring substituted with one, two, three or four substituents $R^{Q2}$; wherein each $R^{Q2}$ is independently selected from the group consisting of F, Cl, Br, I, cyano, hydroxy, $C_1$-$C_6$ alkyl, $C_1$-$C_6$haloalkyl, $C_1$-$C_6$ alkoxy, $C_1$-$C_6$ haloalkoxy, $C_3$-$C_6$ alkenylalkoxy, $C_3$-$C_7$ alkynylalkoxy, and $C_3$-$C_7$ alkynyloxy,
provided that one, two or three substituents $R^{Q2}$ are propargyloxy or allyloxy.

8. A compound of formula (I) according to claim 1, and/or one or more tautomers and/or salts thereof, wherein
$R^1$ is $CH_3$ or $C_1$,
$R^2$ is $CH_3$,
X is NH or O,
$Q^1$ is a phenyl ring substituted with one or more substituents $R^{Q1}$ selected from the group consisting of F, Cl, Br, I, cyano, nitro, amino, hydroxy, $C_1$-$C_4$ alkyl, $C_1$-$C_4$ haloalkyl, $C_1$-$C_4$ alkoxy, $C_1$-$C_4$ haloalkoxy, $C_3$-$C_6$ alkenylalkoxy, $C_3$-$C_7$ alkynylalkoxy, and $C_3$-$C_6$ alkynyloxy,
$Q^2$ is a phenyl ring substituted with one, two, three or four substituents $R^{Q2}$; wherein each $R^{Q2}$ is independently selected from the group consisting of F, Cl, Br, I, cyano, hydroxy, $C_1$-$C_4$ alkyl, $C_1$-$C_4$ haloalkyl, $C_1$-$C_4$ alkoxy, $C_1$-$C_4$ haloalkoxy, $C_3$-$C_6$ alkenylalkoxy, $C_3$-$C_7$ alkynylalkoxy, and $C_3$-$C_6$ alkynyloxy, provided that one, two or three substituents $R^{Q2}$ are propargyloxy or allyloxy.

9. A composition comprising
(a) a fungicidally effective amount of a compound as defined in claim 1,
and one or more further constituents selected from the group consisting of groups (b) and (c):
(b) agrochemically acceptable adjuvants and
(c) other pesticidally active ingredients.

10. A method for controlling one or more plant diseases caused by fungal plant pathogens, comprising
(i) providing a compound of the formula (I) as defined in claim 1, and
(ii) applying to the plant, to a portion of the plant or to plant seeds a fungicidally effective amount the compound provided in (i).

11. A product comprising a compound of the formula (I) as defined in claim 1 for controlling fungi in plants or plant seeds.

12. A method for producing a compound of formula (I) as defined in claim 1, comprising:

(i) providing a compound of formula (Z-ix)

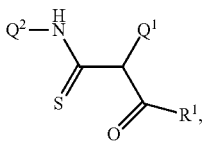

(Z-ix)

(ii) providing a compound of formula (Z-x)

$R^2NH-NH_2$ (Z-x)

(iii) reacting compounds (Z-ix) and (Z-x), thereby obtaining a compound of formula (I).

13. A composition according to claim 9, comprising one or more of a surfactant, liquid diluent, or solid diluent.

14. A compound of formula (I) according to claim 1, which comprises at least one $R^{Q2}$ substituent which is propargyloxy.

15. A compound of formula (I) according to claim 1, which comprises at least one $R^{Q2}$ substituent which is allyloxy.

* * * * *